(12) United States Patent
Malamas et al.

(10) Patent No.: US 7,417,047 B2
(45) Date of Patent: Aug. 26, 2008

(54) AMINO-5-(5-MEMBERED)HETERO-ARYLIMIDAZOLONE COMPOUNDS AND THE USE THEREOF FOR β-SECRETASE MODULATION

(75) Inventors: Michael Sotirios Malamas, Jamison, PA (US); Ping Zhou, Plainsboro, NJ (US); William Floyd Fobare, Lawrenceville, NJ (US); William Ronald Solvibile, East Windsor, NJ (US); Iwan Suwandi Gunawan, Somerset, NJ (US); James Joseph Erdei, Philadelphia, PA (US); Yinfa Yan, Bedminster, NJ (US); Patrick Michael Andrae, Jamesburg, NJ (US); Dominick Anthony Quagliato, Bridgewater, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/478,122

(22) Filed: Jun. 29, 2006

(65) Prior Publication Data
US 2007/0004786 A1    Jan. 4, 2007

Related U.S. Application Data

(60) Provisional application No. 60/695,353, filed on Jun. 30, 2005.

(51) Int. Cl.
A61K 31/4178    (2006.01)
A61K 31/4439    (2006.01)
A61K 31/506     (2006.01)
C07D 403/04     (2006.01)
C07D 401/14     (2006.01)

(52) U.S. Cl. .................. 514/256; 514/341; 514/386; 548/314.7; 546/274.4; 544/333

(58) Field of Classification Search .............. 548/314.7; 514/386, 256, 341; 546/274.4; 544/333
See application file for complete search history.

(56) References Cited

U.S. PATENT DOCUMENTS

| 4,140,793 | A  | 2/1979  | Ward           |
| 4,225,613 | A  | 9/1980  | Ward           |
| 6,054,457 | A  | 4/2000  | Setoi et al.   |
| 6,399,824 | B1 | 6/2002  | Hofmeister et al. |
| 6,656,957 | B1 | 12/2003 | Allgeier et al. |
| 6,974,829 | B2 | 12/2005 | Tung et al.    |
| 7,285,682 | B2 | 10/2007 | Hu             |
| 2005/0282825 | A1 | 12/2005 | Malamas et al. |
| 2005/0282826 | A1 | 12/2005 | Malamas et al. |
| 2006/0111370 | A1 | 5/2006  | Zhu et al.     |
| 2006/0160828 | A1 | 7/2006  | Malamas et al. |
| 2006/0173049 | A1 | 8/2006  | Malamas et al. |
| 2006/0183790 | A1 | 8/2006  | Cole et al.    |
| 2006/0183792 | A1 | 8/2006  | Fobare et al.  |
| 2007/0004730 | A1 | 1/2007  | Zhou           |
| 2007/0027199 | A1 | 2/2007  | Malamas et al. |
| 2007/0072925 | A1 | 3/2007  | Malamas et al. |
| 2007/0191431 | A1 | 8/2007  | Zhou           |
| 2007/0203116 | A1 | 8/2007  | Quagliato et al. |
| 2008/0051390 | A1 | 2/2008  | Malamas et al. |

FOREIGN PATENT DOCUMENTS

| EP | 0861831 A1 | 9/1998 |
| GB | 2013192 A | 8/1979 |
| WO | WO 97/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2004/058727 A1 | 7/2004 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 | 1/2007 |
| WO | WO 2007/016012 A2 | 2/2007 |

OTHER PUBLICATIONS

NINDS Alzheimer's Disease Information Page, retrieved from Internet on Jun. 27, 2007, <http://www.ninds.nih.gov/disorders/alzheimersdisease/alzheimersdisease.htm>.*
Selkoe, Alzheimer's Disease: Genes, Proteins, and Therapy, Apr. 2001, Physiological Reviews, vol. 81(2), 741-766.*
PCT Preliminary Report on Patentability, Written Opinion of the ISR, corresponding PCT international application PCT/US2006/024793, international filing date Jun. 26, 2006.

(Continued)

*Primary Examiner*—Rebecca L Anderson
*Assistant Examiner*—Jason M Nolan
(74) *Attorney, Agent, or Firm*—Joel Silver; Scott Larsen; Andrea Dorigo

(57) ABSTRACT

The present invention provides a 2-amino-5-heteroaryl-5-phenylimidazolone compound of formula I

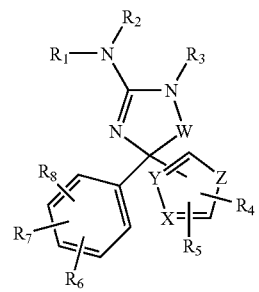

The present invention also provides methods for the use thereof to inhibit β-secretase (BACE) and treat β-amyloid deposits and neurofibrillary tangles.

12 Claims, No Drawings

OTHER PUBLICATIONS

Abbott et al., Molecular Medicine Today, 1996, vol. 2, p. 106-113.
Allimony et al., "Synthesis and antimicrobial activity of some nitrogen heterobicyclic systems: Part I", Indian Journal of Chemistry, 1999, vol. 38B, pp. 445-451.
Fact Sheet Alzheimer's Association, 2006.
Lefrance-Jullien et al., "Design and charaterization of a new cell-permeant inhibitor of the beta-secretase BACE1", British Journal of Pharmacology, 2005, vol. 145, pp. 228-235.
Lyketsos et al., "Position statement of the American Association for Geriatric Psychiatry regarding principles of care for patients with dementia resulting from Alzheimer's Disease", 2006, vol. 14, pp. 561-573.
Alzheimer's Disease, retrieved from internet on Jun. 27, 2007, http://www.mayoclinic.com/health/alzheimers-disease/DA00161/DSECTION-3.
PCT Preliminary Report on Patentability, Written Opinion of the ISR, International Patent Application PCT/US2006/024912, International filing date Jun. 26, 2006.
Su et al. "Drug delivery across the blood-brain barrier: why is it difficult? How to measure and improve it?", Expert Opinion on Drug Delivery, Abstract, 2006, vol. 3, pp. 419-425.
Tao et al., "Synthesis of Conformationally constrained spirohydantoins with a Dibenzo[a,d]heptadiene ring", Synthesis 2000, No. 10, pp. 1449-1453.
Vandana et al., "Transferring coupled liposomes as drug delivery carriers for brain trageting of 5-florouracil", Journal of Drug Targeting, Abstract, 2005, vol. 13 pp. 245-250.
Varghese et al., "Human beta-secretase (BACE) and BACE Inhibitors", J. Med. Chem. 2003, vol. 46(22), pp. 4625-4630.
Xiao et al., "An improved procedure for the synthesis of 4,4-disubstituted-3-oxo-1,2,5-thiadiazolidine 1,1-dioxides", J. Heterocyclic Chem., 2000, vol. 37, pp. 773-777.
Yamada et al., "Hydantoin derivatives, I. Actions on central nervous system of 5,5-diarylhydantoins and 5,5-diarylhydantion-2-imines", Abstract, Oyo Yakuri, 1975, vol. 9(6), pp. 841-847.

* cited by examiner

AMINO-5-(5-MEMBERED)HETERO-ARYLIMIDAZOLONE COMPOUNDS AND THE USE THEREOF FOR β-SECRETASE MODULATION

BACKGROUND OF THE INVENTION

This application claims the benefit under 35 U.S.C. §119 (e) to U.S. Provisional Application No. 60/695,353, filed Jun. 30, 2005, which is hereby incorporated by reference in its entirety.

β-Amyloid deposits and neurofibrillary tangles are two major pathologic characterizations associated with Alzheimer's disease (AD). Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630).

β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324).

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY OF THE INVENTION

The present invention provides a compound of formula I

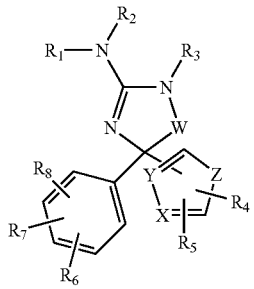

wherein W is CO, CS or $CH_2$;
X is N, NR, NO, S, $SO_m$, O or $CR_9$;
Y is N, NR, NO, S, $SO_m$, O or $CR_{10}$;
Z is C, N, NR, NO, S, $SO_m$, O, $CR_{11}$ or $CR_{11}R_{12}$ with the proviso that at least one of X, Y or Z must be N, NR, NO, S, $SO_m$ or O;
m is 1 or 2;
R is H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl($C_1$-$C_6$)alkyl group each optionally substituted;
$R_1$ and $R_2$ are each independently H, $COR_{14}$, $CO_2R_{15}$ or an optionally substituted $C_1$-$C_4$alkyl group;
$R_3$ is H, $OR_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl ($C_1$-$C_6$)alkyl group each optionally substituted;
$R_4$, $R_5$, $R_9$ and $R_{10}$ are each independently H, halogen, $NO_2$, CN, $OR_{14}$, $CO_2R_{15}$, $COR_{16}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_6$ and $R_8$ are each independently H, halogen, $NO_2$, CN, $OR_{21}$, $NR_{22}R_{23}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_7$ is H, halogen, $NO_2$, CN, $OR_{24}$, $NR_{25}R_{26}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, aryl or heteroaryl group each optionally substituted;
$R_{11}$, $R_{12}$, $R_{13}$, $R_{14}$, $R_{15}$, $R_{16}$, $R_{21}$, $R_{24}$, $R_{27}$, $R_{28}$ and $R_{29}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted;
$R_{17}$, $R_{18}$, $R_{19}$, $R_{20}$, $R_{22}$, $R_{23}$, $R_{25}$, $R_{26}$, $R_{30}$, $R_{31}$, $R_{32}$ and $R_{33}$ are each independently H, $COR_{34}$, $SO_pR_{35}$ or a $C_1$-$C_4$alkyl, $C_2$-$C_6$alkenyl, $C_2$-$C_6$alkynyl, $C_3$-$C_8$ cycloalkyl, cycloheteroalkyl, aryl or heteroaryl group each optionally substituted or $R_{17}$, $R_{18}$; or $R_{19}$, $R_{20}$, or $R_{22}$, $R_{23}$, or $R_{25}$, $R_{26}$, or $R_{30}$, $R_{31}$, or $R_{32}$, $R_{33}$ may be taken together with the atom to which they are attached to form an optionally substituted 5- to 7-membered ring optionally containing an additional heteroatom selected from O, N or S;
$R_{34}$ is H, or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; and
$R_{35}$ is a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; or a tautomer thereof, a stereoisomer thereof or a pharmaceutically acceptable salt thereof.

The present invention also relates to the use of the formula I amino-5-heteroaryl-imidazolone compound for the treatment of β-amyloid deposits and neurofibrillary tangles. The compound of the invention is particularly useful for treating Alzheimer's disease, cognitive impairment, Down's Syndrome, HCHWA-D, cognitive decline, senile dementia, cerebral amyloid angiopathy, degenerative dementia, or other neurodegenerative disorders.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deterioration and death. The exact cause of AD is unknown, but increasing evidence indicates that amyloid beta peptide (A-beta) plays a central role in the pathogenesis of the disease. (D. B. Schenk; R. E. Rydel et al., Journal of Medicinal Chemistry, 1995, 21, 4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type and other neurodegenerative and dementia-inducing disorders. Overexpression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al., Nature, 1999, 402, 537). BACE1 is a membrane-bound aspartic protease with all the known functional properties and characteristics of β-secretase. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that amino-5-heteroarylimidazolone compounds of formula I demonstrate inhibition of β-secretase and the selective inhibition of BACE1. Advantageously, said heteroarylimidazolone compounds may be used as effective therapeutic agents for the treatment, prevention or amelioration of a disease or disorder characterized by elevated β-amyloid deposits or β-amyloid levels in a patient. Accordingly, the present invention provides an amino-pyridine compound of formula I

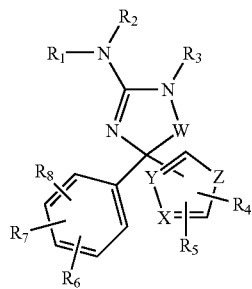

I wherein W is CO, CS or $CH_2$;
X is N, NR, NO, S, $SO_m$, O or $CR_9$;
Y is N, NR, NO, S, $SO_m$, O or $CR_{10}$;
Z is C, N, NR, NO, S, $SO_m$, O, $CR_{11}$ or $CR_{11}R_{12}$ with the proviso that at least one of X, Y or Z must be N, NR, NO, S, $SO_m$ or O;
m is 1 or 2;
R is H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl($C_1$-$C_6$)alkyl group each optionally substituted;
$R_1$ and $R_2$ are each independently H, $COR_{14}$, $CO_2R_{15}$ or an optionally substituted $C_1$-$C_4$alkyl group;
$R_3$ is H, $OR_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl ($C_1$-$C_6$)alkyl group each optionally substituted;
$R_4$, $R_5$, $R_9$ and $R_{10}$ are each independently H, halogen, $NO_2$, CN, $OR_{14}$, $CO_2R_{15}$, $COR_{16}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_6$ and $R_8$ are each independently H, halogen, $NO_2$, CN, $OR_{21}$, $NR_{22}R_{23}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_7$ is H, halogen, $NO_2$, CN, $OR_{24}$, $NR_{25}R_{26}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, aryl or heteroaryl group each optionally substituted;
$R_{11}$, $R_{12}$, $R_{13}$, $R_{14}$, $R_{15}$, $R_{16}$, $R_{21}$, $R_{24}$, $R_{27}$, $R_{28}$ and $R_{29}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted;
$R_{17}$, $R_{18}$, $R_{19}$, $R_{20}$, $R_{22}$, $R_{23}$, $R_{25}$, $R_{26}$, $R_{30}$, $R_{31}$, $R_{32}$ and $R_{33}$ are each independently H, $COR_{34}$, $SO_pR_{35}$ or a $C_1$-$C_4$alkyl, $C_2$-$C_6$alkenyl, $C_2$-$C_6$alkynyl, $C_3$-$C_8$ cycloalkyl, cycloheteroalkyl, aryl or heteroaryl group each optionally substituted or $R_{17}$, $R_{18}$; or $R_{19}$, $R_{20}$, or $R_{22}$, $R_{23}$, or $R_{25}$, $R_{26}$, or $R_{30}$, $R_{31}$, or $R_{32}$, $R_{33}$ may be taken together with the atom to which they are attached to form an optionally substituted 5- to 7-membered ring optionally containing an additional heteroatom selected from O, N or S;
$R_{34}$ is H, or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; and
$R_{35}$ is a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; or a tautomer thereof, a stereoisomer thereof or a pharmaceutically acceptable salt thereof.

It is understood that the claims encompass all possible stereoisomers and prodrugs. Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents. The substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term "alkyl" includes both ($C_1$-$C_{10}$) straight chain and ($C_3$-$C_{12}$) branched-chain (unless defined otherwise) monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Specifically included within the definition of "alkyl" are those alkyl groups that are optionally substituted. Suitable alkyl substitutions include, but are not limited to, CN, OH, halogen, phenyl, carbamoyl, carbonyl, alkoxy or aryloxy.

As used herein the term "haloalkyl" designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like.

The term "alkenyl", as used herein, refers to either a ($C_2$-$C_8$) straight chain or ($C_3$-$C_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term "cycloalkyl", as used herein, refers to a monocyclic, bicyclic, tricyclic, fused, bridged, or spiro monovalent saturated hydrocarbon moiety of 3-10 carbon atoms, unless otherwise specified, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, or the like.

The term "cycloheteroalkyl" as used herein designates a $C_5$-$C_7$cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein $X_1$ is NR', O or S and R is H or an optional substituent as defined hereinbelow.

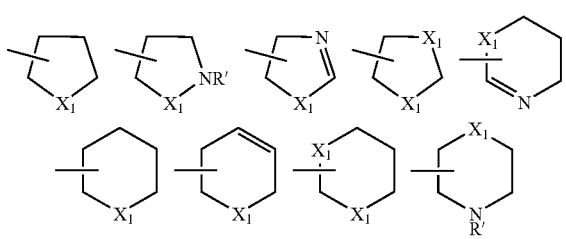

-continued

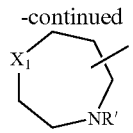

The term "aryl", as used herein, refers to an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. The term "aryl" further includes both unsubstituted carbocylic groups and carbocyclic groups containing 1-5-substitutions.

The term "heteroaryl" as used herein means an aromatic heterocyclic ring system, which may be a single ring (monocyclic) or multiple rings (bicyclic, up to three rings) fused together or linked covalently. Preferably, heteroaryl is a 5- to 6-membered ring. The rings may contain from one to four hetero atoms selected from nitrogen, oxygen, or sulfur, wherein the nitrogen or sulfur atom(s) are optionally oxidized, or the nitrogen atom(s) are optionally quarternized. Any suitable ring position of the heteroaryl moiety may be covalently linked to the defined chemical structure. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, α-carboline, or the like.

The term "halogen", as used herein, designates fluorine, chlorine, bromine, and iodine.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention may exist as one or more tautomers. One skilled in the art will recognize that compounds of formula I may also exist as the tautomer It as shown below.

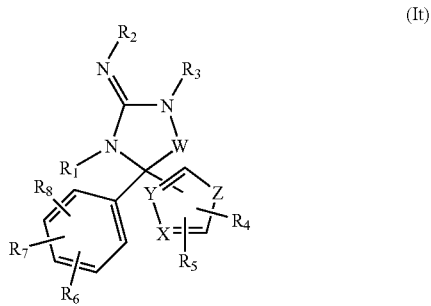
(It)

Tautomereric formula I compounds also include those compounds shown below as Ita, Itb and Itc.

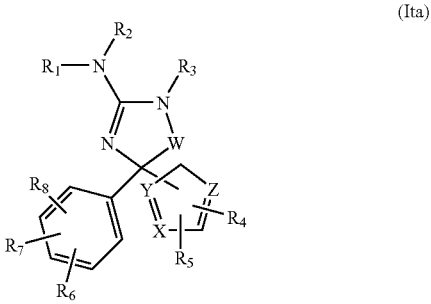
(Ita)

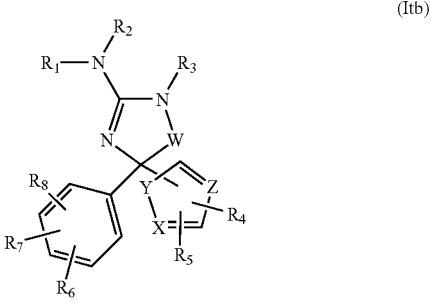
(Itb)

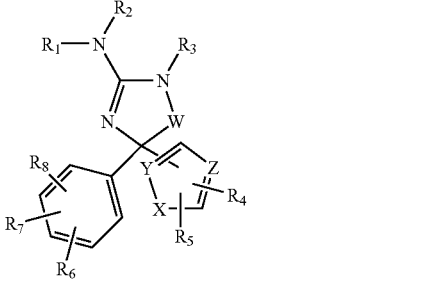
(Itc)

Tautomers often exist in equilibrium with each other. As these tautomers interconvert under environmental and physiological conditions, they provide the same useful biological effects. The present invention includes mixtures of such tautomers as well as the individual tautomers, for example the compounds of Formulas I, It, Ita, Itb and the like.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

Examples of X, Y and Z respectively include: CH, CH and NR; (eg., pyrrol-2-yl or pyrrol-3-yl and such groups N-substituted); S, CH and CH; (eg., thien-2-yl or -3-yl); N, NR and C (eg., the group is bonded via Z, such as N-alkylpyrazol-4-yl); CH, S and N (eg, thiazolyl); which rings are optionally substituted by $R_4$ and $R_5$.

Preferred compounds of formula I are those compounds wherein W is CO; X is $CR_9$; Y is $CR_{10}$ and Z is NR or S. Another group of preferred compounds are those compounds of formula I wherein W is CO; X is N; Y is NR and Z is $CR_{11}R_{12}$. Also preferred are those compounds of formula I wherein $R_7$ is phenyl or heteroaryl.

More preferred compounds of the invention are those compounds of formula I wherein W is CO; X is $CR_9$; Y is $CR_{10}$; Z is NR or S; R is H or $C_1$-$C_4$alkyl and $R_4$ is CN or $COR_{16}$. Another group of more preferred compounds of the invention are those compounds of formula I wherein W is CO; X is N; Y is NR and Z is $CR_{11}R_{12}$; and $R_7$ is phenyl or heteroaryl. A further group of more preferred compounds of the invention are those compounds of formula I wherein W is CO; X is $CR_9$; Y is $CR_{10}$; Z is NR; R is H or $C_1$-$C_4$alkyl; $R_4$ is $COR_{16}$; $R_7$ is phenyl or heteroaryl; $R_1$ and $R_2$ are H; and $R_3$ is methyl.

Preferred compounds of the invention include:
(5S)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;
(5S)-2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one;
2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;
2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one;
2-Amino-3-methyl-5-(3-pyridin-3-ylphenyl)-5-thien-2-yl-3,5-dihydro-4H-imidazol-4-one;
2-Amino-3-methyl-5-(3-pyridin-3-ylphenyl)-5-thien-2-yl-3,5-dihydro-4H-imidazol-4-one;
2-Amino-5-(2',5'-difluoro-1,1'-biphenyl-3-yl)-3-methyl-5-thien-2-yl-3,5-dihydro-4H-imidazol-4-one;
2-Amino-5-(2',5'-difluoro-1,1'-biphenyl-3-yl)-3-methyl-5-thien-3-yl-3,5-dihydro-4H-imidazol-4-one;

2-Amino-5-[3-(2-fluoropyridin-3-yl)phenyl]-3-methyl-5-[3-methyl-1-(2,2,2-trifluoroethyl)-1H-pyrazol-4-yl]-3,5-dihydro-4H-imidazol-4-one;

2-Amino-5-[3-(2-fluoropyridin-3-yl)phenyl]-3-methyl-5-[5-methyl-1-(2,2,2-trifluoroethyl)-1H-pyrazol-4-yl]-3,5-dihydro-4H-imidazol-4-one;

2-Amino-5-[3-(2-fluoropyridin-3-yl)phenyl]-5-(1-isobutyl-1H-pyrazol-4-yl)-3-methyl-3,5-dihydro-4H-imidazol-4-one;

2-Amino-5-(1-butyl-1H-pyrazol-4-yl)-5-[3-(2-fluoropyridin-3-yl)phenyl]-3-methyl-3,5-dihydro-4H-imidazol-4-one;

2-Amino-5-(1-isobutyl-1H-pyrazol-4-yl)-3-methyl-5-(3-pyrimidin-5-ylphenyl)-3,5-dihydro-4H-imidazol-4-one;

2-Amino-5-(1-butyl-1H-pyrazol-4-yl)-3-methyl-5-(3-pyrimidin-5-ylphenyl)-3,5-dihydro-4H-imidazol-4-one;

2-Amino-5-[4-fluoro-3-(2-fluoropyridin-3-yl)phenyl]-3-methyl-5-[1-(2,2,2-trifluoroethyl)-1H-pyrazol-4-yl]-3,5-dihydro-4H-imidazol-4-one;

2-Amino-5-(4-fluoro-3-pyrimidin-5-ylphenyl)-3-methyl-5-[1-(2,2,2-trifluoroethyl)-1H-pyrazol-4-yl]-3,5-dihydro-4H-imidazol-4-one;

2-Amino-5-(1-ethyl-1H-pyrazol-4-yl)-5-(4-fluoro-3-pyrimidin-5-ylphenyl)-3-methyl-3,5-dihydro-4H-imidazol-4-one;

2-Amino-5-(1-ethyl-1H-pyrazol-4-yl)-5-[4-fluoro-3-(2-fluoropyridin-3-yl)phenyl]-3-methyl-3,5-dihydro-4H-imidazol-4-one;

2-amino-5-(5-butylthien-2-yl)-3-methyl-5-phenyl-3,5-dihydro-4H-imidazol-4-one;

methyl 4-[2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;

methyl 4-[(4S)-2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;

methyl 4-[(4R)-2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;

methyl 4-[2-amino-4-(4-fluoro-3-pyrimidin-5-ylphenyl)-1-methyl-5-oxo-4,5-dihydro-1H-imidazol-4-yl]-1-(2,2,2-trifluoroethyl)-1H-pyrrole-2-carboxylate;

methyl 4-{2-amino-4-[4-fluoro-3-(2-fluoropyridin-3-yl)phenyl]-1-methyl-5-oxo-4,5-dihydro-1H-imidazol-4-yl}-1-(2,2,2-trifluoroethyl)-1H-pyrrole-2-carboxylate;

methyl 4-{2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

methyl 4-{2-amino-4-[4-fluoro-3-(2-fluoropyridin-3-yl)phenyl]-1-methyl-5-oxo-4,5-dihydro-1H-imidazol-4-yl}-1-ethyl-1H-pyrrole-2-carboxylate;

isopropyl 4-{2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

2-amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

methyl 4-{(4S)-2-amino-4-[4-fluoro-3-(2-fluoropyridin-3-yl)phenyl]-1-methyl-5-oxo-4,5-dihydro-1H-imidazol-4-yl}-1-(2,2,2-trifluoroethyl)-1H-pyrrole-2-carboxylate;

methyl 4-{(4R)-2-amino-4-[4-fluoro-3-(2-fluoropyridin-3-yl)phenyl]-1-methyl-5-oxo-4,5-dihydro-1H-imidazol-4-yl}-1-(2,2,2-trifluoroethyl)-1H-pyrrole-2-carboxylate;

4-{2-amino-4-[4-ethoxy-3-(2-fluoropyridin-3-yl)phenyl]-1-methyl-5-oxo-4,5-dihydro-1H-imidazol-4-yl}-1-ethyl-N-methyl-1H-pyrrole-2-carboxamide;

isopropyl 4-[2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;

N-{3-[2-amino-4-(1-ethyl-5-propionyl-1H-pyrrol-3-yl)-1-methyl-5-oxo-4,5-dihydro-1H-imidazol-4-yl]-phenyl}-butyramide;

N-{3-[2-amino-4-(1-ethyl-5-propionyl-1H-pyrrol-3-yl)-1-methyl-5-oxo-4,5-dihydro-1H-imidazol-4-yl]-phenyl}-propionamide;

N-{3-[2-amino-4-(1-ethyl-5-propionyl-1H-pyrrol-3-yl)-1-methyl-5-oxo-4,5-dihydro-1H-imidazol-4-yl]-phenyl}-2-methoxy-acetamide;

2-amino-5-(1-ethyl-5-propionyl-1H-pyrrol-3-yl)-3-methyl-5-(3-propoxyphenyl)-3,5-dihydro-4H-imidazol-4-one;

2-amino-5-(1-ethyl-5-propionyl-1H-pyrrol-3-yl)-3-methyl-5-[3-(pentyloxy)phenyl]-3,5-dihydro-4H-imidazol-4-one;

2-amino-5-[3-(3,3-dimethylbutoxy)phenyl]-5-(1-ethyl-5-propionyl-1H-pyrrol-3-yl)-3-methyl-3,5-dihydro-4H-imidazol-4-one;

2-amino-5-(1-ethyl-5-propionyl-1H-pyrrol-3-yl)-5-[3-(2-fluoroethoxy)phenyl]-3-methyl-3,5-dihydro-4H-imidazol-4-one;

2-amino-5-(3-butoxyphenyl)-5-(1-ethyl-5-propionyl-1H-pyrrol-3-yl)-3-methyl-3,5-dihydro-4H-imidazol-4-one;

2-amino-5-[3-(cyclopropylmethoxy)phenyl]-5-(1-ethyl-5-propionyl-1H-pyrrol-3-yl)-3-methyl-3,5-dihydro-4H-imidazol-4-one;

2-amino-5-(1-ethyl-5-propionyl-1H-pyrrol-3-yl)-5-(3-isobutoxyphenyl)-3-methyl-3,5-dihydro-4H-imidazol-4-one;

4-{3-[2-Amino-4-(1-ethyl-5-propionyl-1H-pyrrol-3-yl)-1-methyl-5-oxo-4,5-dihydro-H-imidazol-4-yl]phenoxy}butanenitrile;

2-Amino-5-[3-(2-fluoropyridin-3-yl)phenyl]-3-methyl-5-[1-(3-methylbutyl)-5-propionyl-1H-pyrrol-3-yl]-3,5-dihydro-4H-imidazol-4-one;

2-Amino-5-[1-(3-fluoropropyl)-5-propionyl-1H-pyrrol-3-yl]-5-[3-(2-fluoropyridin-3-yl)phenyl]-3-methyl-3,5-dihydro-4H-imidazol-4-one;

2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one;

2-Amino-5-[3-(2-fluoropyridin-3-yl)phenyl]-3-methyl-5-(5-propionyl-1H-pyrrol-3-yl)-3,5-dihydro-4H-imidazol-4-one;

(5S)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

(5R)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one;

5-(5-Acetyl-1-ethyl-1H-pyrrol-3-yl)-2-amino-5-[3-(2-fluoropyridin-3-yl)phenyl]-3-methyl-3,5-dihydro-4H-imidazol-4-one;

Methyl 4-{(4S)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

Methyl 4-{(4R)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

4-{2-Amino-4-[3-(2-fluoropyridin-3-yl)phenyl]-1-methyl-5-oxo-4,5-dihydro-1H-imidazol-4-yl}-1-ethyl-N-methyl-1H-pyrrole-2-carboxamide;

4-{2-Amino-4-[3-(2-fluoropyridin-3-yl)phenyl]-1-methyl-5-oxo-4,5-dihydro-1H-imidazol-4-yl}-N,1-diethyl-1H-pyrrole-2-carboxamide;
4-{2-Amino-4-[3-(2-fluoropyridin-3-yl)phenyl]-1-methyl-5-oxo-4,5-dihydro-1H-imidazol-4-yl}-1-ethyl-N-propyl-1H-pyrrole-2-carboxamide;
4-{2-Amino-4-[3-(2-fluoropyridin-3-yl)phenyl]-1-methyl-5-oxo-4,5-dihydro-1H-imidazol-4-yl}-N-butyl-1-ethyl-1H-pyrrole-2-carboxamide;
4-{2-Amino-4-[3-(2-fluoropyridin-3-yl)phenyl]-1-methyl-5-oxo-4,5-dihydro-1H-imidazol-4-yl}-1-ethyl-N-isopropyl-1H-pyrrole-2-carboxamide;
4-{2-Amino-4-[3-(2-fluoropyridin-3-yl)phenyl]-1-methyl-5-oxo-4,5-dihydro-1H-imidazol-4-yl}-N-cyclopentyl-1-ethyl-1H-pyrrole-2-carboxamide;
2-Amino-5-[1-ethyl-5-(piperidin-1-ylcarbonyl)-1H-pyrrol-3-yl]-5-[3-(2-fluoropyridin-3-yl)phenyl]-3-methyl-3,5-dihydro-4H-imidazol-4-one;
2-Amino-5-[1-ethyl-5-(morpholin-4-ylcarbonyl)-1H-pyrrol-3-yl]-5-[3-(2-fluoropyridin-3-yl)phenyl]-3-methyl-3,5-dihydro-4H-imidazol-4-one;
4-{2-Amino-4-[3-(2-fluoropyridin-3-yl)phenyl]-1-methyl-5-oxo-4,5-dihydro-1H-imidazol-4-yl}-1-ethyl-N,N-dimethyl-1H-pyrrole-2-carboxamide;
4-{2-Amino-4-[3-(2-fluoropyridin-3-yl)phenyl]-1-methyl-5-oxo-4,5-dihydro-1H-imidazol-4-yl}-1-ethyl-N-(4-fluorobenzyl)-1H-pyrrole-2-carboxamide;
(5S)-2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one;
Methyl 4-{(4S)-2-amino-4-[4-fluoro-3-(2-fluoropyridin-3-yl)phenyl]-1-methyl-5-oxo-4,5-dihydro-1H-imidazol-4-yl}-1-ethyl-1H-pyrrole-2-carboxylate;
(5S)-5-(5-Acetyl-1-ethyl-1H-pyrrol-3-yl)-2-amino-5-[3-(2-fluoropyridin-3-yl)phenyl]-3-methyl-3,5-dihydro-4H-imidazol-4-one;
2-Amino-5-[1-ethyl-5-(methylsulfonyl)-1H-pyrrol-3-yl]-5-[4-fluoro-3-(2-fluoropyridin-3-yl)phenyl]-3-methyl-3,5-dihydro-4H-imidazol-4-one;
Methyl 4-[2-amino-1-methyl-5-oxo-4-(3-pyrimidin-5-ylphenyl)-4,5-dihydro-1H-imidazol-4-yl]-1-(2-fluoroethyl)-1H-pyrrole-2-carboxylate;
Methyl 4-{2-amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;
Methyl 4-{2-amino-4-[3-(6-fluoropyridin-3-yl)phenyl]-1-methyl-5-oxo-4,5-dihydro-1H-imidazol-4-yl}-1-(2-fluoroethyl)-1H-pyrrole-2-carboxylate;
Methyl 4-[2-amino-4-(2',5'-difluorobiphenyl-3-yl)-1-methyl-5-oxo-4,5-dihydro-1H-imidazol-4-yl]-1-(2-fluoroethyl)-1H-pyrrole-2-carboxylate;
Methyl 4-[2-amino-4-(3',5'-difluorobiphenyl-3-yl)-1-methyl-5-oxo-4,5-dihydro-1H-imidazol-4-yl]-1-(2-fluoroethyl)-1H-pyrrole-2-carboxylate;
Methyl 4-[2-amino-4-(3'-cyanobiphenyl-3-yl)-1-methyl-5-oxo-4,5-dihydro-1H-imidazol-4-yl]-1-(2-fluoroethyl)-1H-pyrrole-2-carboxylate;
Methyl 4-[2-amino-4-(5'-cyano-2'-fluorobiphenyl-3-yl)-1-methyl-5-oxo-4,5-dihydro-1H-imidazol-4-yl]-1-(2-fluoroethyl)-1H-pyrrole-2-carboxylate;
Methyl 4-[2-amino-4-(3'-methoxybiphenyl-3-yl)-1-methyl-5-oxo-4,5-dihydro-1H-imidazol-4-yl]-1-(2-fluoroethyl)-1H-pyrrole-2-carboxylate;
Methyl 4-{2-amino-1-methyl-5-oxo-4-[3'-(trifluoromethoxy)biphenyl-3-yl]-4,5-dihydro-1H-imidazol-4-yl}-1-(2-fluoroethyl)-1H-pyrrole-2-carboxylate;
Methyl 4-[2-amino-4-(3',4'-difluorobiphenyl-3-yl)-1-methyl-5-oxo-4,5-dihydro-1H-imidazol-4-yl]-1-(2-fluoroethyl)-1H-pyrrole-2-carboxylate;
Methyl 4-{2-amino-4-[3-(1,3-benzodioxol-5-yl)phenyl]-1-methyl-5-oxo-4,5-dihydro-1H-imidazol-4-yl}-1-(2-fluoroethyl)-1H-pyrrole-2-carboxylate;
4-[2-Amino-4-(3-bromophenyl)-1-methyl-5-oxo-4,5-dihydro-1H-imidazol-4-yl]-1-methyl-1H-pyrrole-2-carbonitrile;
4-[2-Amino-4-(3-bromophenyl)-1-methyl-5-oxo-4,5-dihydro-1H-imidazol-4-yl]-1-(2-fluoroethyl)-1H-pyrrole-2-carbonitrile;
4-[2-Amino-4-(3-bromophenyl)-1-methyl-5-oxo-4,5-dihydro-1H-imidazol-4-yl]-1-propyl-1H-pyrrole-2-carbonitrile;
4-[2-Amino-1-methyl-5-oxo-4-(3-pyrimidin-5-ylphenyl)-4,5-dihydro-1H-imidazol-4-yl]-1-methyl-1H-pyrrole-2-carbonitrile;
4-{2-Amino-4-[3-(2-fluoropyridin-3-yl)phenyl]-1-methyl-5-oxo-4,5-dihydro-1H-imidazol-4-yl}-1-methyl-1H-pyrrole-2-carbonitrile;
4-{2-Amino-4-[3-(2-chloro-5-fluoropyridin-3-yl)phenyl]-1-methyl-5-oxo-4,5-dihydro-1H-imidazol-4-yl}-1-methyl-1H-pyrrole-2-carbonitrile;
4-[2-Amino-1-methyl-5-oxo-4-(3-pyrimidin-5-ylphenyl)-4,5-dihydro-1H-imidazol-4-yl]-1-(2-fluoroethyl)-1H-pyrrole-2-carbonitrile;
4-[2-Amino-1-methyl-5-oxo-4-(3-pyrimidin-5-ylphenyl)-4,5-dihydro-1H-imidazol-4-yl]-1-propyl-1H-pyrrole-2-carbonitrile;
4-{2-Amino-4-[3-(2-fluoropyridin-3-yl)phenyl]-1-methyl-5-oxo-4,5-dihydro-1H-imidazol-4-yl}-1-propyl-1H-pyrrole-2-carbonitrile;
4-{2-Amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carbonitrile;
4-{2-Amino-4-[3-(2-chloro-5-fluoropyridin-3-yl)phenyl]-1-methyl-5-oxo-4,5-dihydro-1H-imidazol-4-yl}-1-propyl-1H-pyrrole-2-carbonitrile;
5-(5-Acetyl-1H-pyrrol-3-yl)-2-amino-5-(3-bromophenyl)-3-methyl-3,5-dihydro-imidazol-4-one;
4-{2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde;
4-[2-Amino-4-(3-bromophenyl)-1-methyl-5-oxo-4,5-dihydro-1H-imidazol-4-yl]-1H-pyrrole-2-carbaldehyde;
4-[2-Amino-4-(3-bromophenyl)-1-methyl-5-oxo-4,5-dihydro-1H-imidazol-4-yl]-1-ethyl-1H-pyrrole-2-carbaldehyde;
4-[2-Amino-4-(3-bromophenyl)-1-methyl-5-oxo-4,5-dihydro-1H-imidazol-4-yl]-1-(2-fluoroethyl)-1H-pyrrole-2-carbaldehyde;
4-{2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde;
4-{2-Amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carbaldehyde;
2-Amino-5-[5-[(diethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one;
2-Amino-5-{1-(2-fluoroethyl)-5-[(isopropylamino)methyl]-1H-pyrrol-3-yl}-5-[3-(2-fluoropyridin-3-yl)phenyl]-3-methyl-3,5-dihydro-4H-imidazol-4-one;
2-Amino-5-[1-(2-fluoroethyl)-5-(pyrrolidin-1-ylmethyl)-1H-pyrrol-3-yl]-5-[3-(2-fluoropyridin-3-yl)phenyl]-3-methyl-3,5-dihydro-4H-imidazol-4-one;

2-Amino-5-[5-[(dimethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one;

2-Amino-5-[5-[(dimethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one;

2-Amino-5-[1-ethyl-5-(1-hydroxypropyl)-1H-pyrrol-3-yl]-5-[3-(2-fluoropyridin-3-yl)phenyl]-3-methyl-3,5-dihydro-4H-imidazol-4-one;

4-{2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde O-methyloxime hydrochloride;

2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one;

2-Amino-5-(3-bromophenyl)-5-(1-ethyl-5-propionyl-1H-pyrrol-3-yl)-3-methyl-3,5-dihydro-4H-imidazol-4-one;

(5S)-2-Amino-5-[3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one;

(5R)-2-Amino-5-[3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one;

2-Amino-5-(1-ethyl-5-propionyl-1H-pyrrol-3-yl)-3-methyl-5-(3-pyrimidin-5-ylphenyl)-3,5-dihydro-4H-imidazol-4-one;

2-Amino-5-(3'-methoxybiphenyl-3-yl)-3-methyl-5-[5-propionyl-1-(2,2,2-trifluoroethyl)-1H-pyrrol-3-yl]-3,5-dihydro-4H-imidazol-4-one;

2-Amino-5-(3',5'-difluorobiphenyl-3-yl)-3-methyl-5-[5-propionyl-1-(2,2,2-trifluoroethyl)-1H-pyrrol-3-yl]-3,5-dihydro-4H-imidazol-4-one;

2-Amino-5-(3'-chlorobiphenyl-3-yl)-3-methyl-5-[5-propionyl-1-(2,2,2-trifluoroethyl)-1H-pyrrol-3-yl]-3,5-dihydro-4H-imidazol-4-one;

2-Amino-5-(3'-chloro-4'-fluorobiphenyl-3-yl)-3-methyl-5-[5-propionyl-1-(2,2,2-trifluoroethyl)-1H-pyrrol-3-yl]-3,5-dihydro-4H-imidazol-4-one;

3'-{2-Amino-1-methyl-5-oxo-4-[5-propionyl-1-(2,2,2-trifluoroethyl)-1H-pyrrol-3-yl]-4,5-dihydro-1H-imidazol-4-yl}biphenyl-3-carbonitrile;

2-Amino-5-(3-bromo-4-fluorophenyl)-3-methyl-5-[5-propionyl-1-(2,2,2-trifluoroethyl)-1H-pyrrol-3-yl]-3,5-dihydro-4H-imidazol-4-one;

2-Amino-5-[4-fluoro-3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one;

2-Amino-5-(4-fluoro-3-pyrimidin-5-ylphenyl)-3-methyl-5-[5-propionyl-1-(2,2,2-trifluoroethyl)-1H-pyrrol-3-yl]-3,5-dihydro-4H-imidazol-4-one;

or a tautomer thereof, a stereoisomer thereof or a pharmaceutically acceptable salt thereof.

Compounds of the invention may be prepared employing conventional methods that utilize readily available reagents and starting materials. The reagents used in the preparation of the compounds of this invention can be either commercially obtained or can be prepared by standard procedures described in the literature. Representative compounds of the present invention can be prepared using the following synthetic schemes. The skilled practitioner will know how to make use of variants of these reaction sequences, which in themselves are well known in the art. For example, compounds of formula I wherein W is CO (Ia) may be prepared by reacting a diketone of formula II with an aminoguanidine derivative of formula III in the presence of a base such as a metal carbonate to give the desired formula Ia compound. The reaction is shown in flow diagram I.

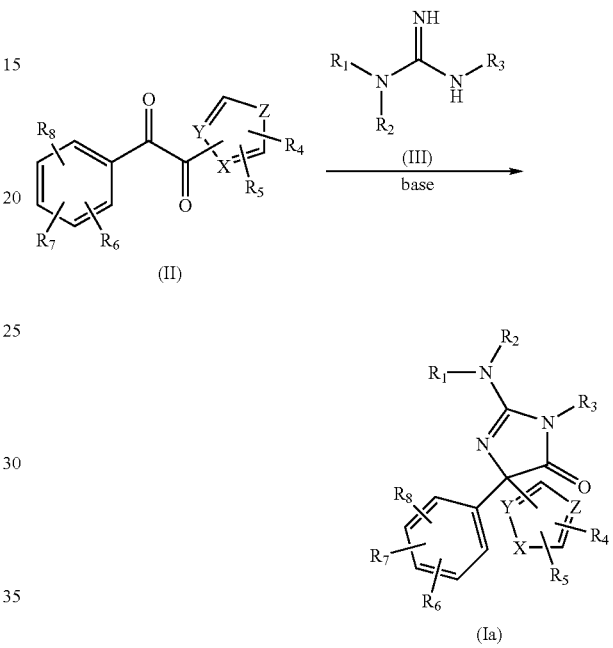

Diketone compounds of formula II may be prepared by reacting an alkyne of formula IV with an oxidizing agent such as Pd(II)Cl/DMSO, N-bromosuccinimide/DMSO, ozone, sodium periodate with ruthenium (IV) oxide hydrate, sulfur trioxide, $KMnO_4$, $I_2$/DMSO, or combinations thereof, preferable $KMnO_4$ and $I_2$/DMSO. The reaction is shown in flow diagram II.

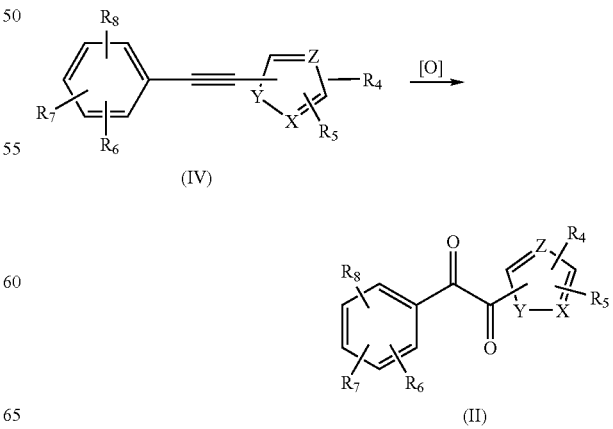

Alkyne compounds of formula IV may be prepared by reacting an aryl compound of formula V wherein L is a leaving group such as Br, I or trifluoromethanesulfonate with a protected acetylene compound of formula VI wherein P is a protecting group such as triaryl(alkyl)silyl or hydroydialkyl (aryl)silyl to give the protected arylalkyne of formula VII; deprotecting the formula VII compound to give the compound of formula VIII using a deprotecting reagent such as a metal or ammonium fluoride, a metal carbonate, for example cesium carbonate or potassium carbonate or a metal hydroxide; and reacting the formula VIII alkyne with a heteroaryl compound of formula IX wherein L represents a leaving group as described hereinabove to give the desired alkyne compound of formula IV. Similarly, compounds of formula IV may be prepared by reversing the order of the coupling the aryl and heteroaryl groups. The reactions are shown in flow diagram III.

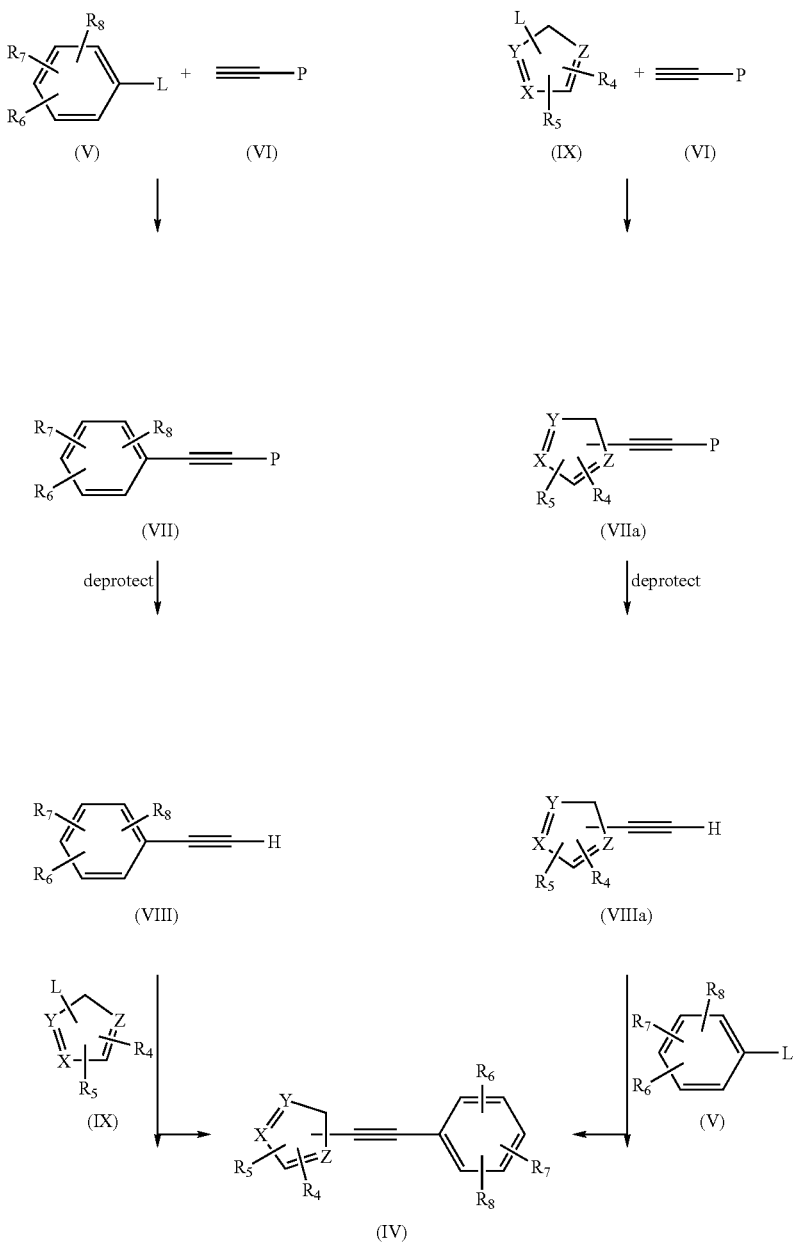

Alternatively, compounds of formula I wherein $R_7$ is aryl or heteroaryl (Ia) may be prepared following the formation of the hydantoin ring by coupling the appropriate hydantoin compound of formula X with an aryl or heteroaryl boronic acid of formula XI to give the desired compounds of formula Ia. The reaction is shown in flow diagram IV wherein L represents a leaving group as described hereinabove.

FLOW DIAGRAM IV

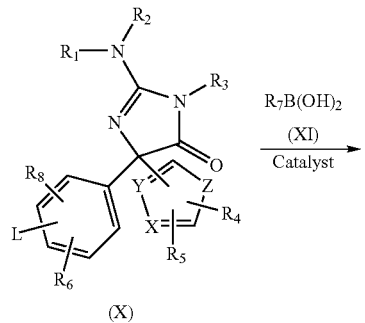

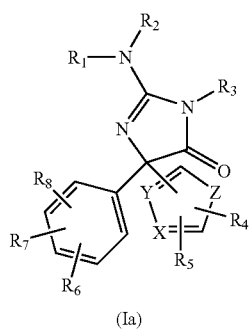

Compounds of formula I wherein W is CS (Ic) may be readily prepared using conventional procedures, such as reacting a compound of formula Ia with $CS_2$, in the presence of a solvent to obtain the desired compound of formula Ic. Similarly, compounds of formula I wherein W is $CH_2$ (Id) may be prepared by reacting a compound of formula Ia with a suitable reducing agent, such as $SnCl_2$, to obtain the desired compound of formula Id. The reactions are shown in flow diagram V.

Advantageously, the compounds of formula I act as BACE inhibitors for the treatment of β-amyloid deposits and neurofibrillary tangles associated with such diseases as Alzheimer's disease, Trisomy 21 (Down's Syndrome), Hereditary Cerebral Hemorrhage with Amyloidosis of the Dutch-type (HCHWA-D), and other neurodegenerative disorders. Accordingly, the present invention provides methods for modulating BACE and treating, preventing, or ameliorating β-amyloid deposits and neurofibrillary tangles associated with diseases and disorders such as Alzheimer's disease, Trisomy 21 (Down's Syndrome), Hereditary Cerebral Hemorrhage with Amyloidosis of the Dutch-type (HCHWA-D), and other neurodegenerative disorders. Such methods generally involve administering to a patient suspected of suffering from or being susceptible to the disease or injury an effective amount of a compound of formula I. Also according to the present invention there is provided a method of treating Alzheimer's disease and related senile dementia's in humans or other mammals which comprises administering to a human or other mammal an effective amount of a compound of the present invention.

The present invention also provides a method for the treatment of a disorder related to or associated with excessive BACE activity in a patient in need thereof which comprises providing said patient a therapeutically effective amount of at least one compound of formula I. Representative disorders include Alzheimer's disease, cognitive impairment, Down's Syndrome, HCHWA-D, cognitive decline, senile dementia, cerebral amyloid angiopathy, degenerative dementia, or other neurodegenerative disorders. Certain of these diseases are characterized by production of β-amyloid deposits or neurofibrillary tangles.

The present invention also provides methods for modulating (and, preferably, inhibiting) the activity of BACE, comprising administering to a patient and/or contacting a receptor thereof with an effective amount of at least one compound of formula I. Certain methods further comprise determining BACE activity, either before or after said contacting step.

The present invention also provides methods of ameliorating β-amyloid deposits in a mammal, comprising administering to said mammal an effective amount of at least one compound of formula I. Further methods ameliorate neurofibrillary tangles in a mammal, and comprise administering to said mammal an effective amount of at least one compound of formula I.

Also provided are methods of ameliorating symptoms of Alzheimer's disease, cognitive impairment, Down's Syn-

FLOW DIAGRAM V

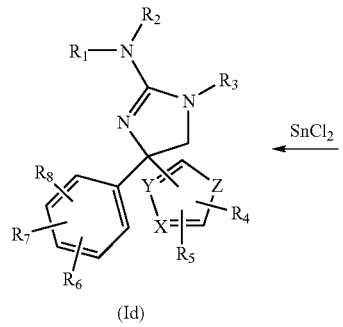 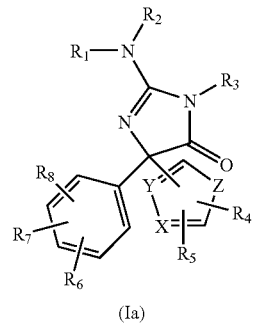 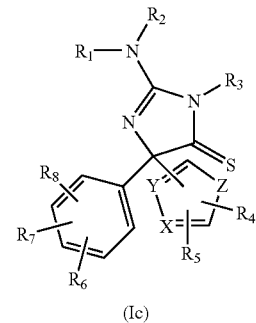

drome, HCHWA-D, cognitive decline, senile dementia, cerebral amyloid angiopathy, degenerative dementia, or other neurodegenerative disorders in a mammal, comprising administering to said mammal an effective amount of at least one compound of formula I.

Further methods prevent Alzheimer's disease, cognitive impairment, Down's Syndrome, HCHWA-D, cognitive decline, senile dementia, cerebral amyloid angiopathy, degenerative dementia, or other neurodegenerative disorders in a mammal that is known to suffer from or suspected to be at risk of suffering from such diseases. These methods comprise administering to said mammal an amount of at least one compound of formula I that is effective to prevent such disease.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The terms "effective amount", "therapeutically effective amount" and "effective dosage" as used herein, refer to the amount of a compound that, when administered to a patient, is effective to at least partially ameliorate (and, in preferred embodiments, cure) a condition from which the patient is suspected to suffer.

It is understood that the effective dosage of the active compounds of this invention may vary depending upon the particular compound utilized, the mode of administration, the condition, and severity thereof, of the condition being treated, as well as the various physical factors related to the individual being treated. For treating Alzheimer's disease and other related senile dementia's, generally, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg preferably from about 3.5 to about 5 mg. In the case of a 70 kg human adult, the total daily dose will generally be from about 7 mg to about 70 mg and may be adjusted to provide the optimal therapeutic result. This regimen may be adjusted to provide the optimal therapeutic response.

In one aspect, the present invention is directed to compositions comprising one or more compounds of formula I and one or more pharmaceutically acceptable carriers.

The present invention also comprises pharmaceutical compositions comprising compounds of the above-described formula I and a pharmaceutically acceptable carrier.

The term "carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and $\beta$-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms TEA, DMSO and DMF designate triethyl amine, dimethyl sulfoxide and N,N-dimethylformamide, respectively. The terms DME and THF designate ethylene glycol dimethyl ether and tetrahydrofuran, respectively. The term TLC designates thin layer chromatography. The term NMR designates proton nuclear magnetic resonance and the term MS designates mass spectroscopy with (+) referring to the positive mode which generally gives a M+1 (or M+H) absorption where M=the molecular mass. All compounds are analyzed at least by MS and NMR.

Proton nuclear magnetic resonance spectra were obtained on a Bruker AVANCE 300 spectrometer at 300 MHz or VARIAN 400 spectrometer at 400 MHz. Spectra are given in ppm (δ) and coupling constants, J values, are reported in Hertz. Tetramethylsilane was used as an internal reference standard. Infrared spectra were obtained on a Nicolet Nexus 470 (ATR) spectrometer. Mass spectra were obtained on a Perkin Elmer Sciex 100.

EXAMPLE 1

Preparation of 2-Amino-3-methyl-5-(1-methyl-1H-pyrazol-4-yl)-5-(3-pyrimidin-5-ylphenyl)-3,5-dihydro-4-imidazol-4-one

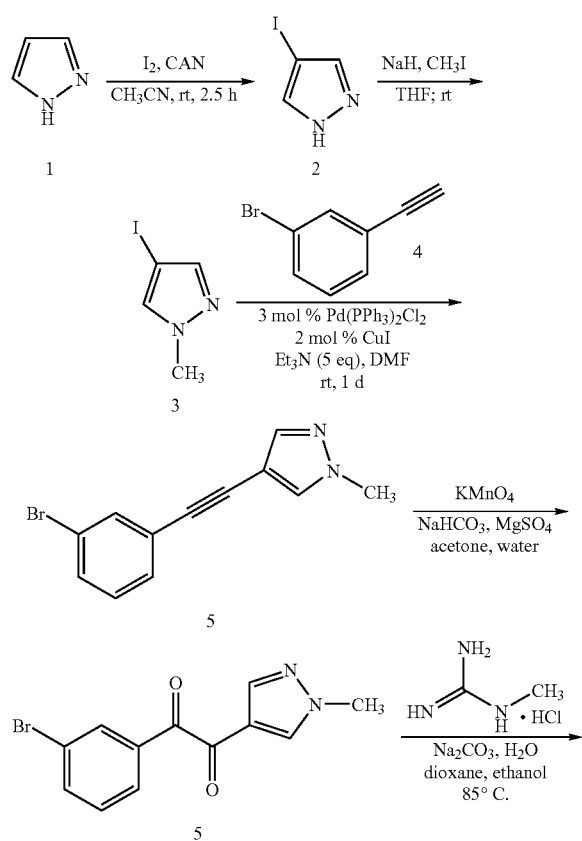

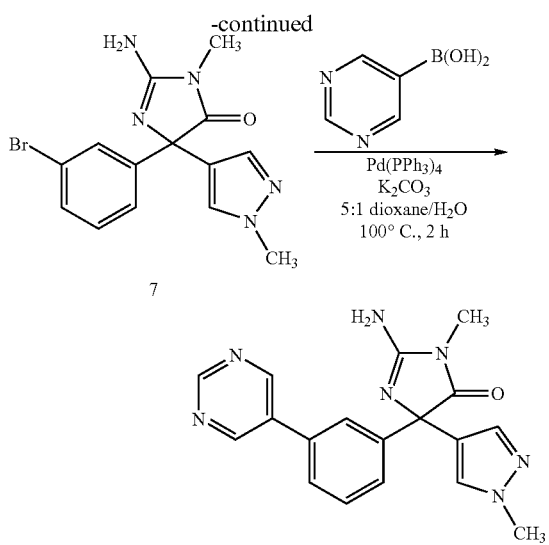

Step a) Preparation of Compound 2:

A mixture of pyrazole (3.00 g, 44.0 mmol), iodine (6.71 g, 26.4 mmol) and ceric ammonium nitrate (14.5 g, 26.4 mmol) in acetonitrile (400 mL) was stirred at room temperature for 2.5 h. The reaction was concentrated and partitioned between ethyl acetate (250 mL) and 5% aqueous sodium bisulfite (250 mL). Water (150 mL) was added and the organic layer was separated and washed with brine (250 mL), dried over magnesium sulfate, filtered and concentrated to afford 2 (7.80 g, 91%) as a white solid: mp 105-108° C.; $^1$H NMR (300 MHz, CDCl$_3$) δ7.63 (s, 2H).

Step b) Preparation of Compound 3:

Sodium hydride (0.680 g of a 60% dispersion in oil, 17.0 mmol) was washed with hexanes (2 mL) diluted with THF (12 mL) and treated with a solution of 2 (3.00 g, 15.5 mmol) in THF (3 mL) over a period of 10 min. After stirring for 4 h at room temperature, a solution of methyl iodide (4.39 g, 31.9 mmol) in THF (3 mL) was added dropwise over a period of 10 min and the mixture stirred at room temperature for 2.5 h. The mixture was diluted with ether (100 mL) then washed with water (50 mL), brine (50 mL), dried over magnesium sulfate, filtered and concentrated to afford 3 (2.95 g, 92%) as an off-white solid: $^1$H NMR (300 MHz, CDCl$_3$) δ 7.49 (s, 1H), 7.41 (s, 1H), 3.92 (s, 3H); ESI MS m/z 209 [C$_4$H$_5$IN$_2$+H]$^+$.

Step c) Preparation of Compound 4:

A mixture of 3 (0.400 g, 1.92 mmol), 3-bromophenylacetylene 4 (0.380 g, 2.12 mmol), bis(triphenylphosphine)palladium(II) chloride (0.040 g, 0.058 mmol), copper (I) iodide (0.007 g, 0.038 mmol) and triethylamine (0.97 g, 9.61 mmol) in dimethylformamide (7 mL) was stirred at room temperature for 4.5 h. The mixture was diluted with ethyl acetate (50 mL), washed with water (50 mL), 5% aqueous lithium chloride (2×50 mL) and brine (50 mL), dried over magnesium sulfate, filtered, and concentrated to afford 0.58 g of an amber syrup. Purification by flash chromatography (silica, 1:4 ethyl acetate/hexanes) afforded 5 (0.27 g, 54%) as an amber syrup: $^1$H NMR (300 MHz, CDCl$_3$) δ 7.64-7.62 (m, 2H), 7.56 (s, 1H), 7.45-7.37 (m, 2H), 7.19 (t, J=7.9 Hz, 1H), 3.92 (s, 3H); ESI MS m/z 261 [C$_{12}$H$_9$BrN$_2$+H]$^+$.

Step d) Preparation of Compound 6:

To a stirred solution of 5 (0.100 g, 0.383 mmol) in acetone (4 mL) was added a solution of sodium bicarbonate (0.019 g, 0.229 mmol) and magnesium sulfate (0.069 g, 0.574 mmol) in water (4 mL), followed by potassium permanganate (0.133 g, 0.843 mmol) in one portion. The reaction mixture was stirred for 20 min at room temperature. After this time the reaction was diluted with 1:1 hexanes/ethyl acetate (4 mL) and water (2 mL) and the solids were removed by filtration. The aqueous layer was separated then extracted with ethyl acetate (2×10 mL), and the combined organic layers washed with water (2×10 mL) and brine (30 mL), dried over magnesium sulfate, filtered and concentrated to afford 6 (0.094 g, 85%) as an off-white solid: $^1$H NMR (300 MHz, CDCl$_3$) δ 8.20 (m, 1H), 8.06 (m, 2H), 7.79 (m, 1H), 7.76 (m, 1H), 7.39 (t, J=7.9 Hz, 1H), 3.92 (s, 3H); ESI MS m/z 293 [C$_{12}$H$_9$BrN$_2$O$_2$+H]$^+$.

Step e) Preparation of Compound 7:

A mixture of 6 (0.400 g, 1.36 mmol) and 1-methylguanidine hydrochloride (0.670 g, 6.14 mmol) in dioxane (18 mL) and ethanol (12 mL) was stirred at room temperature for 5 min. A solution of sodium carbonate (0.650 g, 6.14 mmol) in water (5 mL) was then added and the mixture immersed into an 85° C. oil bath and stirred for 1 h. The mixture was cooled to room temperature, concentrated and the residue partitioned between methylene chloride (100 mL) and water (100 mL). The organic layer was separated, washed with water (100 mL), brine (100 mL), dried over magnesium sulfate, filtered and concentrated. Purification by flash chromatography (silica, 95:5:0.25 methylene chloride/methanol/concentrated ammonium hydroxide) afforded 7 (0.33 g, 70%) as a white solid: $^1$H NMR (300 MHz, CDCl$_3$) δ 7.68 (m, 1H), 7.48-7.37 (m, 4H), 7.18 (t, J=7.9 Hz, 1H), 3.85 (s, 3H), 3.09 (s, 3H); m/z 348 [C$_{14}$H$_{14}$BrN$_5$O+H]$^+$.

Step f) Preparation of 2-Amino-3-methyl-5-(1-methyl-1H-pyrazol-4-yl)-5-(3-pyrimidin-5-ylphenyl)-3,5-dihydro-4-imidazol-4-one A mixture of 7 (0.100 g, 0.287 mmol), 5-pyrimidine boronic acid (0.043 g, 0.345 mmol), tetrakistriphenylphosphinopalladium(0) (0.017 g, 0.0144 mmol) and potassium carbonate (0.099 g, 0.718 mmol) in 5:1 dioxane/water (1.8 mL) was heated at 100° C. for 4 h. The mixture was cooled to room temperature, concentrated and the crude product purified by flash chromatography (silica, 95:5:0.25 methylene chloride/methanol/concentrated ammonium hydroxide) to afford the title compound (0.060 g, 60%) as a white solid: R$_f$ 0.36 (92:8:0.25 methylene chloride/methanol/concentrated ammonium hydroxide); $^1$H NMR (300 MHz, CD$_3$OD) δ 9.13 (s, 1H), 9.01 (s, 2H), 7.75-7.42 (m, 6H), 3.85 (s, 3H), 3.10 (s, 3H); IR (ATR) 1663, 1468, 1413, 1400 cm$^{-1}$; ESI MS m/z 348 [C$_{18}$H$_{17}$N$_7$O+H]$^+$;

EXAMPLES 2-11

Preparation of 2-Amino-3-methyl-5-(substituted Pyrazolyl)-3,5-dihydro-4H-imidazol-4-one Compounds Using essentially the same procedure described in Example 1 and employing the appropriate iodopyrazole derivative and a suitable alkyne intermediate, the compounds shown below were prepared and identified by NMR and mass spectral analyses.

EXAMPLE 2

2-Amino-5-[3-(2-fluoropyridin-3-yl)phenyl]-3-methyl-5-[5-methyl-1-2,2,2-trifluoroethyl)-1H-pyrazol-4-yl]-3,5-dihydro-4H-imidazol-4-one

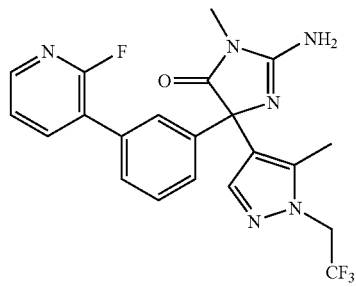

$^1$H NMR (DMSOd$_6$ 300 MHz) δ 2.0 (s, 3H), 2.95 (s, 3H), 5.0 (q, 2H), 6.6 (b, 2H), 7.3 (s, 1H), 7.4 (m, 4H), 7.6 (s, 1H), 8.0 (m, 1H), 8.2 (m, 1H); MS m/e (M)$^+$ 447; mp 235-238° C.

EXAMPLE 3

2-Amino-5-[3-(2-fluoropyridin-3-yl)phenyl]-5-(1-isobutyl-1H-pyrazol-4-yl)-3-methyl-3,5-dihydro-4H-imidazol-4-one

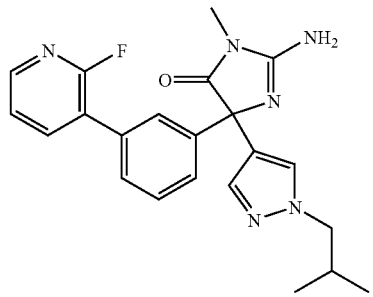

$^1$H NMR (DMSOd$_6$ 300 MHz) δ 0.8 (d, 6H), 2.0 (m, 1H), 2.95 (s, 3H), 3.8 (d, 2H), 6.6 (b, 2H), 7.3 (s, 1H), 7.4 (m, 3H), 7.5 (m, 1H), 7.6 (s, 1H), 7.7 (s, 1H), 8.0 (m, 1H), 8.2 (m, 1H); MS m/e (M)$^+$ 407; mp=94-98° C.

EXAMPLE 4

2-Amino-5-(1-butyl-1H-pyrazol-4-yl)-5-[3-(2-fluoropyridin-3-yl)phenyl]-3-methyl-3,5-dihydro-4H-imidazol-4-one

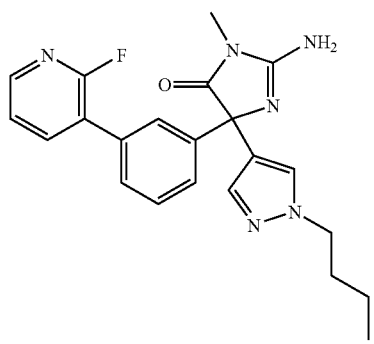

$^1$H NMR (DMSOd$_6$ 300 MHz) δ 0.8 (t, 3H), 1.2 (m, 2H), 1.6 (m, 2H), 2.95 (s, 3H), 4.0 (t, 2H) 6.7 (b, 2H), 7.2 (s, 1H), 7.4 (m, 3H), 7.5 (m, 1H), 7.6 (s, 1H), 7.7 (s, 1H), 8.0 (m, 1H), 8.2 (m, 1H); MS m/e (M)$^+$ 407; mp=88-92° C.

EXAMPLE 5

2-Amino-5-(1-isobutyl-1H-pyrazol-4-yl)-3-methyl-5-(3-pyrimidin-5-ylphenyl)-3,5-dihydro-4H-imidazol-4-one

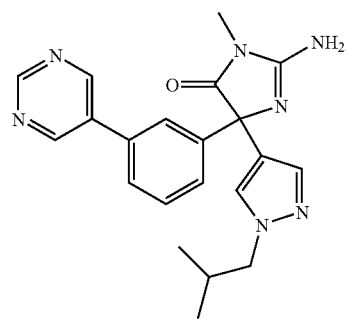

$^1$H NMR (DMSOd$_6$ 300 MHz) δ 0.8 (d, 6H), 2.0 (m, 1H), 2.95 (s, 3H), 3.8 (d, 1H), 6.8 (b, 2H), 7.3 (s, 1H), 7.4 (t, 1H), 7.5 (m, 1H), 7.6 (m, 2H), 7.7 (s, 1H), 8.9 (s, 2H), 9.2 (s, 1H); MS m/e (M)$^+$ 390; mp=118-122° C.

EXAMPLE 6

2-Amino-5-(1-butyl-1H-Pyrazol-4-yl)-3-methyl-5-(3-pyrimidin-5-ylphenyl)-3,5-dihydro-4H-imidazol-4-one

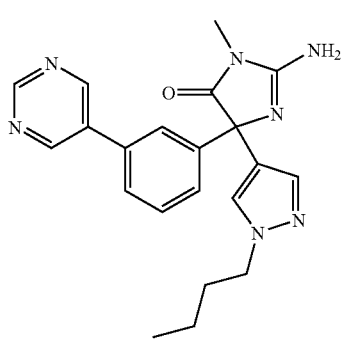

$^1$H NMR (DMSOd$_6$ 300 MHz) δ 0.8 (t, 3H), 1.2 (m, 2H), 1.6 (m, 2H), 2.95 (s, 3H), 4.0 (t, 2H), 6.6 (b, 2H), 7.3 (s, 1H), 7.4 (t, 1H), 7.5 (m, 1H), 7.6 (m, 2H), 7.7 (s, 1H), 8.9 (s, 2H), 9.2 (s, 1H), MS m/e (M)$^+$ 390; mp=94-98° C.

EXAMPLE 7

2-Amino-5-[4-fluoro-3-(2-fluoropyridin-3-yl)phenyl]-3-methyl-5-[1-2,2,2-trifluoroethyl)-1H-pyrazol-4-yl]-3,5-dihydro-4H-imidazol-4-one

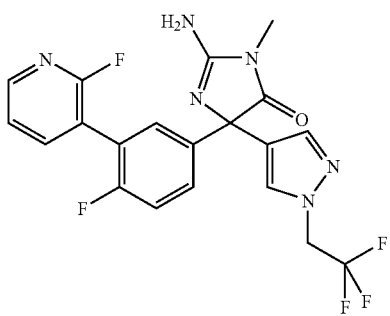

$^1$H NMR (500 MHz, DMSO-d$_6$) δ: 3.10 (s, 3H), 5.12 (q, 2H, J=8.67 Hz), 7.48 (m, 4H), 7.62 (s, 1H), 7.87 (s, 1H), 7.99 (m, 1H), 8.31 (s, 1H), 9.43 (d, 2H); mp>225° C.;

MS (ES) m/z 451 (M+H)$^+$.

EXAMPLE 8

2-Amino-5-(4-fluoro-3-pyrimidin-5-ylphenyl)-3-methyl-5-[1-(2,2,2-trifluoroethyl)-1H-pyrazol-4-yl]-3,5-dihydro-4H-imidazol-4-one

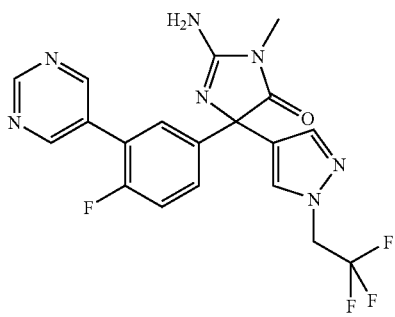

$^1$H NMR (500 MHz, DMSO-$d_6$) δ: 2.92 (s, 3H), 5.03 (q, 2H, J=9.15 Hz), 6.67 (s, 2H), 7.32 (m, 1H), 7.47 (s, 1H), 7.63 (m, 2H), 7.75 (s, 1H), 8.89 (s, 2H), 9.19 (s, 1H); mp 115-117° C.; MS (ES) m/z 434.

EXAMPLE 9

2-Amino-5-(1-ethyl-1H-pyrazol-4-yl)-5-(4-fluoro-3-pyrimidin-5-ylphenyl)-3-methyl-3,5-dihydro-4H-imidazol-4-one

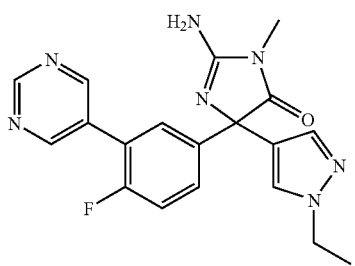

$^1$H NMR (500 MHz, DMSO-$d_6$) δ: 1.26 (t, 3H, J=7.2 Hz), 2.91 (s, 3H), 4.01 (q, 2H, J=7.2 Hz), 6.59 (s, 2H), 7.30 (m, 2H), 7.65 (m, 3H), 8.90 (s, 2H), 9.18 (s, 1H); mp 120-121° C.; MS (ES) m/z 380.

EXAMPLE 10

2-Amino-5-(1-ethyl-1H-pyrazol-4-yl)-5-[4-fluoro-3-(2-fluoropyridin-3-yl)phenyl]-3-methyl-3,5-dihydro-4H-imidazol-4-one

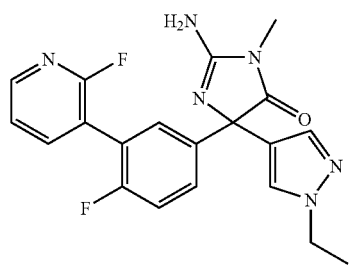

$^1$H NMR (500 MHz, DMSO-$d_6$) δ: 1.26 (t, 3H, J=7.32 Hz), 2.90 (s, 3H), 4.01 (q, 2H, J=7.2 Hz), 6.58 (s, 2H), 7.26 (m, 2H), 7.45 (m, 1H), 7.55 (s, 2H), 7.60 (m, 1H), 7.96 (m, 1H), 8.26 (s, 1H); mp 84-85° C.; MS (ES) m/z 397.

EXAMPLE 11

2-Amino-5-[3-(2-fluoropyridin-3-yl)phenyl]-3-methyl-5-[3-methyl-1-(2,2,2-trifluoroethyl)-1H-pyrazol-4-yl]-3,5-dihydro-4H-imidazol-4-one

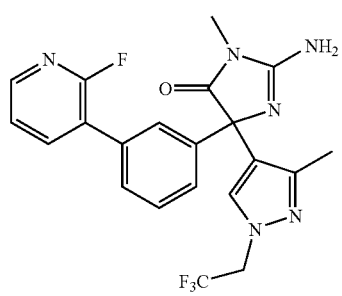

MS m/e (M)$^+$ 447; $^1$H NMR (DMSO $d_6$ 300 MHz) δ 1.8 (s, 3H), 2.95 (s, 3H), 4.95 (q, 2H), 6.6 (b, 2H), 7.4 (m, 5H), 7.6 (s, 1H), 8.0 (m, 1H), 8.2 (m, 1H). mp=128-132° C.

EXAMPLES 12-25

Preparation of 2-Amino-3-methyl-5-thienyl-3,5-dihydro-4H-imidazolone Compounds

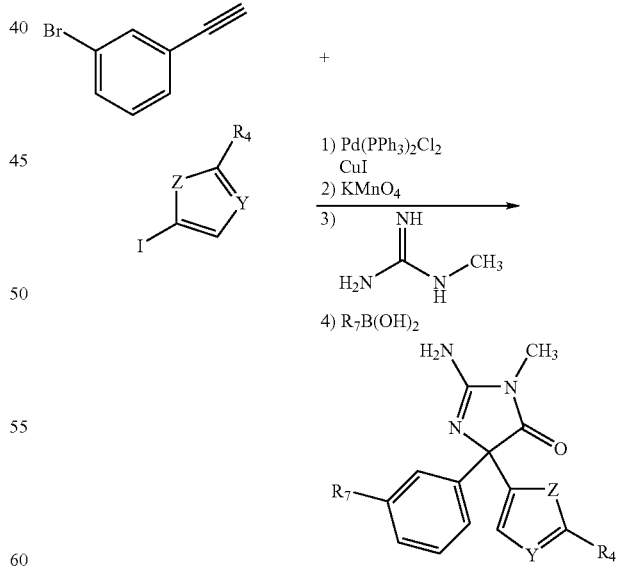

Using essentially the same procedure described in Example 1, Steps b-f, and employing the approriate iodothiophene and a suitable 3-bromophenylalkyne as starting materials, the compounds shown in Table I were obtained and identified by NMR and mass spectral analyses.

TABLE I

| Ex. No | R4 | R7 | Z | Y | mp (° C.) | MS m/z |
|---|---|---|---|---|---|---|
| 12 | H | pyridin-3-yl | S | CH | 219-223 | 349 |
| 13 | H | pyridin-3-yl | CH | S | 248 | 349 |
| 14 | H | 2,5-difluorophenyl | CH | S | 222 | 384 |
| 15 | H | Br | CH | S | — | 350 |
| 16 | H | 2,5-difluorophenyl | S | CH | 209-210 | 384 |
| 17 | CH3 | Br | S | CH | — | 364 |
| 18 | CH3 | pyridin-3-yl | S | CH | 218-220 | 363 |
| 19 | CH3 | pyrimidin-5-yl | S | CH | 133-135 | 364 |
| 20 | H | pyrimidin-5-yl | CH | S | 135 | 350 |
| 21 | H | 3-fluorophenyl | CH | S | 181 | 366* |
| 22 | H | 2,3-difluorophenyl | CH | S | 170 | 384* |
| 23 | H | 3,5-difluorophenyl | CH | S | 217 | 384* |
| 24 | H | 3-cyanophenyl | CH | S | 220 | 373* |
| 25 | H | 2,5-dimethoxyphenyl | CH | S | 143 | 408* |

*(M + H)+

EXAMPLE 26

Preparation of 2-Amino-5-(5-chloro-2-methylthien-3-yl)-3-methyl-5-(3-pyrimidin-5-ylphenyl)-3,5-dihydro-4H-imidazol-4-one

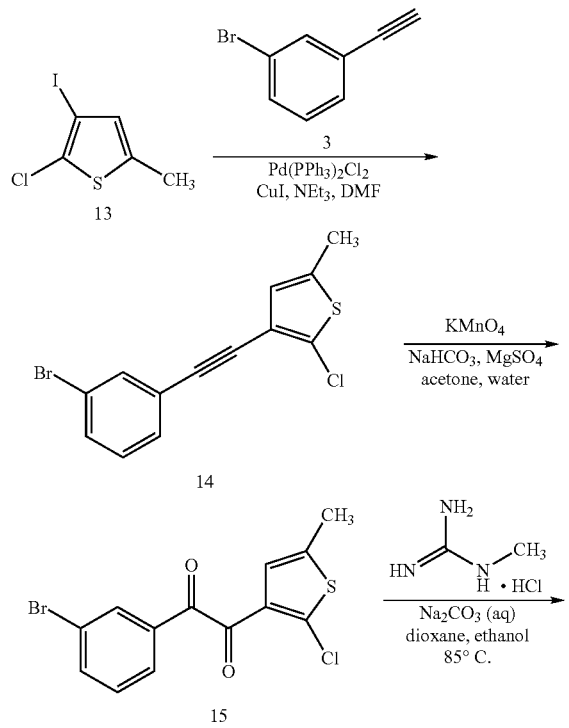

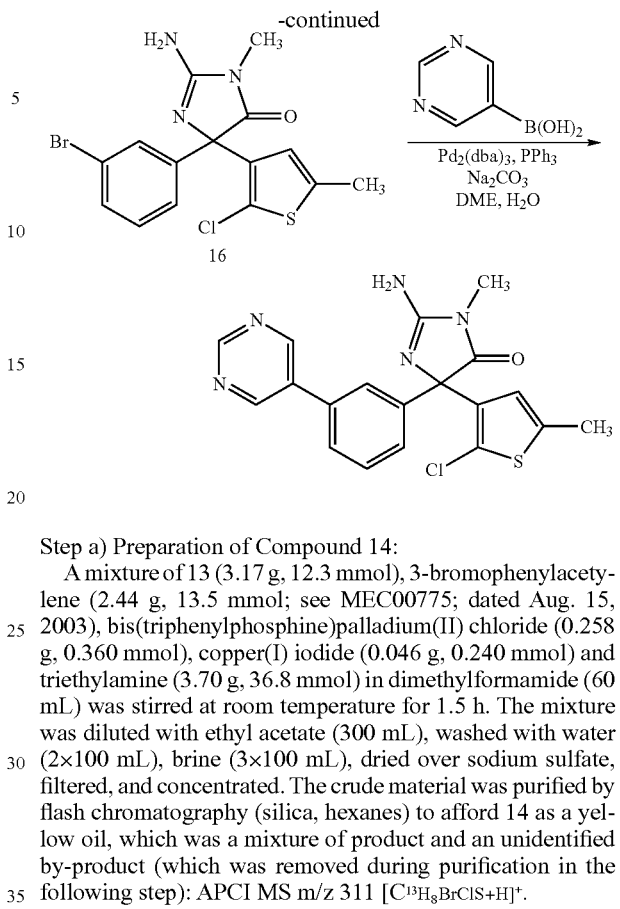

Step a) Preparation of Compound 14:

A mixture of 13 (3.17 g, 12.3 mmol), 3-bromophenylacetylene (2.44 g, 13.5 mmol; see MEC00775; dated Aug. 15, 2003), bis(triphenylphosphine)palladium(II) chloride (0.258 g, 0.360 mmol), copper(I) iodide (0.046 g, 0.240 mmol) and triethylamine (3.70 g, 36.8 mmol) in dimethylformamide (60 mL) was stirred at room temperature for 1.5 h. The mixture was diluted with ethyl acetate (300 mL), washed with water (2×100 mL), brine (3×100 mL), dried over sodium sulfate, filtered, and concentrated. The crude material was purified by flash chromatography (silica, hexanes) to afford 14 as a yellow oil, which was a mixture of product and an unidentified by-product (which was removed during purification in the following step): APCI MS m/z 311 [$C^{13}H_8BrClS+H$]+.

Step b) Preparation of Compound 15:

To a stirred solution of 14 (2.60 g, 8.30 mmol) in acetone (200 mL) was added a solution of sodium bicarbonate (0.418 g, 5.00 mmol) and magnesium sulfate (2.00 g, 16.6 mmol) in water (60 mL), followed by potassium permanganate (3.30 g, 20.9 mmol) in one portion. The reaction mixture was stirred for 1 h at rt. After this time the reaction was diluted with 1:1 hexanes/ethyl acetate (100 mL) and water (50 mL) and the solids were removed by filtration. The aqueous layer was separated then extracted with hexanes (2×75 mL), and the combined organic layers washed with water (2×75 mL), brine (75 mL), dried over sodium sulfate, filtered and concentrated. The resulting crude material was purified by flash chromatography (silica, 90:10 hexanes/ethyl acetate) to afford 15 (1.61 g, 38% over 2 steps) as a yellow oil: $^1$H NMR (500 MHz, CDCl$_3$) δ 8.10 (t, J=1.7 Hz, 1H), 7.87 (dt, J=7.8, 1.2 Hz, 1H), 7.81-7.74 (m, 1H), 7.39 (t, J=7.8 Hz, 1H), 7.06 (d, J=1.2 Hz, 1H), 2.41 (s, 3H).

Step c) Preparation of Compound 16:

A mixture of 15 (1.58 g, 4.60 mmol) and 1-methylguanidine hydrochloride (2.27 g, 20.7 mmol) in dioxane (50 mL) and ethanol (60 mL) was stirred at room temperature for 5 min. A solution of sodium carbonate (2.19 g, 20.7 mmol) in water (15 mL) was then added and the mixture immersed into an 85° C. oil bath and stirred for 45 min. The mixture was cooled to room temperature, concentrated and the residue partitioned between methylene chloride (150 mL) and water (150 mL). The organic layer was separated, washed with water (75 mL), brine (75 mL), dried over sodium sulfate, filtered and concentrated. The crude material was purified by flash chromatography (silica, 95:5:0.5 methylene chloride/ methanol/concentrated ammonium hydroxide) to afford a viscous oil. This oil was dissolved in a minimal amount of methylene chloride, treated with hexanes and then concentrated to afford 16 (0.96 g, 52%) as a white solid: $^1$H NMR (500 MHz, CD$_3$OD) δ 7.70 (br s, 1H), 7.55-7.45 (m, 2H), 7.27 (t, J=7.9 Hz, 1H), 6.12 (br s, 1H), 3.08 (s, 3H), 2.29 (s, 3H); ESI MS m/z 398 [C$_{15}$H$_{13}$BrClN$_3$OS+H]$^+$.

Step d) Preparation of 2-Amino-5-(5-chloro-2-methylthien-3-yl)-3-methyl-5-(3-pyrimidin-5-ylphenyl)-3,5-dihydro-4H-imidazol-4-one Ethylene glycol dimethyl ether (12 mL) was added to a nitrogen purged round bottom flask containing tris(dibenzylideneacetone)dipalladium(0) (0.034 g, 37.3 μmol) and triphenylphosphine (0.019 g, 72.5 μmol) and the mixture stirred for 5 min. 16 (0.30 g, 0.75 mmol), 5-pyrimidine boronic acid (0.111 g, 0.90 mmol), sodium carbonate (0.238 g, 2.25 mmol) and water (5 mL) were then added. The mixture was heated at reflux for 1.5 h, cooled to room temperature and concentrated. The residue was purified by flash chromatography (silica, 95:5:0.5 methylene chloride/methanol/concentrated ammonium hydroxide) and then by semi-preparative chromatography (Method 3) to afford a viscous oil. The oil was free based by partitioning between methylene chloride (20 mL) and 1 N sodium hydroxide (20 mL). The layers were separated and the organic layer dried over sodium sulfate, filtered and concentrated to afford the title product (0.032 g, 11%) as a white solid: mp 141-149° C.; $^1$H NMR (500 MHz, CD$_3$OD) δ 9.13 (s, 1H), 9.03 (s, 2H), 7.87 (br s, 1H), 7.72-7.67 (m, 2H), 7.55 (t, J=7.8 Hz, 1H), 6.19 (s, 1H), 3.11 (s, 3H), 2.29 (s, 3H); IR (ATR) 3342, 3040, 2953, 2918, 1732, 1663, 1601, 1583, 1553, 1467 cm$^{-1}$; ESI MS m/z 398 [C$_{19}$H$_{16}$ClN$_5$OS+H]$^+$;

EXAMPLE 27

Preparation of 2-Amino-5-(2-methylthien-3-yl)-3-methyl-5-(3-pyrimidin-5-ylphenyl)-3,5-dihydro-4H-imidazol-4-one

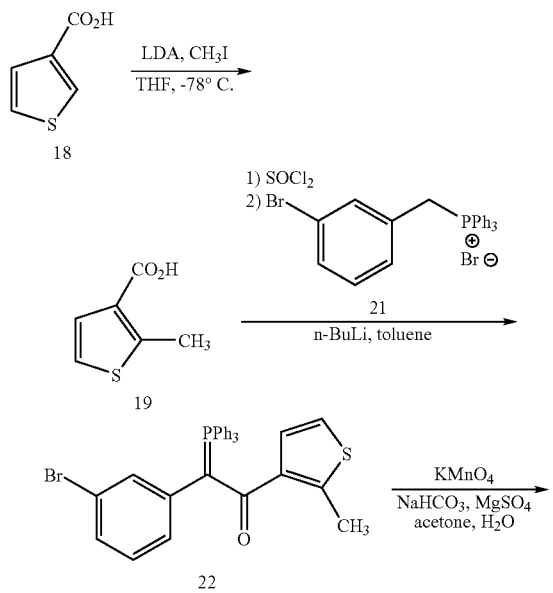

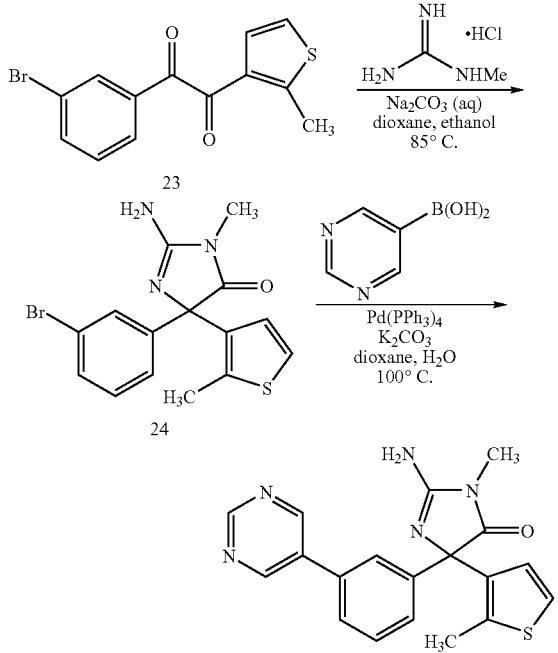

Step a) Preparation of Compound 19:

A solution of diisopropylamine (8.28 g, 81.8 mmol) in THF (190 mL) at −20° C. was treated with n-butyllithium (52 mL of a 1.6 M solution in hexanes, 83.2 mmol) over a period of 20 min, then slowly warmed to 0° C. under stirring for 30 min. This solution was cooled to −78° C. and treated dropwise with a solution of thiophene-3-carboxylic acid (4.99 g, 38.9 mmol) in THF (40 mL) over a period of 10 min. The mixture was stirred at −78° C. for an additional 10 min, then treated with iodomethane (6.16 g, 43.3 mmol) and stirred for 1 h, allowing the solution to slowly warm to rt. Water (200 mL) was added, and the mixture was made acidic by adding 2 N HCl (40 mL). The layers were separated and the aqueous layer was extracted with ether (3×75 mL), then the combined organic layers were dried over sodium sulfate, filtered and concentrated. Purification by flash chromatography (silica, 50:50:1 ethyl acetate/hexanes/acetic acid) afforded 19 (1.12 g, 20%) as a white solid: $^1$H NMR (500 MHz, CDCl$_3$) δ 7.45 (d, J=5.4 Hz, 1H), 7.01 (t, J=5.4 Hz, 1H), 2.77 (s, 3H).

Step b) Preparation of Compound 22:

A solution of 19 (0.908 g, 6.39 mmol) and thionyl chloride (4.59 g, 38.8 mmol) in benzene (7 mL) was heated to reflux for 1 h. The mixture was concentrated, diluted with toluene (20 mL) and again concentrated to afford the acid chloride of 20 (1.10 g, 100%) as a colorless oil. A mixture of 21 (3.27 g, 6.38 mmol) in toluene (30 mL) was treated with n-butyllithium (5.5 mL of a 1.16 M solution in hexanes, 6.38 mmol) and stirred at rt for 15 min. A solution of the acid chloride of 20 (1.10 g, 6.39 mmol) in toluene (8 mL) was added, and the mixture was stirred at rt for 2 h. The reaction was concentrated to afford 22 (4.90 g crude, >100%) as a yellow oil. ESI MS m/z 555 [C$_{31}$H$_{24}$BrOPS+H]$^+$.

Step c) Preparation of Compound 23:

A mixture of 22 (4.50 g, 6.00 mmol) in acetone (20 mL) was treated with a solution of sodium bicarbonate (0.323 g, 3.84 mmol) and magnesium sulfate (1.54 g, 12.8 mmol) in water (10 mL), and the mixture was stirred at rt for 5 min.

Potassium permanganate (2.02 g, 12.8 mmol) was added, and the mixture was heated at 50° C. for 16 h. The reaction was cooled to room temperature, diluted with ether (50 mL) and water (75 mL), and the insoluble material was removed by filtration. The filtrate layers were separated, and the aqueous layer was extracted with ether (2×50 mL). The combined organic extracts were dried over sodium sulfate, filtered, and concentrated to afford 2.19 g of a yellow oil, which was a 2:1 mixture of 23 and 22 as determined by $^1$H NMR analysis. This material was used in the subsequent step without further purification.

Step d) Preparation of Compound 24:

The reaction of 23 (0.113 g, ~67% purity) with 1-methylguanidine hydrochloride was carried out as described in method E to afford 24 (0.0655 g) as an off-white solid: $^1$H NMR (500 MHz, CD$_3$OD) δ 7.56 (t, J=1.8 Hz, 1H), 7.47-7.44 (m, 1H), 7.40-7.37 (m, 1H), 7.25 (t, J=7.9 Hz, 1H), 7.04 (d, J=5.4 Hz, 1H), 6.73 (d, J=5.4 Hz, 1H), 3.10 (s, 3H), 2.09 (s, 3H); ESI MS m/z 364 [C$_{15}$H$_{14}$BrN$_3$OS+H]$^+$.

Step e) Preparation of 2-Amino-5-(2-methylthien-3-yl)-3-methyl-5-(3-pyrimidin-5-ylphenyl)-3,5-dihydro-4H-imidazol-4-one:

A mixture of 24 (0.060 g, 0.166 mmol), 5-pyrimidineboronic acid (0.028 g, 0.224 mmol) and tetrakis(triphenylphosphino)palladium(0) (0.011 g, 92.6 μmol) in dioxane (1.5 mL) was treated with a solution of potassium carbonate (0.074 g, 0.532 mmol) in water (0.3 mL), then heated at reflux for 55 min. The mixture was cooled to room temperature, concentrated, and the residue partitioned between methylene chloride (50 mL) and water (50 mL). The layers were separated, and the aqueous layer was extracted with methylene chloride (2×25 mL). The combined organic extracts were dried over sodium sulfate, filtered, and concentrated. Purification by flash chromatography (silica, 96:4:0.5 methylene chloride/methanol/concentrated ammonium hydroxide) afforded the title product (0.046 g, 76%) as a white solid: mp 154-159° C.: $^1$H NMR (500 MHz, CD$_3$OD) δ 9.12 (s, 1H), 9.01 (s, 2H), 7.73 (d, J=1.8 Hz, 1H), 7.68-7.65 (m, 1H), 7.58-7.51 (m, 2H), 7.05 (s, 1H), 6.77 (d, J=5.3 Hz, 1H), 3.12 (s, 3H), 2.11 (s, 3H); ESI MS m/z 364 [C$_{19}$H$_{17}$N$_5$OS+H

EXAMPLES 28-37

Preparation of 2-Amino-3-methyl-5-(3-heteroarylphenyl)-5-thien-3ylimidazolone Compounds

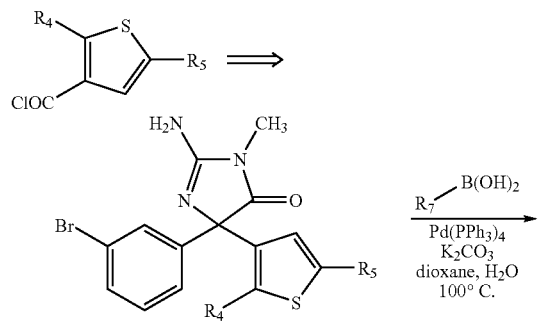

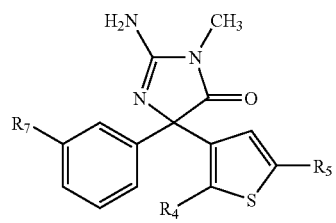

Using essentially the same procedure described in Example 27 and employing the appropriate thien-3-yl carboxylic acid as starting material, the compounds shown in Table II were obtained and identified by NMR and mass spectral analyses.

TABLE II

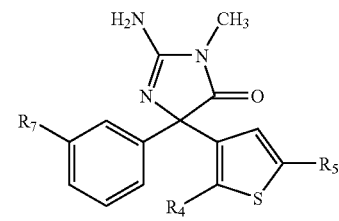

| Ex. No | R4 | R5 | R7 | mp (° C.) | MS m/z |
|---|---|---|---|---|---|
| 28 | H | C$_2$H$_5$ | Br | — | 378 |
| 29 | H | C$_2$H$_5$ | pyrimidin-5-yl | 144-146 | 378 |
| 30 | CH$_3$ | C$_2$H$_5$ | Br | — | 392 |
| 31 | CH$_3$ | C$_2$H$_5$ | pyrimidin-5-yl | 128-134 | 392 |
| 32 | H | Cl | pyrimidin-5-yl | 236-240 | 384 |
| 33 | H | H | 3-pyrazin-2-yl | 223 | 350 |
| 34 | H | H | 2-F-pyridin-3-yl | 213 | 365 |
| 35 | H | H | 6-F-pyridin-3-yl | 228 | 365 |
| 36 | H | H | 6-F-2-CH$_3$-pyridin-3-yl | 140 | 381 |
| 37 | H | H | 5-CH$_3$O-pyridin-3-yl | 197 | 377 |

EXAMPLES 38-40

Preparation of 2-Amino-3-methyl-5-(4-fluoro-3-pyridin-3-ylphenyl)-5-thien-3-ylimidazolone Compounds

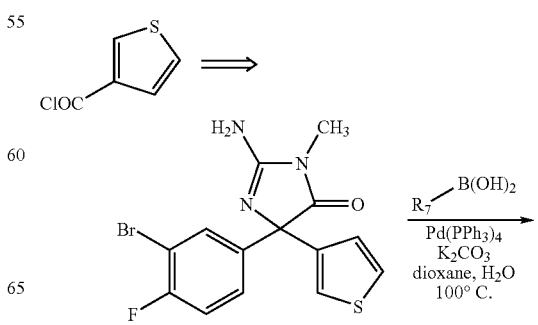

-continued

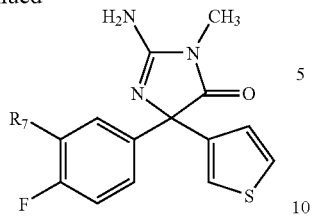

Using essentially the same procedure described in Example 27 and employing the thien-3-yl carboxylic acid and 3-bromo-4-fluorophenylalkyne as starting materials, the compounds shown in Table III were obtained and identified by NMR and mass spectral analyses.

TABLE III

| Ex. No | R7 | mp (° C.) | MS m/z |
|---|---|---|---|
| 38 | 2-CH₃O-pyridin-3-yl | — | 397 |
| 39 | 2-F-pyridin-3-yl | — | 385 |
| 40 | pyridin-3-yl | — | 367 |

EXAMPLE 41

Preparation of 2-Amino-3-methyl-5-(3-pyrimidin-5-ylphenyl)-5-(1,3-thiazol-4-yl)-3,5-dihydro-4H-imidazol-4-one

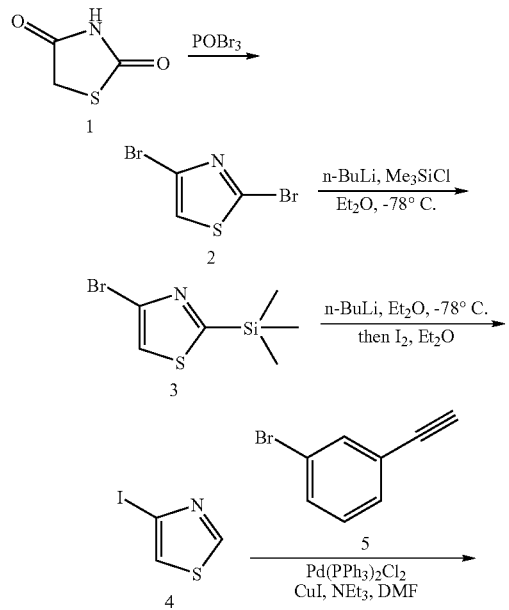

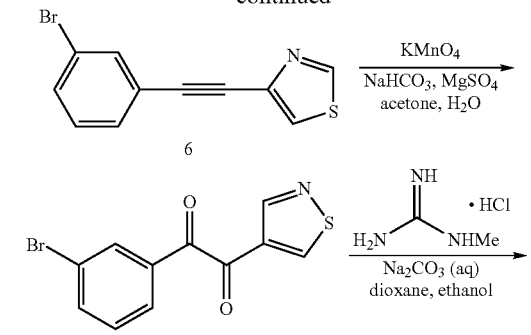

Step a) Preparation of Compound 2:

A mixture of 2,4-thiazolidinedione 1 (2.28 g, 19.5 mmol) and phosphorous oxybromide (25.0 g, 87.0 mmol) was heated at 130° C. for 30 min, then cooled to room temperature. The reaction was diluted with ice water (300 mL) and carefully neutralized by the addition of solid sodium carbonate in small portions. Once neutral, the mixture was extracted with dichloromethane (3×150 mL). The combined organic layers were dried over sodium sulfate, filtered and concentrated. Purification of the residue by flash chromatography (silica, 0:100 to 5:95 ethyl acetate/hexanes) afforded 2 (3.34 g, 71%) as light yellow crystals: $^1$H NMR (500 MHz, CDCl₃) δ 7.21 (s, 1H).

Step b) Preparation of Compound 3:

A solution of 2 (1.10 g, 4.53 mmol) in diethyl ether (8 mL) was added dropwise to a solution of n-BuLi (2.1 mL of a 2.5 M solution in hexanes, 5.3 mmol) at −78° C. over 25 min. The mixture was stirred for 1 h at −78° C., then a solution of chlorotrimethylsilane (0.585 g, 5.38 mmol) in diethyl ether (3 mL) was added dropwise over 20 min. The mixture was stirred for an additional 30 min at −78° C. then quenched by addition of saturated aqueous sodium bicarbonate (20 mL). After warming to room temperature, diethyl ether (100 mL) and water (50 ml) were added, the layers were separated and the aqueous layer was extracted with diethyl ether (2×50 mL). The combined organic extracts were dried over sodium sulfate, filtered and concentrated to afford 3 (0.95 g, 88%) as a red oil: $^1$H NMR (500 MHz, CDCl₃) δ 7.41 (s, 1H), 0.43 (s, 9H).

Step c) Preparation of Compound 4:

A solution of 3 (0.950 g, 4.02 mmol) in diethyl ether (8 mL) was added dropwise to a solution of n-BuLi (3.8 mL of a 1.6

M solution in hexanes, 6.1 mmol) at −78° C. over 20 min. The mixture was stirred for 40 min at −78° C., then a solution of iodine (1.58 g, 6.22 mmol) in diethyl ether (15 mL) was added dropwise over 20 min. The mixture was stirred for an additional 30 min at −78° C. then quenched by addition of saturated aqueous sodium bicarbonate (20 mL). After warming to room temperature, diethyl ether (50 mL) and water (100 mL) were added, the layers were separated and the aqueous layer was extracted with diethyl ether (2×50 mL). The combined organic extracts were dried over sodium sulfate, filtered and concentrated to afford 5 (1.28 g, >100%) as a red oil: $^1$H NMR (300 MHz, CDCl$_3$) δ 8.73 (d, J=1.9 Hz, 1H), 7.51 (d, J=2.0 Hz, 1H).

Step d) Preparation of Compound 6:

A mixture of crude 4 (1.27 g, 4.02 mmol), 3-bromophenyl acetylene 5 (1.10 g, 6.07 mmol) dichlorobis(triphenylphosphino)palladium(II) (0.115 g, 0.164 mmol), copper(I) iodide (0.0248 g, 0.130 mmol), triethylamine (2.19 g, 21.6 mmol) in DMF (20 mL) was stirred at room temperature overnight. The reaction was then diluted with ethyl acetate (500 mL) and washed with water (2×150 mL), 2% aqueous lithium chloride (150 mL), dried over sodium sulfate, filtered, and concentrated. Purification by flash chromatography (silica, 1:19 to 1:9 ethyl acetate/hexanes) afforded 6 (0.376 g, 35%) as a yellow oil: $^1$H NMR (500 MHz, CDCl$_3$) δ 8.82 (d, J=2.0 Hz, 1H), 7.72 (t, J=1.7 Hz, 1H), 7.60 (d, J=2.0 Hz, 1H), 7.48-7.51 (m, 2H), 7.23 (t, J=8.0 Hz, 1H);

ESI MS m/z 264 [C$_{11}$H$_6$BrNS+H]$^+$.

Step e) Preparation of Compound 7:

The reaction of 6 (0.236 g, 0.893 mmol) with potassium permanganate was carried out as described above to afford 7 (0.134 g, 50%) as a yellow solid: $^1$H NMR (500 MHz, CDCl$_3$) δ 8.90 (d, J=1.9 Hz, 1H), 8.53 (d, J=2.0 Hz, 1H), 8.15 (t, J=1.7 Hz, 1H), 7.92 (dt, J=7.7, 1.3 Hz, 1H), 7.77-7.80 (m, 1H), 7.40 (t, J=7.9 Hz, 1H);

ESI MS m/z 296 [C$_{11}$H$_6$BrNO$_2$S+H]$^+$.

Step f) Preparation of Compound 8:

The reaction of 7 with methylguanidine hydrochloride was carried out as described above to afford 8 (0.0965 g, 63%) as an off-white solid: R$_f$ 0.22 (silica, 90:10:0.5 methylene chloride/methanol/concentrated ammonium hydroxide); $^1$H NMR (500 MHz, DMSO-d$_6$) δ 9.01 (d, J=1.5 Hz, 1H), 7.84 (s, 1H), 7.67 (d, J=7.9 Hz, 1H), 7.50 (dd, J=8.0, 1.0 Hz, 1H), 7.32 (t, J=7.9 Hz, 1H), 7.16 (s, 1H), 6.73 (br s, 2H), 2.98 (s, 3H); ESI MS m/z 351, 353 [C$_{13}$H$_{11}$BrN$_4$OS+H]$^+$.

Step g) Preparation of 2-Amino-3-methyl-5-(3-pyrimidin-5-ylphenyl)-5-(1,3-thiazol-4-yl)-3,5-dihydro-4H-imidazol-4-one:

The reaction of 8 with 5-pyrimidine boronic acid was carried out as described above to afford the title product (0.029 g, 27%) as a white solid: mp 234-237° C.; $^1$H NMR (500 MHz, CDCl$_3$) δ 9.10 (s, 1H), 8.92 (s, 2H), 8.80 (d, J=2.0 Hz, 1H), 7.88-7.92 (m, 1H), 7.76-7.82 (m, 1H), 7.49-7.54 (m, 2H), 7.35-7.42 (m, 1H), 3.16 (s, 3H);

ESI MS m/z 351 [C$_{17}$H$_{14}$N$_6$OS+H]$^+$;

EXAMPLE 42

Preparation of 2-Amino-5-(1-ethyl-1H-pyrazol-4-yl)-3-methyl-5-(3-pyrimidin-5-yl)-3,5-dihydro-4H-imidazol-4-one

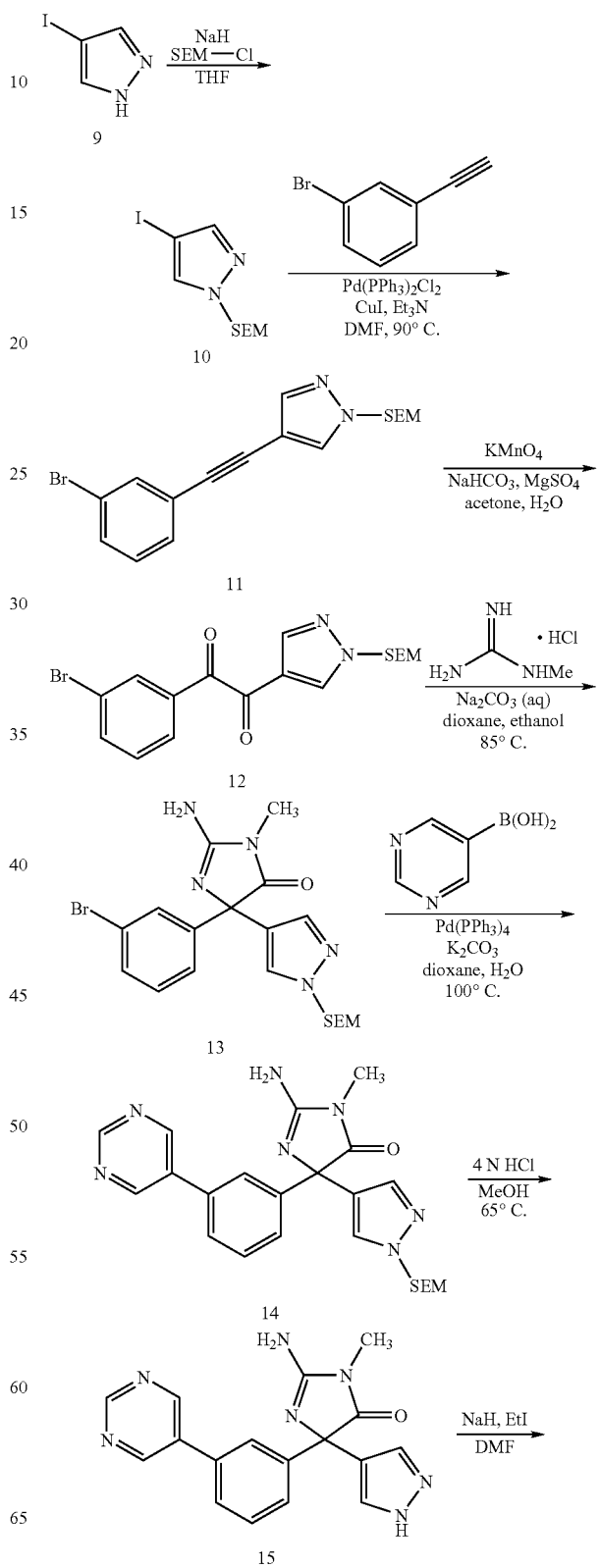

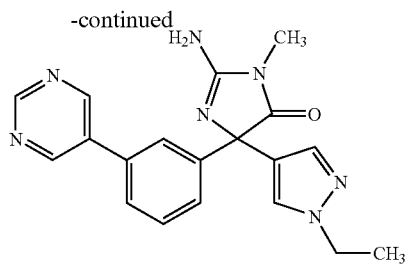

Step a) Preparation of Compound 10:

Sodium hydride (0.11 g of a 60% dispersion in oil, 2.84 mmol) was washed with hexanes, diluted with THF (2 mL) and treated with a solution of 9 (0.50 g, 2.58 mmol) in THF (1 mL) over a period of 5 min. After stirring for 35 min at room temperature, a solution of 2-(trimethylsilyl)ethoxymethyl chloride (0.52 g, 3.10 mmol) in THF (1 mL) was added dropwise over a period of 2 min and the mixture stirred at room temperature for 4.5 h. The mixture was diluted with ether (20 mL) then washed with water (10 mL), brine 10 mL), dried over magnesium sulfate, filtered and concentrated to afford 10 (0.85 g, 100%) as an amber oil: $^1$H NMR (500 MHz, CDCl$_3$) δ 7.65 (s, 1H), 7.55 (s, 1H), 5.41 (s, 2H), 3.58 (m, 2H), 0.91 (m, 2H), 0.50 (s, 9H);

ESI MS m/z 325 [C$_9$H$_{17}$IN$_2$OSi+H]$^+$.

Step b) Preparation of Compound 11:

A mixture of 10 (0.214 g, 0.660 mmol), 3-bromophenyl acetylene (0.144 g, 0.795 mmol), bis(triphenylphosphino) palladium(II) chloride (0.023 g, 32.9 μmol), copper(I) iodide (0.004 g, 20.0 μmol) and triethylamine (0.372 g, 3.68 mmol) in DMF (4 mL) was heated at 90° C. for 30 min. The mixture was cooled to room temperature, ethyl acetate (200 mL) was added, and the solution washed with water (100 mL) and 2% aqueous lithium chloride (2×75 mL). The organic layer was then dried over sodium sulfate, filtered, and concentrated. Purification by flash chromatography (silica, 5:95 ethyl acetate/hexanes) afforded 11 (0.149 g, 60%) as a red oil: $^1$H NMR (500 MHz, CDCl$_3$) δ 7.77 (s, 1H), 7.70 (s, 1H), 7.65 (t, J=1.7 Hz, 1H), 7.47-7.44 (m, 1H), 7.43-7.40 (m, 2H), 7.21 (t, J=7.9 Hz, 1H), 5.43 (s, 2H), 3.59 (t, J=8.2 Hz, 2H), 0.93 (t, J=8.3 Hz, 2H), 0.01 (s, 9H); ESI MS m/z 377 [C$_{17}$H$_{21}$BrN$_2$OSi+H]$^+$.

Step c) Preparation of Compound 12:

The reaction of 11 (0.393 g, 1.04 mmol) with potassium permanganate was performed as described in Example 27, Step c, to afford 12 (0.228 g, 53%) as a yellow solid: $^1$H NMR (500 MHz, CDCl$_3$) δ 8.27 (s, 1H), 8.22 (t, J=1.7 Hz, 1H), 8.13 (s, 1H), 8.01 (dt, J=7.8, 1.2 Hz, 1H), 7.80-7.77 (m, 1H), 7.41 (t, J=7.9 Hz, 1H), 5.48 (s, 2H), 3.64 (t, J=8.3 Hz, 2H), 0.94 (t, J=8.3 Hz, 2H), 0.01 (s, 9H); ESI MS m/z 409 [C$_{17}$H$_{21}$BrN$_2$O$_3$Si+H]$^+$.

Step d) Preparation of Compound 13

The reaction of 12 (0.226 g, 0.552 mmol) with 1-methylguanidine hydrochloride was performed as described in Example 27, Step d, to afford 13 (0.207 g, 80%) as an off-white solid: $^1$H NMR (500 MHz, CDCl$_3$) δ 7.71 (s, 1H), 7.64 (s, 1H), 7.58 (s, 1H), 7.50 (d, J=7.9 Hz, 1H), 7.43 (d, J=7.9 Hz, 1H), 7.21 (t, J=7.9 Hz, 1H), 5.40 (s, 2H), 5.18 (br s, 2H), 3.59 (t, J=8.2 Hz, 2H), 0.92 (t, J=8.2 Hz, 2H), −0.01 (s, 9H); APCI MS m/z 466 [C$_{19}$H$_{26}$BrN$_5$O$_2$Si+H]$^+$.

Step e) Preparation of Compound 14

The reaction of 13 with 5-pyrimidineboronic acid was performed as described in Example 27, Step e, to afford 14 (0.039 g, 81%) as a light yellow solid: $^1$H NMR (500 MHz, CD$_3$OD) δ 9.20 (s, 1H), 8.92 (s, 2H), 7.76 (s, 1H), 7.68-7.64 (m, 2H), 7.59 (s, 1H), 7.50-7.46 (m, 2H), 5.37 (s, 2H), 3.56 (t, J=8.1 Hz, 2H), 3.12 (s, 3H), 0.88 (t, J=8.2 Hz, 2H), −0.05 (s, 9H). ESI MS m/z 464 [C$_{23}$H$_{29}$N$_7$O$_2$Si+H]$^+$.

Step f) Preparation of Compound 15

A mixture of 14 (0.097 g, 0.209 mmol) in methanol (5 mL) was treated with hydrochloric acid (5 mL of a 4 N solution, 20 mmol) and heated to reflux for 24 h. The mixture was concentrated, the residue was re-dissolved in toluene (5 mL), and again concentrated. Purification by flash chromatography (90:10:0.5 methylene chloride/methanol/concentrated ammonium hydroxide) afforded 15 (0.033 g, 47%) as an off-white solid: $^1$H NMR (500 MHz, CD$_3$OD) δ 9.12 (s, 1H), 9.01 (s, 2H), 7.74 (t, J=1.7 Hz, 1H), 7.64 (dd, J=7.6, 1.3 Hz, 1H), 7.61-7.58 (m, 3H), 7.52 (t, J=7.7 Hz, 1H), 3.12 (s, 3H); ESI MS m/z 334 [C$_{17}$H$_{15}$N$_7$O+H]$^+$.

Step g) Preparation of 2-Amino-5-(1-ethyl-1H-pyrazol-4-yl)-3-methyl-5-(3-pyrimidin-5-yl)-3,5-dihydro-4H-imidazol-4-one:

A mixture of sodium hydride (0.004 g, 0.098 mmol) in dimethylformamide (1.2 mL) was treated with a solution of 15 (0.030 g, 0.090 mmol), and the mixture was stirred for 20 min. Iodoethane (0.016 g, 1.01 mmol) was added, and the mixture was stirred at rt for 90 min. Ethyl acetate (20 mL) and 2% aqueous lithium chloride (20 mL) were added, and the layers were separated. The aqueous layer was extracted with ethyl acetate (2×10 mL), and the combined organic extracts were dried over sodium sulfate, filtered, and concentrated. Purification by flash chromatography (95:5:0.5 methylene chloride/methanol/concentrated ammonium hydroxide) afforded the title product (0.009 g, 28%) as an off-white solid: mp 143-147° C.; $^1$H NMR (500 MHz, CD$_3$OD) δ 9.13 (s, 1H), 9.01 (s, 2H), 7.77-7.74 (m, 1H), 7.65 (d, J=7.6 Hz, 1H), 7.62-7.59 (m, 2H), 7.52 (t, J=7.7 Hz, 1H), 7.45 (s, 1H), 4.15 (q, J=7.3 Hz, 2H), 3.12 (s, 3H), 1.42 (t, J=7.3 Hz, 3H); ESI MS m/z 362 [C$_{19}$H$_{19}$N$_7$O+H]$^+$;

EXAMPLE 43

Preparation of 2-Amino-5-(1-ethyl-1H-pyrazol-4-yl)-5-[3-(2-fluoro-pyridin-3-yl)-phenyl]-3-methyl-3,5-dihydro-imidazol-4-one

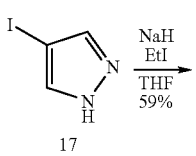

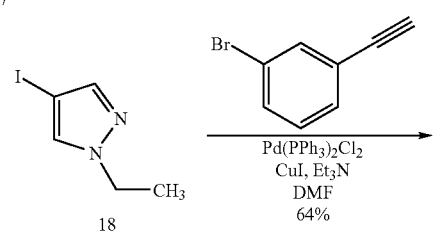

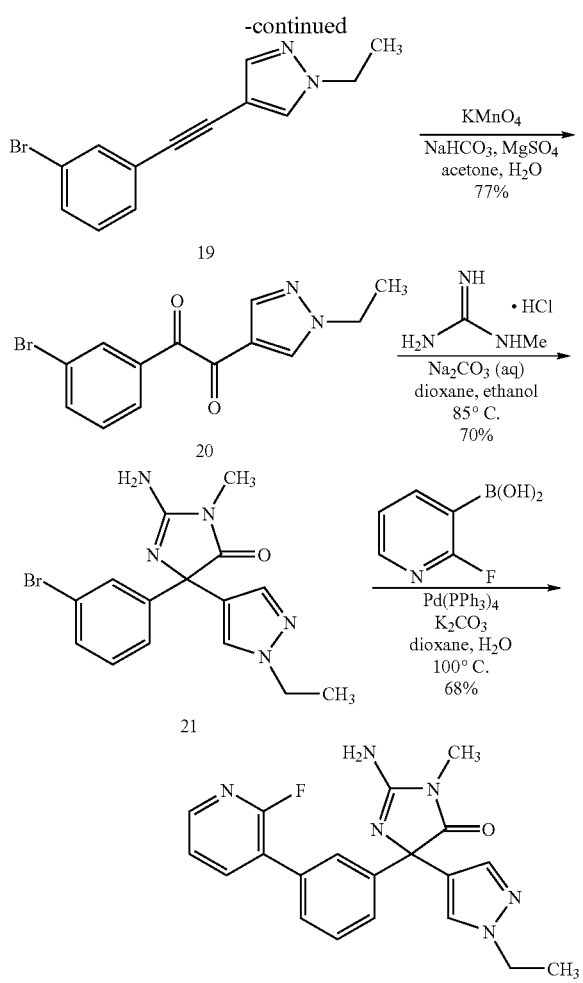

Step a) Preparation of Compound 18

Sodium hydride (0.476 g of a 60% dispersion in oil, 2.84 mmol) was washed with hexanes, diluted with THF (7 mL) and treated with a solution of 17 (1.99 g, 10.3 mmol) in THF (4 mL) over a period of 15 min. After stirring for 4 h at room temperature, a solution of iodoethane (3.12 g, 20.0 mmol) in THF (3 mL) was added dropwise over a period of 10 min and the mixture stirred at room temperature for 3 h. The mixture was diluted with ether (75 mL) and water (75 mL), the layers were separated and the aqueous layer was extracted with ether (2×50 mL). The combined organic extracts were washed with brine (50 mL), dried over sodium sulfate, filtered and concentrated. Purification by flash chromatography (silica, 10:90 to 20:80 ethyl acetate/hexanes) afforded 18 (1.36 g, 59%) as an off-white solid: $^1$H NMR (500 MHz, CDCl$_3$) δ 7.50 (s, 1H), 7.44 (s, 1H), 4.18 (q, J=7.4 Hz, 2H), 1.48 (t, J=7.3 Hz, 3H); ESI MS m/z 223 $[C_5H_7IN_2+H]^+$.

Step b) Preparation of Compound 19

A mixture of 18 (1.36 g, 6.13 mmol), 3-bromophenyl acetylene (1.40 g, 7.73 mmol), bis(triphenylphosphino)palladium(II) chloride (0.132 g, 0.188 mmol), copper(I) iodide (0.025 g, 0.132 mmol) and triethylamine (3.21 g, 31.7 mmol) in DMF (24 mL) was stirred at room temperature for 90 min. Ethyl acetate (500 mL) was added, and the solution washed with water (150 mL) and 2% aqueous lithium chloride (2×100 mL). The organic layer was then dried over sodium sulfate, filtered, and concentrated. Purification by flash chromatography (silica, 10:90 to 20:80 ethyl acetate/hexanes) afforded 19 (1.09 g, 64%) as a reddish-brown solid: $^1$H NMR (500 MHz, CDCl$_3$) δ 7.65 (s, 1H), 7.62 (t, J=1.7 Hz, 1H), 7.59 (s, 1H), 7.44-7.41 (m, 1H), 7.39 (dt, J=7.8, 1.2 Hz, 1H), 7.19 (t, J=7.9 Hz, 1H), 4.18 (q, J=7.3 Hz, 2H), 1.50 (t, J=7.3 Hz, 3H); ESI MS m/z 275 $[C_{13}H_{11}BrN_2+H]^+$.

Step c) Preparation of Compound 20:

To a stirred solution of 19 (1.08 g, 3.92 mmol) in acetone (100 mL) was added a solution of sodium bicarbonate (0.210 g, 2.50 mmol) and magnesium sulfate (0.942 g, 7.82 mmol) in water (40 mL), followed by potassium permanganate (1.25 g, 7.91 mmol) in one portion. The reaction mixture was stirred for 45 min, diluted with 1:1 hexanes/ethyl acetate (150 mL) and water (75 mL), and the solids were removed by filtration. The aqueous layer was separated and extracted with 1:1 hexanes/ethyl acetate (2×75 mL). The combined organic layers were then dried over sodium sulfate, filtered and concentrated. The crude material was purified by flash chromatography (silica, 85:15 to 75:25 hexanes/ethyl acetate) to afford 20 (0.928 g, 77%) as a yellow solid: $^1$H NMR (500 MHz, CDCl$_3$) δ 8.20 (t, J=1.7 Hz, 1H), 8.08 (s, 2H), 7.99 (dt, J=7.8, 1.2 Hz, 1H), 7.78-7.75 (m, 1H), 7.39 (t, J=7.9 Hz, 1H), 4.23 (q, J=7.3 Hz, 2H), 1.54 (t, J=7.3 Hz, 3H); ESI MS m/z 307 $[C_{13}H_{11}BrN_2O_2+H]^+$.

Step d) Preparation of Compound 21

A mixture of 20 (0.926 g, 3.01 mmol) and 1-methylguanidine hydrochloride (1.49 g, 13.6 mmol) in dioxane (40 mL) and ethanol (35 mL) was stirred at room temperature for 5 min. A solution of sodium carbonate (1.45 g, 13.7 mmol) in water (15 mL) was then added and the mixture immersed into an 85° C. oil bath and stirred for 25 min. The mixture was cooled to room temperature, concentrated and the residue partitioned between methylene chloride (75 mL) and water (75 mL). The organic layer was separated, washed with brine (50 mL), dried over sodium sulfate, filtered and concentrated. The crude material was purified by flash chromatography (silica, 96:4:0.5 methylene chloride/methanol/concentrated ammonium hydroxide) to afford a viscous oil. This oil was dissolved in a minimal amount of methylene chloride, treated with hexanes and then concentrated to afford 21 (0.763 g, 70%) as an off-white solid: $^1$H NMR (500 MHz, CD$_3$OD) δ 7.58-7.55 (m, 2H), 7.44-7.41 (m, 3H), 7.24 (t, J=7.9 Hz, 1H), 5.40 (s, 2H), 4.14 (q, J=7.3 Hz, 2H), 3.09 (s, 3H), 1.41 (t, J=7.3 Hz, 3H); APCI MS m/z 362 $[C_{15}H_{16}BrN_5O+H]^+$.

Step e) Preparation of Compound 22

A mixture of 21 (0.152 g, 0.420 mmol), 2-fluoropyridine-3-boronic acid (0.072 g, 0.511 mmol) and tetrakis(triphenylphosphino)palladium(0) (0.026 g, 22.2 µmol) in dioxane (4.2 mL) was treated with a solution of potassium carbonate (0.185 g, 1.34 mmol) in water (0.8 mL), then heated at reflux for 35 min. The mixture was cooled to room temperature, concentrated and the residue partitioned between methylene chloride (50 mL) and water (50 mL). The layers were separated and the aqueous layer was extracted with methylene chloride (2×25 mL). The combined organic extracts were dried over sodium sulfate, filtered and concentrated. Purification by flash chromatography (silica, 96:4:0.5 to 93:7:0.5 methylene chloride/methanol/concentrated ammonium hydroxide) afforded (22 (0.109 g, 68%) as a white solid: R$_f$ 0.40 (90:10:0.5 methylene chloride/methanol/concentrated ammonium hydroxide); mp 122-127° C.; $^1$H NMR (500 MHz, CDCl$_3$) δ 8.17 (d, J=4.6 Hz, 1H), 8.02-7.98 (m, 1H), 7.65 (d, J=1.4 Hz, 1H), 7.60 (s, 1H), 7.52 (m, 2H), 7.47-7.43 (m, 2H), 7.41-7.38 (m, 1H), 4.15 (q, J=7.3 Hz, 2H), 3.10 (s, 3H), 1.42 (t, J=7.3 Hz, 3H); IR (ATR) 3344, 3066, 1665, 1466, 1433, 1399, 1330 cm$^{-1}$; ESI MS m/z 379 $[C_{20}H_{19}FN_6O+H]^+$;

EXAMPLE 44

Preparation of (5R)-2-Amino-5-(1-ethyl-1H-pyrazol-4-yl)-5-[3-(2-fluoropyridin-3-yl)phenyl]-3-methyl-3,5-dihydro-4H-imidazol-4-one (A) and (5S)-2-Amino-5-(1-ethyl-1H-pyrazol-4-yl)-5-[3-(2-fluoropyridin-3-yl)phenyl]-3-methyl-3,5-dihydro-4H-imidazol-4-one (B)

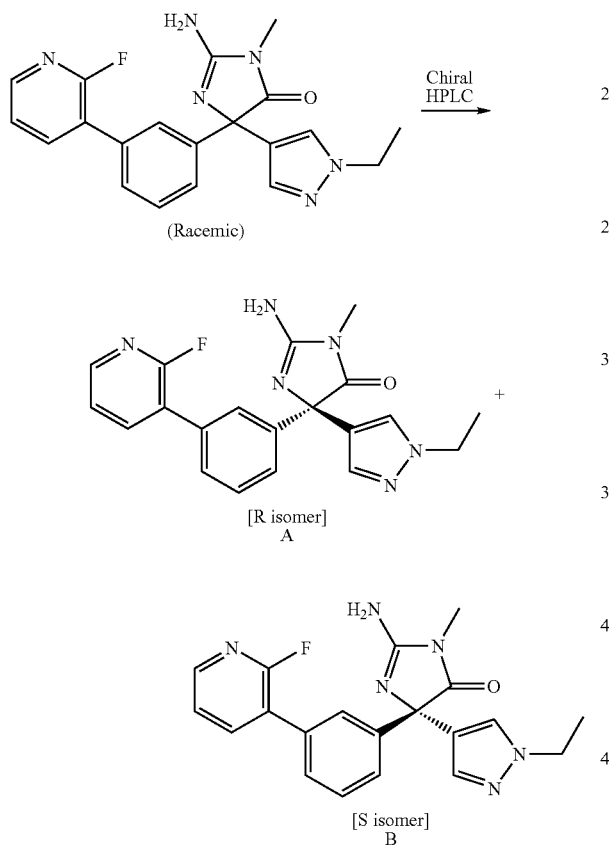

A racemic mixture of 2-amino-5-(1-ethyl-1H-pyrazol-4-yl)-5-[3-(2-fluoro-pyridin-3-yl)-phenyl]-3-methyl-3,5-dihydro-imidazol-4-one was separated by chiral HPLC to give the title enantiomeric products: A (5R)-2-amino-5-(1-ethyl-1H-pyrazol-4-yl)-5-[3-(2-fluoropyridin-3-yl)phenyl]-3-methyl-3,5-dihydro-4H-imidazol-4-one, $^1$H NMR (DMSOd$_6$ 300 MHz) δ 1.1 (t, 3H), 2.95 (s, 3H), 4.05 (q, 2H), 6.28 (s, 1H), 6.35-6.45 (m, 3H), 7.55 (m, 2H), 7.7 (m, 1H), 7.95-8.0 (m, 1H), 8.2 (dd, 1H); MS m/e (M+H)$^+$ 379 and B (5S)-2-Amino-5-(1-ethyl-1H-pyrazol-4-yl)-5-[3-(2-fluoropyridin-3-yl)phenyl]-3-methyl-3,5-dihydro-4H-imidazol-4-one, $^1$H NMR (DMSOd$_6$ 300 MHz) δ 1.1 (t, 3H), 2.95 (s, 3H), 4.05 (q, 2H), 6.28 (s, 2H), 6.35-6.45 (m, 3H), 7.55 (m, 2H), 7.7 (m, 1H), 7.95-8.0 (m, 1H), 8.2 (dd, 1H); MS m/e (M+H)$^+$ 379

EXAMPLE 45

Preparation of 2-Amino-5-(1-ethyl-1H-pyrazol-4-yl)-5-[3-(5-fluoro-pyridin-3-yl)-phenyl]-3-methyl-3,5-dihydro-imidazol-4-one

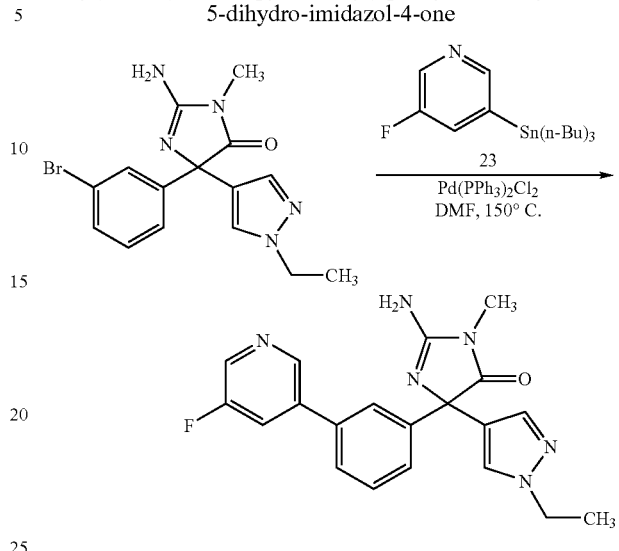

A mixture of 2-amino-5-(1-ethyl-1H-pyrazol-4-yl)-5-[3-bromophenyl]-3-methyl-3,5-dihydro-imidazol-4-one (0.153 g, 0.422 mmol), 23 (0.256 g, 0.663 mmol) and bis(triphenylphosphino)palladium(II) chloride (0.019 g, 27.2 μmol) in DMF (6.5 mL) was heated at 150° C. in a sealed tube for 70 min. The mixture was cooled to room temperature, diluted with ethyl acetate (150 mL) and washed with water (75 mL) and 2% lithium chloride (2×50 mL). The organic layer was dried over sodium sulfate, filtered and concentrated. Purification by flash chromatography (silica, 95:5:0.5 methylene chloride/methanol/concentrated ammonium hydroxide) afforded the title product (0.067 g, 42%) as an off-white solid: mp 216-220° C.; $^1$H NMR (300 MHz, CD$_3$OD) δ 8.63 (s, 1H), 8.44 (d, J=2.6 Hz, 1H), 7.86 (dt, J=9.8, 1.6 Hz, 1H), 7.72 (s, 1H), 7.64-7.55 (m, 3H), 7.51-7.43 (m, 2H), 4.15 (q, J=7.3 Hz, 2H), 3.11 (s, 3H), 1.41 (t, J=7.3 Hz, 3H); IR (ATR) 3120, 1732, 1683, 1474, 1431, 1387, 1320 cm$^{-1}$;
ESI MS m/z 379 $[C_{20}H_{19}FN_6O+H]^+$;

EXAMPLE 46

Preparation of 2-Amino-5-[3-(5-chloropyridin-3-yl)phenyl]-5-(1-ethyl-1H-pyrazol-4-yl)-3-methyl-3,5-dihydro-imidazol-4-one

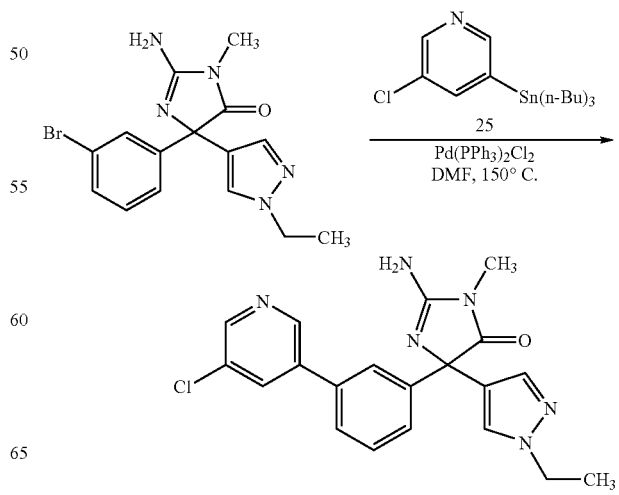

A mixture of 2-amino-5-[3-bromophenyl]-5-(1-ethyl-1H-pyrazol-4-yl)-3-methyl-3,5-dihydro-imidazol-4-one (0.143 g, 0.395 mmol), 25 (0.239 g, 0.594 mmol) and bis(triphenylphosphino)palladium(II) chloride (0.018 g, 25.5 µmol) in DMF (6 mL) was heated at 150° C. in a sealed tube for 70 min. The mixture was cooled to room temperature, diluted with ethyl acetate (150 mL) and washed with water (75 mL) and 2% lithium chloride (2×50 mL). The organic layer was dried over sodium sulfate, filtered and concentrated. Purification by flash chromatography (silica, 95:5:0.5 methylene chloride/methanol/concentrated ammonium hydroxide) afforded the title product (0.064 g, 41%) as an off-white solid: mp 205-210° C.; $^1$H NMR (300 MHz, CD$_3$OD) δ 8.68 (d, J=1.9 Hz, 1H), 8.53 (d, J=2.2 Hz, 1H), 8.10-8.07 (m, 1H), 7.71 (t, J=1.6 Hz, 1H), 7.63-7.54 (m, 3H), 7.51-7.44 (m, 2H), 4.14 (q, J=7.3 Hz, 2H), 3.11 (s, 3H), 1.41 (t, J=7.3 Hz, 3H); IR (ATR) 3275, 3048, 1732, 1669, 1470, 1392, 1325 cm$^{-1}$; ESI MS m/z 395 [C$_{20}$H$_{19}$ClN$_6$O+H]$^+$;

EXAMPLE 47

Preparation of 1-(3-bromophenyl)-2-(1H-pyrrol-3-yl)ethane-1,2-dione

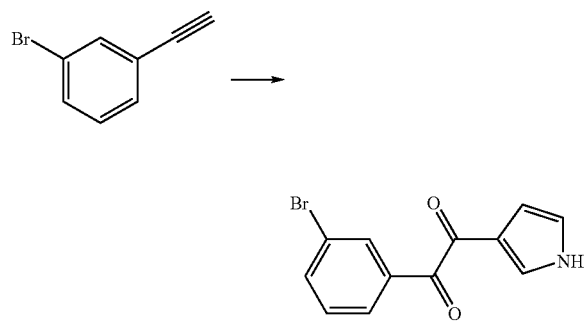

A solution of N-triisopropylsilylpyrrole (3.49 g, 1 mmol), 3-bromo-1-ethynylbenzene (1.81 g, 1 mmol), Pd(PPh$_3$)$_4$ (800 mg) and CuI (185 mg) in CH$_3$CN (15 ml) and triethylamine (35 ml) is refluxed for 5 h. The reaction mixture is cooled to room temperature and the solvent is evaporated on a rotary evaporator. The crude material is purified by flash chromatographied (silica gel, 100% hexane) to afford 3-[(3-bromophenyl)ethynyl]-1-(triisopropylsilyl)-1H-pyrrole (2.7 g, 85%) as a clear oil.

To a solution of 3-[(3-bromophenyl)ethynyl]-1-(triisopropylsilyl)-1H-pyrrole (2.7 g, 8.5 mmol) in acetone (100 mml) is added a solution of MgSO$_4$ (1.53 g, 12.75 mmol) and NaHCO$_3$ (316 mg, 3.76 mmol) in water (50 ml), followed by the addition of KMnO$_4$ (2.68 g, 17 mmol) in one portion at room temperature. After refluxing for 5 h, the reaction mixture is cooled to room temperature and extracted with ether (2×50 mL), the combined organic extracts are dried over MgSO$_4$. The crude material is purified flash chromatography (silica gel, EtOAc/hexane: 30/70 to 50/50) to afford the title compound as a yellow solid (42%). mp: 111-113° C. MS (−) ES: 276 (M−H)$^-$.

EXAMPLE 48

Preparation of 1-(3-bromophenyl)-2-(1-ethyl-1H-pyrrol-3-yl)ethane-1,2-dione

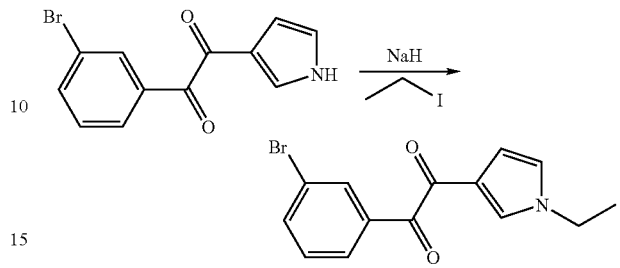

The title compound is prepared by using essentially the same procedure as in Example 1, step b, affording an oil (56%). MS (+) ES: 306 (M+H)$^+$.

EXAMPLE 49

Preparation of 1-(3-bromophenyl)-2-[1-(2,2,2-trifluoroethyl)-1H-pyrrol-3-yl]ethane-1,2-dione

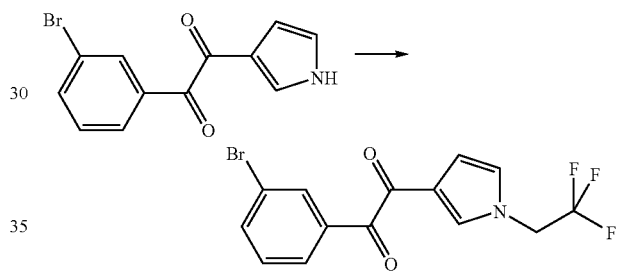

To a solution of 1-(3-bromophenyl)-2-(1H-pyrrol-3-yl)ethane-1,2-dione (93 mg, 0.33 mmol) in DMF (5.0 mL) was added 2,2,2-trifluoroethyl 4-methylbenzenesulfonate (170 mg, 0.66 mmol), K$_2$CO$_3$ (100 mg, 0.73 mmol) and Et$_4$NCl (5.5 mg, 0.033 mmol) at room temperature. After heating at 80° C. for 3 days, the reaction mixture is cooled, diluted with H$_2$O, EtOAc. The two layers are separated and the aqueous layer is extracted with EtOAc. The combined organic extracts are washed with 1N HCl aqueous H$_2$O, brine, dried (MgSO$_4$) and concentrated. The crude material is purified by chromatography (silica gel, EtOAc/hexane: 20/80) to give the title compound (190 mg, 65%) as a solid. mp: 105-106° C. MS (+) ES: 418 (M+CH$_3$COO)$^-$.

EXAMPLE 50

Preparation of 2-Amino-5-(3-bromophenyl)-5-(1-ethyl-1H-Pyrrol-3-yl)-3-methyl-3,5-dihydro-4H-imidazol-4-one

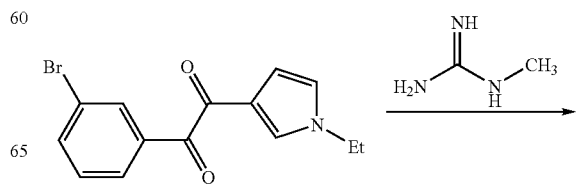

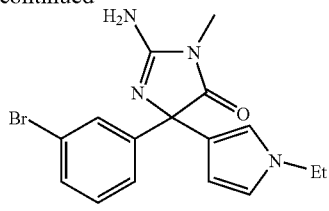

The title compound was prepared using essentially the same procedure described in Example 21, step c, to give the title product as a solid (82%), mp 138-140° C., MS (+) ES: 361 (M+H)+.

EXAMPLE 51

Preparation of 2-Amino-5-(3-bromophenyl)-3-methyl-5-[1-(2,2,2-trifluoroethyl)-1H-pyrrol-3-yl]-3,5-dihydro-4H-imidazol-4-one

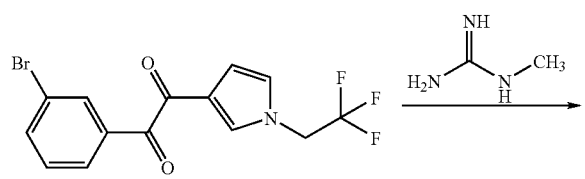

The title compound was prepared using essentially the same procedure described in Example 21, step c, to give the title product a solid (70%). mp: 74-76° C. MS (+) ES: 415 (M+H)+.

EXAMPLE 52

Preparation of 2-amino-5-(1-ethyl-1H-pyrrol-3-yl)-3-methyl-5-(3-pyrimidin-5-ylphenyl)-3,5-dihydro-4H-imidazol-4-one

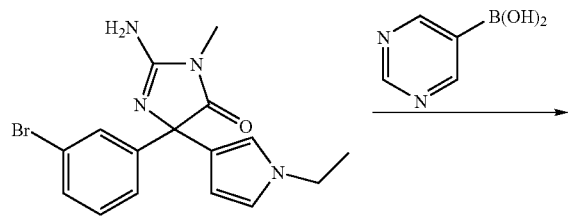

To a solution of 2-amino-5-(3-bromophenyl)-5-(1-ethyl-1H-pyrrol-3-yl)-3-methyl-3,5-dihydro-4H-imidazol-4-one (80 mg, 0.22 mmol) in DME (3 mL) is added pyrimidin-5-ylboronic acid (57 mg, 0.44 mmol), tetrakis(triphenylphosphine)palladium (25 mg, 0.022 mmo) and a solution sodium carbonate (93 mg, 0.88 mmol) in H2O (0.5 mL) at room temperature. The reaction mixture is refluxed for 1 h and cooled. After evaporation of the solvent, the crude material is purified by chromatography (silica gel, EtOAc/2M ethanolic NH3: 92/8) to give the title compound (60 mg, 75%) as a solid. mp: 100-102° C.; MS(+) ES: 361 (M+H)+.

EXAMPLES 53-55

Preparation of 2-amino-5-(1-substituted-1H-pyrrol-3-yl)-5-(3-substituted-phenyl)-3-methyl-3,5-dihydro-4H-imidazol-4-one Compounds

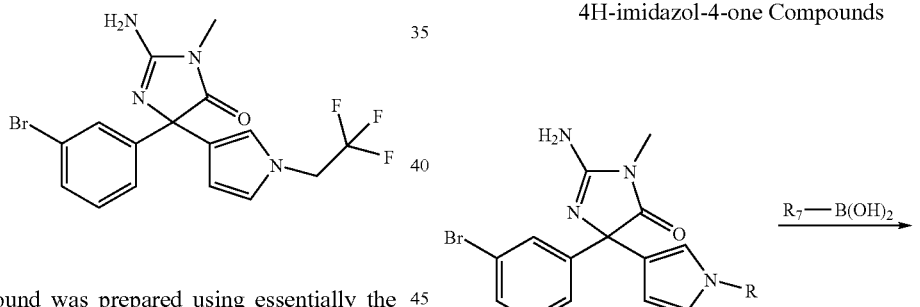

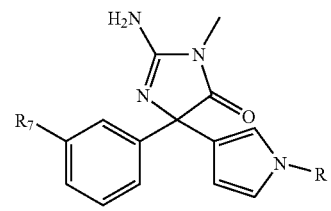

Using essentially the same procedure described in Example 52 and employing the appropriated 5-(3-bromophenyl)hydantoin and a suitable boronic acid reagent, the compounds shown in Table IV were obtained and identified by NMR and mass spectral analyses.

TABLE IV

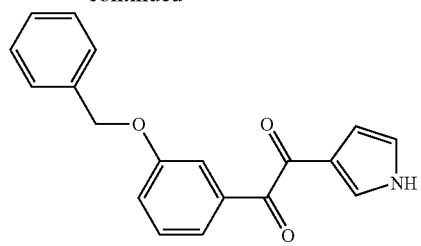

| Ex. No | R | R7 | mp (° C.) | M + H |
|---|---|---|---|---|
| 53 | $C_2H_5$ | 2-fluoropyridin-2-yl | 103-105 | 378 |
| 54 | $CH_2CF_3$ | pyrimidin-5-yl | 103-105 | 415 |
| 55 | $CH_2CF_3$ | 2-fluoropyridin-2-yl | 104-106 | 432 |

EXAMPLE 56

Preparation of 3-benzyloxy-1-ethynylbenzene

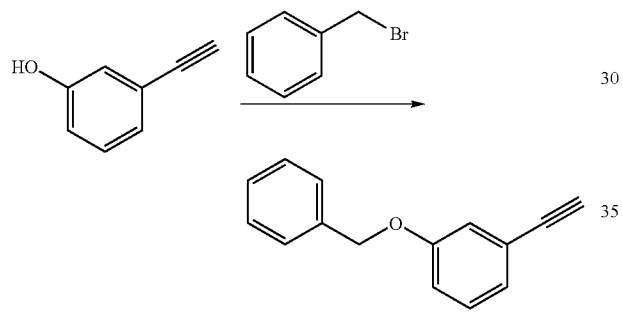

A mixture of 3-hydroxy-1-ethynylbenzene (4.36 g, 37 mmol), benzylbromide (6.95 g, 4.1 mmol) and $K_2CO_3$ (10.2 g, 7.4 mmol) in acetanitrile (50 ml) is stirred at room temperature for 24 hr. The insoluble material is removed by filtration and filtrate is concentrated. The crude material is purified by flash chromatography (silica gel, hexane/EtOAc: 95/5) to afford the title compound as a clear oil 5.2 g (68%).

$^1$HNMR (400 MHz, $CDCl_3$): δ (ppm) 3.05 (s, 1H), 5.05 (s, 2H), 6.98 (d, 1H) 7.00-7.50 (m, 8H).

EXAMPLE 57

Preparation of 1-[3-(benzyloxy)phenyl]-2-(1H-pyrrol-3-yl)ethane-1,2-dione

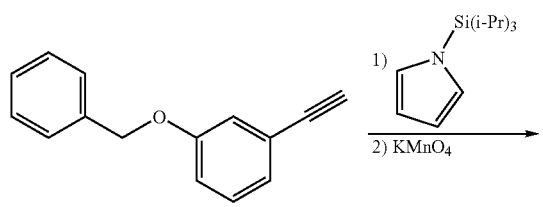

The title compound was prepared using essentially the same procedure described in Example 47 to give the title product as a solid (29%) mp 124-125° C., MS (+) ES: 306 (M+H)$^+$.

EXAMPLE 58

Preparation of 2-amino-5-(3-benzyloxyphenyl)-5-(1H-pyrrol-3-yl)-3-methyl-3,5-dihydro-4H-imidazol-4-one

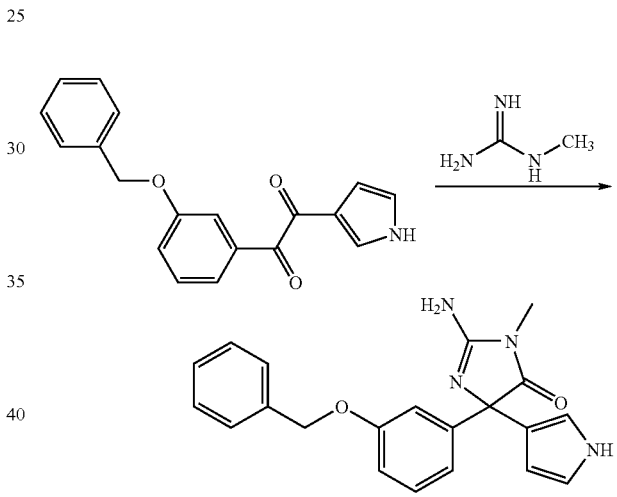

The title compound was prepared using essentially the same procedure described in Example 21, step c, to give the title product as a solid (38%) mp 98-100° C. MS (+) ES: 361 (M+H)$^+$.

EXAMPLE 59

Preparation of 2-amino-5-(3-hydroxyphenyl)-5-(1H-pyrrol-3-yl)-3-methyl-3,5-dihydro-4H-imidazol-4-one

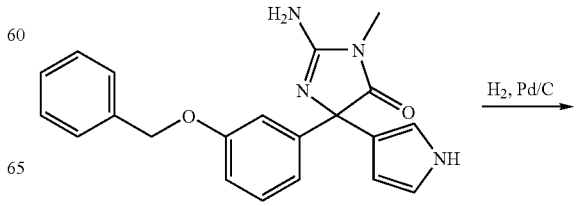

-continued

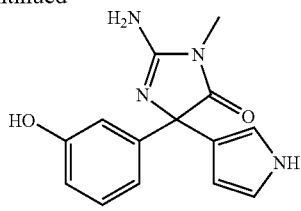

A mixture of 2-amino-5-(3-benzyloxyphenyl)-5-(1H-pyrrol-3-yl)-3-methyl-3,5-dihydro-4H-imidazol-4-one (70 mg, 0.2 mmol) and Pd/C (8 mg) in ethanol (10 ml) is hydrogenated at 45 psi overnight. The catalyst is removed by filtration and the filtrate is concentrated. The crude material is purified by flash chromatography (silica gel, EtOAc/2.0M ethanolic $NH_3$: 90/10 to 80/20) to afford the title compound as a solid, 49 mg (93%) mp 142-145° C., MS (+) ES: 271 (M+H)$^+$.

EXAMPLE 60

Preparation of 3-(3-ethynylphenyl)-2-fluoropyridine

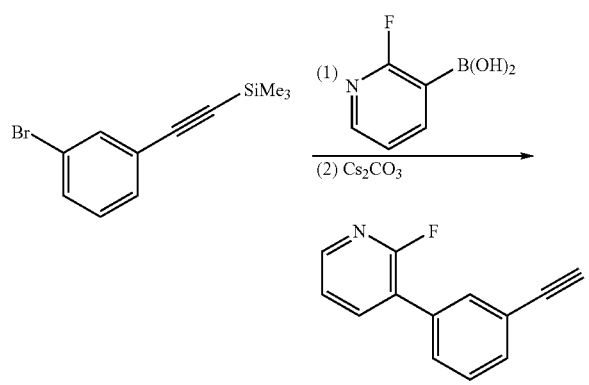

To a solution of [(3-bromophenyl)ethynyl](trimethyl)silane (2.28 g, 9.0 mmol) in DME (150 mL) is added (2-fluoropyridin-3-yl)boronic acid (1.41 g, 10.0 mmol), tetrakis(triphenylphosphine)palladium (0.52 g, 0.5 mmol) and a solution of sodium carbonate (3.8 g, 36.0 mmol) in $H_2O$ (15 mL) at room temperature. After refluxing for 3 h, the reaction mixture is cooled, quenched with saturated sodium carbonate, diluted with EtOAc. The two layers are separated and the aqueous layer is extracted with EtOAc. The combined organic extracts are washed with brine, dried ($MgSO_4$) and concentrated. The crude mixture is purified by chromatography (silica gel, EtOAc/hexane: 5/95) to give the 2-fluoro-3-{3-[(trimethylsilyl)ethynyl]phenyl}pyridine (2.25 g, 91%) as an oil. MS(+) APPI: 270 (M+H)$^+$.

To a solution of 2-fluoro-3-{3-[(trimethylsilyl)ethynyl]phenyl}pyridine (2.20 g, 8.1 mmol) in MeOH/$CH_2Cl_2$ (1/1, 60 mL) is added $Cs_2CO_3$ (3.17 g, 9.7 mmol) at room temperature. After stirring for 1 h, the reaction mixture is diluted with $CH_2Cl_2$ and passed through a thin layer of silica gel. The solution is concentrated and the crude material is purified by chromatography (silica gel, EtOAc/hexane: 20/80) to give the title compound (1.23 g, 77%) as a solid. mp: 45-47° C. MS (+) EI: 198 M$^+$.

EXAMPLE 61

Preparation of 1-(cyclopropylmethoxy)-3-ethynylbenzene

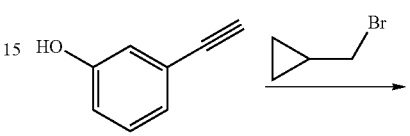

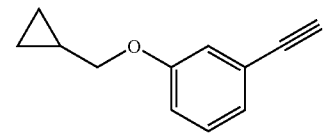

To a solution of 3-ethynylphenol (1.18 g, 10.0 mmol) in acetone (30 mL) is added (bromomethyl)cyclopropane (1.02 mL, 10.0 mmol), sodium iodide (0.75 g, 5.0 mmol) and $Cs_2CO_3$ (6.52 g, 20.0 mmol) at room temperature. After refluxing over night, the reaction mixture is cooled, diluted with $Et_2O$ (300 mL) and pass through a thin layer of silica gel. The solution is concentrated. The crude material is purified by chromatography (silica gel, EtOAc/hexane: 1/99) to give the title compound (1.45 g, 84%) as an oil. MS(+) APPI: 173 (M+H)$^+$.

EXAMPLE 62

Preparation of 1-(2-fluoroethyl)-4-iodo-1H-pyrazole

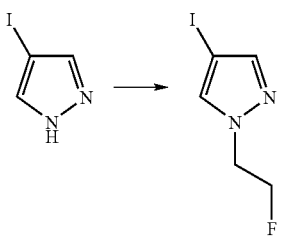

A solution of 4-iodo-1H-pyrazole (1.10 g, 5.7 mmol) in anhydrous DMF (25 mL) is treated with NaH (0.23 g, 60% in mineral oil, 5.7 mmol). After stirring for 20 minutes at room temperature, the reaction mixture is treated with 1-iodo-2-fluoroethane (1.0 g, 5.7 mmol) and stirred over night at room temperature. The reaction is quenched with $H_2O$ and diluted with EtOAc. The two layers are separated and the aqueous is extracted with EtOAc. The combined organic extracts are washed with $H_2O$, brine, dried ($Na_2SO_4$) and concentrated. The crude material is purified by chromatography (silica gel, EtOAc/hexane: 15/85) to afford the title compound (1.08 g, 79%) as an oil. MS (+) ES 240 (M+H)$^+$.

EXAMPLE 63

Preparation of 4-iodo-1-(2,2,2-trifluoroethyl)-1H-pyrazole

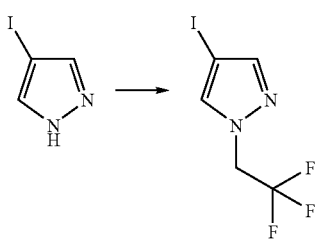

A mixture of 4-iodo-1H-pyrazole (960 mg, 5 mmol), 2,2,2-trifluoroethyl iodide (3.13 g, 15 mmol) and $Cs_2CO_3$ (2.4 g, 7.7 mmol) in DMF (5 ml) is heated at 60° C. with stirring overnight. After cooling, the reaction mixture is partitioned between water (50 ml) and ether (20 ml). The organic layer is separated, dried ($MgSO_4$) and concentrated to afford the title compound as an oil which solidified upon standing 1.0 g (72%). $^1$HNMR ($CDCl_3$): δ (ppm) 4.70 (m, 2H), 7.56 (s, 1H), 7.59 (s, 1H).

EXAMPLE 64

Preparation of 2-fluoro-3-(3-{[1-(2-fluoroethyl)-1H-pyrazol-4-yl]ethynyl}phenyl)pyridine

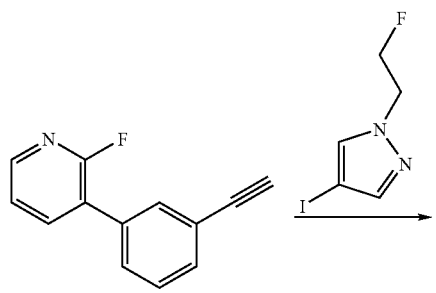

To a solution of 1-(2-fluoroethyl)-4-iodo-1H-pyrazole (148 mg, 0.62 mmol) in DMF (5.0 mL) is added dichlorobis(triphenylphosphine)palladium (16 mg, 0.022 mmol), copper iodide (3 mg, 0.015 mmol), TEA (0.53 mL, 3.8 mmol) and 3-(3-ethynylphenyl)-2-fluoropyridine (150 mg, 0.76 mmol). The reaction mixture is heated at 65° C. for 3 h, cooled and quenched with $H_2O$. The aqueous layer is extracted with EtOAc. The combined organic extracts are washed with brine, dried ($MgSO_4$) and concentrated. The crude material is purified by chromatography (silica gel, EtOAc/hexane: 30/70) to afford the title compound (145 mg, 76%) as an oil. MS (+) ES: 310 (M+H)$^+$.

EXAMPLE 65

Preparation of 2-fluoro-3-(3-{[1-(2,2,2-trifluoroethyl)-1H-pyrazol-4-yl]ethynyl}phenyl)pyridine

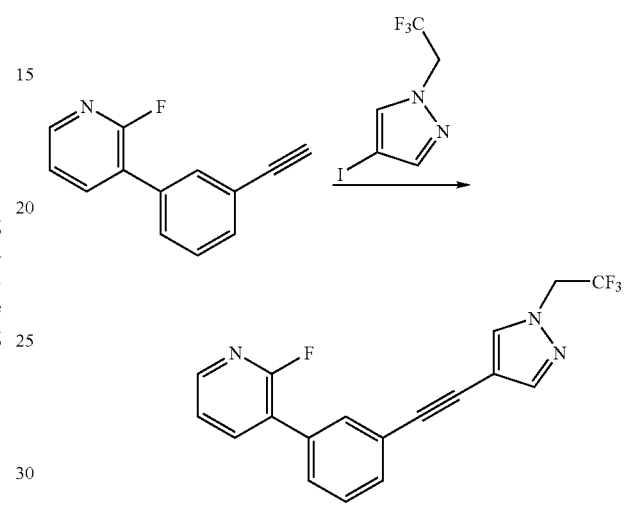

The title compound was prepared using essentially the same procedure described in Example 64 to give the title compound as an oil (59%) MS (+) ES: 346 (M+H)$^+$.

EXAMPLE 66

Preparation of 4-{[3-(cyclopropylmethoxy)phenyl]ethynyl}-1-(2-fluoroethyl)-1H-pyrazole

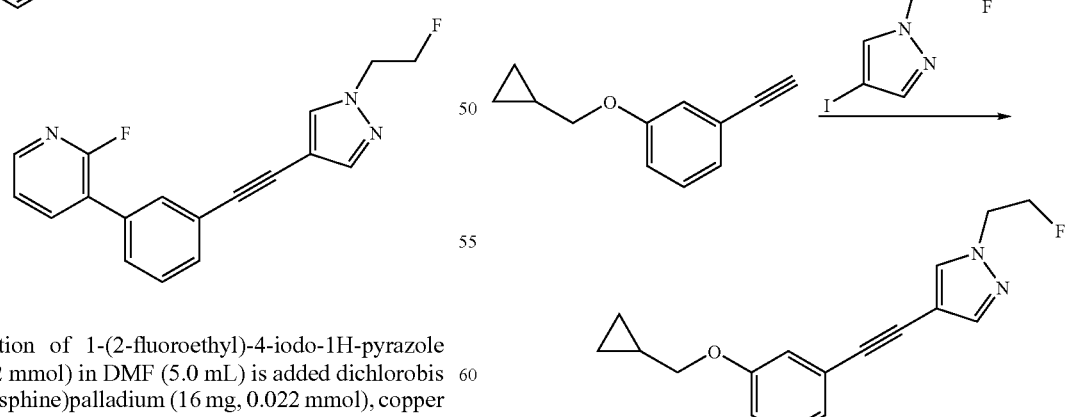

The title compound was prepared using essentially the same procedure described in Example 64 to give the title compound as an oil (72%). MS (+) ES: 285 (M+H)$^+$.

EXAMPLE 67

Preparation of 4-{[3-(cyclopropylmethoxy)phenyl]ethynyl}-1-(2,2,2-trifluoroethyl)-1H-pyrazole

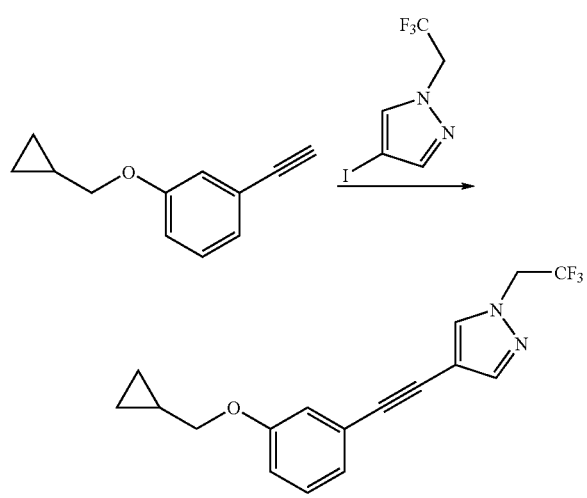

The title compound was prepared using essentially the same procedure described in Example 64 to give the title compound as a solid (81%) mp: 63-65° C.,
MS (+) ES: 346 (M+H)⁺.

EXAMPLE 68

Preparation of 2-amino-5-[1-(2-fluoroethyl)-1H-pyrazol-4-yl]-5-[3-(2-fluoropyridin-3-yl)phenyl]-3-methyl-3,5-dihydro-4H-imidazol-4-one

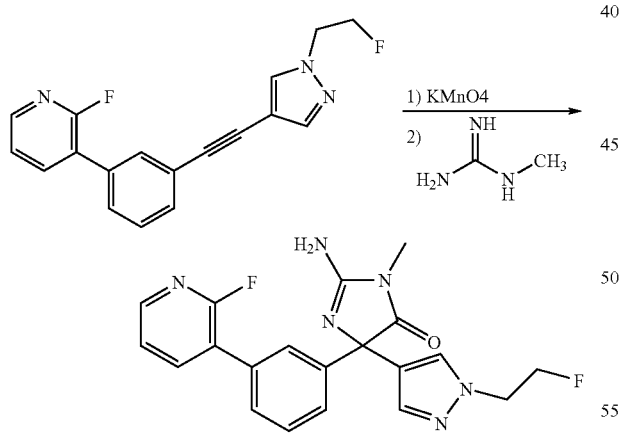

To a solution of 2-fluoro-3-(3-{[1-(2-fluoroethyl)-1H-pyrazol-4-yl]ethynyl}phenyl)pyridine (140 mg, 0.45 mmol) in acetone (7 mL) is added a warm (~40° C.) solution of NaHCO₃ (23 mg, 0.27 mmol) and MgSO₄ (82 mg, 0.68 mmol) in H₂O (7 mL) followed by the addition of solid potassium permanganate (156 mg, 0.99 mmol) in one portion. After stirring at room temperature for 30 minutes, the reaction mixture is extracted with Et₂O/hexane (1/1) until no product left in aqueous layer. The combined organic extracts are dried (MgSO₄) and concentrated to dryness to afford 1-[1-(2-fluoroethyl)-1H-pyrazol-4-yl]-2-[3-(2-fluoropyridin-3-yl)phenyl]ethane-1,2-dione (95 mg, 62%) as an oil. MS (+) ES: 342 (M+H)⁺.

To a solution of 1-[1-(2-fluoroethyl)-1H-pyrazol-4-yl]-2-[3-(2-fluoropyridin-3-yl)phenyl]ethane-1,2-dione (90 mg, 0.26 mmol) in EtOH (5.0 mL) is added N-methylguanidine hydrochloride (31 mg, 0.29 mmol) and a solution of Na₂CO₃ (54 mg, 0.52 mmol) in H₂O (0.5 mL). After refluxing for 2 h, the solvent is removed on a rotary evaporator. The crude mixture is purified by chromatography (silica gel, EtOAc/2.0M methanolic NH₃: 90/10) to give the title compound (74 mg, 72%) as a solid. mp: 195-197° C. MS (−) ES: 395 (M−H)⁻.

EXAMPLE 69

Preparation of 2-amino-5-[3-(2-fluoropyridin-3-yl)phenyl]-3-methyl-5-[1-(2,2,2-trifluoroethyl)-1H-pyrazol-4-yl]-3,5-dihydro-4H-imidazol-4-one

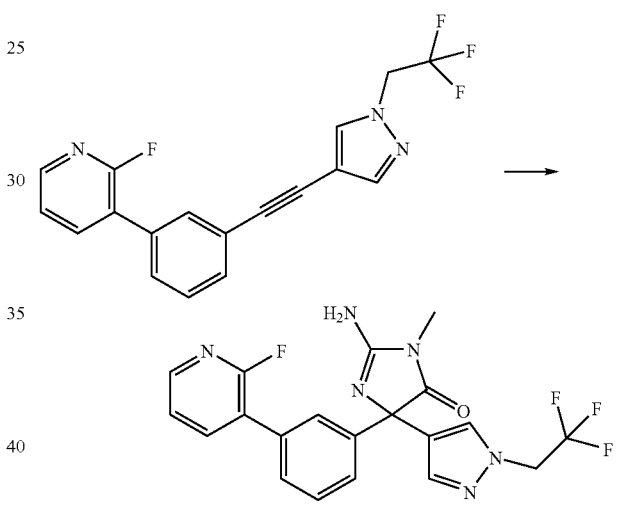

The title compound was prepared using essentially the same procedure described in Example 68 to give the title compound as an oil (77%) mp: 104-106° C., MS (−) ES: 431 (M−H)⁻.

EXAMPLE 70

Preparation of 2-amino-5-[3-(cyclopropylmethoxy)phenyl]-5-[1-(2-fluoroethyl)-1H-pyrazol-4-yl]-3-methyl-3,5-dihydro-4H-imidazol-4-one

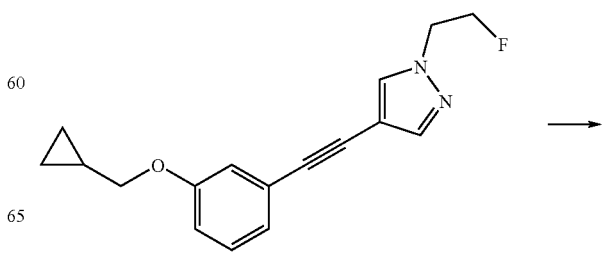

-continued

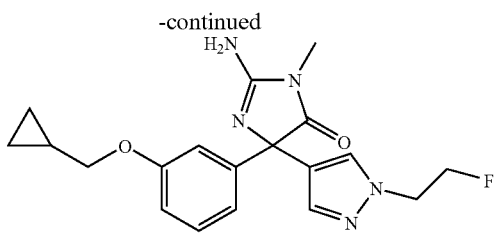

The title compound was prepared using essentially the same procedure described in Example 68 to give the title compound as an oil (78%). mp: 70-72° C.

MS (−) ES: 370 (M−H)⁻.

EXAMPLE 71

Preparation of 2-amino-5-[3-(cyclopropylmethoxy)phenyl]-3-methyl-5-[1-(2,2,2-trifluoroethyl)-1H-pyrazol-4-yl]-3,5-dihydro-4H-imidazol-4-one

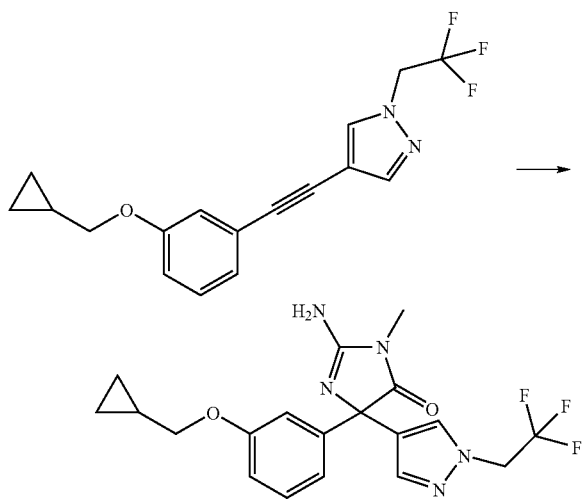

The title compound was prepared using essentially the same procedure described in Example 68 to give the title compound as an oil (73%) mp 78-80° C., MS (+) ES: 408 (M+H)⁺.

EXAMPLE 72

Preparation of 1-(Difluoromethoxy)-4-ethynylbenzene

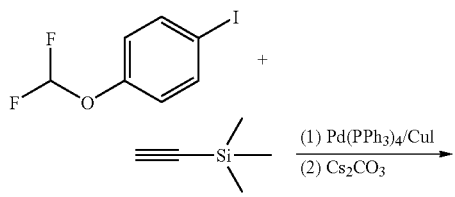

-continued

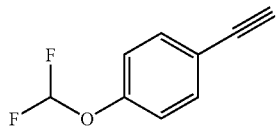

A solution of 1-(difluoromethoxy)-4-iodobenzene (12.7 g, 50 mmol) in triethylamine (175 mL) was treated with tetrakis(triphenylphosphine)palladium (4.0 g, 3.5 mmol), copper iodide (925 mg, 4.85 mmol), and a solution of ethynyl(trimethyl)silane (6.9 mL, 50 mmol) in acetonitrile at room temperature, stirred for 1 h at 60° C. and concentrated in vacuo. The resultant residue was dissolved in Et₂O, filtered and the filtrated was concentrated in vacuo. This residue was purified by chromatography (silica gel, EtOAc/hexane: 5/95) to give {[4-(difluoromethoxy)-phenyl]ethynyl}(trimethyl)silane (11.5 g, 96%) as an oil.

A solution of {[4-(difluoromethoxy)phenyl]ethynyl}(trimethyl)silane (10.0 g, 41.7 mmol) in MeOH/CH₂Cl₂ (1/1) was treated with cesium carbonate (16.3 g, 50 mmol) at room temperature, stirred for 1.5 h, diluted with CH₂Cl₂ and filtered through a pad of silica gel. The filtrate was concentrated to dryness to give the title compound (6.8 g, 97%) as an oil, identified by NMR and mass spectral analyses.

MS (+) EI:168.

EXAMPLES 73-78

Preparation of 2-amino-5-[4-(difluoromethoxy)phenyl]-5-heteroaryl-3-methyl-3,5-dihydro-4H-imidazol-4-one Compounds

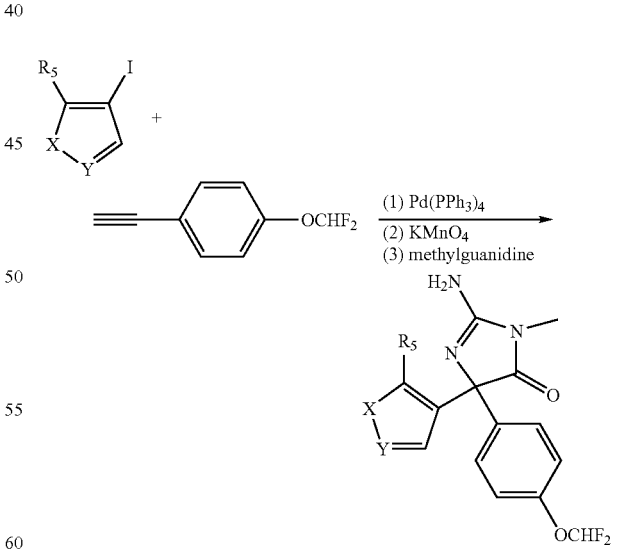

Using essentially the same procedure described in Example 68 and employing 1-(difluoromethoxy)-4-ethynylbenzene and the desired iodoheteroaryl reagent, the compounds shown in Table V were obtained and identified by NMR and mass spectral analyses.

TABLE V

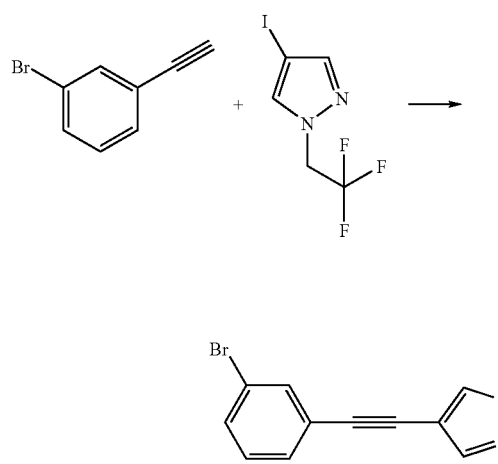

| Ex. No | X | Y | R | R5 | mp °C. | M + H |
|---|---|---|---|---|---|---|
| 73 | NR | N | 2-fluoroethyl | H | 140-142 | 368 |
| 74 | NR | N | 2,2,2-trifluoroethyl | H | 70-72 | 404 |
| 75 | NR | N | benzyl | H | 74-76 | 412 |
| 76 | NR | N | pentyl | H | 138-140 | 392 |
| 77 | NR | CH | H | propionyl | 108-110 | 377 |
| 78 | NR | CH | methyl | propionyl | 171-173 | 389* |

*(M − H)−

EXAMPLE 79

Preparation of 4-[(3-bromophenyl)ethynyl]-1-(2,2,2-trifluoroethyl)-1H-pyrazole

To a solution of 4-iodo-1-(2,2,2-trifluoroethyl)-1H-pyrazole (4.14 g, 15 mmol) in triethylamine (53 mL) is added tetrakis(triphenylphosphine)paddadium (1.20 g, 1.04 mmol), copper iodide (0.28 g, 1.46 mmol) and a solution of 1-bromo-3-ethynylbenzene (2.78 g, 15 mmol) in acetonitrile (15 mL) at room temperature. After heating for 1 hour at 80° C., the reaction mixture is cooled and concentrated. The crude material is purified by chromatography (silica gel, EtOAc/hexane: 5/95) to give the title compound as a solid (4.91 g, 99%). mp: 107-109° C. MS (+) EI: 328 M+.

EXAMPLE 80

Preparation of 1-(3-bromophenyl)-2-[1-(2,2,2-trifluoroethyl)-1H-pyrazol-4-yl]ethane-1,2-dione

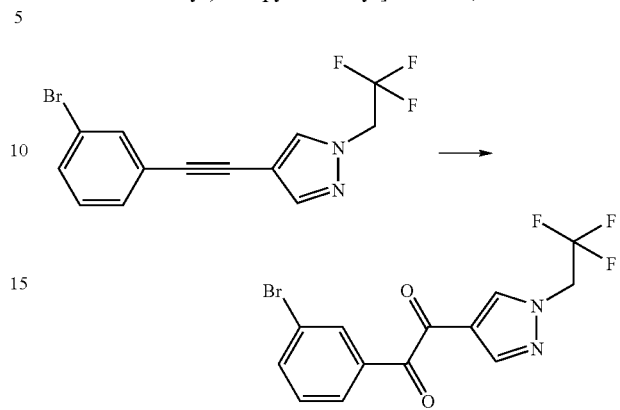

To a solution of 4-[(3-bromophenyl)ethynyl]-1-(2,2,2-trifluoroethyl)-1H-pyrazole (4.90 g, 14.9 mmol) in acetone (150 mL) is added a warm (~40° C.) solution of NaHCO$_3$ (0.75 g, 8.9 mmol) and MgSO$_4$ (2.70 g, 22.4 mmol) in H$_2$O (150 mL) followed by the addition of solid potassium permanganate (5.2 g, 32.8 mmol) in one portion. After stirring for 40 minutes at room temperature, the reaction mixture is extracted with a solution of Et$_2$O/hexane (1/1) until no product left in aqueous layer. The combined organic extracts is dried (MgSO$_4$) and concentrated to dryness to afford the title compound (4.4 g, 82%) as a solid. mp: 66-67° C. MS (−) ES: 359 (M−H)−.

EXAMPLE 81

Preparation of 2-amino-5-(3-bromophenyl)-3-methyl-5-[1-(2,2,2-trifluoroethyl)-1H-pyrazol-4-yl]-3,5-dihydro-4H-imidazol-4-one

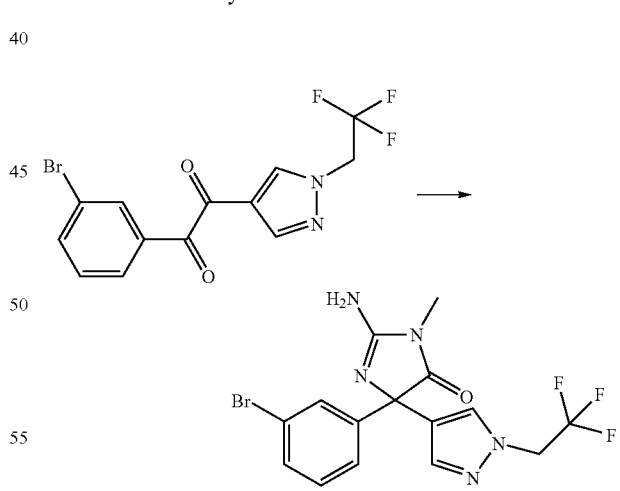

To a solution of 1-(3-bromophenyl)-2-[1-(2,2,2-trifluoroethyl)-1H-pyrazol-4-yl]ethane-1,2-dione (2.4 g, 6.7 mmol) in EtOH (70 mL) is added N-methylguanidine hydrochloride (0.8 g, 7.3 mmol) and a solution of Na$_2$CO$_3$ (1.41 g, 13.3 mmol) in H$_2$O (7 mL). After refluxing for 1 h, the reaction mixture is concentrated. The crude material is purified by chromatography (silica gel, EtOAc/2.0M methanolic NH$_3$: 90/10) to give the title compound (2.2 g, 79%) as a solid. mp: 80-82° C. MS (+) ES: 416 (M+H)+.

EXAMPLES 82-89

Preparation of 2-amino-3-methyl-5-(3-arylphenyl)-5-[1-(2,2,2-trifluoroethyl)-1H-pyrazol-4-yl]-3,5-dihydro-4H-imidazol-4-ones

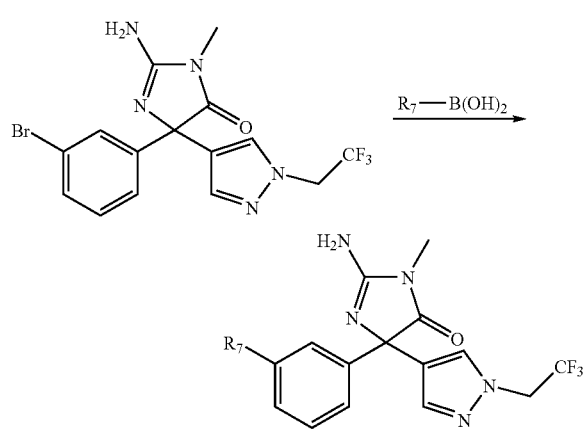

A solution of 2-amino-5-(3-bromophenyl)-3-methyl-5-[1-(2,2,2-trifluoroethyl)-1H-pyrazol-4-yl]-3,5-dihydro-4H-imidazol-4-one (104 mg, 0.25 mmol) in ethylene glycol dimethyl ether was treated with the appropriate boronic acid (0.5 mmol), tetrakis(triphenylphosphine)palladium (29 mg, 0.03 mmol) and 2.0M aqueous sodium carbonate (0.5 mL, 1.0 mmol) at room temperature. The reaction mixture was refluxed for 3 hour and cooled. After evaporation of the solvent, the crude mixture was purified by chromatography (silica gel, EtOAc/2.0M ethanolic $NH_3$: 92/8) to give the compounds shown in Table VI. These compounds were identified by NMR and mass spectral analyses.

TABLE VI

| Ex. No. | R7 | mp (° C.) | (M + H)+ |
|---|---|---|---|
| 82 | 3-methoxyphenyl | 95-97 | 444 |
| 83 | 3-ethoxyphenyl | 88-90 | 458 |
| 84 | 2,5-difluorophenyl | 98-100 | 448* |
| 85 | 5-fluoro-2-methoxyphenyl | 104-106 | 462 |
| 86 | 5-cyano-2-fluorophenyl | 118-120 | 457 |
| 87 | 2,3-difluorophenyl | 103-105 | 450 |
| 88 | pyridin-3-yl | 202-204 | 415 |
| 89 | 3-pyrimidin-5-yl | 223-225 | 416 |

*(M − H)−

EXAMPLE 90

Preparation of 4-(3-benzyloxyphenylethynyl)-1-(2,2,2-trifluoroethyl)-1H-pyrazole

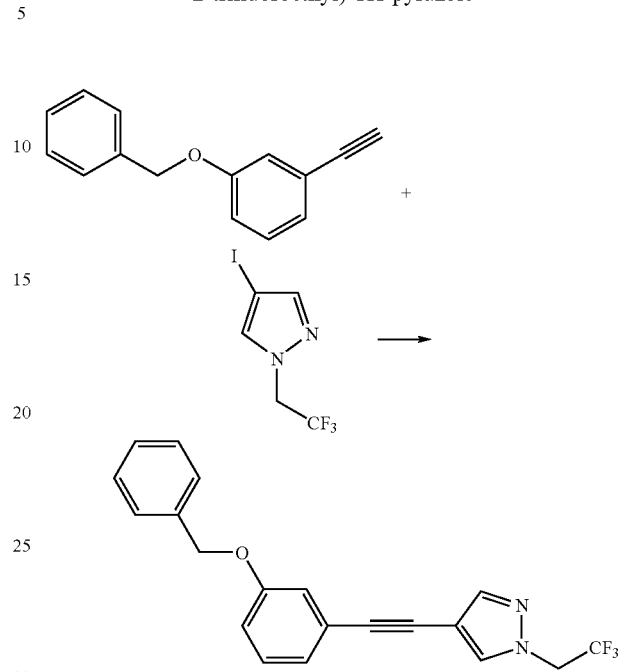

The title compound is prepared using essentially the same procedure described in Example 79 to give the title compound as a yellow solid (70%), mp: 84-86° C. $^1$HNMR ($CDCl_3$): δ (ppm) 4.67 (q, 2H), 5.07 (s, 2H), 6.95 (d, 1H), 7.00-7.50 (m, 8H), 7.70 (d, 2H).

EXAMPLE 91

Preparation of 1-(3-benzyloxyphenyl)-2-[1-2,2,2-trifluoroethyl)-1H-pyrazol-4-yl]ethane-1,2-dione

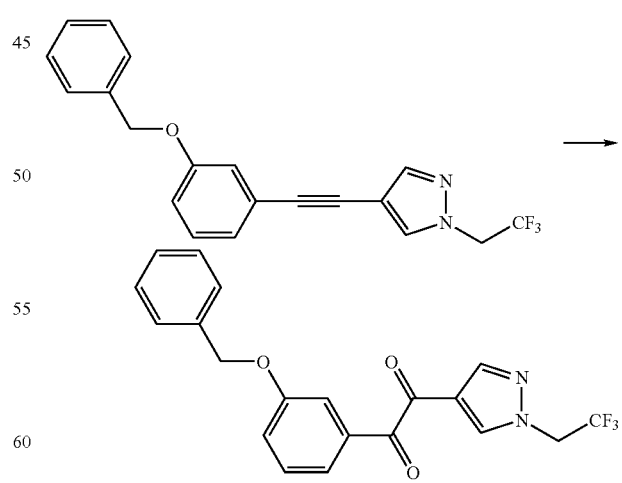

The title compound is prepared using essentially the same procedure described in Example 80 to give the title compound as a a solid (92%). $^1$HNMR ($DMSO-d_6$): δ (ppm) 5.15 (s, 2H), 5.20 (q, 2H), 7.20-7.50 (m, 9H), 8.16 (s, 1H), 8.64 (s, 1H).

EXAMPLE 92

Preparation of 2-amino-5-[3-(benzyloxy)phenyl]-3-methyl-5-[1-(2,2,2-trifluoroethyl)-1H-pyrazol-4-yl]-3,5-dihydro-4H-imidazol-4-one

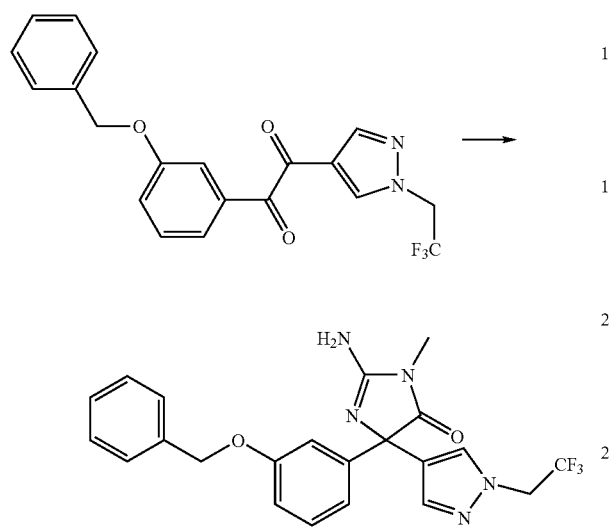

The title compound is prepared using essentially the same procedure described in Example 81 to give the title compound as a a solid (68%) mp: 85-87° C.,
MS (+) ES: 444 (M+H)+.

EXAMPLE 93

Preparation of 2-amino-5-(3-hydroxyphenyl)-3-methyl-5-[1-(2,2,2-trifluoroethyl)-1H-pyrazol-4-yl-3,5-dihydro-4H-imidazol-4-one

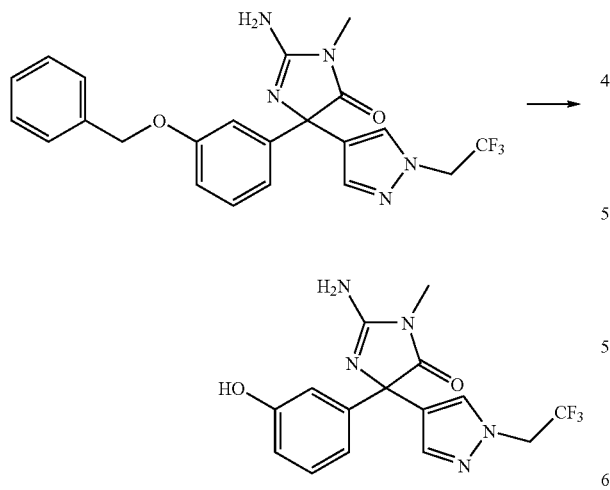

A mixture of 2-amino-5-[3-(benzyloxy)phenyl]-3-methyl-5-[1-(2,2,2-trifluoroethyl)-1H-pyrazol-4-yl]-3,5-dihydro-4H-imidazol-4-one (330 mg, 0.74 mmol) and Pd/C (33 mg) in ethanol (10 ml) is hydrogenated at 45 psi overnight. After removal of the catalyst by filtration, the filtrate is concentrated. The crude material is purified by flash chromatography (silica gel, EtOAc/2.0M ethanolic $NH_3$: 90/10 to 80/20) to afford the title compound as a solid 250 mg (95%). mp: 118-120° C. MS (+) ES: 354 (M+H)+.

EXAMPLE 94

Preparation of 4-(3-bromo-4-fluorophenylethynyl)-1-isopropyl-1H-pyrazole

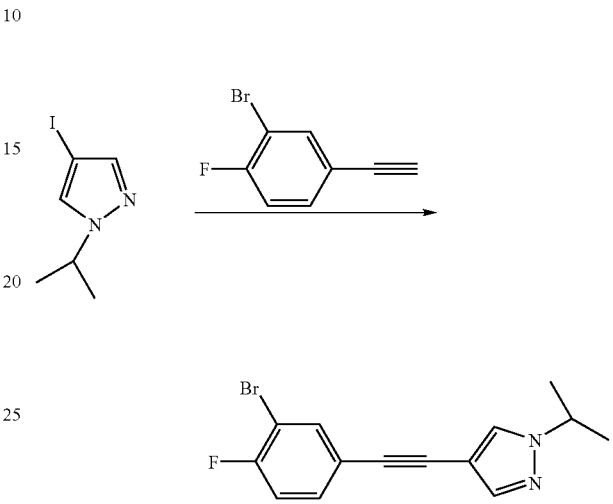

The title compound is prepared using essentially the same procedure described in Example 64 to give the title compound as a solid (55%). $^1$HNMR (DMSO-$d_6$): δ (ppm) 1.36 (d, 6H), 4.46 (m, 1H), 7.38 (t, 1H), 7.48 (m, 1H), 7.65 (s, 1H), 7.77 (d, 1H), 8.11 (s, 1H).

EXAMPLE 95

Preparation of 2-amino-5-(3-bromo-4-fluorophenyl)-5-(1-isopropyl-1H-pyrazol-4-yl)-3-methyl-3,5-dihydro-4H-imidazol-4-one

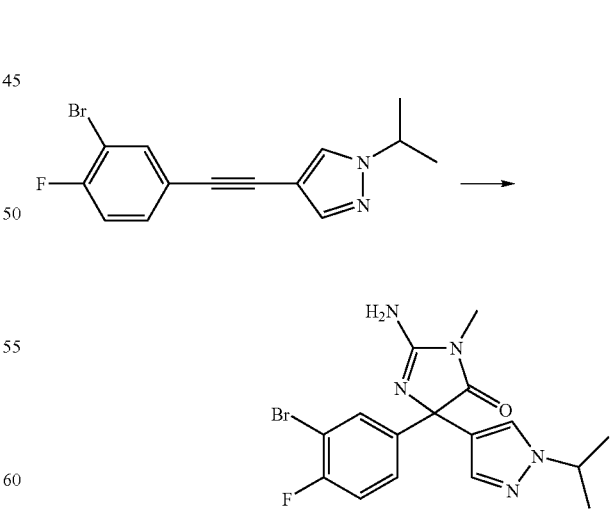

The title compound is prepared using essentially the same procedure described in Example 68 to give the title compound as a solid (80%) mp: 80-82° C.,
MS (+) ES: 395 (M+H)+.

EXAMPLES 96-98

Preparation of 2-amino-5-(4-fluoro-3-substituted-phenyl)-5-(1-isopropyl-1H-Pyrazol-4-yl)-3-methyl-3,5-dihydro-imidazol-4-one Compounds

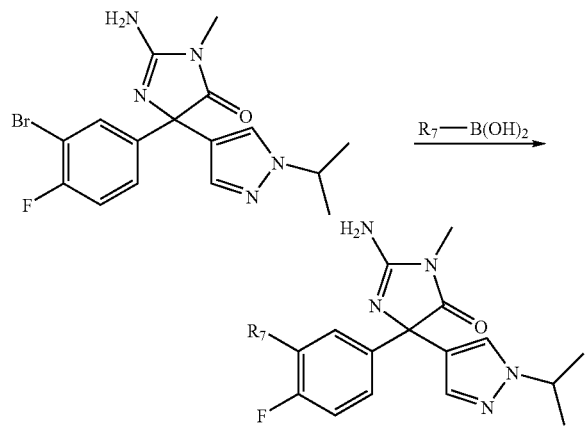

Using essentially the same procedure described in Example 82 and employing the appropriated boronic acid reagent, the compounds shown in Table VII were obtained and identified by NMR and mass spectral analyses.

TABLE VII

| Ex. No. | R7 | mp (° C.) | (M + H)+ |
|---|---|---|---|
| 96 | pyrimidin-5-yl | 110-113 | 394 |
| 97 | 2-fluoropyridin-3-yl | 115-117 | 411 |
| 98 | 3-methoxyphenyl | 112-114 | 422 |

EXAMPLES 99-108

Preparation of 2-amino-5-(3-heteroarylphenyl)-5-(1-substituted-1H-pyrazol-4-yl)-3-methyl-3,5-dihydro-imidazol-4-one Compounds

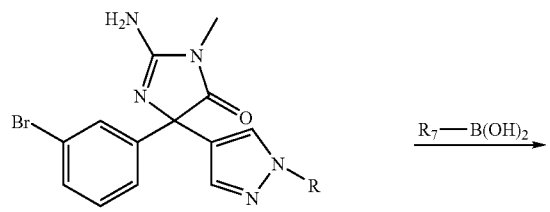

-continued

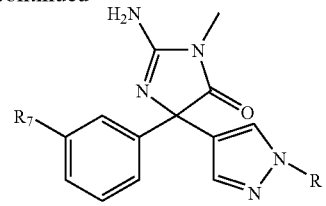

Using essentially the same procedures described in Examples 1 and 62-75 and employing the appropriate 5-pyrazol-4-yl hydantoin substrate and boronic acid reagent, the compounds shown in Table VIII were obtained and identified by NMR and mass spectral analyses.

TABLE VIII

| Ex. No. | R | R7 | mp (° C.) |
|---|---|---|---|
| 99 | 2-ethylbutyl | 2-fluoropyridin-3-yl | 75-80 |
| 100 | cyclopentyl | 2-fluoropyridin-3-yl | 106-109 |
| 101 | 3,3-dimethylbutyl | 2-fluoropyridin-3-yl | 100-103 |
| 102 | 3-methylbutyl | 2-fluoropyridin-3-yl | 86-90 |
| 103 | benzyl | 2-fluoropyridin-3-yl | 94-97 |
| 104 | 2-cyclohexylethyl | 2-fluoropyridin-3-yl | 88-90 |
| 105 | cyclopentyl | pyrimidin-5-yl | 112-115 |
| 106 | 3,3-dimethylbutyl | pyrimidin-5-yl | 93-96 |
| 107 | 2-cyclohexylethyl | pyrimidin-5-yl | 102-105 |
| 108 | 3-methylbutyl | pyrimidin-5-yl | 87-90 |

EXAMPLE 109

Preparation of 2-Amino-5-(5-butylthien-2-yl)-3-methyl-5-phenyl-3,5-dihydro-4H-imidazol-4-one

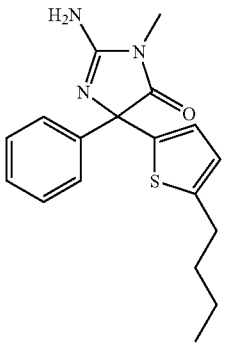

Step a) (5-Butyl-thiophen-2-yl)-oxo-acetic acid ethyl ester

To a 0° C. solution containing 2-butyl-thiophene (5 g, 35.6 mmol) dissolved in benzene (90 mL) and diethyloxalate (5.1 g, 35.6 mmol) was added (dropwise) a solution containing TiCl$_4$ (6.7 g, 35.6 mmol) dissolved in benzene (10 mL). The reaction was let stir at 5° C. for 1 h then poured into water (300 mL) and extracted with ether. The organic layer was separated, washed with brine, then dried over MgSO₄, filtered and stripped. The residue was purified by flash chromatography on silica gel in hexane/ethyl acetate 20:1. A yellow oil (4 g, 46% yield) was recovered. MS m/e 241 (M)⁺; ¹HNMR (400 MHz, DMSO-d₆, 300 MHz) δ 0.9 (t, 3H), 1.4 (m, 5H), 1.6 (m, 2H), 2.9 (t, 2H), 4.4 (t, 2H), 7.1 (s, 1H), 7.9 (s, 1H).

Step b) (5-Butyl-thiophen-2-yl)-oxo-acetic acid

To solution containing (5-butyl-thiophen-2-yl)-oxo-acetic acid ethyl ester (Step a, 1 g, 4.2 mmol) dissolved in ethanol 10 mL) was added K₂CO₃ 2N (10 mL). The reaction was stirred at room temperature 6 h. The ethanol was removed under reduce pressure and the residue taken in water (50 mL) then washed with ether. The aqueous was separated and made acidic with concentrated HCl then extracted with CHCl₃ (2×). The organic layers were separated and combined and dried over MgSO₄, then filtered and stripped. A white solid (0.6 g, 67% yield) was recovered. MS m/e 211 (M)⁻; ¹HNMR (DMSO-d₆ 300 MHz) δ 0.9 (t, 3H), 1.3 (m, 2H), 1.6 (m, 2H), 2.8 (t, 2H), 4.3 (b, 1H), 7.1 (s, 1H), 7.9 (s, 1H).

Step c) 1-(5-Butyl-thiophen-2-yl)-2-phenyl-ethane-1,2-dione

Into a flask containing THF (60 mL) was added copper (II) bromide (5.7 g, 40 mmol) followed by lithium bromide (6.8 g, 80 mmol). The reaction was cooled to 0° C. and a solution of 4-methyl-phenylmagnesium bromide (1N) in ether (48 mmol) was added dropwise. The reaction was stirred 10 min and a solution containing (5-butyl-thiophen-2-yl)-oxo-acetyl chloride was added dropwise over 20 min at 0° C. The reaction was poured into HCl 1N (aqueous) and extracted with ether. The organic layer was separated and washed with NaOH 2.5N (aqueous), then brine and dried over MgSO₄, filtered and stripped. MS m/e 273 (M)⁻; ¹HNMR (DMSO-d₆, 300 MHz) δ 0.9 (t, 3H), 1.3 (m, 2H), 1.6 (m, 2H), 2.8 (t, 2H), 7.0 (s, 1H), 7.6 (t, 2H), 7.7 (s, 1H), 7.8 (m, 1H), 7.9 (d, 2H).

Step d) 2-Amino-5-(5-butylthien-2-yl)-3-methyl-5-phenyl-3,5-dihydro-4H-imidazol-4-one 1-(5-butyl-thiophen-2-yl)-2-phenyl-ethane-1,2-dione was dissolved in a solution containing ethanol (15 mL) and water (3 mL). Into this mixture was added 1-methylguanidine hydrochloride (0.32 g, 3 mmol), and followed by K₂CO₃ (1.2 g, 0.9 mmol). The reaction was set to reflux 3 h, and then cooled to room temperature and the ethanol removed under reduced pressure. The crude product was taken in water (50 mL) and extracted with CHCl₃ (3×). The organic layers were separated and combined, then dried over MgSO₄, filtered and stripped. The crude product was purified by flash chromatography on silica gel in 10% methanol/ethyl acetate. A white solid was obtained. MS m/e 328 (M)⁺; ¹HNMR (DMSO-d₆, 300 MHz) δ 0.9 (m, 3H), 1.2 (m, 2H), 1.5 (m, 1H), 2.6 (t, 2H), 2.95 (s, 3H), 6.5 (s, 1H), 6.6 (b, 2H), 6.8 (s, 1H), 7.2 (m, 3H), 7.5 (m, 2H).

EXAMPLE 110

Preparation of 2-Amino-5-[5-(4-fluorophenyl)thien-2-yl]-5-(4-methoxy-3-methylphenyl)-3-methyl-3,5-dihydro-4H-imidazol-4-one

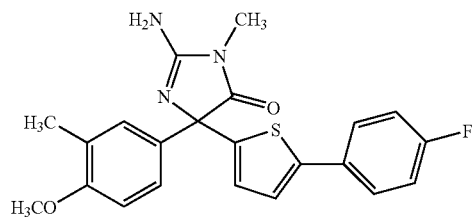

Step a) 1-[5-(4-Fluorophenyl)thien-2-yl]-2-(4-methoxy-3-methylphenyl)ethane-1,2-dione One equivalent of 4-methoxy-3-methyl-benzyl-triphenyl-phosphonium chloride was reacted with 5-(4-fluoro-phenyl)-thiophene-2-carboxylic acid chloride (3 mmol) to give 1-[5-(4-fluorophenyl)thien-2-yl]-2-(4-methoxy-3-methylphenyl) ethane-1,2-dione as a yellow solid (0.26 g, 25% yield, mp 165° C.); MS m/e (M–H)⁻ 354; ¹H NMR (400 MHZ, CDCl₃) δ ppm 2.21(s, 3H), 3.90 (s, 3H), 6.82(d, 1H), 7.10 (t, 2H), 7.25 (d, 1H), 7.61 (m, 2H), 7.70 (d, 1H), 7.85 (m, 1H), 7.91(m, 1H).

Step b) 2-Amino-5-[5-(4-fluorophenyl)thien-2-yl]-5-(4-methoxy-3-methylphenyl)-3-methyl-3,5-dihydro-4H-imidazol-4-one Using substantially the same procedure described in Example 1, step d, and employing 1-[5-(4-fluorophenyl) thien-2-yl]-2-(4-methoxy-3-methylphenyl)ethane-1,2-dione and 1-methylguanidine hydrochloride, the title compound was obtained as a white solid; mp 110° C.; MS m/e (M–H)⁻ 408; ¹H NMR (400 MHZ, DMSO-d₆) δ 2.05 (s, 3H), 2.90 (s, 3H), 3.70 (s, 3H), 6.70 (bs, 2H), 6.80 (d, 1H), 6.90 (d, 1H), 7.19 (m, 2H), 7.21 (m, 1H), 7.22 (m, 1H), 7.30 (m, 1H), 7.58 (m, 2H).

EXAMPLE 111

Preparation of 2-Amino-5-[4-(4-fluorophenyl)thien-2-yl]-5-(4-methoxy-3-methylphenyl)-3-methyl-3,5-dihydro-4H-imidazol-4-one

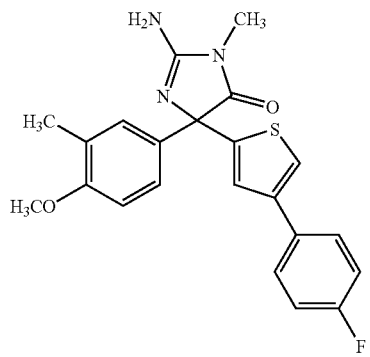

Step a) 4-(4-Fluorophenyl)thiophene-2-benzoyl chloride 4-(4-Fluorophenyl)thiophene-2-carboxcylic acid (1 g, 4.5 mmol) was dissolved in 10 mL of CH₂Cl₂ with 1 drop DMF, to this was then added oxalyl chloride (1.1 g, 9.0 mmol). The reaction was stirred at room temperature for 16 h then stripped of solvent under reduced pressure. The product was carried to the next step without any further purification.

Step b) 1-[4-(4-Fluorophenyl)thien-2-yl]-2-(4-methoxy-3-methylphenyl)ethane-1,2-dione Using substantially the same procedure described in Exmple 93, step a, and employing 4-(4-fluorophenyl)thiophene-2-benzoyl chloride and 3-methyl, 4-methoxy-benzyl triphenylphosphonium chloride, 1-[4-(4-fluorophenyl)thien-2-yl]-2-(4-methoxy-3-methylphenyl)ethane-1,2-dione was obtained as a yellow solid, $^1$H NMR (DMSOd$_6$ 300 MHz) δ 2.2 (s, 3H), 3.9 (s, 3H), 7.15 (dd, 1H), 7.22 (t, 2H), 7.8 (m, 4H), 8.2 (s, 1H), 7.79 (s, 1H).

Step c) 2-Amino-5-[4-(4-fluorophenyl)thien-2-yl]-5-(4-methoxy-3-methylphenyl)-3-methyl-3,5-dihydro-4H-imidazol-4-one Using essentially the same procedure described in Example 93, step b, and employing 1-[4-(4-fluorophenyl)thien-2-yl]-2-(4-methoxy-3-methylphenyl)ethane-1,2-dione and methylguanidine, the title product was obtained as a tan solid, MS m/e (M)⁻ 408; $^1$H NMR (DMSOd$_6$ 300 MHz) δ 2.1 (s, 3H), 2.98 (s, 3H), 3.7 (s, 3H), 6.8 (b, 2H), 6.6 (dd, 1H), 7.2 (t, 2H), 7.3 (m, 3H), 7.6 (m, 3H).

EXAMPLE 112

Preparation of 2-Amino-5-(3bromophenyl)-5-[5-(2-ethyl-[1,3]dioxolan-2-yl)-thiophen-3-yl]-3-methyl-3,5-dihydro-imidazol-4-one

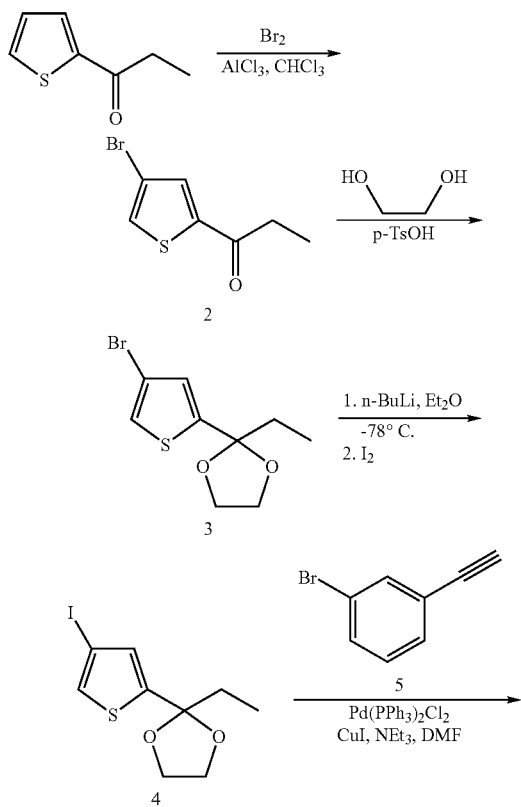

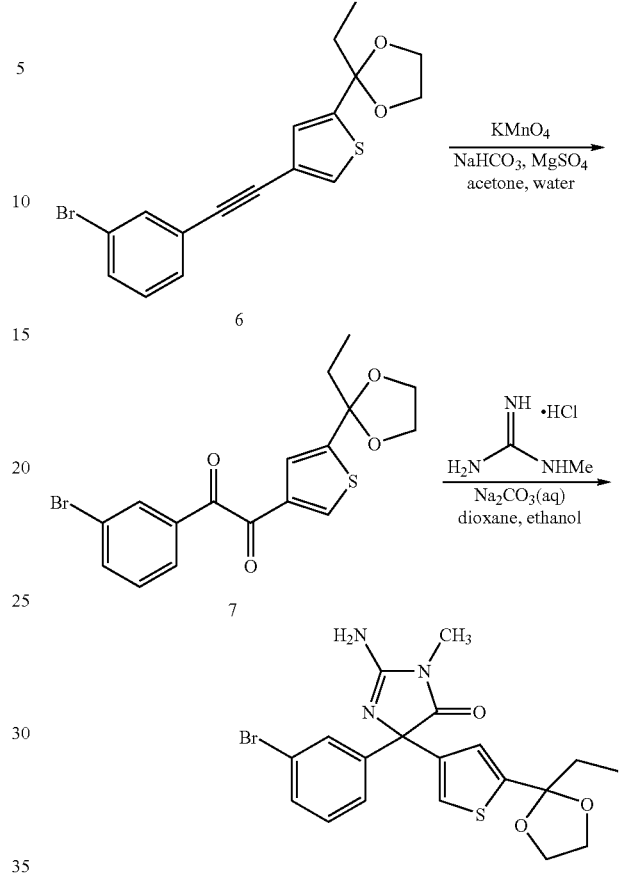

Step a) A stirred suspension of aluminum trichloride (6.27 g, 47.1 mmol) in chloroform at room temperature was treated sequentially with 2-(1-propionyl)thiophene (3.00 g, 21.4 mmol) and bromine (3.60 g, 22.4 mmol), stirred for 17 h, poured into iced water and diluted with methylene chloride. The phases were separated and the aqueous phase was extracted with methylene chloride. The extracts and the organic phase were combined, washed with water and brine, dried over sodium sulfate and concentrated to afford 2 (5.51 g, 117%) as a dark orange oil:
$^1$H NMR (300 MHz, CDCl$_3$) δ 7.59 (d, J=1.1 Hz, 1H), 7.51 (d, J=1.1 Hz, 1H), 2.91 (q, J=7.3 Hz, 2H), 1.23 (t, J=7.3 Hz, 3H); ESI MS m/z 219 [C$_7$H$_7$BrOS+H]⁺.

Step b) A mixture of 2 (5.51 g, ca. 85% purity, 21.4 mmol), ethylene glycol (2.02 g, 32.6 mmol) and p-toluene sulfonic acid (0.40 g, 2.14 mmol) in benzene was heated under Dean-Stark conditions for 22 h. The reaction was then cooled to room temperature and the solvents evaporated. Purification of the resultant concentrate by flash chromatography (silica, 90:10 hexanes/ethyl acetate) afforded 3 (4.96 g, 88%) as an orange liquid: $^1$H NMR (300 MHz, CDCl$_3$) δ 7.13 (d, J=1.4 Hz, 1H), 6.92 (d, J=1.4 Hz, 1H), 4.06-3.92 (m, 4H), 1.99 (q, J=7.4 Hz, 2H), 0.94 (t, J=7.4 Hz, 3H).

Step c) A solution of 3 (2.00 g, 7.60 mmol) in ether at −78° C. was treated dropwise with n-BuLi (4.20 mL of a 1.98 M solution in hexanes, 8.30 mmol), stirred for 30 min, treated dropwise with a solution of iodine (2.10 g, 8.3 mmol) in ether, stirred at −60° C. for a further 30 min, treated with saturated ammonium chloride solution and diluted with ethyl acetate. The phases were separated. The organic phase was washed sequentially with 10% aqueous sodium thiosulfate, water and brine, dried over sodium sulfate and concentrated. Purification of the resultant concentrate by flash chromatography (silica, 90:10 hexanes/ethyl acetate) afforded 4 (1.62 g, 68%) as an orange oil which was a 3:1 mixture of product to starting material: $^1$H NMR (500 MHz, CDCl$_3$) δ 7.29 (d, J=1.4 Hz, 1H), 6.99 (d, J=1.4 Hz, 1H), 4.04-3.94 (m, 4H), 1.99 (q, J=7.4 Hz, 2H), 0.93 (t, J=7.4 Hz, 3H).

Step d) A mixture of 4 (1.62 g, 5.20 mmol), 3-bromophenylethyne (1.04 g, 5.70 mmol), dichloro(bistriphenylphosphine)palladium(II) (0.11 g, 0.15 mmol), copper(I) iodide (0.02 g, 0.10 mmol) and triethylamine (2.63 g, 26.0 mmol) in dimethylformamide was stirred at room temperature for 30 min and diluted with water and ethyl acetate. The phases were separated. The organic phase was washed with brine, dried over sodium sulfate and concentrated. Purification of the resultant concentrate by flash chromatography (silica, 95:5 to 90:10 hexanes/ethyl acetate) afforded 6 (1.07 g, 57%) as a colorless liquid: $^1$H NMR (500 MHz, CDCl$_3$) δ 7.64 (t, J=1.7 Hz, 1H), 7.47-7.44 (m, 1H), 7.42 (d, J=1.3 Hz, 1H), 7.42-7.40 (m, 1H), 7.20 (t, J=7.9 Hz, 1H), 7.09 (d, J=1.3 Hz, 1H), 4.04-3.95 (m, 4H), 2.02 (q, J=7.5 Hz, 2H), 0.95 (t, J=7.5 Hz, 3H); ESI MS m/z 363 [C$_{17}$H$_{15}$BrO$_2$S+H]$^+$.

Step e) A stirred solution of 6 (1.05 g, 2.89 mmol) in acetone was treated with a solution of sodium bicarbonate (0.145 g, 1.73 mmol) and magnesium sulfate (0.690 g, 5.78 mmol) in water, followed by potassium permanganate (1.14 g, 7.20 mmol) in one portion. The reaction mixture was stirred for 1 h, treated with a further portion of potassium permanganate (0.45 g, 2.84 mmol), stirred for an additional 2.25 h, diluted with 1:1 hexanes/ethyl acetate and water) and filtered. The filtrate was separated and the aqueous layer was extracted with ethyl acetate. The extracts were combined with the filtrate organic layer, washed with brine, dried over sodium sulfate and concentrated. Purification of the resultant concentrate by flash chromatography (silica, 90:10 to 80:20 hexanes/ethyl acetate) afforded 7 (0.63 g, 55%) as a yellow oil:

$^1$H NMR (300 MHz, CDCl$_3$) δ 8.15 (t, J=1.7 Hz, 1H), 8.12 (d, J=1.4 Hz, 1H), 7.96-7.92 (m, 1H), 7.82-7.76 (m, 1H), 7.55 (d, J=1.4 Hz, 1H), 7.39 (t, J=7.9 Hz, 1H), 4.07-3.96 (m, 4H), 2.03 (q, J=7.5 Hz, 2H), 0.96 (t, J=7.5 Hz, 3H); ESI MS m/z 395 [C$_{17}$H$_{15}$BrO$_4$S+H]$^+$.

Step f) A mixture of 7 (0.63 g, 1.59 mmol) and 1-methylguanidine hydrochloride (0.78 g, 7.15 mmol) in dioxane and ethanol was stirred at room temperature for 5 min, treated with a solution of sodium carbonate (0.75 g, 7.15 mmol) in water, stirred and heated at 80° C. for 1 h, cooled to room temperature and concentrated in vacuo. The resultant residue was partitioned between methylene chloride and water. The organic layer was separated and washed with water and brine, dried over sodium sulfate and concentrated. Purification of the resultant concentrate by flash chromatography (silica, 95:5:0.5 methylene chloride/methanol/concentrated ammonium hydroxide) afforded a viscous oil, which was coevaporated from methylene chloride and hexanes to afford the title compound (0.55 g, 77%) as a white solid: $^1$H NMR (300 MHz, CDCl$_3$) δ 7.70 (br s, 1H), 7.50-7.39 (m, 2H), 7.25-7.14 (m, 2H), 6.95 (br s, 1H), 4.03-3.90 (m, 4H), 3.10 (s, 3H), 1.99 (q, J=7.5 Hz, 2H), 0.90 (t, J=7.5 Hz, 3H); ESI MS m/z 450 [C$_{19}$H$_{20}$BrN$_3$O$_3$S+H]$^+$.

EXAMPLES 113 and 114

Preparation of 2-Amino-5-[5-(2-ethyl-[1,3]dioxolan-2-yl)-thiophen-3-yl]-5-(3-heteroarylphenyl)-3-methyl-3,5-dihydro-imidazol-4-one Compounds

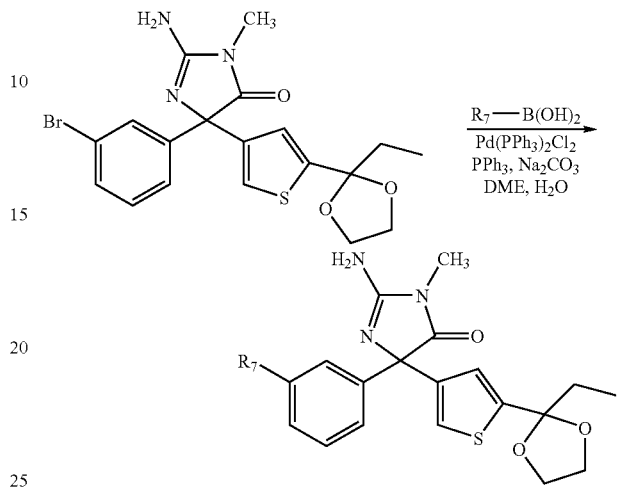

Using essentially the same procedure described in Example 75 and employing the appropriate heteroaryl boronic acid the compounds shown in Table IX are obtained and identified by NMR and mass spectral analyses.

TABLE IX

| Ex. No. | R7 | mp (° C.) |
|---|---|---|
| 113 | 2-fluoropyridin-3-yl | 93-103 |
| 114 | pyrimidin-5-yl | 105-112 |

EXAMPLE 115

Preparation of 2-Amino-5-[3-(2-fluoro-pyridin-3-yl)-phenyl]-3-methyl-5-(5-propionyl-thiophen-3-yl)-3,5-dihydro-imidazol-4-one

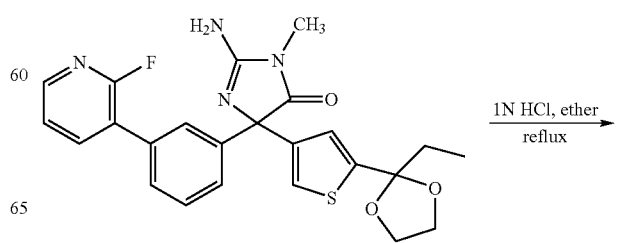

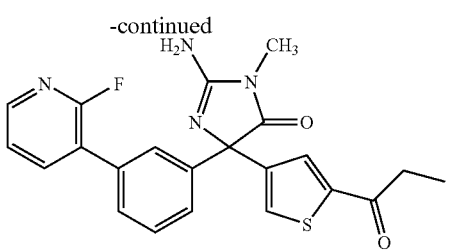

A mixture of 2-amino-5-[5-(2-ethyl-[1,3]dioxolan-2-yl)-thiophen-3-yl]-5-[3-(2-fluoro-pyridin-3-yl)-phenyl]-3-methyl-3,5-dihydro-imidazol-4-one (0.11 g, 0.23 mmol) in diethyl ether and 1 N HCl was heated at reflux temperature for 1 h, cooled to room temperature, diluted with methylene chloride and basified to pH 9 using 2 N sodium hydroxide. The phases were separated. The organic phase was washed with brine, dried over sodium sulfate and concentrated in vacuo. The resultant concentrate was freeze dried from 1:1 acetonitrile/water (4 mL) to afford the title compound as a white solid, 0.069 g (71% yield), mp 98-112° C.; $^1$H NMR (500 MHz, CDCl$_3$) δ 8.19 (dt, J=4.7, 1.4 Hz, 1H), 7.85-7.81 (m, 1H), 7.78-7.69 (m, 3H), 7.61-7.55 (m, 1H), 7.52-7.48 (m, 1H), 7.43 (t, J=7.7 Hz, 1H), 7.29-7.23 (m, 1H), 3.12 (s, 3H), 2.88 (q, J=7.3 Hz, 2H), 1.17 (t, J=7.3 Hz, 3H); ESI MS m/z 423 [C$_{22}$H$_{19}$FN$_4$O$_2$S+H].

EXAMPLE 116

Preparation of 2-Amino-3-methyl-5-(5-propionyl-thiophen-3-yl)-5-(3-pyrimidin-5-yl-phenyl)-3,5-dihydro-imidazol-4-one

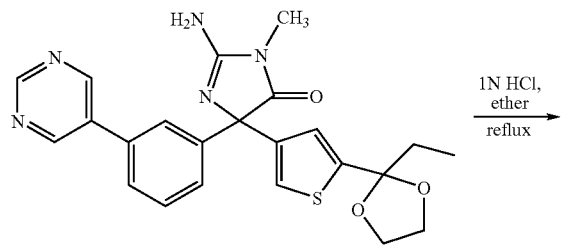

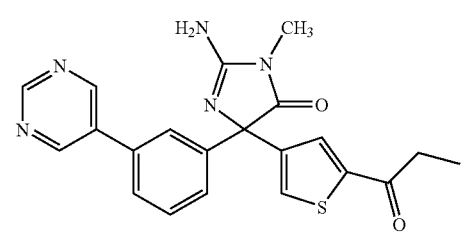

Using essentially the same procedure described in Example 115 and employing 2-amino-5-[5-(2-ethyl-[1,3]dioxolan-2-yl)-thiophen-3-yl]-3-methyl-5-(3-pyrimidin-5-yl-phenyl)-3,5-dihydro-imidazol-4-one as starting material, the title product was obtained as a white solid, mp 167-172° C.; $^1$H NMR (500 MHz, CDCl$_3$) δ 9.19 (s, 1H), 8.92 (s, 2H), 7.76-7.72 (m, 3H), 7.66-7.63 (m, 1H), 7.51-7.48 (m, 2H), 3.15 (s, 3H), 2.87 (q, J=7.3 Hz, 2H), 1.17 (t, J=7.3 Hz, 3H); ESI MS m/z 406 [C$_{21}$H$_{19}$N$_5$O$_2$S+H]$^+$;

EXAMPLE 117

Preparation of 2-Amino-3-methyl-5-phenyl-5-(5-propionyl-3-thienyl)-3,5-dihydro-4H-imidazol-4-one

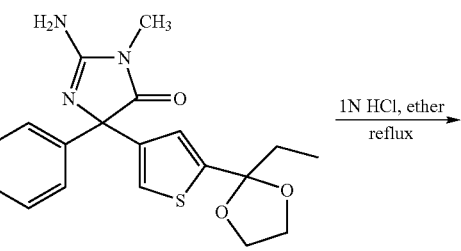

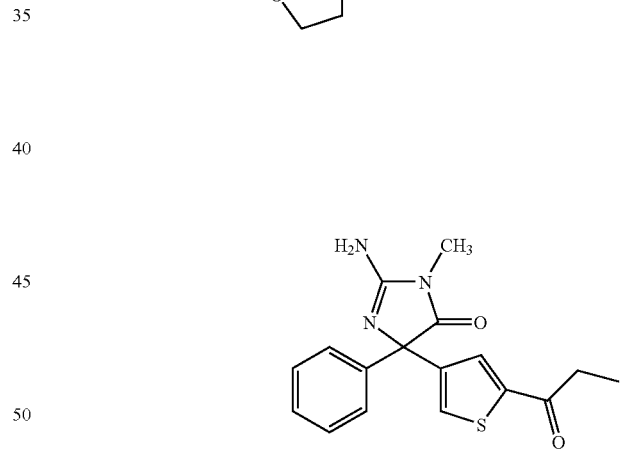

Using essentially the same procedure described in Example 115 and employing 2-amino-5-[5-(2-ethyl-[1,3]dioxolan-2-yl)-thiophen-3-yl]-3-methyl-5-phenyl-3,5-dihydro-imidazol-4-one as starting material, the title product was obtained; $^1$H NMR (DMSOd$_6$ 300 MHz) □ 0.98 (s, 3H), 2.76 (q, 2H), 3.9 (s, 3H), 4.5 (s, 2H), 4.6 (m, 2H), 6.65 (brs, 2H), 7.2 (m, 1H), 7.25 (t, 1H), 7.4 (d, 1H), 7.7 (d, 1H); MS m/e (M+H)$^+$ 328

EXAMPLE 118
Preparation of Methyl 4-[2-Amino-4-(4-fluoro-3-pyrimidinyl-5-phenyl)-1-methyl-5-oxo-4,5-dihydro-1H-imidazol-4-yl]-1-(2-fluoroethyl)-1H-pyrrole-2-carboxylate
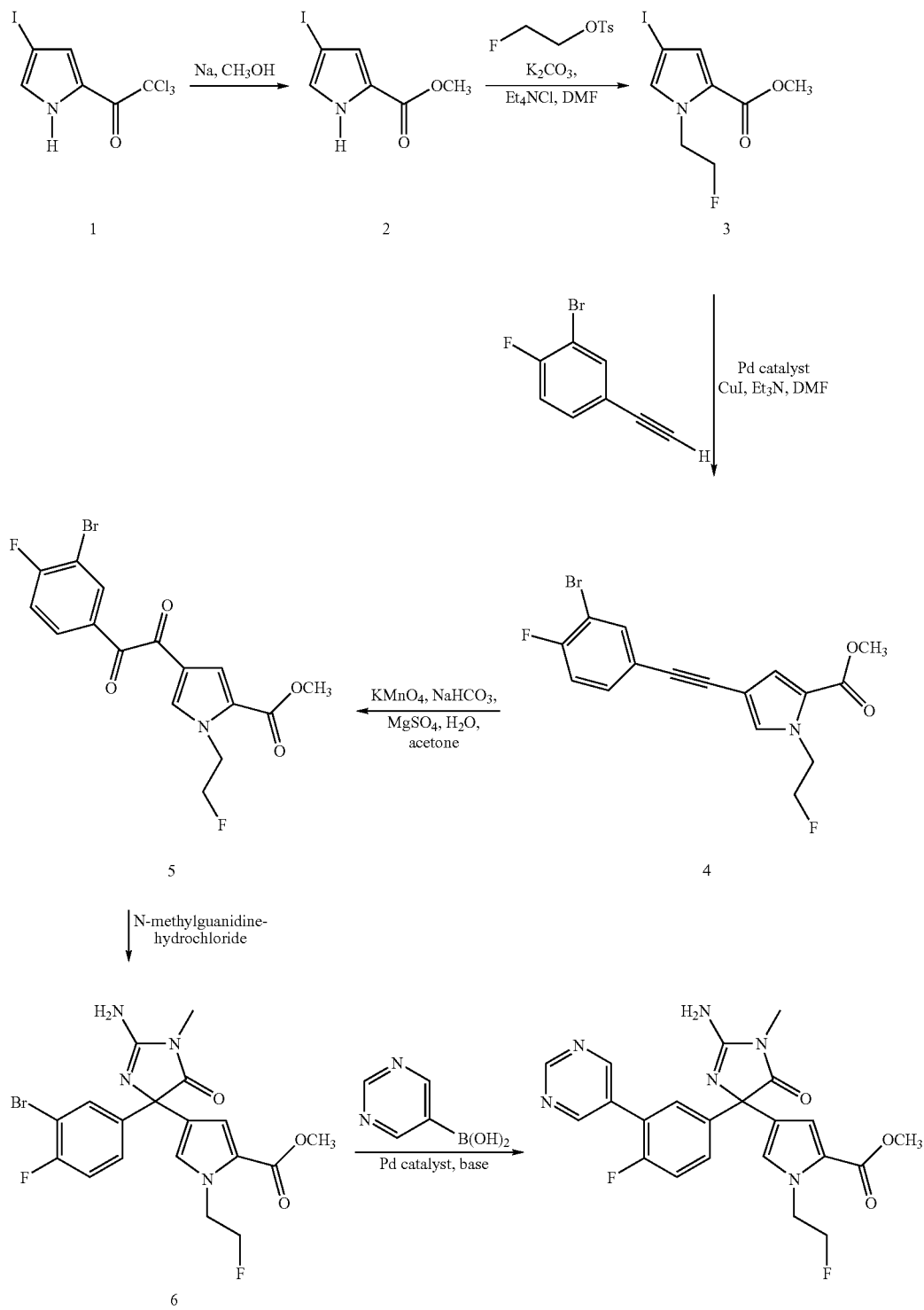

Step a) 4-Iodo-1H-pyrrole-2-carboxylic acid methyl ester

To a solution of 300 mL of dry methanol was added 0.52 gm (0.023 mol) of sodium and the solution was stirred until all sodium was reacted. The solution was cooled to 0° C. and 19.5 gm (0.057 mol) of 2,2,2-trichloro-1-(4-iodo-1H-pyrrol-2-yl)-ethanone was added as a solid over a 15 min period. After 15 min at 0° C. the solution was warmed to room temperature and stirred for an additional 2 h. The solvents were removed at reduced pressure and the residue dissolved in diethyl ether. The ether layer was washed with $H_2O$, saturated brine, dried ($Na_2SO_4$) and the solvents removed at reduced pressure. The solid was recystallized from hot hexanes-trace EtOAc to yield 13.7 gm (95% yield) of a light brown solid. This was used without further purification.

Step b) 1-(2-Fluoro-ethyl)-4-iodo-1H-pyrrole-2-carboxylic acid methyl ester

To a solution of 2.87 gm (0.013 mol) of toluene-4-sulfonic acid 2-fluoro-ethyl ester in 50 mL of DMF was added 1.81 gm (0.013 mol) of potassium carbonate, 0.2 gm (1.2 mmol) of tetraethylammonium chloride and 3.0 gm (0.012 mol) of 4-iodo-1H-pyrrole-2-carboxylic acid methyl ester. The reaction mixture was heated to 70° C. for 18 h. The reaction mixture was cooled and added to 350 mL of EtOAc. The organic layer was washed 3 times (100 mL) with $H_2O$, once with saturated brine, dried ($Na_2SO_4$) and the solvents removed at reduced pressure. Chromatography on silica gel using a gradient of hexanes to 2%-3% EtOAc-hexanes yielded 3.2 gm (90% yield) of a white solid (m.p. 49-50.5° C.). $^1H$ NMR (400 MHz, $CDCl_3$) δ: 3.80 (s, 3H), 4.58 (m, 2H), 4.63 (m, 1H), 4.76 (m, 1H,), 6.93 (s, 1H), 7.06 (s, 1H).

Step c) 4-(3-Bromo-4-fluoro-phenylethynyl)-1-(2-fluoro-ethyl)-1H-pyrrole-2-carboxylic acid methyl ester To a solution of 0.88 gm (4.44 mmol) of 2-bromo-4-ethynyl-1-fluoro-benzene, 0.129 gm (0.185 mmol) bis-triphenylphosphine-palladium dichloride, 0.021 gm (0.11 mmol), 2.8 mL (0.02 mol) of triethylamine in 25 mL of DMF was added 1.10 gm (3.70 mmol) of 1-(2-fluoro-ethyl)-4-iodo-1H-pyrrole-2-carboxylic acid methyl ester. The mixture was allowed to stir at room temperature for 2 h. The mixture was added to 300 mL of EtOAc and washed twice with $H_2O$ (100 mL), once with saturated brine, dried ($Na_2SO_4$) and the solvents removed at reduced pressure. Chromatography on silica gel using a gradient of 2%-4% EtOAc-hexanes yielded 0.96 gm (71% yield) of a yellow oil. $^1H$ NMR (400 MHz, $CDCl_3$) δ: 3.82 (s, 3H), 4.61 (m, 2H), 4.66 (m, 1H), 4.75 (m, 1H,), 7.06 (s, 1H), 7.09 (d, 1H, J=1.74 Hz), 7.14 (s, 1H), 7.37 (m, 1H), 7.67 (dd, 1H, J=1.97, 6.61 Hz).

Step d) 4-[2-(3-Bromo-4-fluoro-phenyl)-2-oxo-acetyl]-1-(2-fluoro-ethyl)-1H-Pyrrole-2-carboxylic acid methyl ester To a solution of 0.95 gm (2.6 mmol) of 4-(3-bromo-4-fluoro-phenylethynyl)-1-(2-fluoro-ethyl)-1H-pyrrole-2-carboxylic acid methyl ester in 20 mL of acetone was added 0.46 (3.85 mmol) $MgSO_4$. While stirring at room temperature 0.13 gm (1.54 mmol) of $NaHCO_3$ in 12 mL of distilled $H_2O$ was added and then 0.89 gm (5.65 mmol) of $KMnO_4$ was added as a solid over a 5 minute period. The mixture was allowed to stir at room temperature for 3 h. 150 mL of 1:1 EtOAc-hexanes was added and the mixture was filtered through celite. The organic layer was diluted with 200 mL of EtOAc and washed twice with $H_2O$ (100 mL), saturated brine then dried ($Na_2SO_4$) and the solvents were removed at reduced pressure. This was used without further purification. $^1H$ NMR (400 MHz, $CDCl_3$) δ: 3.82 (s, 3H), 4.63 (s, 2H), 4.69 (m, 1H), 4.75 (m, 1H,), 7.06 (s, 1H), 7.20 (d, 1H, J=8.4 Hz), 7.22 (d, 1H, J=1.8 Hz), 8.0 (m, 1H), 8.28 (dd, 1H, J=2.1, 6.72 Hz).

Step e) 4-[2-Amino-4-(3-bromo-4-fluoro-phenyl)-1-methyl-5-oxo-4,5-dihydro-1H-imidazol-4-yl]-1-(2-fluoro-ethyl)-1H-pyrrole-2-carboxylic acid methyl ester To a solution of 0.742 gm (1.85 mmol) of 4-[2-(3-bromo-4-fluoro-phenyl)-2-oxo-acetyl]-1-(2-fluoro-ethyl)-1H-pyrrole-2-carboxylic acid methyl ester in 18 mL of MeOH and 21 mL of dioxane in a pressure tube was added 0.40 gm (3.7 mmol) of N-methylguanidine hydrochloride. After stirring at room temperature for 15 min, 0.41 gm (3.9 mmol) of $Na_2CO_3$ in 5.2 mL of $H_2O$ was added and the reaction mixture was sealed and heated to 85° C. for 4 h. The mixture was cooled and the solvents removed at reduced pressure. The residue was taken up in $CH_2Cl_2$ (200 mL) and washed with $H_2O$ (100 mL), saturated brine, dried ($Na_2SO_4$) and the solvent removed at reduced pressure. Chromatography on silica gel using a gradient of EtOAc to 3% MeOH-EtOAc yielded 0.64 gm (76% yield) of a white foam. $^1H$ NMR (400 MHz, $CDCl_3$) δ: 3.08 (s, 3H), 3.76 (s, 3H), 4.52 (m, 1H), 4.59 (m, 2H,), 4.71 (m, 1H), 6.92 (s, 1H), 6.94 (s, 1H), 7.04 (t, 1H, J=8.47 Hz), 7.50 (m, 1H), 8.28 (dd, 1H, J=2.2, 4.41 Hz).

Step f) 4-[2-Amino-4-(4-fluoro-3-pyrimidin-5-yl-phenyl)-1-methyl-5-oxo-4,5-dihydro-1H-imidazol-4-yl]-1-(2-fluoro-ethyl)-1H-pyrrole-2-carboxylic acid methyl ester In a pressure tube was put 2 mL of MeOH and 2 mL of toluene. The solution was degassed with argon and 7.5 mg (0.008 mmol) of $Pd_2(dba)_3$ and 8.6 mg of triphenylphosphine was added under an argon atmosphere. After 15 min stirring at room temperature, 47.0 mg (0.38 mmol) of 5-pyrimidyl-boronic acid, 83 mg (0.78 mmol) of $Na_2CO_3$, and 125 mg (0.27 mmol) of 4-[2-Amino-4-(3-bromo-4-fluoro-phenyl)-1-methyl-5-oxo-4,5-dihydro-1H-imidazol-4-yl]-1-(2-fluoro-ethyl)-1H-pyrrole-2-carboxylic acid methyl ester was added and the reaction sealed heated to 110° C. for 18 h. The reaction mixture was cooled, diluted with 100 mL of $CHCl_3$, filtered through celite and the solvent removed at reduced pressure. Chromatography on silica gel using a gradient of EtOAc to 2%-8% MeOH-EtOAc yielded 0.08 gm (64% yield) of a white solid (mp 88-90° C.). $^1H$ NMR (500 MHz, $CDCl_3$) δ: 3.15 (s, 3H), 3.73 (s, 3H), 4.50 (m, 1H), 4.58 (m, 2H), 4.68 (m, 1H), 6.96 (s, 2H), 7.16 (t, 1H, J=8.66 Hz), 7.65 (m, 2H), 8.88 (m, 2H), 9.15 (s, 1H). MS (ESI) m/z 455.1 ([M+H])$^+$; MS (ESI) m/z 453.1 ([M−H])$^−$.

EXAMPLE 119

Preparation of Methyl 4-[(4S)-2-Amino-4-(4-fluoro-3-pyrimidinyl-5-phenyl)-1-methyl-5-oxo-4,5-dihydro-1H-imidazol-4-yl]-1-(2-fluoroethyl)-1H-pyrrole-2-carboxylate (A) and of Methyl 4-[(4R)-2-Amino-4-(4-fluoro-3-pyrimidinyl-5-phenyl)-1-methyl-5-oxo-4,5-dihydro-1H-imidazol-4-yl]-1-(2-fluoroethyl)-1H-Pyrrole-2-carboxylate (B)

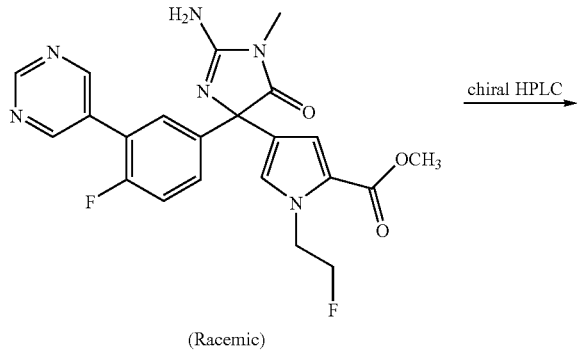

(Racemic)

-continued

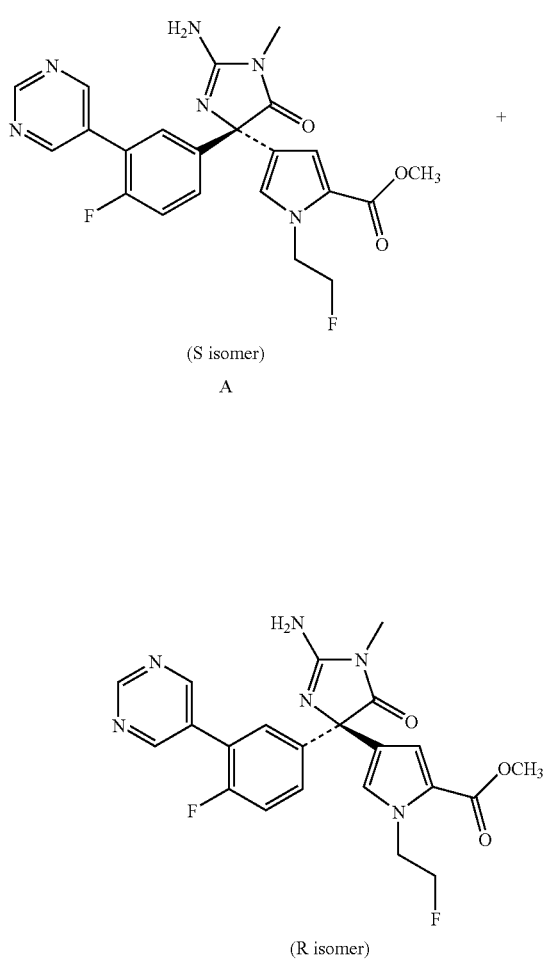

(S isomer)
A (R isomer)
B

A racemic mixture of methyl 4-[2-Amino-4-(4-fluoro-3-pyrimidinyl-5-phenyl)-1-methyl-5-oxo-4,5-dihydro-1H-imidazol-4-yl]-1-(2-fluoroethyl)-1H-pyrrole-2-carboxylate was separated by chiral HPLC to give the title enantiomeric products:

A: Methyl 4-[(4S)-2-Amino-4-(4-fluoro-3-pyrimidinyl-5-phenyl)-1-methyl-5-oxo-4,5-dihydro-1H-imidazol-4-yl]-1-(2-fluoroethyl)-1H-pyrrole-2-carboxylate; mp 186-188° C.; [α]$_D$ –83.2 (c 1.0, MeOH); MS (ESI) m/z (M+H)$^+$ 455.2; $^1$H NMR (500 MHz, CDCl$_3$) δ 3.15 (s, 3H), 3.73 (s, 3H), 4.50 (m, 1H), 4.58 (m, 2H), 4.68 (m, 1H), 6.96 (s, 2H), 7.16 (t, 1H, J=8.66 Hz), 7.65 (m, 2H), 8.88 (m, 2H), 9.15 (s, 1H); and B: Methyl 4-[(4R)-2-Amino-4-(4-fluoro-3-pyrimidinyl-5-phenyl)-1-methyl-5-oxo-4,5-dihydro-1H-imidazol-4-yl]-1-(2-fluoroethyl)-1H-pyrrole-2-carboxylate; mp 186-188° C.; [α]$_D$ +72.8 (c 1.0, MeOH); MS (ESI) m/z (M+H)$^+$ 455.1; $^1$H NMR (500 MHz, CDCl$_3$) δ 3.15 (s, 3H), 3.73 (s, 3H), 4.50 (m, 1H), 4.58 (m, 2H), 4.68 (m, 1H), 6.96 (s, 2H), 7.16 (t, 1H, J=8.66 Hz), 7.65 (m, 2H), 8.88 (m, 2H), 9.15 (s, 1H).

EXAMPLES 120-128

Preparation of Alkyl 4-[2-Amino-4-(3-heteroarylphenyl)-1-methyl-5-oxo-4,5-dihydro-1H-imidazol-4-yl]-1-(substituted)-1H-pyrrole-2-carboxylate Compounds

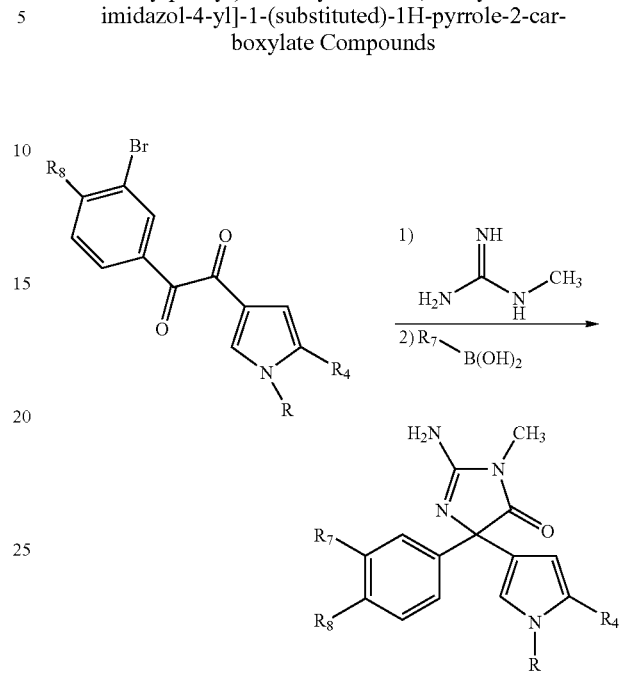

Using essentially the same procedure described in Example 118 and employing the appropriate dione and a suitable heteroaryl boronic acid, the compounds shown in Table X are obtained and identfied by NMR and mass spectral analyses.

TABLE X

| Ex. No | R | R4 | R7 | R8 | mp (° C.) |
|---|---|---|---|---|---|
| 120 | CH$_2$CF$_3$ | CO$_2$CH$_3$ | 2-F-pyridin-3-yl | F | 124-128 |
| 121 | CH$_2$CF$_3$ | CO$_2$CH$_3$ | pyrimidin-5-yl | F | 182-184 |
| 122 | CH$_2$CH$_2$F | CO$_2$CH$_3$ | 2-F-pyridin-3-yl | F | 127-128 |
| 123 | CH$_2$CH$_3$ | CO$_2$CH$_3$ | 2-F-pyridin-3-yl | F | 113-115 |
| 124 | CH$_2$CH$_2$F | CO$_2$CH(CH$_3$)$_2$ | 2-F-pyridin-3-yl | F | 117-118 |
| 125 | CH$_2$CH$_3$ | CO$_2$C$_2$H$_5$ | 2-F-pyridin-3-yl | F | 114-115 |
| 126* | CH$_2$CF$_3$ | CO$_2$CH$_3$ | 2-F-pyridin-3-yl | F | 124-126 |
| 127 | CH$_2$CH$_2$F | CO$_2$CH(CH$_3$)$_2$ | pyrimidin-5-yl | F | 167-170 |
| 128 | CH$_2$CH$_3$ | CONHCH$_3$ | 2-F-pyridin-3-yl | OC$_2$H$_5$ | 148-150 |

*R isomer

EXAMPLE 129

Preparation of N-{3-[2-amino-4-(1-ethyl-5-propionyl-1H-pyrrol-3-yl)-1-methyl-5-oxo-4,5-dihydro-1H-imidazol-4-yl]-phenyl}-butyramide

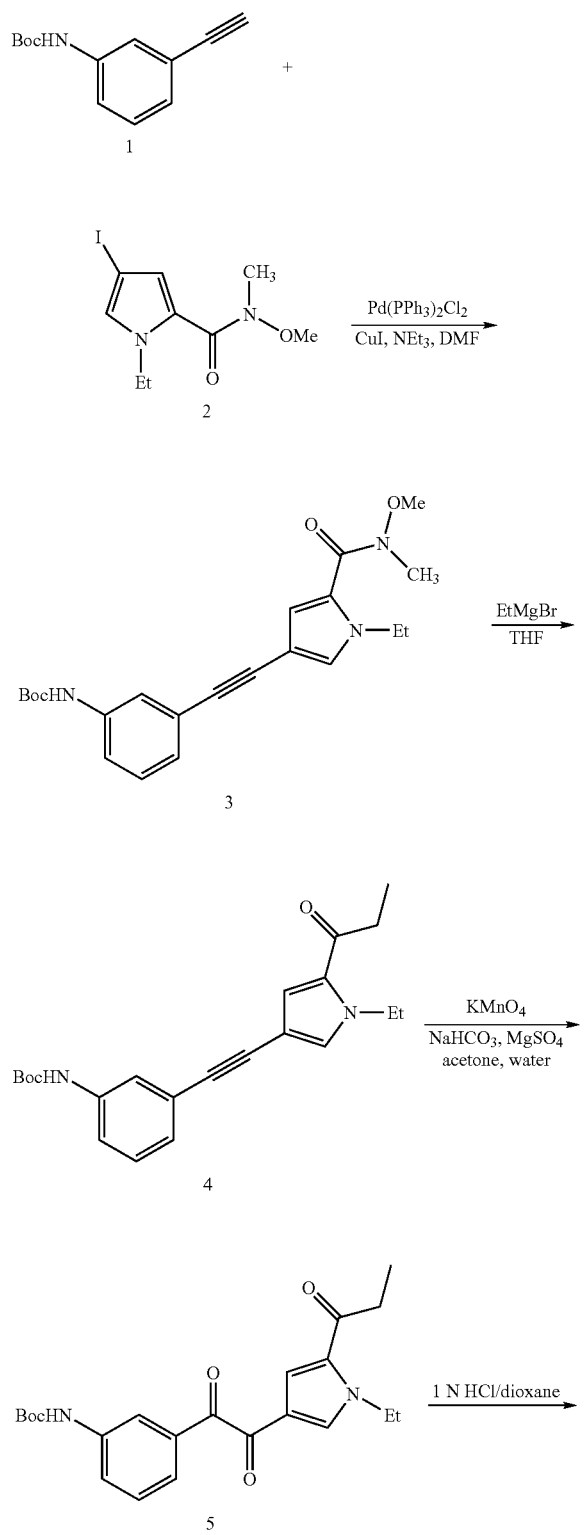

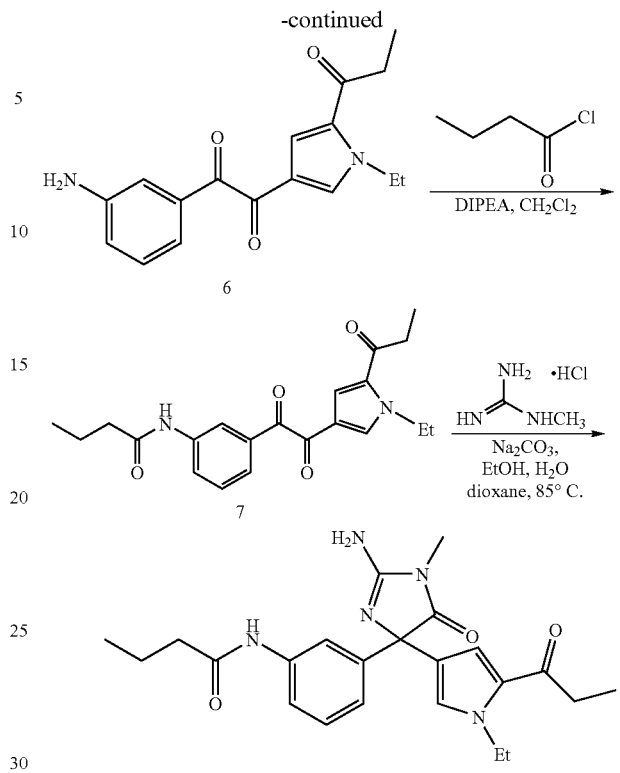

Step a) Preparation of Compound 3

A mixture of 1 (Prepared according to the procedure described in Gang, L. et al., *J. Med. Chem*. 2003, 46, 4232-4235; 4.08 g, 18.9 mmol), 2 (5.30 g, 17.2 mmol), dichlorobis(triphenylphosphine)palladium(II) (0.36 g, 0.51 mmol), copper(I) iodide (0.064 g, 0.34 mmol) and triethylamine (8.7 g, 86.0 mmol) in dimethylformamide (100 mL) was stirred at room temperature for 1.5 h and then at 40° C. for a further 1 h. After this time, the reaction was cooled to room temperature and diluted with ethyl acetate (300 mL) and water (150 mL). The organic layer was separated and washed with water (100 mL) and brine (100 mL), dried over sodium sulfate, filtered and concentrated. Purification by flash chromatography (silica, 80:20 to 50:50 hexanes/ethyl acetate) afforded 2 (4.80 g, 70%) as a dark red oil: $^1$H NMR (500 MHz, CDCl$_3$) δ 7.56 (br s, 1H), 7.25-7.20 (m, 2H), 7.14 (dt, J=7.2, 1.5 Hz, 1H), 7.06 (d, J=1.7 Hz, 1H), 7.02 (d, J=1.7 Hz, 1H), 6.45 (br s, 1H), 4.32 (q, J=7.2 Hz, 2H), 3.70 (s, 3H), 3.34 (s, 3H), 1.52 (s, 9H), 1.40 (t, J=7.2 Hz, 3H).

Step b) Preparation of Compound 4

A mixture of 3 (4.20 g, 10.6 mmol) in tetrahydrofuran (55 mL) was cooled to 0° C. Ethyl magnesium bromide (7.8 mL of a 3.0 M solution in diethyl ether, 23.3 mmol) was added and the mixture stirred at 0° C. for 5 min and then at room temperature for 1.5 h. The reaction mixture was then quenched with saturated aqueous ammonium chloride (30 mL) and then diluted with ethyl acetate (200 mL). The organic layer was separated and washed with water (50 mL) and brine (50 mL), dried over sodium sulfate, filtered and concentrated. Purification by flash chromatography (silica, 80:20 hexanes/ethyl acetate) afforded 4 (2.18 g, 56%) as a pale yellow solid: $^1$H NMR (500 MHz, CDCl$_3$) δ 7.56 (br s, 1H), 7.27-7.21 (m, 2H), 7.14 (dt, J=7.2, 1.5 Hz, 1H), 7.10-

7.08 (m, 2H), 6.48 (br s, 1H), 4.37 (q, J=7.1 Hz, 2H), 2.82 (q, J=7.4 Hz, 2H), 1.54 (s, 9H), 1.38 (t, J=7.1 Hz, 3H), 1.19 (t, J=7.4 Hz, 3H).

Step c) Preparation of Compound 5

A mixture of 4 (0.500 g, 1.36 mmol), potassium permanganate (0.537 g, 3.40 mmol), sodium bicarbonate (0.068 g, 0.82 mmol) and magnesium sulfate (0.327 g, 2.72 mmol) in acetone (60 mL) and water (30 mL) was stirred at ambient temperature for 1.5 h. The mixture was heated at 40° C. for an additional 2.5 h. The reaction was cooled to room temperature, diluted with 1:1 ethyl acetate/hexanes (200 mL) and filtered. The filtrate was then separated and the organic layer was washed with brine (3×40 mL), dried over sodium sulfate, filtered and concentrated to afford 5 (0.450 g, 83%) as a yellow solid: $^1$H NMR (300 MHz, CDCl$_3$) δ 7.93 (t, J=1.8 Hz, 1H), 7.79 (d, J=7.7 Hz, 1H), 7.69 (dd, J=7.8, 1.1 Hz, 1H), 7.56 (d, J=1.6 Hz, 1H), 7.49 (d, J=1.7 Hz, 1H), 7.43 (t, J=7.9 Hz, 1H), 6.62 (s, 1H), 4.39 (dd, J=14.3, 7.2 Hz, 2H), 2.86 (dd, J=14.7, 7.4 Hz, 2H), 1.52 (s, 9H), 1.40 (t, J=7.1 Hz, 3H), 1.19 (t, J=7.4 Hz, 3H).

Step d) Preparation of Compound 6

A mixture of 5 (0.450 g, 0.88 mmol) and 4 M HCl/dioxane (2.25 mL) in dioxane (7 mL) was stirred at room temperature for 3 h then heated to 50° C. for 1 h. After this time additional 4 M HCl/dioxane (2.25 mL) and dioxane (10 mL) were added and the mixture was stirred at room temperature for an additional 17 h. The reaction mixture was then concentrated to half the original volume then diluted with ether (50 mL). The resulting precipitate was filtered and washed with ether to afford 6 (0.164 g, 56%) as a yellow solid: $^1$H NMR (400 MHz, CDCl$_3$) δ 8.11 (s, 1H), 7.89 (s, 1H), 7.72 (s, 1H), 7.60 (s, 1H), 7.47 (s, 2H), 4.38-4.36 (m, 2H), 2.83 (dd, J=14.2, 7.0 Hz, 2H), 1.38-1.33 (m, 3H), 1.21-1.15 (m, 3H).

Step e) Preparation of Compound 7

A mixture of 6 (0.164 g, 0.49 mmol), and diisopropylethylamine (0.158 g, 1.23 mmol) in methyelene chloride was cooled to 0° C. then butyryl chloride (0.56 ml, 0.54 mmol) was added and the mixture was stirred at room temperature for 1 h. After this time the mixture was diluted with methylene chloride (50 mL) and washed with aqueous 1 N HCl solution (50 mL), saturated aqueous sodium bicarbonate solution (50 mL) and brine (50 mL). The organic layer was dried over sodium sulfate, filtered and concentrated. Purification by flash chromatography (silica, 1:4 ethyl acetate/hexanes) afforded 7 (0.154 g, 85%) as a yellow solid: $^1$H NMR (400 MHz, CDCl$_3$) δ 8.05-8.00 (m, 2H), 7.76 (d, J=7.8 Hz, 1H), 7.57 (d, J=1.7 Hz, 1H), 7.54-7.43 (m, 2H), 7.37 (s, 1H), 4.39 (dd, J=14.3, 7.2 Hz, 2H), 2.90-2.82 (m, 2H), 2.35 (t, J=7.3 Hz, 2H), 1.83-1.70 (m, 2H), 1.50-1.38 (m, 3H), 1.28-1.12 (m, 3H), 1.03-0.96 (m, 3H); ESI MS m/z 369 [C$_{21}$H$_{24}$N$_2$O$_4$+H]$^+$.

Step f) Preparation of N-{3-[2-amino-4-(1-ethyl-5-propionyl-1H-pyrrol-3-yl)-1-methyl-5-oxo-4,5-dihydro-1H-imidazol-4-yl]-phenyl}-butyramide A mixture of 7 (0.154 g, 0.42 mmol) and 1-methylguanidine hydrochloride (0.206 g, 1.88 mmol) in dioxane (4.0 mL) and ethanol (1.6 mL) was stirred at room temperature for 5 min. A solution of sodium carbonate (0.199 g, 1.88 mmol) in water (4.0 mL) was then added, the flask immersed into an oil bath at 85° C. and the contents stirred for 2 h. After this time the reaction mixture was cooled to room temperature and concentrated. The residue obtained was diluted with methylene chloride (50 mL) and water (25 mL). The organic layer was separated and washed with water (25 mL) and brine (50 mL), dried over sodium sulfate, filtered and concentrated. Purification by flash chromatography (silica, 95:5:0.25 methylene chloride/methanol/concentrated ammonium hydroxide) afforded the title product as a glass (0.120 g, 67%). A portion of the glass (0.050 g) was triturated with methelyene chloride and hexanes to afford the title product (0.027 g) as a white solid: mp 201-205° C.; $^1$H NMR (500 MHz, CD$_3$OD) δ 7.58 (d, J=8.0 Hz, 1H), 7.54 (s, 1H), 7.25 (t, J=7.9 Hz, 1H), 7.10 (d, J=7.8 Hz, 1H), 7.04 (dd, J=7.4, 1.8 Hz, 2H), 4.31 (dd, J=14.2, 7.1 Hz, 2H), 3.10 (s, 3H), 2.80-2.75 (m, 2H), 2.31 (t, J=7.3 Hz, 2H), 1.71-1.67 (m, 2H), 1.29 (t, J=7.1 Hz, 3H), 1.12 (t, J=7.4 Hz, 3H), 0.98 (t, J=7.4 Hz, 3H), ESI MS m/z 424 [C$_{23}$H$_{29}$N$_5$O$_3$+H]$^+$.

EXAMPLE 130

Preparation of N-{3-[2-amino-4-(1-ethyl-5-propionyl-1H-pyrrol-3-yl)-1-methyl-5-oxo-4,5-dihydro-1H-imidazol-4-yl]-phenyl)-propionamide

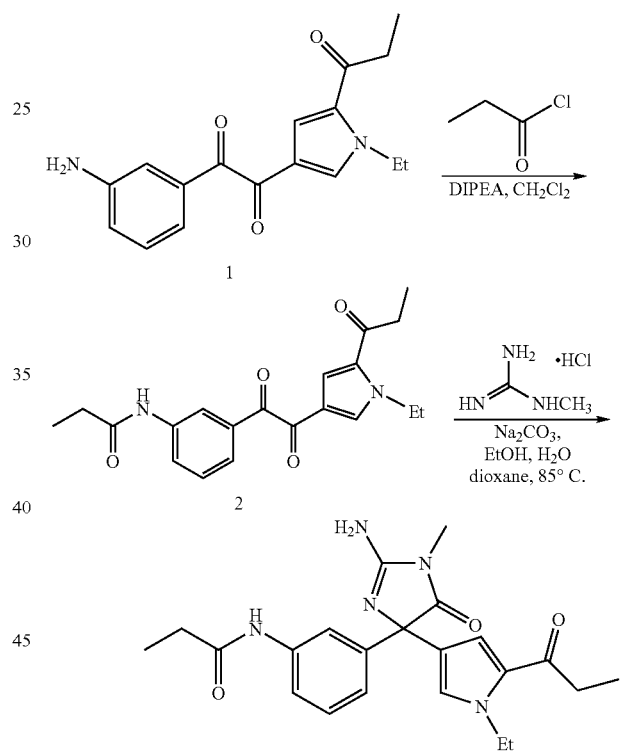

Step a) Preparation of Compound 2

A mixture of 1 (0.250 g, 0.75 mmol), and diisopropylethylamine (0.243 g, 1.88 mmol) in methylene chloride was cooled to 0° C. then propionyl chloride (0.076 g, 0.82 mmol) was added and the mixture stirred at room temperature for 1 h. After this time the mixture was diluted with methylene chloride (50 mL) and washed with aqueous 1 N HCl (50 mL), saturated aqueous sodium bicarbonate (50 mL) and brine (50 mL). The organic layer was dried over sodium sulfate, filtered and concentrated. Purification by flash chromatography (silica, 1:4 ethyl acetate/hexanes) afforded 2 (0.238 g, 89%) as a yellow solid: $^1$H NMR (500 MHz, CDCl$_3$) δ 8.03 (d, J=7.6 Hz, 1H), 7.99 (s, 1H), 7.77 (d, J=7.8 Hz, 1H), 7.57 (d, J=1.7 Hz, 1H), 7.49 (d, J=1.8 Hz, 1H), 7.47 (d, J=7.9 Hz, 1H), 7.23 (s, 1H), 4.39 (dd, J=14.3, 7.2 Hz, 2H), 2.87 (dd, J=14.8, 7.4 Hz, 2H), 2.42 (dd, J=15.1, 7.5 Hz, 2H), 1.41 (t, J=7.1 Hz, 3H), 1.26 (t, J=7.5 Hz, 3H), 1.19 (t, J=7.4 Hz, 3H); ESI MS m/z 355 $[C_{20}H_{22}N_2O_4+H]^+$.

Step b) Preparation of N-{3-[2-amino-4-(1-ethyl-5-propionyl-1H-pyrrol-3-yl)-1-methyl-5-oxo-4,5-dihydro-1H-imidazol-4-yl]-phenyl}-propionamide A mixture of 2 (0.079 g, 0.22 mmol) and 1-methylguanidine hydrochloride (0.110 g, 1.01 mmol) in dioxane (2.0 mL) and ethanol (0.8 mL) was stirred at room temperature for 5 min. A solution of sodium carbonate (0.107 g, 1.01 mmol) in water (2.0 mL) was then added, the flask immersed into an oil bath at 85° C. and stirred at this temperature for 2 h. After this time the reaction mixture was cooled to room temperature and concentrated. The residue obtained was diluted with methylene chloride (50 mL) and water (25 mL). The organic layer was separated and washed with water (25 mL) and brine (50 mL), dried over sodium sulfate, filtered and concentrated. Purification by flash chromatography (silica, 95:5:0.25 methylene chloride/methanol/concentrated ammonium hydroxide) afforded the title product (0.055 g, 61%) as a colorless oil, which was solidified from methylene chloride and hexanes to afford the title product (0.033 g) as a white solid: mp 120-141° C.; $^1$H NMR (500 MHz, CDCl$_3$) δ 7.57 (s, 1H), 7.49 (d, J=8.1 Hz, 1H), 7.36 (d, J=7.9 Hz, 1H), 7.19 (s, 1H), 6.92 (dd, J=10.5, 1.7 Hz, 2H), 4.28 (dd, J=14.2, 7.1 Hz, 2H), 3.13 (s, 3H), 2.75 (dd, J=14.8, 7.4 Hz, 2H), 2.36 (dd, J=15.1, 7.6 Hz, 2H), 1.33 (t, J=7.1 Hz, 3H), 1.22 (t, J=7.5 Hz, 3H), 1.12 (t, J=7.4 Hz, 3H), ESI MS m/z 410 $[C_{22}H_{27}N_5O_3+H]^+$.

EXAMPLE 131

Preparation of N-{3-[2-amino-4-(1-ethyl-5-propionyl-1H-pyrrol-3-yl)-1-methyl-5-oxo-4,5-dihydro-1H-imidazol-4-yl]-phenyl}-2-methoxy-acetamide

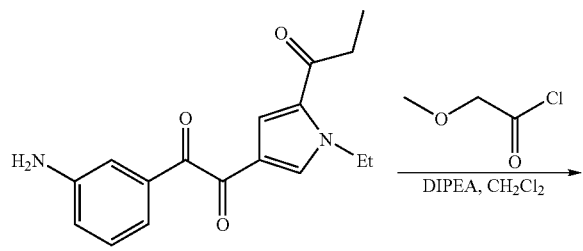

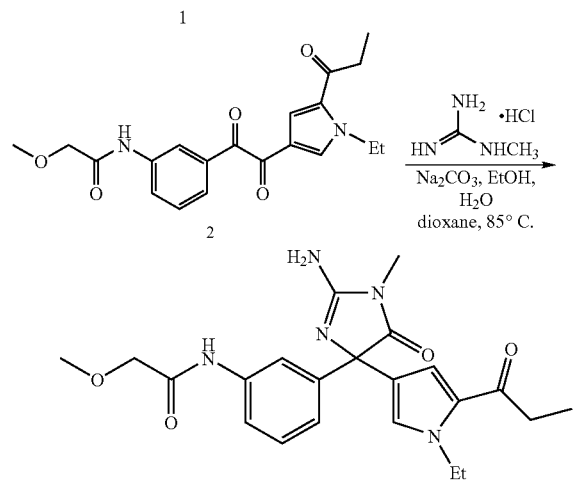

Step a) Preparation of Compound 2

A mixture of 1 (0.250 g, 0.75 mmol), and diisopropylethylamine (0.243 g, 1.88 mmol) in methyelene chloride was cooled to 0° C. then methoxyacetyl chloride (0.089 g, 0.82 mmol) was added and the mixture stirred at room temperature for 1 h. After this time the mixture was diluted with methylene chloride (50 mL) and washed with aqueous 1 N HCl (50 mL), saturated aqueous sodium bicarbonate (50 mL) and brine (50 mL). The organic layer was dried over sodium sulfate, filtered and concentrated. Purification by flash chromatography (silica, 1:4 ethyl acetate/hexanes) afforded 2 (0.260 g, 94%) as a yellow solid: $^1$H NMR (500 MHz, CDCl$_3$) δ 8.40 (s, 1H), 8.11 (d, J=8.1 Hz, 1H), 8.04 (t, J=1.8 Hz, 1H), 7.80 (d, J=7.9 Hz, 1H), 7.58 (d, J=1.7 Hz, 1H), 7.51-7.48 (m, 2H), 4.40 (dd, J=14.3, 7.1 Hz, 2H), 4.03 (s, 2H), 3.52 (s, 3H), 2.86 (dd, J=14.8, 7.4 Hz, 2H), 1.41 (t, J=7.2 Hz, 3H), 1.19 (t, J=7.4 Hz, 3H); ESI MS m/z 371 $[C_{20}H_{22}N_2O_5+H]^+$.

Step b) Preparation of N-{3-[2-amino-4-(1-ethyl-5-propionyl-1H-pyrrol-3-yl)-1-methyl-5-oxo-4,5-dihydro-1H-imidazol 4-yl]-phenyl]-2-methoxy-acetamide A mixture of 2 (0.087 g, 0.23 mmol) and 1-methylguanidine hydrochloride (0.116 g, 1.06 mmol) in dioxane (2.0 mL) and ethanol (0.8 mL) was stirred at room temperature for 5 min. A solution of sodium carbonate (0.112 g, 1.06 mmol) in water (2.0 mL) was then added, the flask immersed into an oil bath at 85° C. and stirred at this temperature for 2 h. After this time the reaction mixture was cooled to room temperature and concentrated. The residue obtained was diluted with methylene chloride (50 mL) and water (25 mL). The organic layer was separated and washed with water (25 mL) and brine (50 mL), dried over sodium sulfate, filtered and concentrated. Purification by flash chromatography (silica, 95:5:0.25 methylene chloride/methanol/concentrated ammonium hydroxide) afforded the title product (0.065 g, 66%) as a colorless oil, which was solidified from methylene chloride and hexanes to afford the title product (0.042 g) as a white solid: mp 95-115° C.; $^1$H NMR (500 MHz, CDCl$_3$) δ 8.26 (s, 1H), 7.61-7.59 (m, 2H), 7.38 (d, J=7.9 Hz, 1H), 7.31 (t, J=8.3 Hz, 1H), 6.91 (dd, J=10.1, 1.8 Hz, 2H), 4.29 (dd, J=14.3, 7.1 Hz, 2H), 3.98 (d, J=1.6 Hz, 2H), 3.49 (s, 3H), 3.12 (s, 3H), 2.76 (dd, J=14.8, 7.4 Hz, 2H), 1.33 (t, J=7.1 Hz, 3H), 1.13 (t, J=7.4 Hz, 3H), ESI MS m/z 426 $[C_{22}H_{27}N_5O_4+H]^+$.

EXAMPLE 132

Preparation of 2-Amino-5-(1-ethyl-5-propionyl-1H-pyrrol-3-yl)-3-methyl-5-(3-propoxyphenyl)-3,5-dihydro-4H-imidazol-4-one

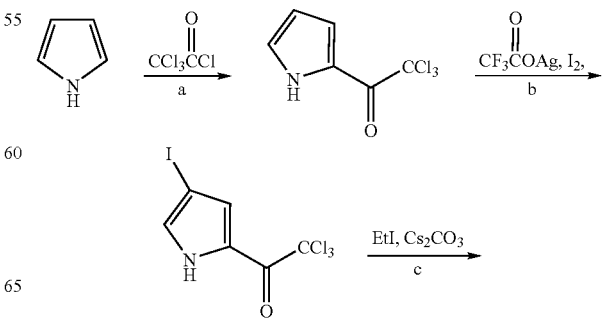

-continued

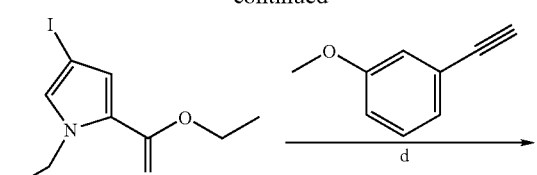

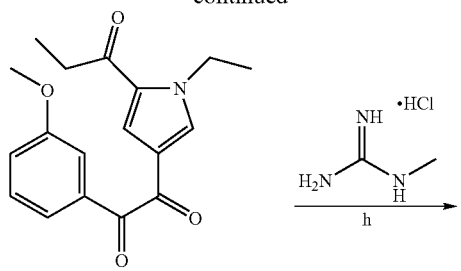

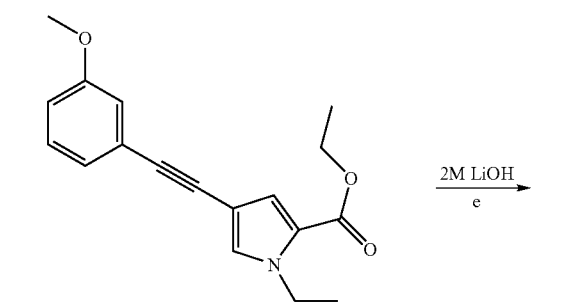

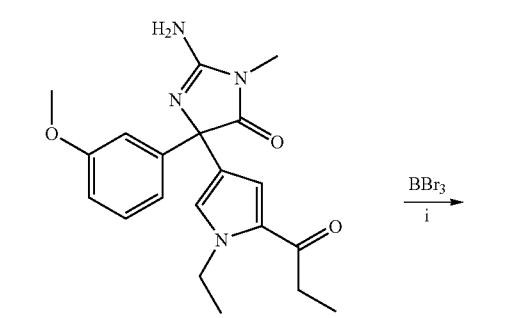

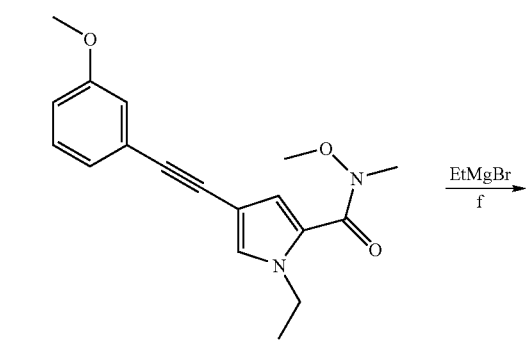

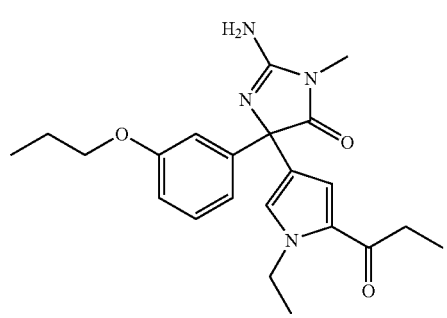

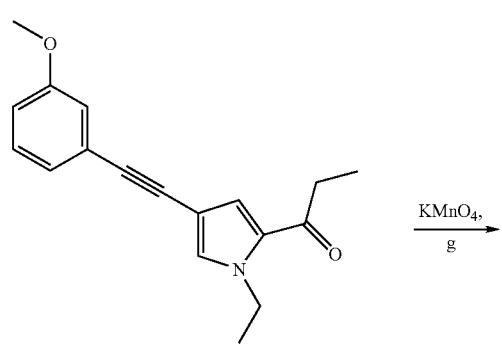

Step a) Preparation of 2,2,2-Trichloro-1 (1H-pyrrol-2-yl) ethanone

Under a nitrogen atmosphere to a solution of trichloroacetyl chloride (45 g, 246 mmol) in ether was added dropwise a solution of pyrrole (15.6 g, 233 mmol) in ether over 3 hours. The heat of reaction caused the mixture to reflux during the addition. Following the addition the mixture was stirred for 1 hour. Under cooling (5° C.) a solution of potassium carbonate (20 g, 145 mmol) in water was added slowly. The layers were separated and the organic phase was washed with brine, dried (MgSO$_4$), filtered, treated with charcoal and filtered. The solvent was removed in vacuo and the residue was dissolved in hexane. The dark colored solution was cooled in the refrigerator and the product crystallized (38 g, 77% yield, tan solid), $^1$H NMR (400 MHZ, DMSOd$_6$) δ 6.31-6.33 (m, 1H), 7.27-7.31 (m, 2H), MS m/e (M–H)$^-$209.9.

Step b) Preparation of 2,2,2-Trichloro-1 (4-iodo-1H-pyrrol-2-yl)ethanone

Under a nitrogen atmosphere to a cold (0° C.) suspension of 2,2,2-Trichloro-1 (1H-pyrrol-2-yl)ethanone (21.1 g, 99.3 mmol) and silver trifluoroacetate (23.2 g, 105 mmol) in chloroform was added iodine (25.4 g, 100 mmol) portionwise over 10 minutes. The mixture was allowed to warm to room temperature and stirred for 2 hours. This was filtered through celite and washed with chloroform. The organic phase was washed sequentially with 5% Na$_2$S$_2$O$_5$, water, brine, dried (MgSO$_4$) and filtered. Evaporation and trituration with 80% hexane/ether (80 mL) gave the title compound as a white solid (25.5 g, 78% yield), mp 140° C., $^1$H NMR (400 MHZ, CDCl$_3$) δ 7.2 (m, 2H), 7.4 (m, 1H), (9.5 (bs, 1H), MS m/e (M+H)$^+$ 339.

Step c) Preparation of Ethyl-4-iodo-1H-pyrrole-2-carboxylic acid ethyl ester

Under a nitrogen atmosphere to a solution of 2,2,2-trichloro-1 (4-iodo-1H-pyrrol-2-yl)ethanone (9 g, 26.6 mmol) in DMF (30 mL) was added Cs$_2$CO$_3$ (17.4 g, 53.2 mmol) and stirred for 10 minutes. To this was then added a solution of iodoethane (8.72 g, 55.86 mmol) in DMF (10 mL). The new mixture was stirred at room temperature for 20 hours. A worked up TLC sample indicated the reaction was complete. DMF was removed in vacuo and the residue was taken back in a mixture of saturated aqueous NH$_4$Cl: H$_2$O (1:1, 200 mL) solution and extracted with ether. The combined ether extracts were washed with 5% Na$_2$S$_2$O$_5$, dried (MgSO$_4$) and filtered. Evaporation and purification by flash chromatography (hexane/ethyl acetate 9.7/0.3) gave light yellow oil (7 g, 89% yield), $^1$H NMR (400 MHZ, CDCl$_3$) δ 1.3 (t, 3H), 1.35 (t, 3H), 4.22 (q 2H), 4.3 (q, 2H), 6.85 (s, 1H), 7.0 (s, 1H), MS m/e (M)$^+$ 293.

Step d) Preparation of 1-Ethyl-4-(3-methoxy-phenylethynyl)-1H-pyrrole-2-carboxylic acid ethyl ester:

Argon was gently bubbled to a mixture of ethyl-4-iodo-1H-pyrrole-2-carboxylic acid ethyl ester (4.1 g, 14 mmol), CuI (0.14 g, 0.76 mmol), Et$_3$N (40 ml, 287 mmol) and tetrakis(triphenylphosphosphine)palladium (0) (0.64 g, 0.554 mmol) in ACN (20 mL) over 5 minutes. A prepared solution of 1-ethynyl-3-methoxy-benzene (2.03 g, 15.4 mmol) in ACN (5 mL) was added into it and the new mixture was reflux under Nitrogen for 3 hours. The resulting brown colored reaction mixture was cooled to room temperature and concentrated in vacuo. The concentrate was diluted with water and extracted with ether. The combined ether extracts were washed with saturated aqueous solution of NH$_4$Cl, brine, dried (MgSO$_4$) and filtered. Evaporation and purification by flash chromatography on silica gel (Hexane/EtOAc 9.7/0.3) gave the title compound as a yellow brownish oil (3.6 g, 84% yield), $^1$H NMR (400 MHZ, CDCl$_3$) δ 1.31-1.34 (t, 3H), 1.38-1.40 (t, 3H), 3.78 (s, 3H), 4.25-4.27 (q, 2H), 4.30-4.33 (q, 2H), 6.83 (m, 1H), 6.89 (m, 1H), 7.06 (m, 3H), 7.19 (m, 1H), MS m/e (M+H)$^+$ 298.1.

Step e) Preparation of 1-Ethyl-4-(3-methoxy-phenylethynyl)-1H-pyrrole-2-carboxylic acid methyl amide:

To a solution of 1-ethyl-4-(3-methoxy-phenylethynyl)-1H-pyrrole-2-carboxylic acid ethyl ester (3.5 g, 11.76 mmol) in dioxane (70 mL) was added LiOH (2M, 35 mL). The reaction mixture was stirred at room temperature for 3 days, and then concentrated in vacuo. The residue was dissolved in H$_2$O (30 ml) and extracted with ether. Under cooling the aqueous was acidified with HCl (3N) and extracted with EtOAc. The organic extracts were dried over MgSO$_4$. Evaporation and recrystallzation from ether and hexane gave the 1-ethyl-4-(3-methoxy-phenylethynyl)-1H-pyrrole-2-carboxylic acid intermediate as light yellow solid (2.55 g, 79% yield), mp 129° C., $^1$H NMR (400 MHZ, CDCl$_3$) δ 1.26 (t, 3H), 3.73 (s, 3H), 4.26-4.28 (q, 2H), 6.96-6.97 (m, 2H), 6.99-7.0 (m, 2H), 7.23-7.24 (m, 1H), 7.46 (s, 1H), 12.46 (bs, 1H), MS m/e (M–H)$^-$ 268.1.

This intermediate (2.5 g, 9.28 mmol) was treated with oxalyl chloride (4.1 mL, 46.4 mmol), DMF (2 drops) in methylene chloride (70 mL) and stirred at room temperature for 2 hours to give 1-ethyl-4-(3-methoxy-phenylethynyl)-1H-pyrrole-2-carboxylic acid chloride (2.7 g, 9.38 mmol) after a usual workup. 1-Ethyl-4-(3-methoxy-phenylethynyl)-1H-pyrrole-2-carboxylic acid chloride (2.7 g, 9.38 mmol) was diluted with methylene chloride (35 mL) and added to a prepared solution of N,O, dimethyl-hydroxylamine hydrochloride (4.6 g, 46.4 mmol) and diisopropyl-ethyl amine (13 mL, 74.3 mmol) in methylene chloride (35 mL) over 5 minutes. The reaction was complete after 4 hours. Solvent was removed in vacuo and the residue was taken back in a mixture of saturated aqueous NH$_4$Cl: H$_2$O (1:1, 150 mL) solution and extracted with ether. Combined ether extracts were washed with brine dried (MgSO$_4$) and filtered. Evaporation and purification by flash chromatography (hexane/ethyl acetate 9/1) gave the title compound as a light yellow oil (2.48 g g, 82% yield), $^1$H NMR (400 MHZ, CDCl$_3$) □ 1.35-1.37 (t, 3H), 3.31 (s, 3H), 3.67 (s, 3H), 3.78 (s, 3H), 4.29-4.30 (q, 2H), 6.83 (m, 1H), 6.99 (m, 2H), 7.01 (m, 2H), 7.19 (m, 1H), MS m/e (M+H)$^+$ 313.1.

Step f) Preparation of 1-[1-Ethyl-4-(3-methoxy-phenylethynyl)-1H-pyrrol-2-yl]-propan-1-one:

Under a nitrogen atmosphere to a cold (0° C.) solution of 1-ethyl-4-(3-methoxy-phenylethynyl)-1H-pyrrole-2-carboxylic acid methyl amide (2.48 g, 7.93 mmol) in THF (40 ml) was added EtMgBr solution (1 molar in THF, 16 mL) over 10 minutes. The mixture was allowed to warm to room temperature and stirred for 18 hours, then poured into ice/1 N HCl solution and extracted with ether. The combined ether extracts were washed with brine, dried over MgSO$_4$ and evaporated to dryness. The resultant residue was purified by flash chromatography (hexane/ethyl acetate 9.5/0.5) to give the title compound as an off white solid (1.8 g, 80% yield), mp 64° C., $^1$H NMR (400 MHZ, CDCl$_3$) δ 1.16 (t, 3H), 1.35 (t, 3H), 2.8 (q, 2H), 3.79 (s, 3H), 4.35 (q 2H), 6.85 (m, 1H), 6.99-7.03 (m, 2H), 7.05 (m, 2H), 7.08 (m, 1H), MS m/e (M+H)$^+$ 282.1.

Step g) Preparation of 1-(1-Ethyl-5-propionyl-1H-pyrrol-3yl)-2-(3-methoxy-phenyl)-ethane-1,2-dione:

To a solution of 1-[1-ethyl-4-(3-methoxy-phenylethynyl)-1H-pyrrol-2-yl]-propan-1-one. (1.8 g, 6.39 mmol) in acetone was added MgSO$_4$ (1 g, 8.95 mmol) followed by an aqueous solution of NaHCO$_3$ (0.32 g, 3.83 mmol) in H$_2$O and KMnO$_4$ (2 g, 12.78 mmol). The suspension was stirred for 20 hours, then diluted with H$_2$O and ether and filtered through a pad of solka floc. The organic phase was separated, washed with brine, dried over MgSO$_4$ and evaporated to dryness to afford the title compound as a light yellow solid (1.5 g, 75% yield), mp 97° C., $^1$H NMR (400 MHZ, CDCl$_3$) δ 1.16 (t, 3H), 1.38 (t, 3H), 2.83 (q, 2H), 3.84 (s, 3H), 4.36 (q, 2H), 7.18 (m, 1H), 7.36 (m, 1H), 7.39 (m, 1H), 7.47-7.55 (m, 3H), MS m/e (M+H)$^+$ 314.1

Step h) Preparation of 2-Amino-5-(1-ethyl-5-propionyl-1-H-pyrrol-3-yl)-5-(3-methoxy-phenyl)-3-methyl-3,5-dihydro-imidazol-4-one:

Using essentially the same procedure described in Example 107, step b, and employing 1-(1-ethyl-5-propionyl-1H-pyrrol-3yl)-2-(3-methoxy-phenyl)-ethane-1,2-dione (1.5 g, 4.78 mmol), the title product was obtained as a white solid (1.37 g, 77% yield), mp 79° C., $^1$H NMR (400 MHZ, DMSO-d$_6$) δ 1.0 (t, 3H), 1.18 (t, 3H), 2.70 (q, 2H), 2.93 (s, 3H), 3.69 (s, 3H), 4.22 (q, 2H), 6.55 (bs, 2H), 6.78 (m, 1H), 6.9 (s, 1H), 7.02 (m, 2H), 7.06 (m, 1H), 7.19 (m, 1H), MS m/e (M+H)$^+$ 369.2.

Step i) Preparation of 2-Amino-5-(1-ethyl-5-propionyl-1-H-pyrrol-3-yl)-5-(3-hydroxy-phenyl)-3-methyl-3,5-dihydro-imidazol-4-one:

Boron tribromide (1M in dichloromethane, 21 mL, 21.17 mmol) was added dropwise to a cold (−78° C.) suspension of 2-amino-5-(1-ethyl-5-propionyl-1-H-pyrrol-3-yl)-5-(3-methoxy-phenyl)-3-methyl-3,5-dihydro-imidazol-4-one (1.3 g, 3.52 mmol) in CH$_2$Cl$_2$. The mixture was allowed to warm to room temperature, stirred for 20 h, and poured slowly into cold (0° C.) ethyl ether, treated slowly with methanol over a 10 minute period, basified to pH 8 at 0° C. with saturated aqueous NaHCO$_3$ and extracted with CHCl$_3$. The combined CHCl$_3$ extracts were washed with brine, dried over MgSO$_4$ and evaporated to dryness. The resultant residue was purifiied by flash chromatography (ethyl acetate/methylene chloride/methyl alcohol/triethyl amine, 5/4.4/0.5/0.1) to give the title compound as a white solid (0.95 g, 72% yield), mp 101° C., $^1$H NMR (400 MHZ, DMSO-d$_6$) δ 0.99 (t, 3H), 1.17 (t, 3H), 2.66-2.68 (q, 2H), 2.90 (s, 3H).4.19-4.21 (q, 2H), 6.5 (bs, 2H), 6.55 (m, 1H), 6.84-6.88 (m, 3H), 7.01 (m, 2H), 9.21 (bs, 1H), MS m/e (M−H)$^-$ 353.1.

Step j) Preparation of 2-Amino-5-(1-ethyl-5-propionyl-1H-pyrrol-3-yl)-3-methyl-5-(3-propoxyphenyl)-3,5-dihydro-4H-imidazol-4-one:

Under a nitrogen atmosphere, a solution of 2-amino-5-(1-ethyl-5-propionyl-1-H-pyrrol-3-yl)-5-(3-hydroxy-phenyl)-3-methyl-3,5-dihydro-imidazol-4-one (0.08 g, 0.225 mmol) in DMF (5 mL) was treated with Cs$_2$CO$_3$ (0.15 g, 0.45 mmol) and iodopropane (0.046 g, 0.27 mmol). The reaction mixture was sealed and stirred at room temperature for 20 hours. The solvent was removed in vacuo and the residue was dissolved in CHCl$_3$ and filtered. The filtrate was evaporated. The resultant residue was purified by combi flash chromatography (ethyl acetate/methylene chloride/methyl alcohol/triethyl amine, 5/4.4/0.5/0.1) to give the title compound as a white solid (0.04 g, 45% yield), mp 95° C., $^1$H NMR (400 MHZ, DMSO-d$_6$) δ 0.89-0.99 (dt, 6H), 1.15 (t, 3H), 1.64-1.66 (m, 2H), 2.64-2.68 (m, 2H), 2.9 (s, 3H), 3.81 (m, 2H), 4.20 (m, 2H), 6.50 (bs, 2H), 6.72-6.74 (m, 1H), 6.87 (s, 1H), 7.0-7.02 (m, 3H), 7.14 (m, 1H), MS m/e (M+H)$^+$ 397.

EXAMPLES 133-140

Preparation of 2-Amino-5-(1-ethyl-5-propionyl-1H-pyrrol-3-yl)-3-methyl-5-(3-propoxyphenyl)-3,5-dihydro-4H-imidazol-4-one

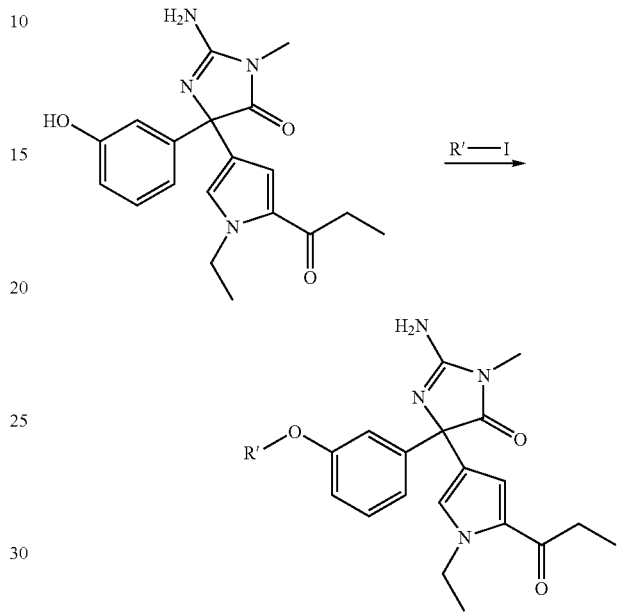

Using essentially the same procedure described in Example 132, step j, and employing the appropriate alkyl iodide, the compounds shown on Table XI were obtained and identfied by NMR and mass spectral analyses.

TABLE XI

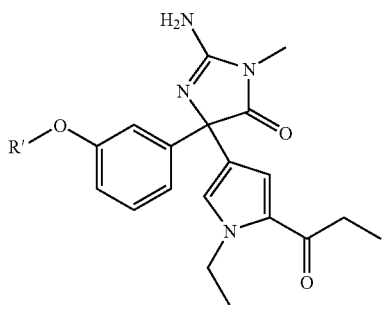

| Ex. No. | R' | mp (° C.) | (M − H)$^-$ |
|---|---|---|---|
| 133 | pentyl | 70 | 423.2 |
| 134 | 3,3-dimethylbutyl | 93 | 437.2 |
| 135 | 2-fluoroethyl | 76 | 399.2 |
| 136 | butyl | 76 | 411.2* |
| 137 | cyclopropylmethyl | 86 | 407.2 |
| 138 | isobutyl | 78 | 411.2* |
| 139 | CN—CH$_2$—CH$_2$—CH$_2$—CH$_2$ | 68 | 421.2* |
| 140 | CH$_2$=CH—CH$_2$—CH$_2$—CH$_2$ | 69 | 423.2* |

*(M + H)$^+$

EXAMPLE 141

Preparation of 2-Amino-3-methyl-5-(3-propoxyphenyl)-5-thien-2-yl-3,5-dihydro-4H-imidazol-4-one

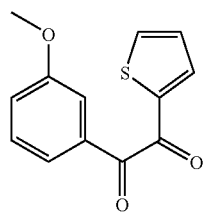 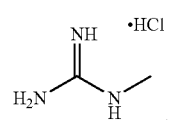

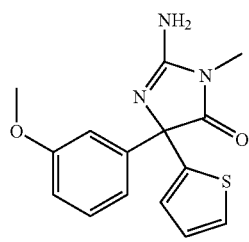 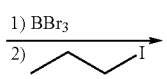

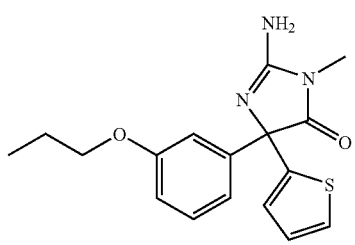

Using essentially the same procedure described in Example 132 and employing 3-methoxyphenyl)-2-thien-2-ylethane-1,2-dione as starting material, the title product was obtained as a white solid, mp 79-81° C., identified by NMR and mass spectral analyses. $^1$HNMR (DMSOd$_6$ 300 MHz) δ 0.9 (t, 3H), 1.75 (m, 2H), 2.95 (s, 3H), 3.9 (q, 2H), 6.8 (b, 3H) 7.0 (m, 1H), 7.1 (m, 3H), 7.2 (m, 1H), 7.35 (m, 1H);
MS m/e (M)$^+$ 330

EXAMPLES 142-148

Preparation of 2-Amino-3-methyl-5-(3-alkoxyphenyl)-5-thien-3-yl-3,5-dihydro-4H-imidazol-4-one Compounds

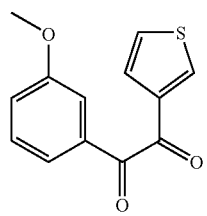 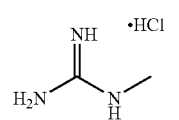

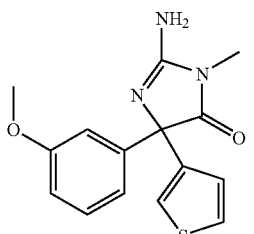 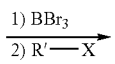

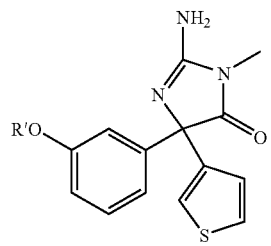

Using essentially the same procedure described in Example 109 and employing 1-(3-methoxyphenyl)-2-thien-3-ylethane-1,2-dione as starting material and the desired alkyl halide, R'X, wherein X is Cl, Br or I, the compounds shown in Table XII were obtained and identified by NMR and mass spectral analyses.

TABLE XII

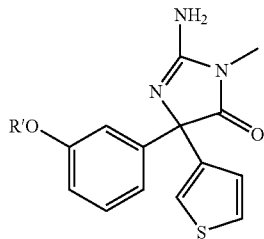

| Ex. No. | R' | mp (° C.) | M + m/e |
|---|---|---|---|
| 142 | methyl | 159-162 | 302.1 |
| 143 | propyl | 161-163 | 328 |
| 144 | 3-methylbutyl | 84-88 | 358 |
| 145 | pyridin-3-ylmethyl | 210-213 | 379 |
| 146 | 4,4,4-trifluorobutyl | 94-97 | 398 |
| 147 | cyclohexylmethyl | 88-90 | 384 |
| 148 | isobutyl | 70-73 | 344 |

EXAMPLE 149

Preparation of 2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one

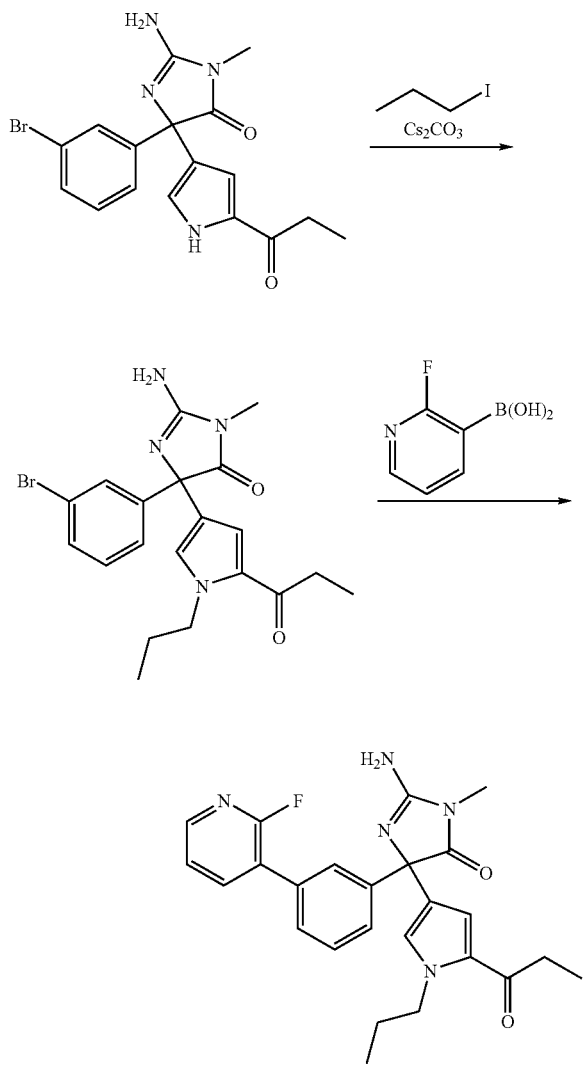

Step a) Preparation of 2-Amino-5-(3-bromophenyl)-3-methyl-5-(5-propionyl-1-propyl-1H-pyrrol-3-yl)-3,5-dihydro-imidazol-4-one Under a nitrogen atmosphere, to a solution of 2-amino-5-(3-bromo-phenyl)-3-methyl-5-(5-propionyl-1H-pyrrol-3-yl)-3,5-dihydro-imidazol-4-one (0.2 g, 0.51 mmol) in DMF (5 mL) was added Cs$_2$CO$_3$ (0.33 g, 1.02 mmol) and iodopropane (0.12 g, 0.70 mmol). The reaction mixture was sealed and stirred at room temperature for 20 hours. DMF was removed in vacuo, the residue was taken back CHCl$_3$ and filtered. Evaporation and purification by combi flash chromatography (methylene chloride/methyl alcohol/triethyl amine, 9.5/0.4/0.1) gave the title compound as a white solid (0.16 g, 72% yield), mp 260° C., $^1$H NMR (400 MHZ, CDCl$_3$) δ 0.73 (t, 3H), 1.01 (t, 3H), 1.03 (q, 2H), 2.66 (m, 2H), 2.91 (s, 3H), 4.12 (q, 2H), 6.6 (bs, 2H), 6.87 (s, 1H), 6.98 (s, 1H), 7.23 (m, 1H), 7.37 (m, 1H), 7.45 (m, 1H), 7.57 (m, 1H), MS m/e (M–H)$^-$ 429.1.

Step b) Preparation of 2-Amino-5-[3-(2-fluoropyridin-3-yl)phenyl]-3-methyl-5-(5-propionyl-1-propyl-1H-pyrrol-3-yl)-3,5-dihydro-imidazol-4-one Using essentially the same procedure described in Example 43, step e, and employing 2-fluoro-pyridin-3-yl boronic acid and 2-amino-5-(3-bromophenyl)-3-methyl-5-(5-propionyl-1-propyl-1H-pyrrol-3-yl)-3,5-dihydro-imidazol-4-one as reactants, the title product was obtained as a white solid, mp 118° C., $^1$H NMR (400 MHZ, DMSO-d$_6$) δ 0.73 (t, 3H), 0.96 (t, 3H), 1.54 (m, 2H), 2.67 (m, 2H), 2.92 (s, 3H), 4.13 (m, 2H), 6.60 (bs, 2H), 6.92 (s, 1H), 7.01 (s, 1H), 7.41 (m, 3H), 7.53 (m, 1H), 7.67 (m, 1H), 7.97 (m, 1H), 8.19, (m, 1H), m/e (M–H)$^-$ 446.2.

EXAMPLE 150

Preparation of 2-Amino-5-[3-bromophenyl]-5-[1-(2-fluoroethyl)-5-propionyl-1H-pyrrol-3-yl)-3-methyl-3,5-dihydro-4H-imidazol-4-one

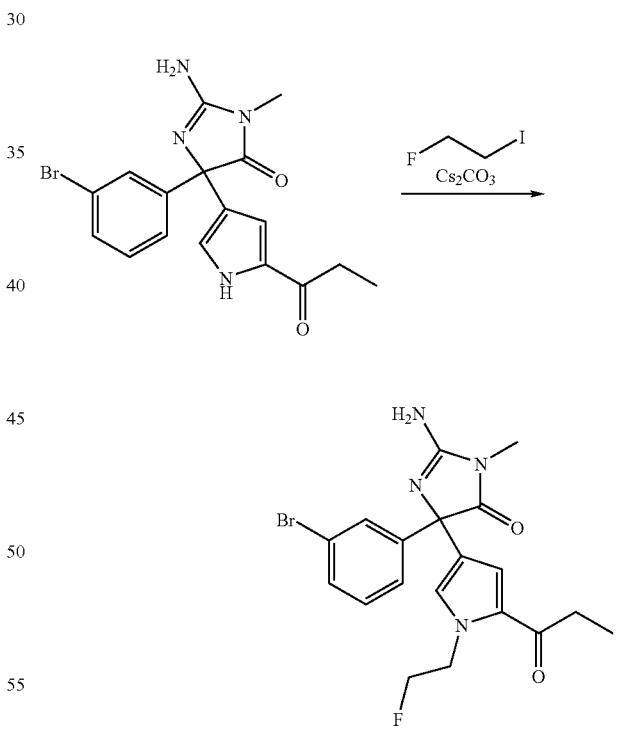

Using essentially the same procedure described in Example 149, step a, and employing 2-fluoro-1-iodoethane, the title compound was obtained and identified by NMR and mass spectral analyses. $^1$HNMR (DMSOd$_6$ 300 MHz) δ 0.98 (s, 3H), 2.76(q, 2H), 3.9(s, 3H), 4.5(s, 2H), 4.6(m, 2H), 6.65 (brs, 2H), 6.9(s, 1H), 7.1(s, 1H), 7.2(t, 1H), 7.4(m, 1H), 7.55(m, 1H), 7.6(s, 1H); MS m/e (M+H)$^+$ 435

EXAMPLE 151

Preparation of 2-Amino-5-[3-(2,5-difluoropyridin-3-yl)phenyl]-5-[1-(2-fluoro-ethyl)-5-propionyl-1H-pyrrol-3-yl)-3-methyl-3,5-dihydro-4H-imidazol-4-one

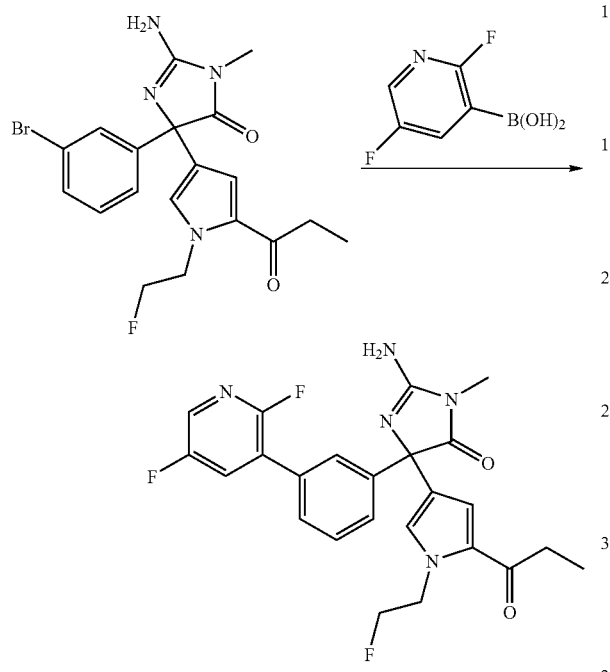

Using essentially the same procedure described in Example 149, step b, and employing 2,5-difluoropyridin-3-ylboronic acid, the title compound was obtained and identified by NMR and mass spectral analyses. ¹HNMR (DMSOd₆ 300 MHz) δ 0.98 (s, 3H), 2.76(q, 2H), 3.9(s, 3H), 4.45(s, 2H), 4.6(m, 2H), 6.6(brs, 2H), 6.95 (s, 1H), 7.4 (m, 2H), 7.6(d, 1H), 7.78(s, 1H), 8.0(m, 1H), 8.2(d, 1H); MS m/e (M+H)⁺ 470

EXAMPLES 152-182

Preparation of 2-Amino-5-[3-(2-fluoropyridin-3-yl)phenyl]-3-methyl-5-(5-carbonyl-1-sustituted-1H-pyrrol-3-yl)-3,5-dihydro-4H-imidazol-4-one Compounds

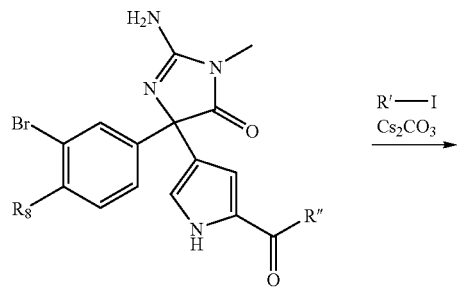

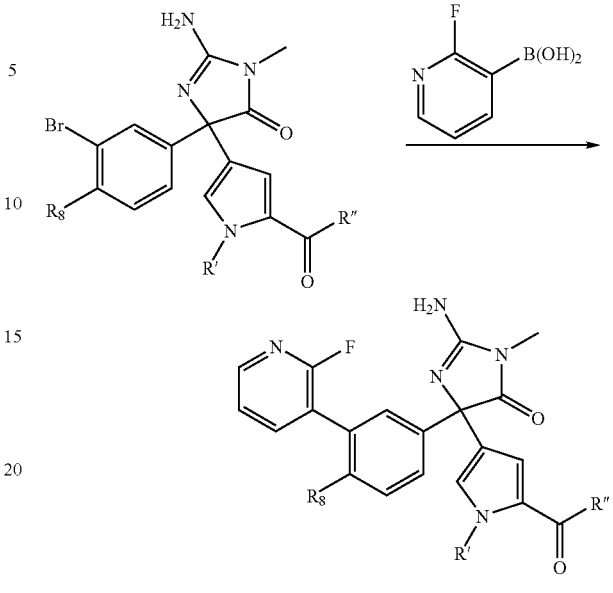

Using essentially the same procedures described hereinabove in Examples 132 and 149, the compounds shown in Table XIII were obtained and identfied by NMR and mass spectral analyses.

TABLE XIII

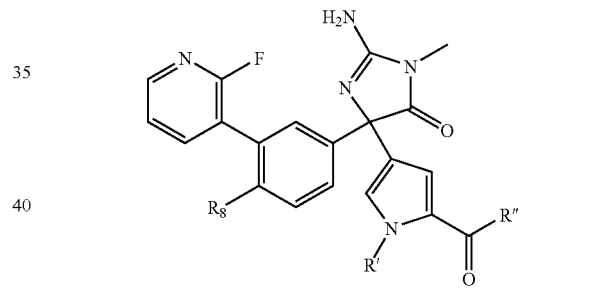

| Ex. No | R8 | R' | R" | mp °C. |
|---|---|---|---|---|
| 152 | H | 3-F-propyl | ethyl | 105 |
| 153 | H | 3-CH₃-butyl | ethyl | — |
| 154 | H | H | ethyl | — |
| 155 | H | ethyl | ethyl | 126-128 |
| 156 | H | ethyl | methyl | 123-124 |
| 157 | H | ethyl | NHCH₃ | 138-140 |
| 158 | H | ethyl | NHC₂H₅ | 132-135 |
| 159 | H | ethyl | NH-n-propyl | 120-123 |
| 160 | H | ethyl | NH-n-butyl | 118-120 |
| 161 | H | ethyl | NH-isopropyl | 121-123 |
| 162 | H | ethyl | NH-cyclopentyl | 127-128 |
| 163 | H | ethyl | N-piperidinyl | 111-113 |
| 164 | H | ethyl | N-morpholinyl | 108-109 |
| 165 | H | ethyl | N(CH₃)₂ | >200 |
| 166 | H | ethyl | NH-(4-F-benzyl) | 110-112 |
| 167 | H | 2-fluoroethyl | ethyl | 100 |
| 168 | H | ethyl | propyl | 82-84 |
| 169 | H | ethyl | pentyl | 71-73 |
| 170 | H | ethyl | phenyl | 104-106 |
| 171 | H | ethyl | cyclohexyl | 94-100 |
| 172 | H | ethyl | cyclopropyl | 98-100 |
| 173 | H | ethyl | isopropyl | 85-88 |
| 174 | H | ethyl | sec-butyl | 210-211 |
| 175 | H | H | ethyl | 121-125 |
| 176 | H | 4,4,4-trifluorobutyl | ethyl | 91-94 |

TABLE XIII-continued

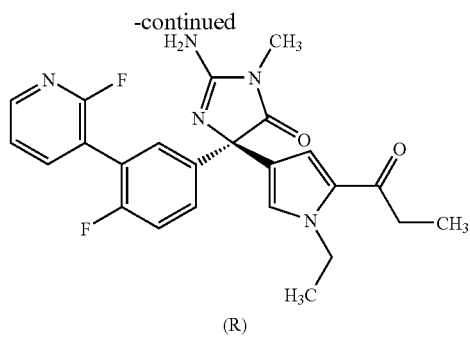

| Ex. No | R8 | R' | R" | mp °C. |
|---|---|---|---|---|
| 177 | H | cyclopropylmethyl | ethyl | 111-114 |
| 178 | H | 4-fluorobutyl | ethyl | 105 |
| 179 | H | isobutyl | ethyl | 98-102 |
| 180 | H | methyl | ethyl | 107-111 |
| 181 | H | benzyl | ethyl | 93-96 |
| 182 | H | 1,3-thiazol-4-ylmethyl | ethyl | 116-120 |

EXAMPLE 183

Preparation of (5S)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one (A) and (5R)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one (B)

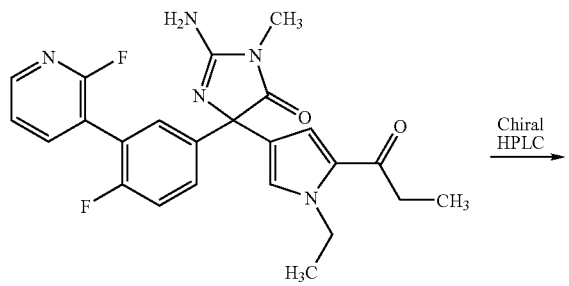

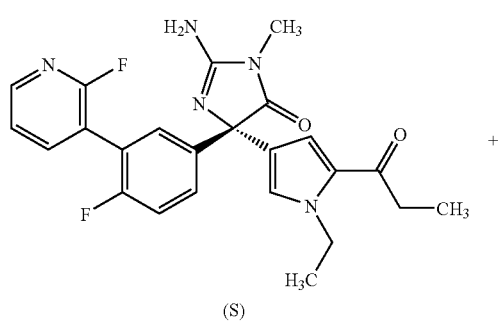

A racemic mixture of 2-amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one was separated by chiral HPLC using a Chiralcel AD, 2×25 cm column with 20% EtOH in hexane to give the title products: (A) (5S)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one, mp 114-116° C.; MS (ES) m/z 452.1 [M+H] and (B) (5R)-2-amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one, mp 114-117° C.; MS (ES) m/z 452.1 [M+H].

EXAMPLE 184

Preparation of Methyl 4-{(4S)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-Pyrrole-2-carboxylate (A) and Methyl 4-{(4R)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate (B)

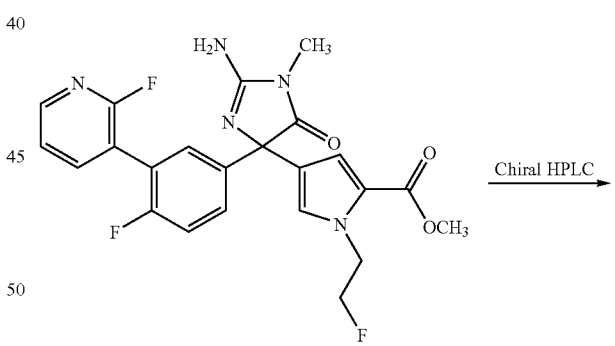

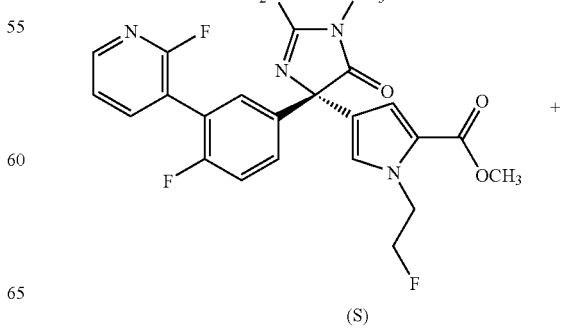

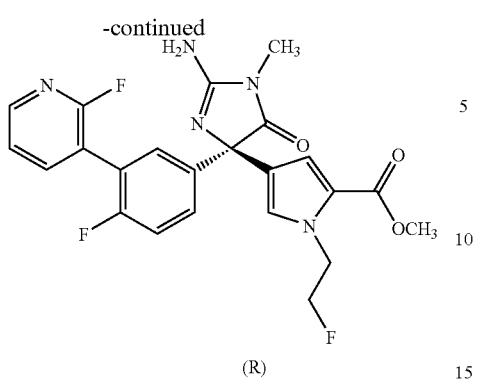

(R)

A racemic mixture of methyl 4-{2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate was separated by chiral HPLC using a Chiralcel AD, 2×25 cm column with 15% EtOH in hexane to give the title products: (A) Methyl 4-{(4S)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate, mp 111-113° C.; $[\alpha]_D^{25}$=-65.6° (c=1% solution, MeOH); MS (APPI) m/z 472 [M+H]$^+$ and (B) methyl 4-{(4R)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate, mp 110-114° C.; $[\alpha]_D^{25}$=+68.2° (c=1% solution, MeOH); MS (APPI) m/z 472 [M+H]$^+$.

EXAMPLE 185

Preparation of (5S)-2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one

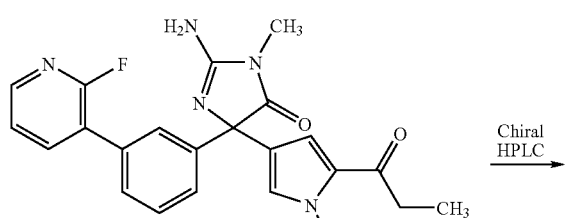

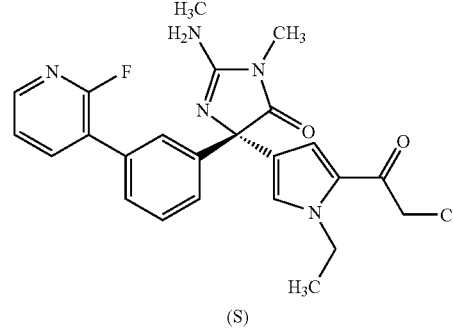

(S)

A racemic mixture of 2-amino-5-(1-ethyl-5-propionyl-1H-pyrrol-3-yl)-5-[3-(2-fluoropyridin-3-yl)phenyl]-3-methyl-3,5-dihydro-4H-imidazol-4-one was separated by chiral HPLC using a Chiralcel AD, 2×25 cm column with 20% EtOH in hexane to give the title product, mp 94-97° C.; $[\alpha]_D^{25}$=-68.85° (c=5.47 MG/0.7 ML, MeOH); MS (ES) m/z 432.1 [M+H]$^+$.

EXAMPLE 186

Preparation of Methyl 44(4S)-2-amino-4-[4-fluoro-3-(2-fluoropyridin-3-yl)phenyl]-1-methyl-5-oxo-4,5-dihydro-1H-imidazol-4-yl}-1-ethyl-1H-pyrrole-2-carboxylate

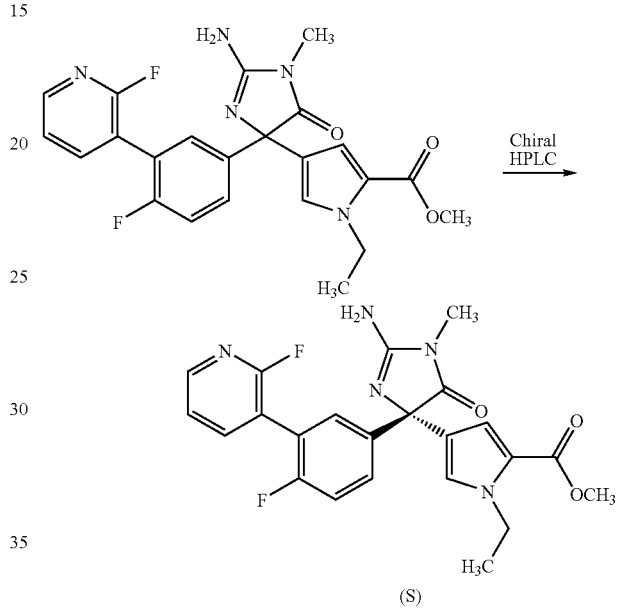

(S)

A racemic mixture of methyl 4-{2-amino-4-[4-fluoro-3-(2-fluoropyridin-3-yl)phenyl]-1-methyl-5-oxo-4,5-dihydro-1H-imidazol-4-yl}-1-ethyl-1H-pyrrole-2-carboxylate was separated by chiral HPLC using a Chiralcel AD, 2×25 cm column with 20% EtOH in hexane to give the title product, mp 114-117° C.; $[\alpha]_D^{25}$=-63.2° (c=1% solution, MeOH); MS (APPI) m/z 454 [M+H]$^+$.

EXAMPLE 187

Preparation of (5S)-5-(5-Acetyl-1-ethyl-1H-pyrrol-3-yl)-2-amino-5-[3-(2-fluoropyridin-3-yl)phenyl]-3-methyl-3,5-dihydro-4H-imidazol-4-one

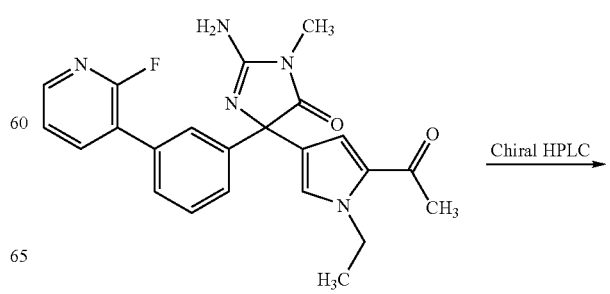

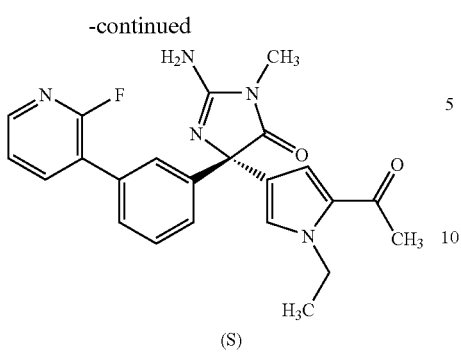

A racemic mixture of 5-(5-acetyl-1-ethyl-1H-pyrrol-3-yl)-2-amino-5-[3-(2-fluoropyridin-3-yl)phenyl]-3-methyl-3,5-dihydro-4H-imidazol-4-one was separated by chiral HPLC using a Chiralcel AD, 2×25 cm column with 20% EtOH in hexane to give the title product, mp 109-111° C.; $[\alpha]_D^{25}$=−60.60°, (c=8.85 MG/0.885 ML, MeOH);

MS (ES) m/z 418.2 $[M+H]^+$.

EXAMPLE 188

Preparation of 2-Amino-5-[1-ethyl-5-(methylsulfonyl)-1H-pyrrol-3-yl]-5-[4-fluoro-3-(2-fluoropyridin-3-yl)phenyl]-3-methyl-3,5-dihydro-4H-imidazol-4-one

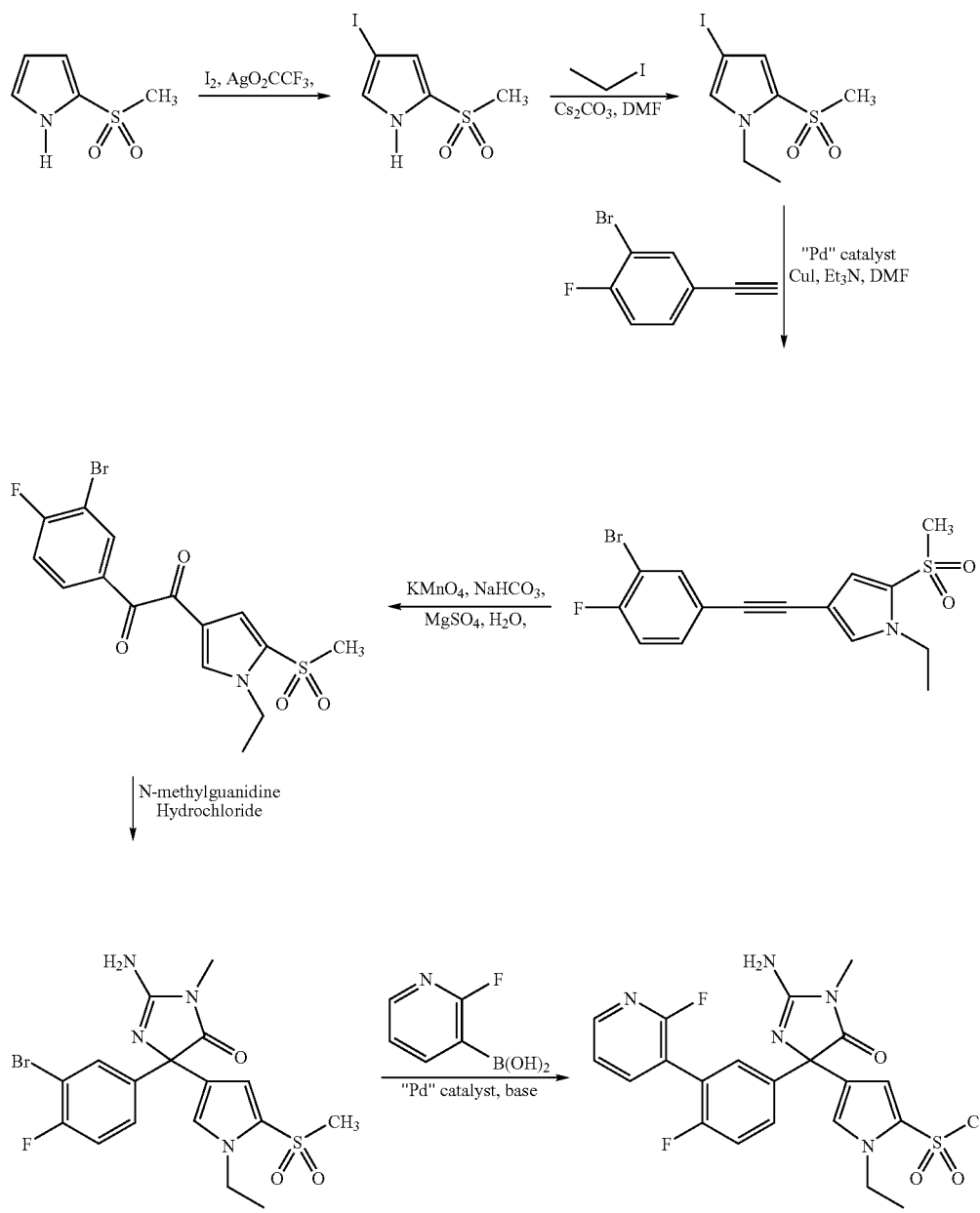

Step 1: 4-Iodo-2-methanesulfonyl-1H-pyrrole

A solution of 2-(methylsulfonyl)pyrrole (0.3 g, 2.06 mmol) in DMF at –10° C. was treated with N-iodosuccinimide (0.49 g, 2.17 mmol), stirred at –10° C. for 3.5 h, poured into $CH_2Cl_2$, washed sequentially with 20% $Na_2CO_3$ and brine. The organic phase was dried ($Na_2SO_4$) and concentrated in vacuo. Chromatography of the resultant residue (silica gel, 5%-40% EtOAc-hexanes as eluent) yielded 0.14 gm (25% yield) of a white solid. $^1H$ NMR (400 MHz, $CDCl_3$) δ: 3.09 (s, 3H), 6.93 (dd, 1H, J=1.5, 2.5 Hz), 7.03 (dd, 1H, J=1.5, 2.8 Hz).

Step 2: 1-Ethyl-4-iodo-2-methanesulfonyl-1H-pyrrole

A solution of 4-iodo-2-methanesulfonyl-1H-pyrrole (0.14 g, 0.52 mmol) in DMF was treated with $Cs_2CO_3$ (0.84 g, 2.58 mmol) and ethyl iodide (0.161 g, 1.03 mmol). The reaction mixture was diluted with EtOAc and washed sequentially with water and brine. The organic phase was separated, dried ($Na_2SO_4$) and concentrated in vacuo. Chromatography of the resultant residue (silica gel, 10%-30% EtOAc-hexanes as eluent) yielded an oil; $^1H$ NMR (400 MHz, $CDCl_3$) δ: 1.47 (t, 3H, J=7.3 Hz), 3.09 (s, 3H), 4.26 (q, 2H, J=7.3 Hz), 6.90 (m, 1H), 6.95 (s, 1H).

Step 3: 4-(3-Bromo-4-fluoro-phenylethynyl)-1-ethyl-2-methanesulfonyl-1H-pyrrole

A solution of 1-ethyl-4-iodo-2-methanesulfonyl-1H-pyrrole (0.28 g, 0.94 mmol) in DMF was treated with dichlorobis(triphenylphosphine)-palladium(II) (0.033 g, 0.05 mmol), triphenylphosphine (0.0054 g, 0.028 mmol) and triethylamine (0.68 mL, 4.9 mmol), treated dropwise with a solution of 2-bromo-4-ethynyl-1-fluorobenzene (0.28 g, 1.4 mmol) in DMF, stirred at room temperature for 18 h, poured into EtOAc and washed sequentially with water and brine. The organic phase is separated, dried ($Na_2SO_4$) and concentrated in vacuo. Chromatography of the resultant residue (silica gel, 2%-20% EtOAC-hexanes as eluent) yielded an oil; $^1H$ NMR (400 MHz, $CDCl_3$) δ: 1.50 (t, 3H, J=7.3 Hz), 3.12 (s, 3H), 4.28 (q, 2H, J=7.3 Hz), 7.01 (d, 1H, J=1.8 Hz), 7.07 (t, 1H, J=8.5 Hz), 7.12 (d, 1H, J=1.8 Hz), 7.37 (m, 1H), 7.66 (dd, 1H, J=2.1, 6.6 Hz).

Step 4: 1-(3-Bromo-4-fluoro-phenyl)-2-(1-ethyl-5-methanesulfonyl-1H-pyrrol-3-yl)-ethane-1,2-dione A solution of 4-(3-bromo-4-fluoro-phenylethynyl)-1-ethyl-2-methanesulfonyl-1H-pyrrole (0.35 g, 0.93 mmol) in acetone was treated with $NaHCO_3$ (0.047 g, 0.56 mmol) and $MgSO_4$ (0.17 g, 1.4 mmol), treated with $KMnO_4$ (0.32 g, 2.05 mmol) and water, stirred at room temperature for 2 h and fitered. The filtercake was washed with EtOAC, dried overnight and washed with EtOAc a second time. The combined filtrates were washed with $H_2O$ and brine, dried ($Na_2SO_4$) and concentrated in vacuo to yield 0.32 gm (86% yield) of an oil. This was used as is in Step 5.

Step 5: 2-Amino-5-(4-bromo-3-fluoro-phenyl)-5-(1-ethyl-5-methanesulfonyl-1H-pyrrol-3-yl)-3-methyl-3,5-dihydro-imidazol-4-one A solution of 1-(3-bromo-4-fluoro-phenyl)-2-(1-ethyl-5-methanesulfonyl-1H-pyrrol-3-yl)-ethane-1,2-dione (0.32 g, 0.79 mmol) in dioxane and EtOH was treated with N-methylguanidine hydrochloride (0.17 g, 1.6 mmol) and $Na_2CO_3$ (0.18 g, 1.66 mmol), heated to 105° C. for 18 h and concentrated in vacuo. The residue was dissolved in $CHCl_3$, washed with $H_2O$ and brine, dried ($Na_2SO_4$) and evaporated to dryness at reduced pressure. Chromatography of this residue (silica gel, EtOAc and 1%-2% MeOH-EtOAc as eluent) yielded a solid; $^1H$ NMR (400 MHz, $CDCl_3$) δ: 1.44 (t, 3H, J=7.3 Hz), 3.08 (s, 3H), 3.10 (s, 3H), 3.97 (brs, 2H), 4.21 (q, 2H, J=7.3 Hz), 6.85 (d, 1H, J=2.1 Hz), 6.90 (d, 1H, J=2.1 Hz), 7.06 (t, 1H, J=8.5 Hz), 7.51 (m, 1H), 7.77 (dd, 1H, J=2.3, 6.6 Hz).

Step 6: 2-Amino-5-[1-ethyl-5-(methylsulfonyl)-1H-pyrrol-3-yl]-5-[4-fluoro-3-(2-fluoropyridin-3-yl)phenyl]-3-methyl-3,5-dihydro-4H-imidazol-4-one A degassed solution of dichlorobis(triphenylphosphine)-palladium(II) (0.016 g, 0.023 mmol), triphenylphosphine (0.012 g, 0.046 mmol) in 2.0 mL of 50:50 EtOH-toluene was treated with $Na_2CO_3$ (0.19 g, 1.8 mmol), 2-fluoropyrinine-3-boronic acid (0.097 g, 0.69 mmol) and a solution of 2-amino-5-(4-bromo-3-fluoro-phenyl)-5-(1-ethyl-5-methanesulfonyl-1H-pyrrol-3-yl)-3-methyl-3,5-dihydro-imidazol-4-one (0.21 g, 0.46 mmol) in 1 mL of degassed 50:50 EtOH-toluene, stirred at 100° C. for 18 h and concentrated in vacuo. The residue was dissolved in $CHCl_3$, washed with $H_2O$ and brine, dried ($Na_2SO_4$) and evaporated to dryness at reduced pressure. Chromatography of the resultant residue (silica gel, EtOAc and 1%-4% MeOH-EtOAc as eluent) yielded the title product, 0.16 gm (74% yield) as a light yellow solid mp 193-195° C. $^1H$ NMR (400 MHz, DMSO-$d_6$) δ: 1.27 (t, 3H, J=7.2 Hz), 2.91 (s, 3H), 3.15 (s, 3H), 4.21 (q, 2H, J=7.2 Hz), 6.63 (d, 1H, J=2.1 Hz), 7.06 (d, 1H, J=2.1 Hz), 7.27 (t, 1H, J=9.3 Hz), 7.45 (m, 1H), 7.63 (m, 1H), 7.97 (m, 1H), 8.27 (m, 1H); MS (ESI) m/z 474.1 ([M+H]$^+$; MS (ESI) m/z 472.1 ([M−H])$^-$.

EXAMPLES 189-199

Preparation of Methyl 4-[2-amino-1-methyl-5-oxo-4-(3-heteroarylphenyl)-4,5-dihydro-1H-imidazol-4-yl]-1-(2-fluoroethyl)-1H-pyrrole-2-carboxylate Compounds

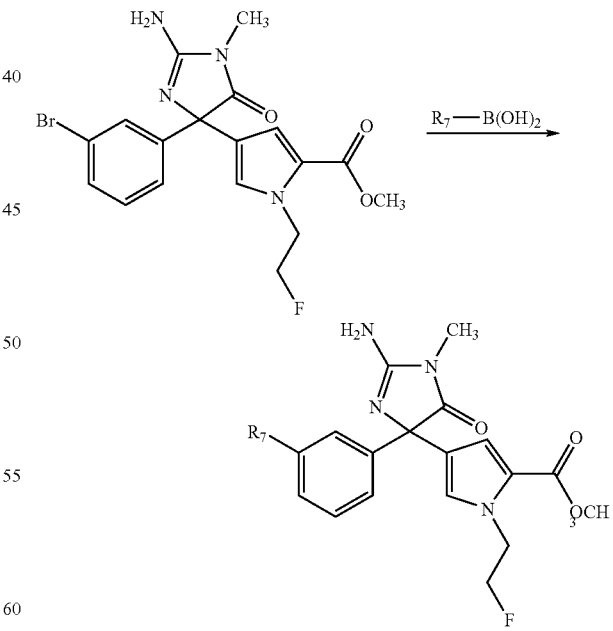

Using essentially the same procedure described in Example 188, Step 6, and employing 4-[2-amino-4-(4-bromo-phenyl)-1-methyl-5-oxo-4,5-dihydro-1H-imidazol-4-yl]-1-(2-fluoro-ethyl)-1H-pyrrole-2-carboxylic acid methyl ester as substrate and the appropriate heteroarylboronic acid, the compounds shown on Table XIV were obtained and identified by HNMR and mass spectral analyses.

TABLE XIV

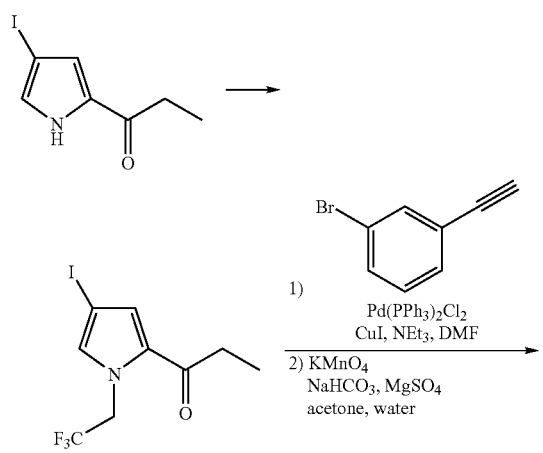

| Ex. No. | R7 | mp (° C.) | (M + H)+ |
|---|---|---|---|
| 189 | pyrimidin-5-yl | 181-184 | 435.1 |
| 190 | 2-fluoropyridin-3-yl | 100 | 452.1 |
| 191 | 6-fluoropyridin-3-yl | 206-210 | 454.1 |
| 192 | 2,5-difluorophenyl | 166-170 | 471.1 |
| 193 | 3,5-difluorophenyl | 173-176 | 471.1 |
| 194 | 3-cyanophenyl | 98-101 | 460.1 |
| 195 | 5-cyano-2-fluorophenyl | 147-150 | 478.1 |
| 196 | 3-methoxyphenyl | 121-124 | 465.5 |
| 197 | 3-(trifluoromethoxy)phenyl | 154-157 | 503.1 |
| 198 | 3,4-difluorophenyl | 125-128 | 471.1 |
| 199 | 1,3-benzodioxol-5-yl | 137-140 | 479.1 |

EXAMPLE 200

Preparation of 2-Amino-5-[5-propionyl-1-(2,2,2-trifluoroethyl)-1H-pyrrol-3-yl]-5-[3-(2-fluoropyridin-3-yl)phenyl]-3-methyl-3,5-dihydro-4H-imidazol-4-one

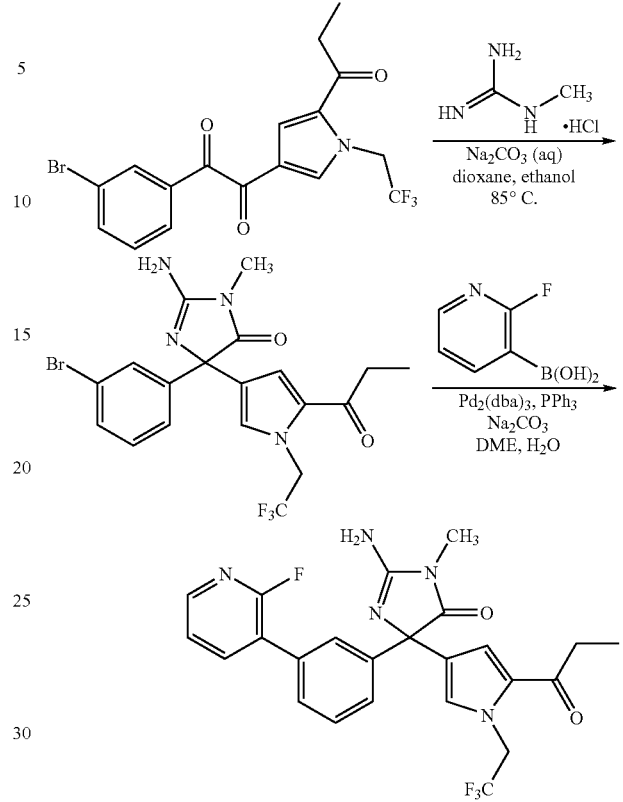

Step a) Preparation of 1-[4-Iodo-1-(2,2,2-trifluoro-ethyl)-1H-pyrrole-2-yl)-propan-1-one:

A mixture of 1-(4-Iodo-1H-pyrrol-2-yl)-propan-1-one (3.8 g, 15.3 mmol), 2-Iodo-1,1,1-trifluoroethane (3.83 g, 18.3 mmol) and $Cs_2CO_3$ (5.96 g, 183 mmol) in 20 ml DMF is heated with stirring to 60° C. for until the reaction is finished (TLC). The mixture then is cooled to room temperature and partitioned between water (200 ml) and ether (100 ml), the ether phase is separated and dried with $MgSO_4$. The product is purified by flash chromatography with solvent EtOAc/hexane (10/90) to afford the product as an oil which solidified upon standing 1.8 g (35%). $^1$HNMR (DMSO-$d_6$): δ (ppm) 1.00 (t, 3H), 2.79 (q, 2H), 5.29 (q, 2H), 7.36 (s, 1H), 7.39 (s, 1H).

Step b) Preparation of 1-(3-bromo-phenyl)-2-[5-propionyl-1-(2,2,2-trifluoro-ethyl)-1H-pyrrole-3-yl]-ethane-1,2-dione:

A mixture of 1-[4-Iodo-1-(2,2,2-trifluoro-ethyl)-1H-pyrrole-2-yl)-propan-1-one (4.8 g, 0.145 mol), 1-bromo-3-ethynyl-benzene (2.62 g, 0.145 mol) CuI (137 mg, 0.725 mmol) and $Pd(PPh_3)_4$ (670 mg, 0.58 mmol) in a mixture of triethylamine (50 ml) and acetonitrile (20 ml) is heated to reflux for 2 hours before cooled down to room temperature. The volatile solvent is removed under reduced pressure, and the residue is partitioned between ethyl acetate (50 ml) and water (200 ml). The organic phase is dried with $MgSO_4$ and is purified by flash chromatography with EtOAc/hexane (10/90-20/80) as eluent to afford the alkyne product as a yellow solid 4.6 g (82%). This solid stirred with $KMnO_4$ (4.73 g, 2.5 mol), $NaHCO_3$ (604 mg, 7.2 mmol) and $MgSO_4$ (2.16 g, 18 mmol) in a mixture of acetone (200 ml) and water (100 ml) at room temperature for two hours. The mixture is extracted with ether (2×50 ml) to afford the product as a yellow oil 4.5 g (90%).

$^1$HNMR (DMSO-d$_6$): δ (ppm) 1.03 (t, 3H), 2.92 (q, 2H), 5.38 (q, 2H) 7.56 (t, 1H), 7.74 (s, 1H), 7.92 (d, 1H), 7.95 (d, 2H), 8.06 (s, 1H), 8.12 (s, 1H).

Step c) Preparation of 2-amino-5-(3-bromophenyl)-5-(1-ethyl-5-propionyl-1H-pyrrol-3-yl)-3-methyl-3,5-dihydro-4H-imidazol-4-one:

A mixture of 1-(3-bromo-phenyl)-2-[5-propionyl-1-(2,2,2-trifluoro-ethyl)-1H-pyrrole-3-yl]-ethane-1,2-dione (4.5 g, 0.0108 mol), methylguanidine (2.36 g, 0.0216 mol) and sodium carbonate (2.28 g, 0.0216 mol) in 100 ml ethanol is heated to reflux for three hours. The solvent is evaporated to dryness and the residue is flash chromatographed on silica gel with eluent EtOAc/Ethanol (containing 2 mol ammonia) to afford the product 3.8 gram (75%) as an off-white solid, mp 100-102° C.,

MS (+) ES 471 [M+H]$^+$.

Step d) Preparation of 2-amino-5-[5-propionyl-1-(2,2,2-trifluoroethyl)-1H-pyrrol-3-yl]-5-[3-(2-fluoropyridin-3-yl)phenyl]-3-methyl-3,5-dihydro-4H-imidazol-4-one:

A mixture of 2-amino-5-(3-bromophenyl)-5-(1-ethyl-5-propionyl-1H-pyrrol-3-yl)-3-methyl-3,5-dihydro-4H-imidazol-4-one (471 mg, 1 mmol), (2-fluoropyridin-3-yl)boronic acid (280 mg, 2 mmol), Pd(PPh$_3$)$_2$Cl$_2$ (35 mg, 0.05 mmol), PPh$_3$ (26.1 mg, 0.1 mmol) and sodium carbonate (315 mg, 3 mmol) in a mixture of toluene/ethanol (50/50) (30 ml) is heated to 110° C. for three hours. The cooled mixture is partitioned between methelene chloride (50 ml) and water (150 ml), the organic phase is separated and dried with MgSO$_4$. The product is purified by flash chromatography with solvent EtOAc/Ethanol (containing 2.0M ammonia) (90/10) to afford the title product as a white solid, 430 mg (89% yield), mp 108-110° C., MS (+) ES 488 [M+H]$^+$.

EXAMPLES 201-208

Preparation of 2-amino-5-[5-propionyl-1-(2,2,2-trifluoroethyl)-1H-pyrrol-3-yl]-5-[3-(heteroaryl)phenyl]-3-methyl-3,5-dihydro-4H-imidazol-4-one Compounds

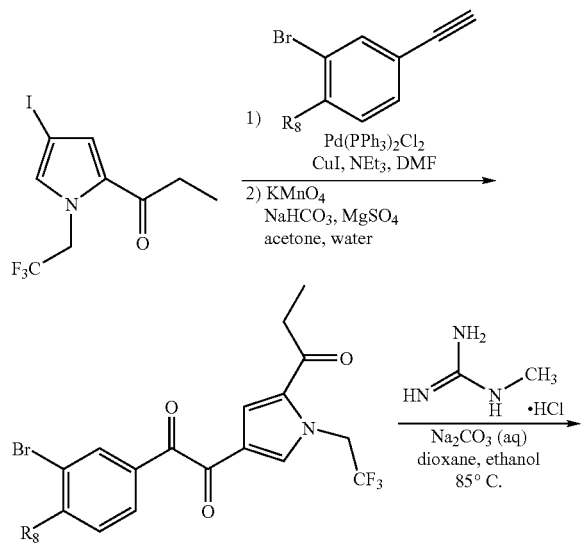

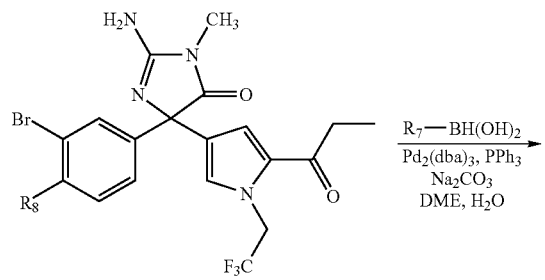

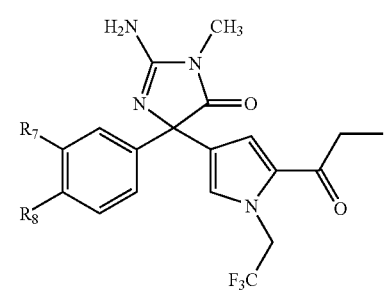

Using essentially the same procedure described in Example 200 and employing the appropriately substituted bromoethynylbenzene and a suitable heteroaryl- or arylboronic acid, the compounds shown in Table XV were obtained and identified by NMR and mass spectral analyses.

TABLE XV

| Ex. No | R7 | R8 | mp ° C. | M + H |
|---|---|---|---|---|
| 201 | pyrimidin-5-yl | H | 135-137 | 471.2 |
| 202 | 3-methoxyphenyl | H | 103-105 | 499.1 |
| 203 | 3,5-difluorophenyl | H | 104-106 | 505.1 |
| 204 | 3-chlorophenyl | H | 108-110 | 503.1 |
| 205 | 3-chloro-4-fluorophenyl | H | 107-108 | 521.0 |
| 206 | 3-cyanophenyl | H | 112-114 | 494.1 |
| 207 | 2-fluoropyridin-3-yl | F | 122-124 | 506.1 |
| 208 | pyrimidin-5-yl | F | 225-226 | 489.2 |

EXAMPLES 209-212

Preparation of 2-Amino-5-[3-(2-fluoropyridin-3-yl)phenyl]-3-methyl-5-(5-carbonyl-1-substituted-1H-pyrrol-3-yl)-3,5-dihydro-4H-imidazol-4-one Compounds

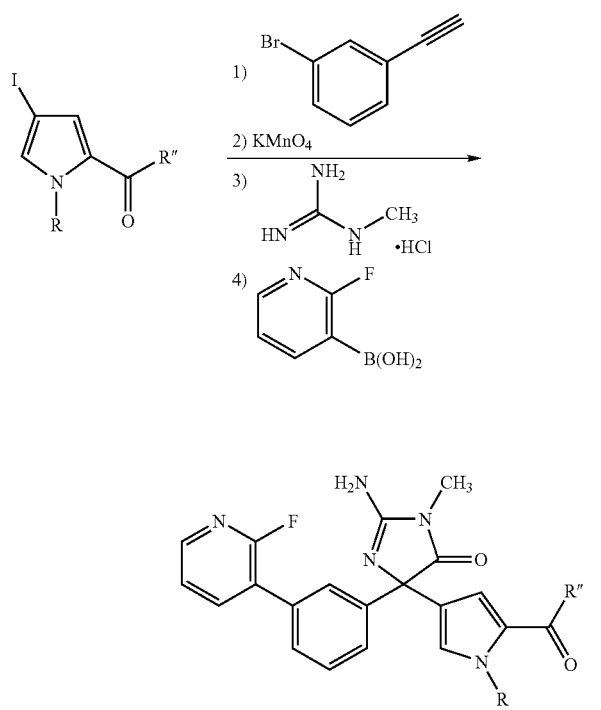

Using essentially the same procedure described in Example 200 and employing the appropriately substituted iodopyrrole, the compounds shown in Table XVI were obtained and identified by NMR and mass spectral analyses.

TABLE XVI

| Ex. No | R | R" | mp °C. |
|---|---|---|---|
| 209 | 3-fluoropropyl | H | 202-204 |
| 210 | 3-fluoropropyl | methyl | 218-221 |
| 211 | H | ethyl | — |
| 212 | 2,2-difluoroethyl | ethyl | — |

EXAMPLE 213

Preparation of 5-[5-acetyl-1-(3-fluoropropyl)-1H-pyrrol-3-yl]-2-amino-5-(3-hydroxyphenyl)-3-methyl-3,5-dihydro-4H-imidazol-4-one

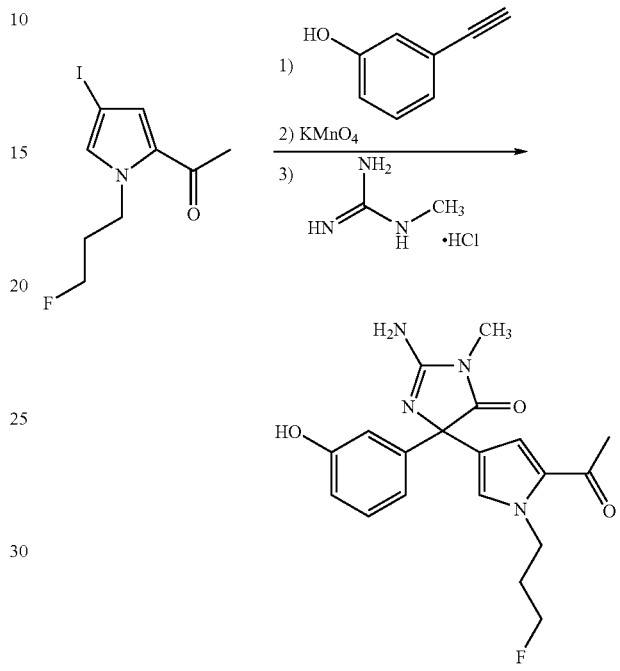

Using essentially the same procedure described in Example 200 and employing the appropriately substituted iodopyrrole and 3-hydroxyphenylethyne, the title compound was obtained as a yellow solid and identified by NMR and mass spectral analyses.

EXAMPLE 214

Preparation of 3-[(3-{4-[5-Acetyl-1-(3-fluoropropyl)-1H-pyrrol-3-yl]-2-amino-1-methyl-5-oxo-4,5-dihydro-1H-imidazol-4-yl}phenoxy)methyl]benzamide

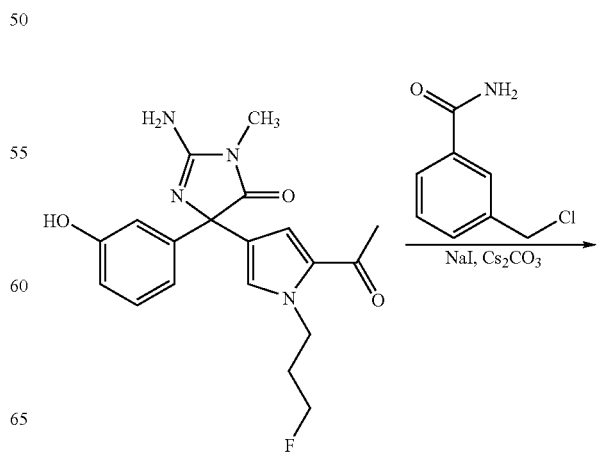

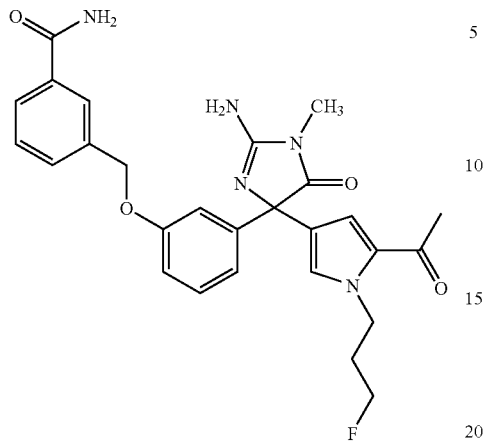

A mixture of 5-[5-acetyl-1-(3-fluoropropyl)-1H-pyrrol-3-yl]-2-amino-5-(3-hydroxyphenyl)-3-methyl-3,5-dihydro-4H-imidazol-4-one, 3-(chloromethyl)benzamide, sodium iodide, and cesium carbonate in dimethylformamide was heated to 45° C. for 16 hours. The cooled reaction mixture was poured into ethyl acetate and washed with water. The organic phase was dried over sodium sulfate and evaporated. The resultant residue was purified by HPLC using a CN bonded phase preparative column and by precipitation from hexane to give the title product as a white solid, identified by NMR and mass spectral analyses.

EXAMPLE 215

Preparation of 5-[5-Acetyl-1-(3-fluoropropyl)-1H-pyrrol-3-yl]-2-amino-3-methyl-5-[3-(2-morpholin-4-yl-2-oxoethoxy)phenyl]-3,5-dihydro-4H-imidazol-4-one

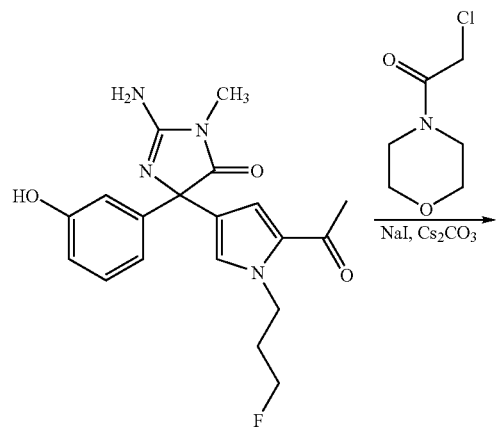

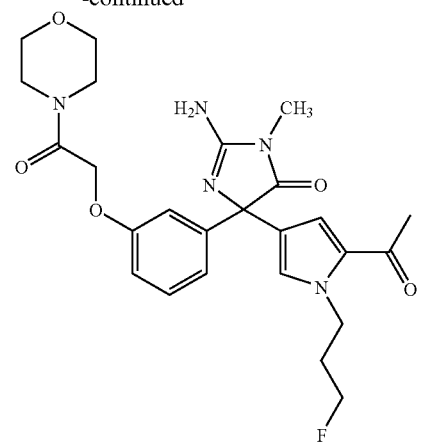

Using essentially the same procedure described in Example T and employing 2-chloro-1-morpholinoethanone, the title compound was obtained as a white solid, identified by NMR and mass spectral analyses.

EXAMPLE 216

Preparation of 442-Amino-1-methyl-5-oxo-4-[3-(phenylethynyl)phenyl]-4,5-dihydro-1H-imidazol-4-yl}-1-(3-fluoropropyl)-1H-pyrrole-2-carbaldehyde

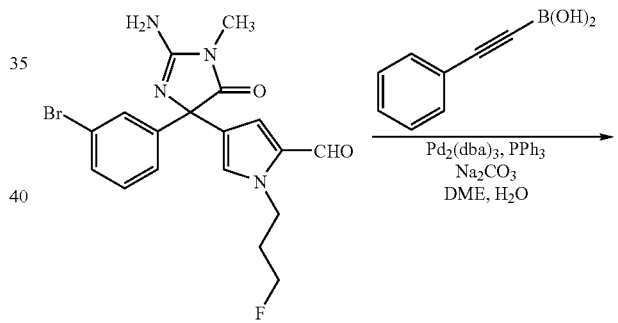

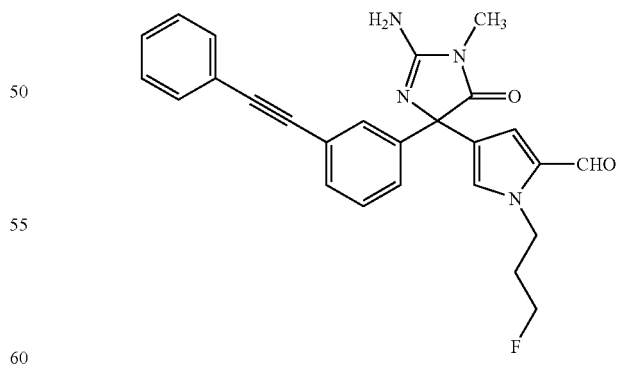

Using essentially the same procedure described in Example 200 and employing 4-{2-amino-1-methyl-5-oxo-4-(3-bromophenyl)-4,5-dihydro-1H-imidazol-4-yl}-1-(3-fluoropropyl)-1H-pyrrole-2-carbaldehyde and phenylethyneboronic acid, the title compound was obtained as a white solid, mp 85-90° C., identified by NMR and mass spectral analyses.

EXAMPLE 217

Preparation of 2-Amino-5-[1-ethyl-5-(methoxymethyl)-1H-pyrrol-3-yl]-5-[3-(2-fluoropyridin-3-yl)phenyl]-3-methyl-3,5-dihydro-4H-imidazol-4-one

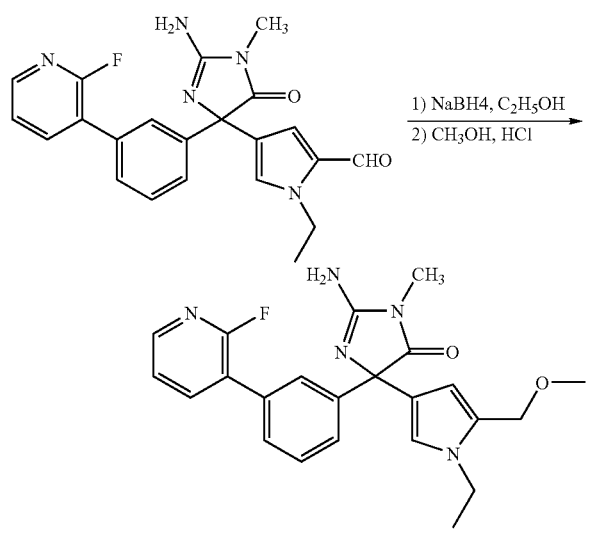

A solution of 4-{2-amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde in dry ethanol was treated with 2 equivalents of sodium borohydride at 0° C., allowed to come to room temperature, quenched with water and evaporated to dryness under reduced pressure. The resultant residue is dispersed in water and extracted with ethyl acetate. The extracts are combined, dried over MgSO4 and concentrated in vacuo. The resultant residue was dissolved in 0.5M methanolic HCl, stirred overnight and evaporated to dryness under reduced pressure. This residue was dissolved in chloroform, washed with dilute sodium bicarbonate, dried over sodium sulfate and concentrated in vacuo. The resultant residue was purified using flash chromatography and was crystallized from ethylacetate/hexane to give the title compound as a solid, mp 154-157° C., identfied by NMR and mass spectral analyses.

EXAMPLES 218-221

Preparation of 2-Amino-5-[1-ethyl-5-(alkoxymethyl)-1H-pyrrol-3-yl]-5-[3-(2-fluoropyridin-3-yl)phenyl]-3-methyl-3,5-dihydro-4H-imidazol-4-one

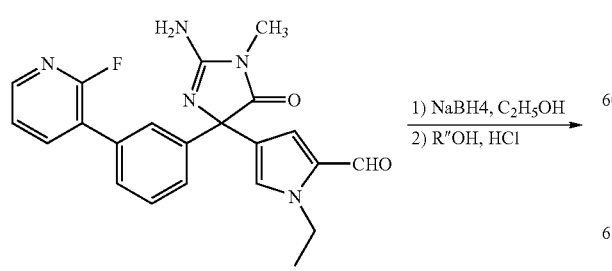

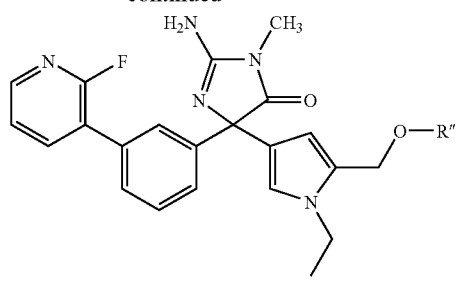

Using essentially the same procedure described in Example 217 and employing the desired alcohol, R"OH, the compounds shown in Table XVii were obtained and identified by NMR and mass spectral analyses.

TABLE XVII

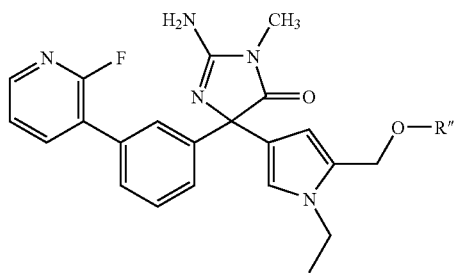

| Ex. No | R" | mp ° C. |
|---|---|---|
| 218 | ethyl | 135-141 |
| 219 | propyl | 128-131 |
| 220 | isopropyl | 126-128 |
| 221 | n-butyl | — |

EXAMPLE 222

Preparation of 4-(2-Amino-4-[3-(2-fluoropyridin-3-yl)phenyl-1-methyl-5-oxo-4,5-dihydro-1H-imidazol-4-yl]-1-(3-fluoropropyl)-1H-pyrrole-2-carbaldehyde oxime

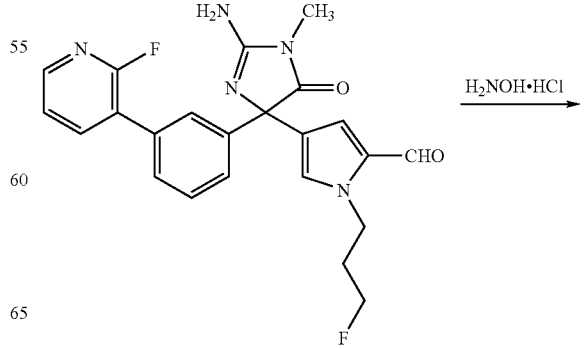

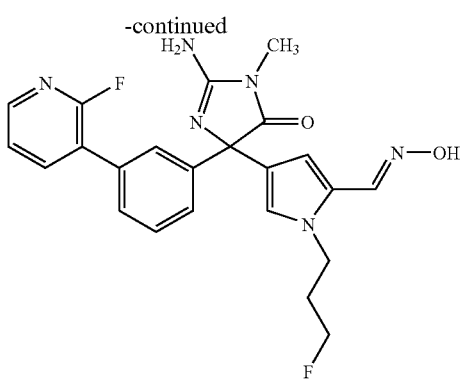

A solution of 4-{2-amino-4-[3-(2-fluoropyridin-3-yl)phenyl]-1-methyl-5-oxo-4,5-dihydro-1H-imidazol-4-yl}-1-(3-fluoropropyl)-1H-pyrrole-2-carbaldehyde in dry tetrahydrofuran was treated with 1.1 equivalent of hydroxylamine hydrochloride, warmed to 45° C. for 2 hours and concentrated in vacuo. The resultant residue was dissolved in chloroform, washed with water, dried over sodium sulfate and concentrated in vacuo. This residue was purified by HPLC (CN bonded stationary phase, gradient 30% to 60% of (20% MeOH/methylene chloride) and hexane to afford the title compound as a white amorphous solid, mp 119-123° C., identified by NMR and mass spectral analyses.

EXAMPLE 223

Preparation of 2-Amino-5-[1-ethyl-5-(4-hydroxybenzyl)-1H-pyrrol-3-yl]-5-[3-(2-fluoropyridin-3-yl)phenyl]-3-methyl-3,5-dihydro-4H-imidazol-4-one

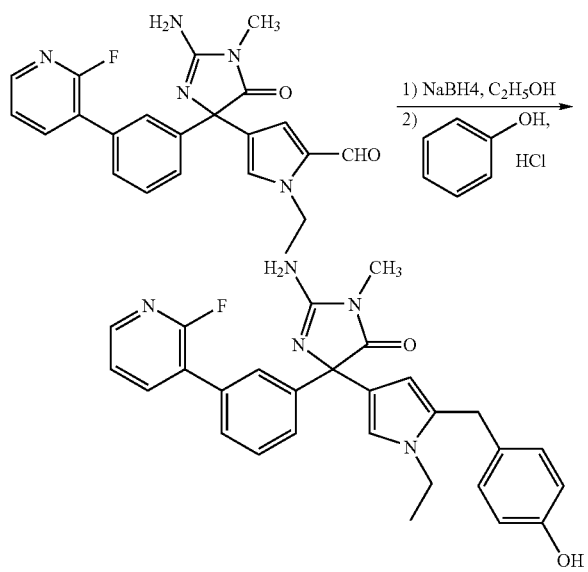

Using essentially the same procedure described in Example 217 and employing phenolic HCl in step 2, the title compound was obtained and identified by NMR and mass spectral analyses. $^1$H NMR (400 MHz, DMSO-d$_6$) δ: 1.04 (t, 3H, J=7.2 Hz), 2.88 (s, 3H), 3.66 (q, 2H, J=7.2 Hz), 3.67 (s, 2H), 5.60 (d, 1H, J=1.9 Hz), 6.52 (d, 2H, J=1.9 Hz), 6.61 (d, 2H, J=8.5 hZ), 6.68 (d, 2H, J=8.5 hZ), 7.38-7.52 (series of m, 4H), 7.66 (s, 1H), 7.94 (m, 1H), and 8.20 (m, 1H).

EXAMPLE 224

Preparation of (5S)-2-amino-5-[3-(2-fluoropyridin-3-yl)phenyl]-3-methyl-5-[5-propionyl-1-(2,22-trifluoroethyl)-1H-pyrrol-3-yl]-3,5-dihydro-4H-imidazol-4-one (A) and (5R)-2-amino-5-[3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one (B)

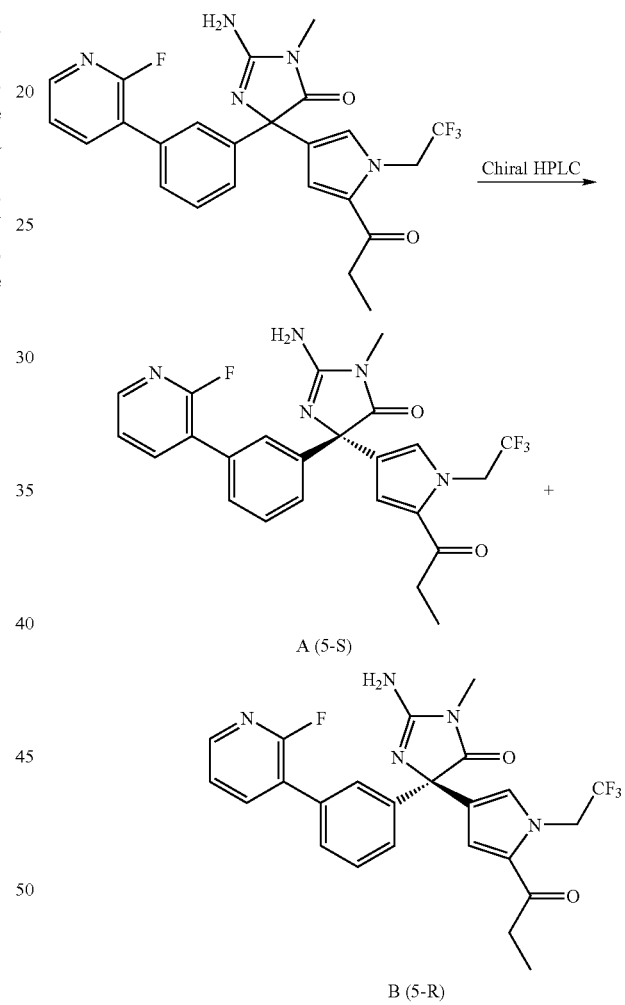

A racemic mixture of 2-amino-5-(1-ethyl-5-propionyl-1H-pyrrol-3-yl)-5-[3-(2-fluoropyridin-3-yl)phenyl]-3-methyl-3,5-dihydro-4H-imidazol-4-one is chirally separated on Chiralcel AD, 50×5 cm, mobile phase 100% ethanol, [α]$_{25}$=−75 (1% DMSO) the S enantiomer title product A is obtained as a white solid, mp 108-110° C., MS (+) ES 488 [M+H]$^+$ and, using mobile phase 100% ethanol, [α]$_{25}$ =+71.8 (1% DMSO), the R enantiomer title product B is obtained as a white solid, mp 108-110° C.,

MS (+) ES 488 [M+H]$^+$.

EXAMPLE 225

Preparation of 4-[2-Amino-1-methyl-5-oxo-4-(3-pyrimidin-5-ylphenyl)-4,5-dihydro-1H-imidazol-4-yl]-1-methyl-1H-pyrrole-2-carbonitrile

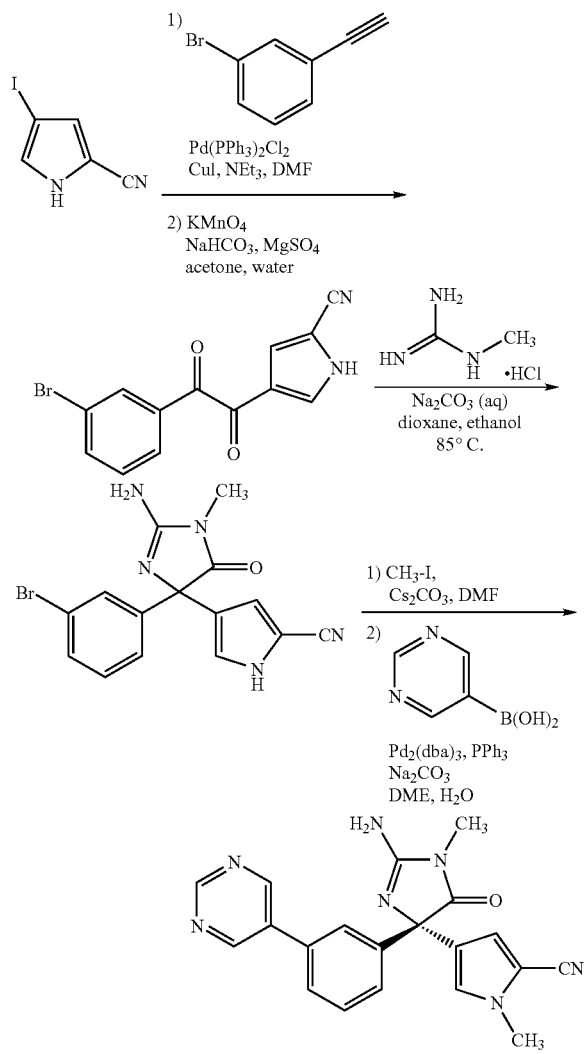

Step a-1) Preparation of 4-(3-Bromo-phenylethynyl)-1H-pyrrole-2-carbonitrile

The dimethylformamide was vigorously deoxygenated with nitrogen gas before use in this reaction. To a solution of 2-cyano-4-iodopyrrole (2.30 g, 10.52 mmol) in dimethylformamide was added dichloropalladium(II) bistriphenylphosphine (185 mg), copper(I) iodide (50 mg) and finally triethylamine (3.85 mL). After stirring ten minutes, 1-bromo-3-ethynyl-benzene (2.38 g, 13.15 mmol) was added. This mixture was stirred overnight at room temperature under nitrogen atmosphere. The reaction mixture was diluted with ethyl acetate and washed with 2% aqueous lithium chloride and 5% aqueous sodium chloride. The organic phase was dried (Na$_2$SO$_4$), filtered and evaporated. The residue was purified by flash chromatography (silica gel, 20% ethyl acetate/hexane) to afford 4-(3-bromo-phenylethynyl)-1H-pyrrole-2-carbonitrile as a yellow solid, 2.84 g, 99% yield.

Step a-2) Preparation of 4-[2-(3-Bromophenyl)-2-oxo-acetyl]-1H-pyrrole-2-carbonitrile A solution of 4-(3-bromo-phenylethynyl)-1H-pyrrole-2-carbonitrile (2.85 g, 10.52 mmol) in acetone was treated with a 45° C. solution of magnesium sulfate (1.90 g, 15.78 mmol) and sodium bicarbonate (0.53 g, 6.31 mmol) in water, immediately treated with KMnO$_4$ (3.74 g, 23.67 mmol), stirred for 15 minutes (TLC (silica gel, 25% ethyl acetate/hexane) indicated complete clean conversion), diluted with EtOAc and washed with water until the washings were colorless. The organic phase was dried (MgSO$_4$), filtered and evaporated. The resultant residue was crystallized to purity from warm ethyl acetate/hexane to afford 4-[2-(3-bromophenyl)-2-oxo-acetyl]-1H-pyrrole-2-carbonitrile as a yellow crystalline solid, 2.68 g, 84% yield.

Step b) Preparation of 4-[2-Amino-4-(3-bromophenyl)-1-methyl-5-oxo-4,5-dihydro-1H-imidazol-4-yl]-1H-pyrrole-2-carbonitrile A mixture of 4-[2-(3-bromophenyl)-2-oxo-acetyl]-1H-pyrrole-2-carbonitrile (2.73 g, 9.0 mmol) and methyl guanidine hydrochloride (1.972 g, 18.0 mmol) in dioxane/ethanol (40 mL/20 mL) was treated with a solution of sodium carbonate (1.91 g, 18.0 mmol) in water. The reaction mixture was heated to 80° C. for ten hours (TLC indicated complete conversion to one more polar material), concentrated in vacuo and redissolved in 5% methanol/chloroform. This solution was dried (Na$_2$SO$_4$), filtered and evaporated. The resultant residue was purified by flash chromatography (silica gel, 5% methanol/chloroform as eluent) to give 4-[2-amino-4-(3-bromophenyl)-1-methyl-5-oxo-4,5-dihydro-1H-imidazol-4-yl]-1H-pyrrole-2-carbonitrile as a beige glass, 2.40 g (74.5% yield).

Step c-1) Preparation of 4-[2-Amino-4-(3-bromophenyl)-1-methyl-5-oxo-4,5-dihydro-1H-imidazol-4-yl]-1-methyl-1H-pyrrole-2-carbonitrile To a solution of 4-[2-amino-4-(3-bromophenyl)-1-methyl-5-oxo-4,5-dihydro-1H-imidazol-4-yl]-1H-pyrrole-2-carbonitrile (0.50 g, 1.40 mmol) in dimethylformamide was added cesium carbonate (0.639 g, 1.96 mmol) and methyl iodide (96 μL, 1.54 mmol). The reaction mixture was stirred overnight at room temperature while protected from moisture, diluted with chloroform and washed well with water. The organic phase was dried (Na$_2$SO$_4$), filtered through a short column of silica gel and evaporated to afford the desired compound as a tan solid, 0.524 g (quantitative yield).

Step c-2) Preparation of 4-[2-Amino-1-methyl-5-oxo-4-(3-pyrimidin-5-ylphenyl)-4,5-dihydro-1H-imidazol-4-yl]-1-methyl-1H-pyrrole-2-carbonitrile The toluene/ethanol (1/1) solvent mixture was deoxygenated vigorously with nitrogen gas prior to using in this reaction. A mixture of 4-[2-amino-4-(3-bromophenyl)-1-methyl-5-oxo-4,5-dihydro-1H-imidazol-4-yl]-1-methyl-1H-pyrrole-2-carbonitrile (173 mg, 0.465 mmol), sodium carbonate (148 mg, 1.394 mmol), pyrimidine-5-boronic acid (86.4 mg, 0.697 mmol) and tetrakis(triphenylphosphine)palladium(0) (27 mg, 0.023 mmol) in toluene/ethanol (1/1) solvent mixture (10 mL) was heated in a 100° C. oil bath for eight hours. TLC (5% methanol/chloroform) shows complete conversion to a new material. The solvent was removed by evaporation and the residue dissolved in chloroform and washed with water. The organic phase was dried (Na$_2$SO$_4$), filtered and evaporated. The resultant residue was purified by HPLC (Luna CN column, normal mobile phase). Crystallization from warm ethyl acetate/hexane afforded the title product as a pure crystalline material, mp 214-225° C.; MS (ES) m/z 370.1.

EXAMPLES 226-232

Preparation of 4-[2-Amino-1-methyl-5-oxo-4-(3-heteroarylphenyl)-4,5-dihydro-1H-imidazol-4-yl]-1-alkyl-1H-pyrrole-2-carbonitrile Compounds

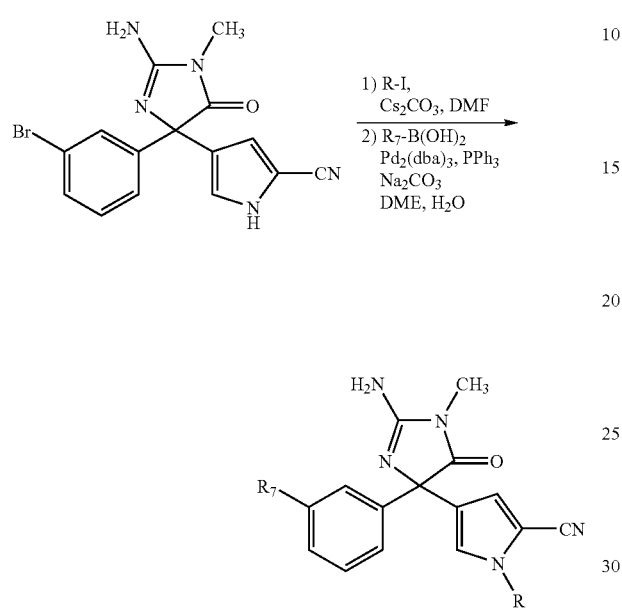

Using essentially the same procedure described in Example 225 and employing the appropriate alkyl iodide and a suitable heteroarylboronic acid, the compounds shown on Table XVIII were obtained and identified by NMR and mass spectral analyses.

TABLE XVIII

| Ex. No | R | R7 | mp °C. | MS m/z |
|---|---|---|---|---|
| 226 | $CH_3$ | 2-fluoropyridin-3-yl | 213-220 | 387.1 |
| 227 | $CH_3$ | 2-chloro-5-fluoropyridin-3-yl | >225 | 421.0 |
| 228 | $CH_2CH_2F$ | pyrimidin-5-yl | 193-194 | 402.1 |
| 229 | propyl | pyrimidin-5-yl | 165-166 | — |
| 230 | propyl | 2-fluoropyridin-3-yl | 187-188 | — |
| 231 | $CH_2CH_2F$ | 2-fluoropyridin-3-yl | 175-177 | — |
| 232 | propyl | 2-chloro-5-fluoropyridin-3-yl | 132-134 | — |

EXAMPLE 233

Preparation of 4-{2-amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde

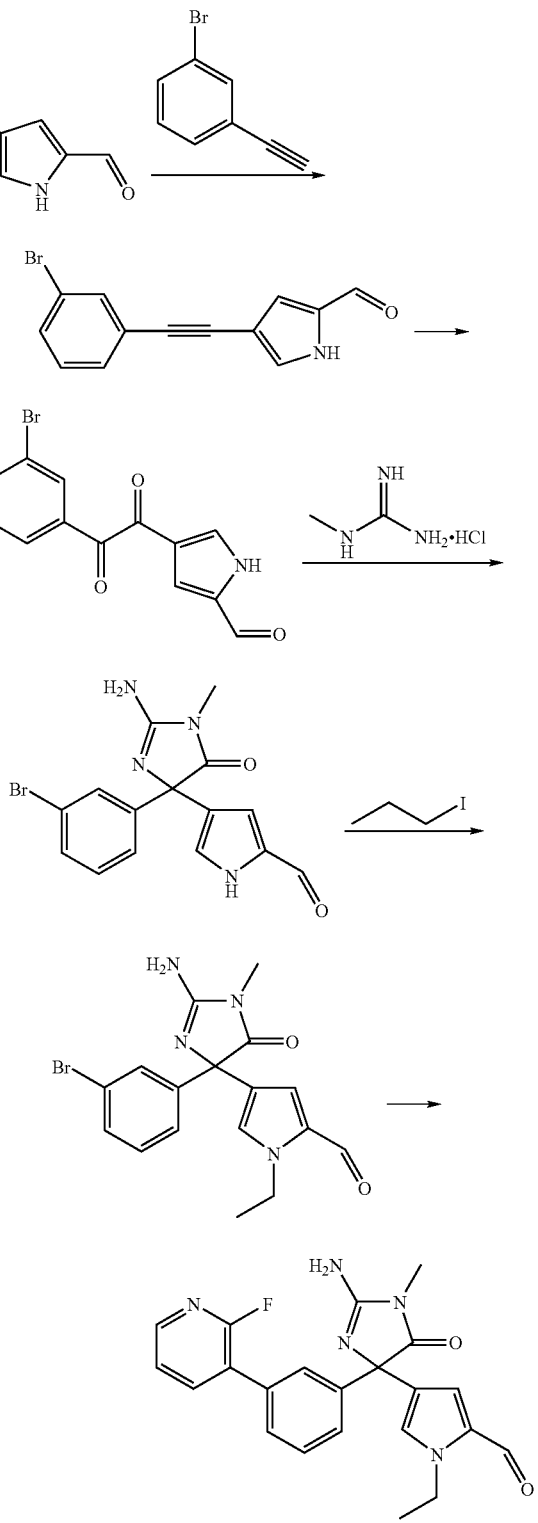

Step a) Preparation of 4-[(3-Bromophenyl)ethynyl]-1H-pyrrole-2-carbaldehyde

A solution of 4-iodo-1H-pyrrole-2-carbaldehyde (0.50 g; 2.262 mmol) and bis(triphenylphosphine)palladium-(II) chloride (0.079 g; 0.113 mmol)) in DMF (15 mL; degassed with nitrogen for 30 minutes) was stirred at ambient temperature for 15 minutes. Then the following were added: 1-bromo-3-ethynylbenzene (0.61 g; 3.394 mmol), copper iodide (43 mg; 0.226), and triethylamine (1.58 mL, 11.3 mmol). The course of the reaction was followed with TLC (4:1, hexane: ethyl acetate). After 2 hours the reaction mixture was diluted with water and the organic material was extracted into dichloromethane. The organic extracts were washed with water and brine, dried over MgSO$_4$, filtered, and evaporated. The residue was chromatographed on silica gel using 3:1 hexane: ethyl acetate to yield 0.58 g (93%) of the title compound as a yellow crystalline solid, mp 152-156° C.; MS (ES) m/z 272.0, [M−H]−.

Step b) Preparation of 4-[(3-Bromophenyl)(oxo)acetyl]-1H-pyrrole-2-carbaldehyde

To DMSO was added 4-[(3-bromophenyl)ethynyl]-1H-pyrrole-2-carbaldehyde (1.50 g; 5.47 mmol), and palladium (II)chloride (97 mg; 0.547 mmol). The resulting solution was stirred at 140° C. for one hour. The mixture was cooled to ambient temperature and diluted with water. The product was extracted into chloroform and dried over MgSO$_4$. The resulting solid was chromatographed on silica gel using 7:3 hexane: ethyl acetate to give 1.21 g of the title compound as a greenish crystalline solid (72% yield), mp 202-203° C.; MS (ES) m/z 304.0, [M−H]−.

Step c) Preparation of 4-[2-Amino-4-(3-bromophenyl)-1-methyl-5-oxo-4,5-dihydro-1H-imidazol-4-yl]-1H-pyrrole-2-carbaldehyde To a solution of 4-[(3-bromophenyl)(oxo)acetyl]-1H-pyrrole-2-carbaldehyde (0.10 g; 0.32 mmol), and sodium carbonate (0.038 g; 0.359 mmol) in ethanol (5 mL), was added 1-methylguanidine hydrochloride (0.039 g; 0.359 mmol). The mixture was stirred at 85° C. for four hours. The ethanol was evaporated and the residue was taken up in chloroform and washed twice with water. The solution was dried over MgSO$_4$, filtered and evaporated. The product was crystalized by cooling a hot, saturated ethyl acetate solution to give the title compound, 0.085 g (72% yield), mp 142-151° C.; MS (ES) m/z 361.0, [M+H]+.

Step d) Preparation of 4-[2-Amino-4-(3-bromophenyl)-1-methyl-5-oxo-4,5-dihydro-1H-imidazol-4-yl]-1-ethyl-1H-pyrrole-2-carbaldehyde In DMF, (7 mL) is dissolved 4-[2-amino-4-(3-bromophenyl)-1-methyl-5-oxo-4,5-dihydro-1H-imidazol-4-yl]-1H-pyrrole-2-carbaldehyde (1.50 g; 4.15 mmol). To this solution is added cesium carbonate (1.35 g; 4.15 mmol) and iodoethane (0.43 mL; 5.4 mmol), and the mixture is stirred for 20 hours at room temperature. The mixture is diluted to 50 mL with chloroform, washed twice with water, dried over MgSO$_4$, filtered, and evaporated. The residue was crystallized in ethyl acetate to give the title product as light-brown crystals, 1.18 g (73% yield), mp 194-195° C.; MS (ES) m/z 387.0, [M−H]−.

Step e) Preparation of 4-{2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde A 1:1 mixture of toluene and ethanol was sparged with nitrogen for 30 minutes. To the solvent was added 4-[2-amino-4-(3-bromophenyl)-1-methyl-5-oxo-4,5-dihydro-1H-imidazol-4-yl]-1-ethyl-1H-pyrrole-2-carbaldehyde (1.10 g; 3.04 mmol), 2-fluoro-3-pyridineboronic acid (0.69 g; 4.9 mmol), sodium carbonate (1.03 g; 9.75 mmol), and tetrakis[triphenylphosphine]-palladium(0) (0.53 g; 0.46 mmol). This mixture was heated at reflux temperature for three hours. The solvents were evaporated and the residue was crystallized in CHCl$_3$ and water to give the title as grey crystals, 0.91 g (74% yield), mp 198-201° C.; MS (ES) m/z 406.2, [M+H]+.

EXAMPLE 234

Preparation of 4-[2-Amino-4-[3-(2-fluoropyridin-3-yl)phenyl]-1-methyl-5-oxo-4,5-dihydro-1H-imidazol-4-yl)-1-(2-fluoroethyl)-1H-pyrrole-2-carbaldehyde

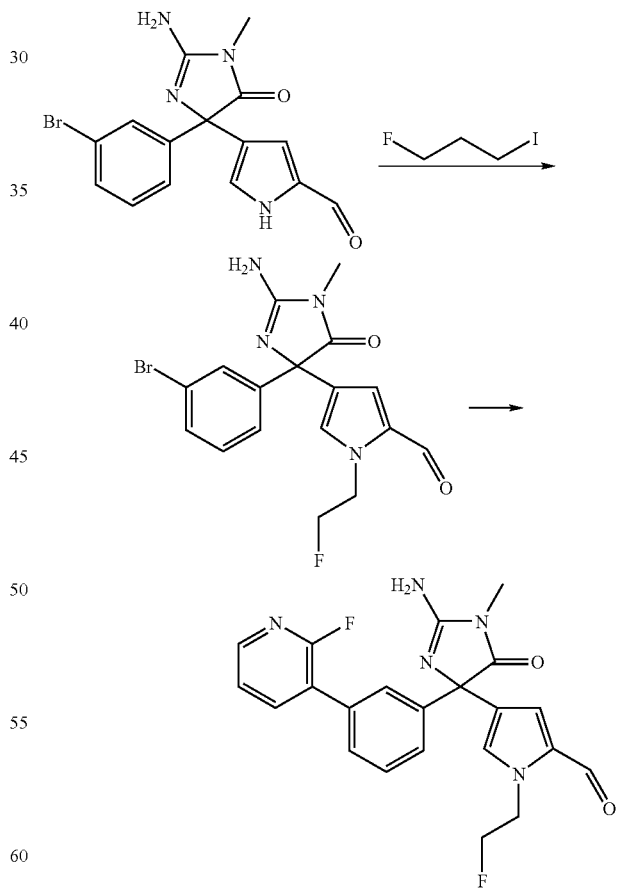

Using essentially the same procedure described in Example 233 and employing 2-fluoroethyl iodide as reagent, the title compound was obtained, mp 218-221° C.; MS (APPI) m/z 424, [M+H]+.

EXAMPLE 235

Preparation of 2-Amino-5-[5-[(diethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one

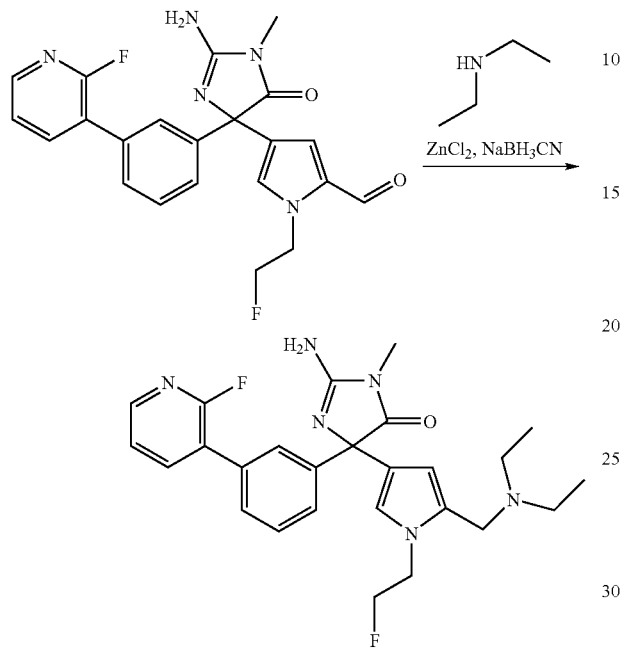

To a glass tube was added methanol (0.5 mL), 4-{2-amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carbaldehyde (0.05 g; 0.12 mmol), diethylamine (43 µL; 0.41 mmol), and 1.8 mL of a methanolic solution of $ZnCl_2$ (0.1 M), and $NaBH_3CN$ (0.2 M). The mixture was stirred 24 hours at room temperature. The solvent was evaporated and the residue was dissolved in chloroform, washed with 0.1 N NaOH solution, dried over $MgSO_4$, and evaporated to give the title compound as an amorphous white solid, 0.021 g (37% yield), mp 121-140° C.; MS (ES) m/z 479.2, [M−H]−.

EXAMPLES 236-238

Preparation of 2-Amino-5-[5-[(substitutedamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one Compounds

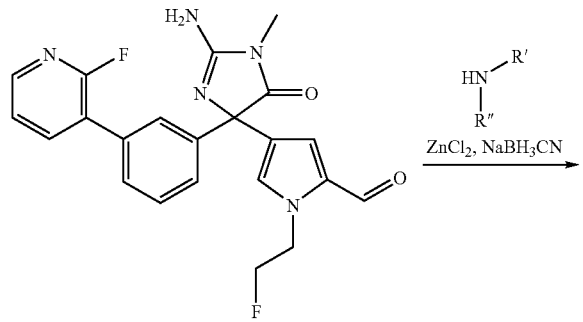

-continued

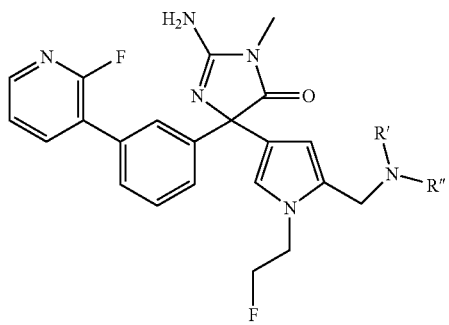

Using essentially the same procedure described in Example 235 and employing the appropriate amine, the compounds shown on Table XIX were obtained and identified by NMR and mass spectral analyses.

TABLE XIX

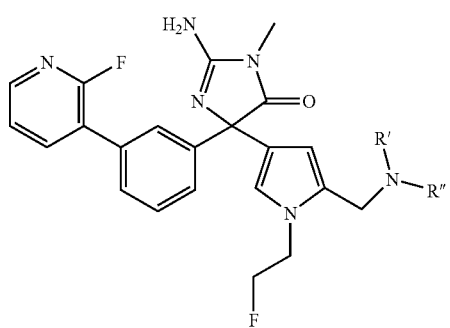

| Ex. No | R' | R" | mp ° C. | MS m/z |
|---|---|---|---|---|
| 236 | H | isopropyl | 98-99 | 465.2 |
| 237 | —CH₂CH₂CH₂CH₂— | | 110-120 | 477.2 |
| 238 | CH₃ | CH₃ | 118-121 | 451.1 |

EXAMPLE 239

Preparation of 2-Amino-5-[1-ethyl-5-(hydroxymethyl)-1H-pyrrol-3-yl]-5-[3-(2-fluoropyridin-3-yl)phenyl]-3-methyl-3,5-dihydro-4H-imidazol-4-one

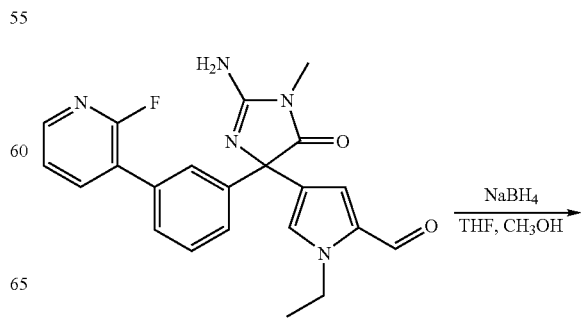

-continued

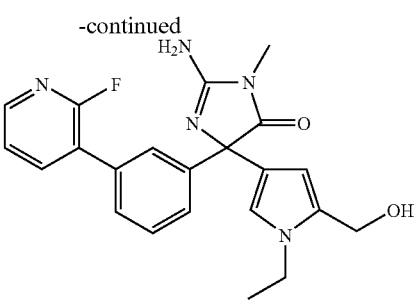

A solution of 4-{2-amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde (0.071 g; 0.25 mmol) in THF (20 mL) and methanol (5 mL) was stirred at ambient temperature as an excess of $NaBH_4$ (0.071 g; 1.88 mmol) was added. After one hour the solvents were evaporated and the residue was taken up into dichloromethane and washed with water. The dichloromethane phase was dried over $MgSO_4$, filtered, and evaporated. The resultant residue was crystallized from ethyl acetate and hexane to obtain the title product as a white solid, mp 170-172° C.; MS (ES) m/z 406.1; [M−H]−

EXAMPLE 240

Preparation of 2-Amino-5-[1-ethyl-5-(1-hydroxypropyl)-1H-pyrrol-3-yl]-5-[3-(2-fluoropyridin-3-yl)phenyl]-3-methyl-3,5-dihydro-4H-imidazol-4-one

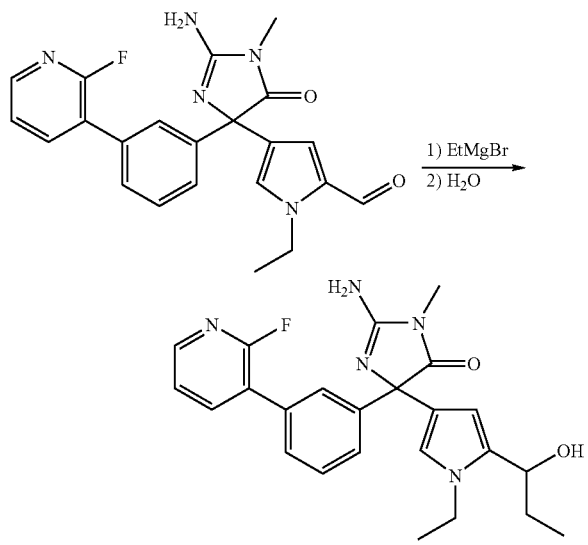

A mixture of 4-{2-amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde (0.10 g; 0.25 mmol) in THF (5 mL; anhydrous) was stirred and cooled to −15° C. To this was added an excess of EtMgBr (3.1 eq; 0.25 mL of 3.0 M solution in hexane), dropwise. The mixture was stirred at −15° C. for one hour. The reaction was worked up by carefully adding 1.0 mL of saturated aqueous ammonium chloride solution, diluting with dichloromethane (30 mL) and washing with water. The organic phase was dried over $MgSO_4$, filtered and evaporated. Two products were separated from the crude mixture by chromatography on silica gel. The column was eluted with a chloroform/methanol mixture on a gradient (9:1 through 7:3). The more polar product was isolated and crystallized from ethyl acetate/hexane to give the title product as white crystals, 0.05 g (46% yield), mp 115-121° C.; MS (ES) m/z 434.2; [M−H]−

EXAMPLE 241

Preparation of 442-Amino-4-[3-(2-fluoropyridin-3-yl)phenyl]-1-methyl-5-oxo-4,5-dihydro-1H-imidazol-4-yl-1-ethyl-1H-pyrrole-2-carbaldehyde O-methyloxime hydrochloride

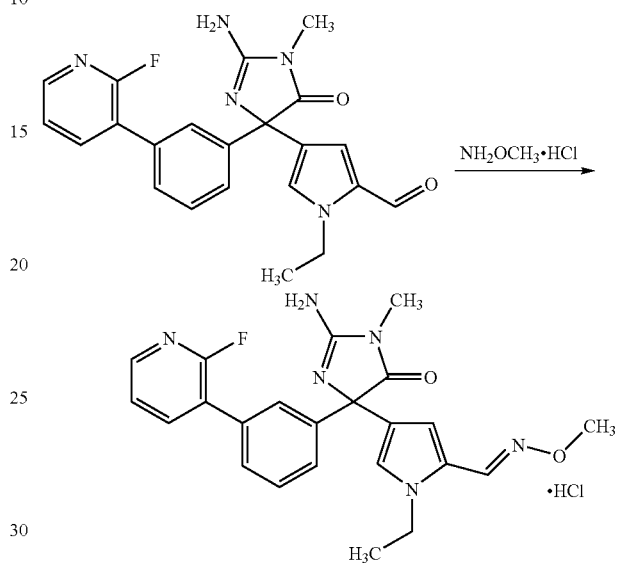

A stirred suspension of 4-{2-amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde (0.10 g; 0.25 mmol), in THF (5 mL), was added methoxylamine hydrochloride (0.021 g; 0.25 eq). The mixture was stirred at reflux temperature for 2 hours. The mixture was cooled and the solvent was evaporated. The residue was dissolved in dichloromethane and washed with water. The dichloromethane solution was dried over $MgSO_4$, filtered and evaporated. The resultant residue was crystallized from ethyl acetate and hexane to yield the title compound, 0.069 g (64% yield), mp 190-193° C., MS (ES) m/z 433.1; [M−H]−

EXAMPLE 242

Preparation of (5S)-2-Amino-5-[3-(2,5-difluoropyridin-3-yl)phenyl]-5-[1-(2-fluoroethyl)-5-propionyl-1H-pyrrol-3-yl]-3-methyl-3,5-dihydro-4H-imidazol-4-one (A) and (5R)-2-Amino-5-[3-(2,5-difluoropyridin-3-yl)phenyl]-5-[1-(2-fluoroethyl)-5-propionyl-1H-pyrrol-3-yl]-3-methyl-3,5-dihydro-4H-imidazol-4-one (B)

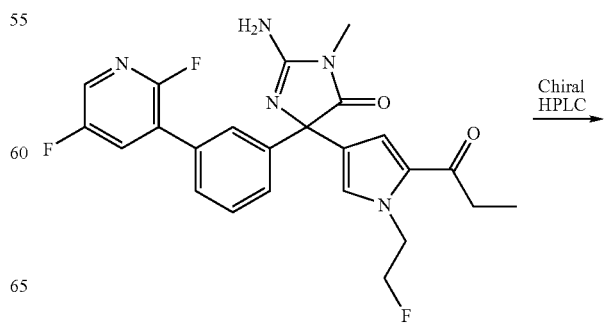

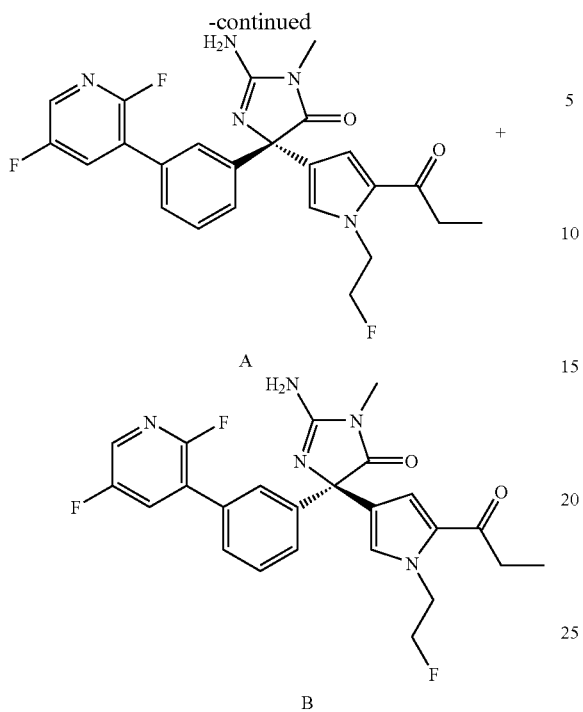

A

B

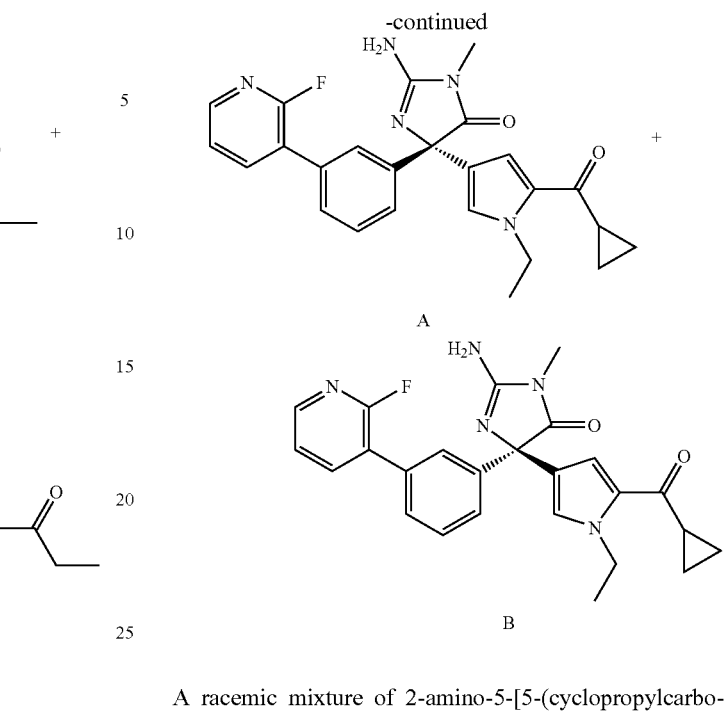

A

B

A racemic mixture of 2-amino-5-[3-(2,5-difluoropyridin-3-yl)phenyl]-5-[1-(2-fluoroethyl)-5-propionyl-1H-pyrrol-3-yl]-3-methyl-3,5-dihydro-4H-imidazol-4-one was separated by chiral HPLC using a Chiralcel AD, 0.46×25 cm (column) with mobile phase 8:2 hexane:isopropanol (0.1% diethtylamine) to give the title products: A (5S) isomer, $^1$H NMR (DMSOd$_6$ 300 MHz) δ 0.98 (s, 3H), 2.76 (q, 2H), 3.9 (s, 3H), 4.45 (s, 2H), 4.6 (m, 2H), 6.6 (brs, 2H), 6.95 (s, 1H), 7.4 (m, 2H), 7.6 (d, 1H), 7.78 (s, 1H), 8.0 (m, 1H), 8.2 (d, 1H); MS m/e (M+H)$^+$ 470; [α]=−72.2 (1% solution in MeOH) and B (5R) isomer, $^1$H NMR (DMSOd$_6$300 MHz) δ 0.98 (s, 3H), 2.76 (q, 2H), 3.9 (s, 3H), 4.45 (s, 2H), 4.6 (m, 2H), 6.6 (brs, 2H), 6.95 (s, 1H), 7.4 (m, 2H), 7.6 (d, 1H), 7.78 (s, 1H), 8.0 (m, 1H), 8.2 (d, 1H); MS m/e (M+H)$^+$ 470; [α]=+77.2 (1% solution in MeOH).

A racemic mixture of 2-amino-5-[5-(cyclopropylcarbonyl)-1-ethyl-1H-pyrrol-3-yl]-5-[3-(2-fluoropyridin-3-yl)phenyl]-3-methyl-3,5-dihydro-4H-imidazol-4-one was separated by chiral HPLC using a Chiralcel AD, 5×25 cm (column) with mobile phase 22% EtOH in hexane to give the title products: A (5S) isomer, $^1$H NMR (DMSOd$_6$ 300 MHz) δ 0.9 (m, 4H), 1.05 (t, 3H), 1.1 (m. 1H), 3.95 (s, 3H), 4.1 (q, 2H), 6.6 (brs, 2H), 7.05 (s, 1H), 7.1 (s, 1H), 7.4 (m, 3H), 7.6 (m, 1H), 7.7 (s, 1H), 8.0 (m, 1H), 8.2 (m, 1H); MS m/e (M+H)$^+$ 446; [α]=−73 (1% solution in MeOH); and B (5R) isomer, $^1$H NMR (DMSOd$_6$ 300 MHz) δ 0.9 (m, 4H), 1.05 (t, 3H), 1.1 (m. 1H), 3.95 (s, 3H), 4.1 (q, 2H), 6.6 (brs, 2H), 7.05 (s, 1H), 7.1 (s, 1H), 7.4 (m, 3H), 7.6 (m, 1H), 7.7 (s, 1H), 8.0 (m, 1H), 8.2 (m, 1H); MS m/e (M+H)$^+$ 446; [α]=+70.4 (1% solution in MeOH).

EXAMPLE 243

Preparation of (5S)-2-Amino-5-[5-(cyclopropylcarbonyl)-1-ethyl-1H-pyrrol-3-yl]-5-[3-(2-fluoropyridin-3-yl)phenyl]-3-methyl-3,5-dihydro-4H-imidazol-4-one (A) and (5R)-2-Amino-5-[5-(cyclopropylcarbonyl)-1-ethyl-1H-pyrrol-3-yl]-5-[3-(2-fluoropyridin-3-yl)phenyl]-3-methyl-3,5-dihydro-4H-imidazol-4-one (B)

EXAMPLE 244

Preparation of (5S)-2-Amino-5-[3-(2-fluoropyridin-3-yl)phenyl]-3-methyl-5-(5-propionyl-3-thienyl)-3,5-dihydro-4H-imidazol-4-one (A) and (5R)-2-Amino-5-[3-(2-fluoropyridin-3-yl)phenyl]-3-methyl-5-(5-propionyl-3-thienyl)-3,5-dihydro-4H-imidazol-4-one (B)

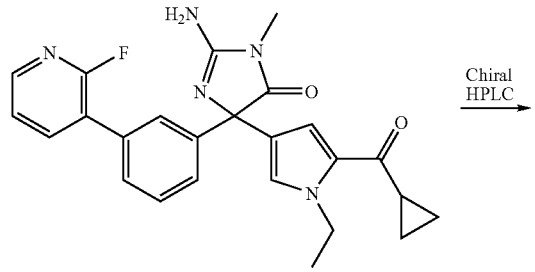

Chiral HPLC →

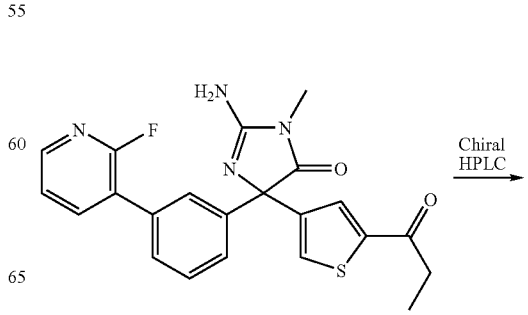

Chiral HPLC →

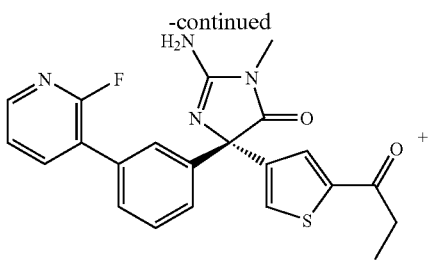

A

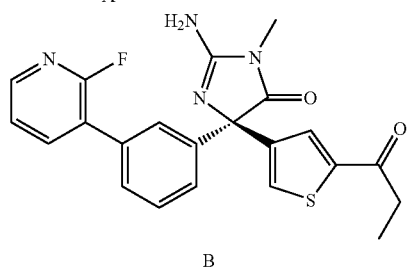

B

A racemic mixture of 2-amino-5-[3-(2-fluoropyridin-3-yl) phenyl]-3-methyl-5-(5-propionyl-3-thienyl)-3,5-dihydro-4H-imidazol-4-one was separated by chiral HPLC using a Chiralcel AD, 0.46×10 cm (column) with mobile phase 100% EtOH with 0.1% DEA to give the title products: A (5S) isomer, $^1$H NMR (500 MHz, CDCl$_3$) δ 8.19 (dt, J=4.7, 1.4 Hz, 1H), 7.85-7.81 (m, 1H), 7.78-7.69 (m, 3H), 7.61-7.55 (m, 1H), 7.52-7.48 (m, 1H), 7.43 (t, J=7.7 Hz, 1H), 7.29-7.23 (m, 1H), 3.12 (s, 3H), 2.88 (q, J=7.3 Hz, 2H), 1.17 (t, J=7.3 Hz, 3H); ESI MS m/z 423; [α]=−78.6 (1% solution in MeOH); and B (5R) isomer, $^1$H NMR (500 MHz, CDCl$_3$) δ 8.19 (dt, J=4.7, 1.4 Hz, 1H), 7.85-7.81 (m, 1H), 7.78-7.69 (m, 3H), 7.61-7.55 (m, 1H), 7.52-7.48 (m, 1H), 7.43 (t, J=7.7 Hz, 1H), 7.29-7.23 (m, 1H), 3.12 (s, 3H), 2.88 (q, J=7.3 Hz, 2H), 1.17 (t, J=7.3 Hz, 3H); ESI MS m/z 423; [α]=+71.8 (1% solution in MeOH).

EXAMPLE 245

Preparation of (5R)-2-Amino-3-methyl-5-phenyl-5-(5-propionyl-3-thienyl)-3,5-dihydro-4H-imidazol-4-one (A) and (5S)-2-Amino-3-methyl-5-phenyl-5-(5-propionyl-3-thienyl)-3,5-dihydro-4H-imidazol-4-one

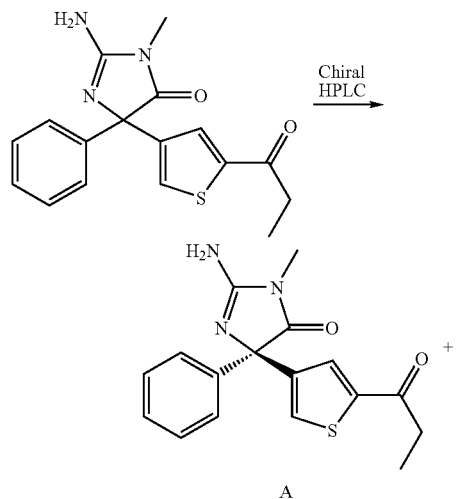

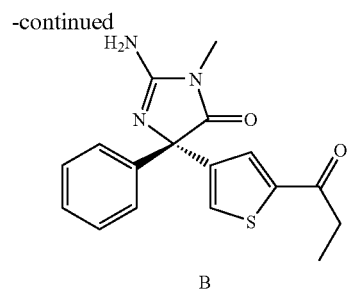

B

A racemic mixture of 2-amino-3-methyl-5-phenyl-5-(5-propionyl-3-thienyl)-3,5-dihydro-4H-imidazol-4-one was separated by chiral HPLC using a Chiralcel AD, 0.46×10 cm (column) with mobile phase 12% IPA with DEA in CO$_2$ to give the title products: A (5R) isomer, $^1$H NMR (DMSOd$_6$ 300 MHz) δ 0.98 (s, 3H), 2.76 (q, 2H), 3.9 (s, 3H), 4.45 (s, 2H), 4.6 (m, 2H), 6.6 (brs, 2H), 6.95 (s, 1H), 7.4 (m, 2H), 7.6 (d, 1H), 7.78 (s, 1H), 8.0 (m, 1H), 8.2 (d, 1H); MS m/e (M+H)+328; [α]=+74.8 (1% solution in MeOH); and B (5S) isomer, $^1$H NMR (DMSOd$_6$ 300 MHz) δ 0.98 (s, 3H), 2.76 (q, 2H), 3.9 (s, 3H), 4.45 (s, 2H), 4.6 (m, 2H), 6.6 (brs, 2H), 6.95 (s, 1H), 7.4 (m, 2H), 7.6 (d, 1H), 7.78 (s, 1H), 8.0 (m, 1H), 8.2 (d, 1H); MS m/e (M+H)$^+$ 328; [α]=−76 (1% solution in MeOH).

EXAMPLE 246

Preparation of (5S)-5-[5-Acetyl-1-(3-fluoropropyl)-1H-pyrrol-3-yl]-2-amino-5-[3-(2-fluoropyridin-3-yl) phenyl]-3-methyl-3,5-dihydro-4H-imidazol-4-one (A) and (5R)-5-[5-Acetyl-1-(3-fluoropropyl)-1H-pyrrol-3-yl]-2-amino-5-[3-(2-fluoropyridin-3-yl) phenyl]-3-methyl-3,5-dihydro-4H-imidazol-4-one (B)

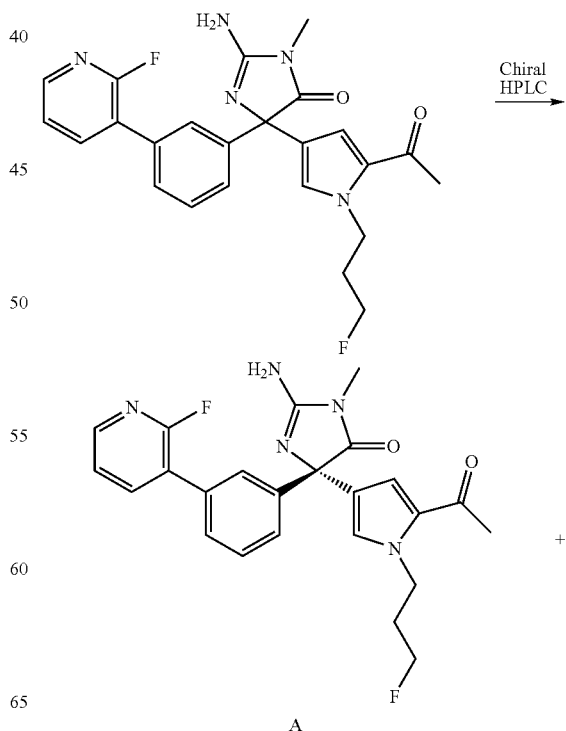

-continued

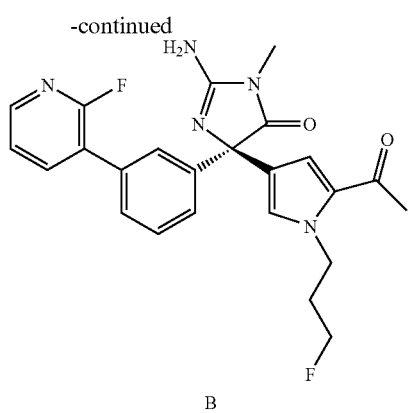

B

A racemic mixture of 5-[5-acetyl-1-(3-fluoropropyl)-1H-pyrrol-3-yl]-2-amino-5-[3-(2-fluoropyridin-3-yl)phenyl]-3-methyl-3,5-dihydro-4H-imidazol-4-one was separated by chiral HPLC to give the title products: A (5S) isomer, $[\alpha]_D^{25}=-64.20°$ (c=5.3 MG/0.7 ML, MeOH); MS (APPI) m/z 452; and B (5R) isomer, $[\alpha]_D^{25}=+62.87°$ (c=5.5 MG/0.7 ML, MeOH); MS (APPI) m/z 452.

EXAMPLE 247

Preparation of 4-{(4S)-2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde

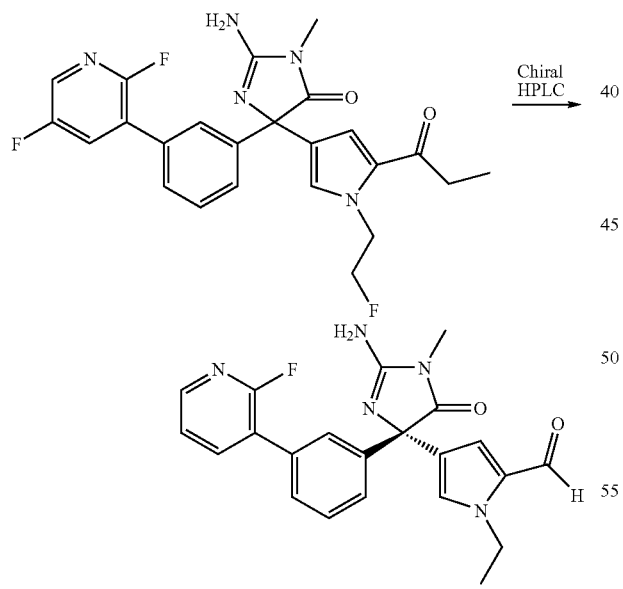

A racemic mixture of 4-{2-amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde was separated by chiral HPLC to give the title product, identified by NMR and mass spectral analyses. $[\alpha]_D^{25}=-73.0$ (1% solution in DMSO).

EXAMPLE 248

Preparation of (5S)-2-Amino-5-[1-(3-fluoropropyl)-5-(2-oxopropyl)-1H-pyrrol-3-yl]-5-[3-(2-fluoropyridin-3-yl)phenyl]-3-methyl-3,5-dihydro-4H-imidazol-4-one

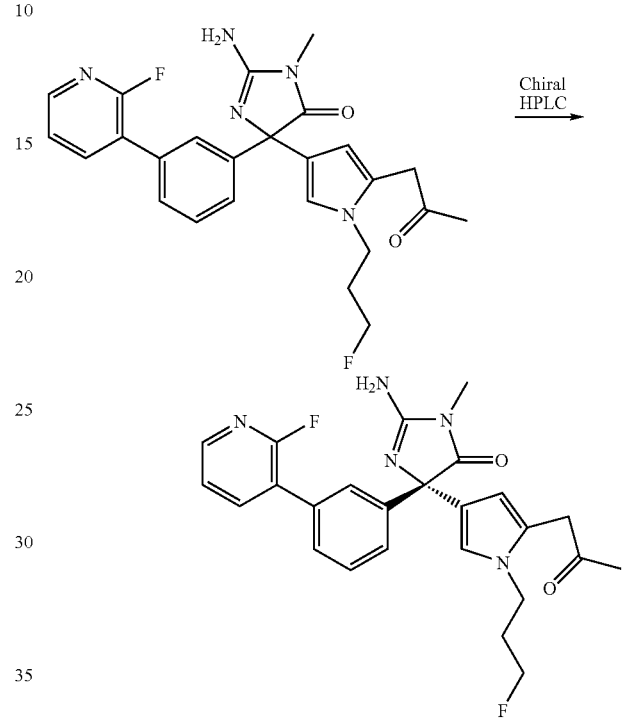

A racemic mixture of 2-amino-5-[1-(3-fluoropropyl)-5-(2-oxopropyl)-1H-pyrrol-3-yl]-5-[3-(2-fluoropyridin-3-yl)phenyl]-3-methyl-3,5-dihydro-4H-imidazol-4-one was separated by chiral HPLC to give the title product as a yellow solid, mp 147-150° C., identified by NMR and Mass spectral analyses. $[\alpha]_D^{25}=-78.0$ (1% solution in DMSO).

EXAMPLE 249

Preparation of (5S)-5-(5-acetyl-1-methyl-1H-pyrrol-3-yl)-2-amino-3-methyl-5-phenyl-3,5-dihydro-4H-imidazol-4-one (A) and (5R)-5-(5-acetyl-1-methyl-1H-Pyrrol-3-yl)-2-amino-3-methyl-5-phenyl-3,5-dihydro-4H-imidazol-4-one (B)

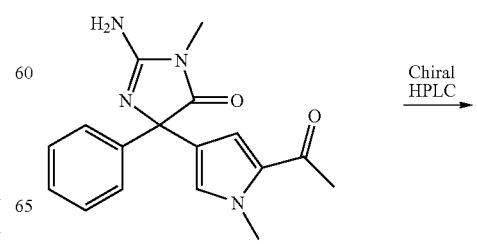

-continued

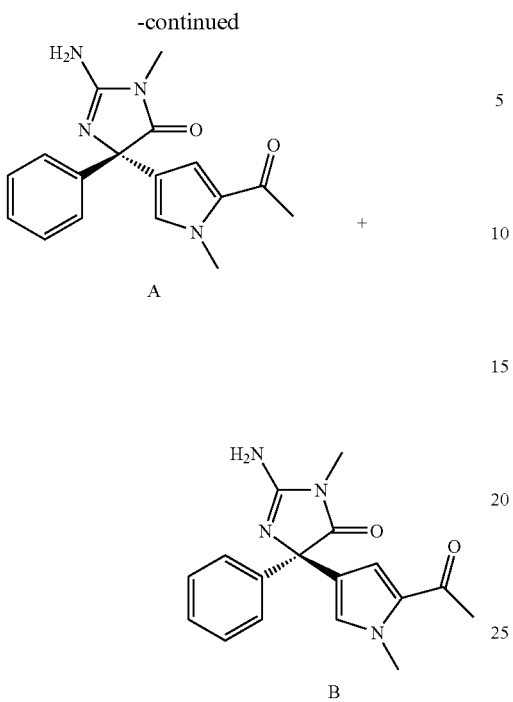

A

B

A racemic mixture of 5-(5-acetyl-1-methyl-1H-pyrrol-3-yl)-2-amino-3-methyl-5-phenyl-3,5-dihydro-4H-imidazol-4-one was separated by chiral HPLC using a Chiralcel AD column to give the title products: A (5S) isomer, $[\alpha]^D_{25}=-100.0$ (1% solution in DMSO); MS (APPI) m/z 311; and B (5R) isomer, $[\alpha]^D_{25}=+90.0$ (1% solution in DMSO); MS (APPI) m/z 311.

EXAMPLE 250

Preparation of (5S)-2-Amino-5-[1-(4-fluorobutyl)-5-propionyl-1H-pyrrol-3-yl]-5-[3-(2-fluoropyridin-3-yl)phenyl]-3-methyl-3,5-dihydro-4H-imidazol-4-one (A) and (5R)-2-Amino-5-[1-(4-fluorobutyl)-5-propionyl-1H-pyrrol-3-yl]-5-[3-(2-fluoropiridin-3-yl)phenyl]-3-methyl-3,5-dihydro-4H-imidazol-4-one (B)

-continued

A

B

A racemic mixture of 2-amino-5-[1-(4-fluorobutyl)-5-propionyl-1H-pyrrol-3-yl]-5-[3-(2-fluoropyridin-3-yl)phenyl]-3-methyl-3,5-dihydro-4H-imidazol-4-one was separated by chiral HPLC using a Chiralcel AD column to give the title products: A (5S) isomer, $[\alpha]^D_{25}=-72.20°$ (c=1% solution MeOH); and B (5R) isomer, $[\alpha]^D_{25}=+74.0$ (1% solution in DMSO). Both isomers were identified by NMR and mass spectral analyses.

EXAMPLE 251

Preparation of (5S)-2-Amino-5-[1-(cyclopropylmethyl)-5-propionyl-1H-pyrrol-3-yl]-5-[3-(2-fluoropyridin-3-yl)phenyl]-3-methyl-3,5-dihydro-4H-imidazol-4-one (A) and (5R)-2-Amino-5-[1-(cyclopropylmethyl)-5-propionyl-1H-pyrrol-3-yl]-5-(3-(2-fluoropyridin-3-yl)phenyl]-3-methyl-3,5-dihydro-4H-imidazol-4-one (B)

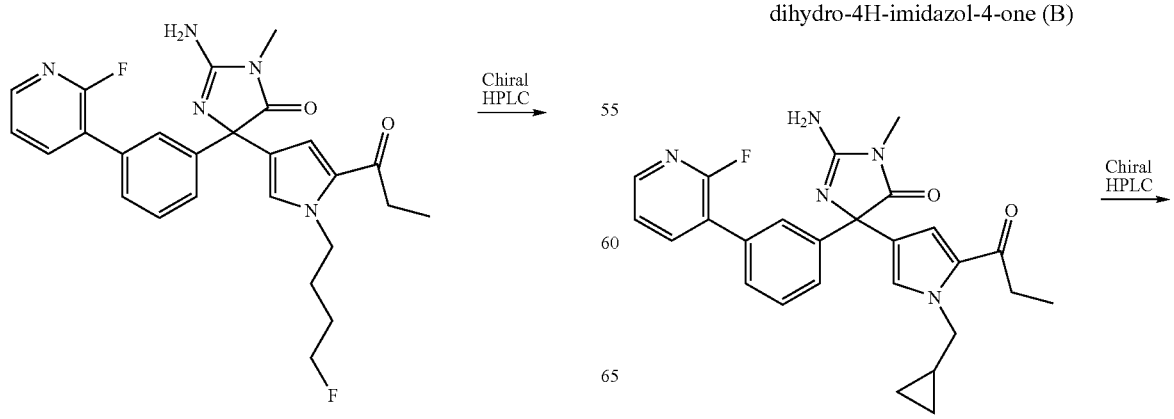

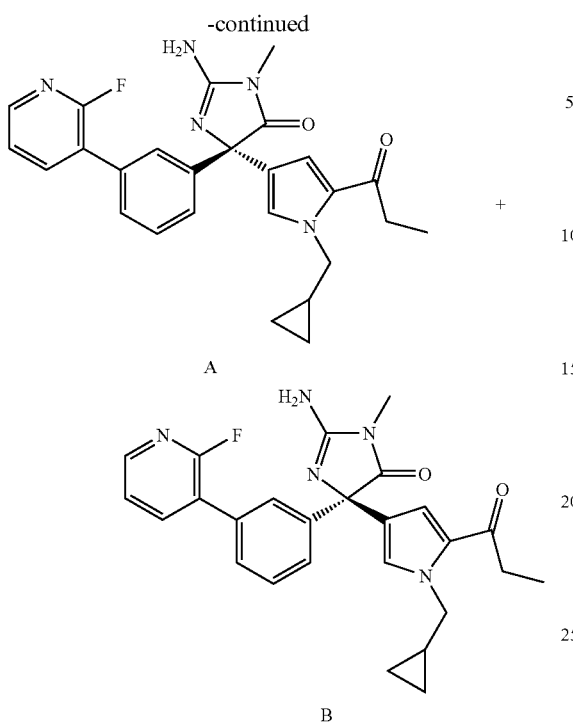

A

B

A racemic mixture of 2-amino-5-[1-(cyclopropylmethyl)-5-propionyl-1H-pyrrol-3-yl]-5-[3-(2-fluoropyridin-3-yl)phenyl]-3-methyl-3,5-dihydro-4H-imidazol-4-one was separated by chiral HPLC using a Chiralcel AD column to give the title products: A (5S) isomer, $[\alpha]^D_{25}=-72.2°$ (c=1% solution MeOH); and B (5R) isomer, $[\alpha]^D_{25}=+79.0$ (1% solution in DMSO). Both isomers were identified by NMR and mass spectral analyses.

EXAMPLE 252

Preparation of (5S)-2-Amino-5-[3-(2-fluoropyridin-3-yl)phenyl]-3-methyl-5-[5-propionyl-1-(4,4,4-trifluorobutyl)-1H-pyrrol-3-yl]-3,5-dihydro-4H-imidazol-4-one (A) and (5R)-2-Amino-5-[3-(2-fluoropyridin-3-yl)phenyl]-3-methyl-5-[5-propionyl-1-(4,4,4-trifluorobutyl)-1H-pyrrol-3-yl]-3,5-dihydro-4H-imidazol-4-one (B)

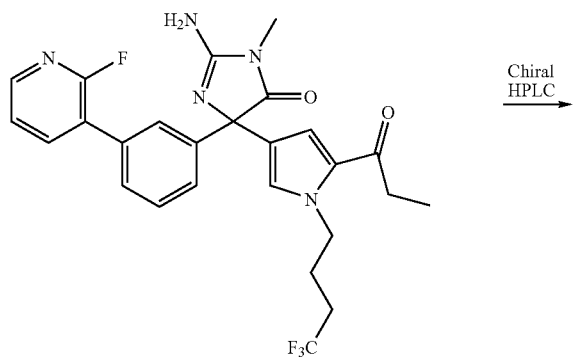

Chiral HPLC →

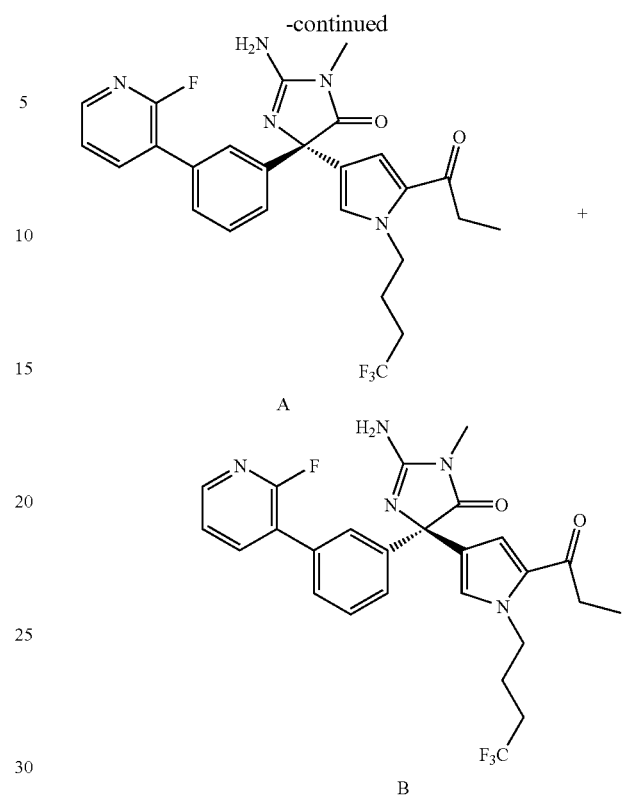

A

B

A racemic mixture of 2-amino-5-[3-(2-fluoropyridin-3-yl)phenyl]-3-methyl-5-[5-propionyl-1-(4,4,4-trifluorobutyl)-1H-pyrrol-3-yl]-3,5-dihydro-4H-imidazol-4-one was separated by chiral HPLC using a Chiralcel AD column to give the title products: A (5S) isomer, $[\alpha]^D_{25}=-62.500°$ (c=1% solution MeOH); and B (5R) isomer, $[\alpha]^D_{25}=+67.0$ (1% solution in DMSO). Both isomers were identified by NMR and mass spectral analyses.

EXAMPLE 253

Preparation of (5S)-2-Amino-5-[1-(2,2-difluoroethyl)-5-propionyl-1H-pyrrol-3-yl]-5-[3-(2-fluoropyridin-3-yl)phenyl]-3-methyl-3,5-dihydro-4H-imidazol-4-one (A) and (5R)-2-Amino-5-[1-(2,2-difluoroethyl)-5-propionyl-1H-pyrrol-3-yl]-5-[3-(2-fluoropyridin-3-yl)phenyl]-3-methyl-3,5-dihydro-4H-imidazol-4-one (B)

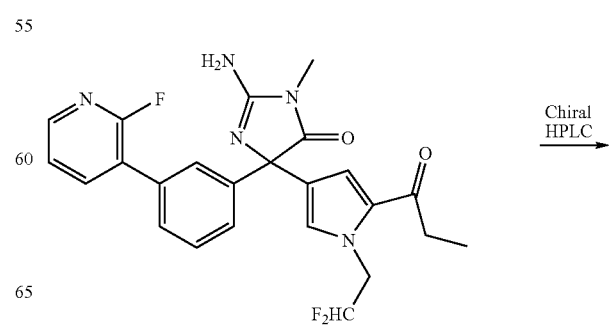

Chiral HPLC →

-continued

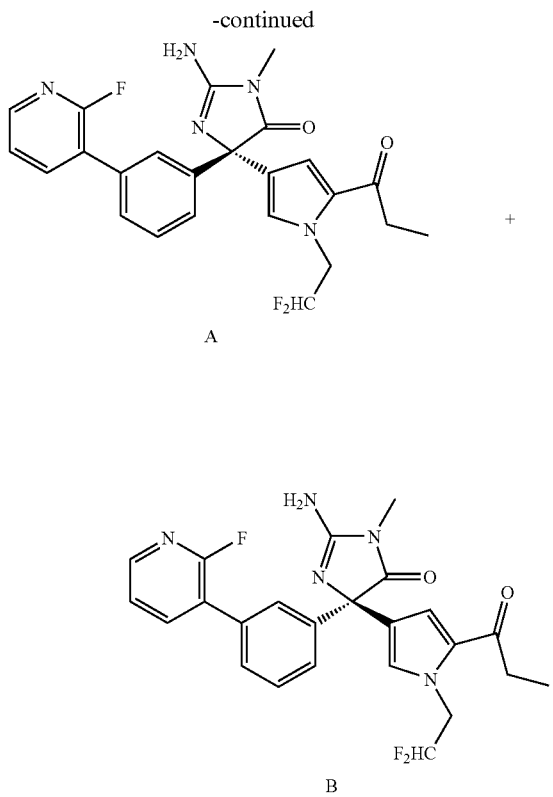

A racemic mixture of 2-amino-5-[1-(2,2-difluoroethyl)-5-propionyl-1H-pyrrol-3-yl]-5-[3-(2-fluoropyridin-3-yl)phenyl]-3-methyl-3,5-dihydro-4H-imidazol-4-one was separated by chiral HPLC using a Chiralcel AD column to give the title products: A (5S) isomer, $[\alpha]^D{}_{25}$=−78.0 (1% solution in DMSO); and B (5R) isomer, $[\alpha]^D{}_{25}$=+66.0 (1% solution in DMSO). Both isomers were identified by NMR and mass spectral analyses.

EXAMPLE 254

Preparation of (A) (5S)-2-Amino-5-[3-(2-fluoro-pyridin-3-yl)-phenyl]-3-methyl-5-(5-propionyl-1-propyl-1H-pyrrol-3-yl)-3,5-dihydro-imidazol-4-one (A) and (5R)-2-Amino-5-[3-(2-fluoro-pyridin-3-yl)-phenyl]-3-methyl-5-(5-propionyl-1-propyl-1H-Pyrrol-3-yl)-3,5-dihydro-imidazol-4-one (B)

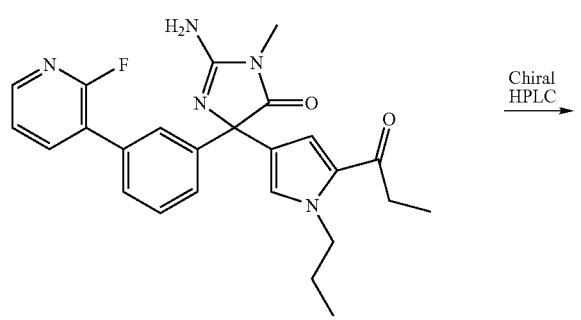

-continued

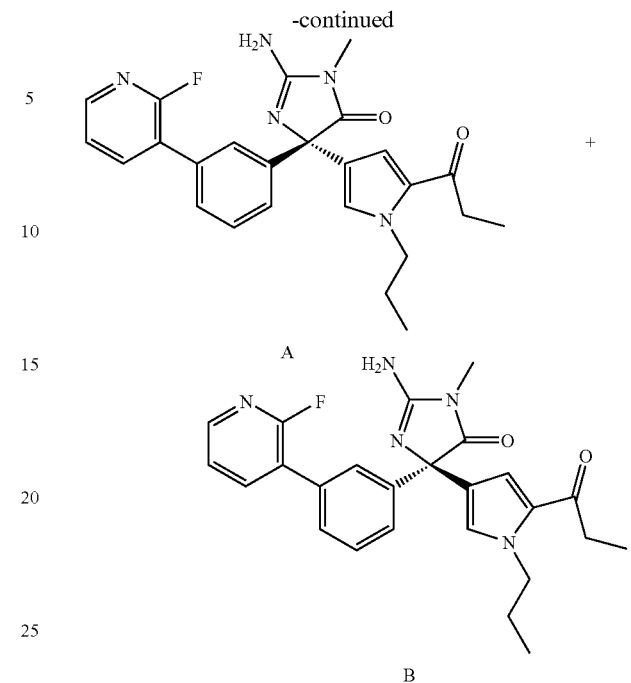

A racemic mixture of 2-amino-5-[3-(2-fluoro-pyridin-3-yl)-phenyl]-3-methyl-5-(5-propionyl-1-propyl-1H-pyrrol-3-yl)-3,5-dihydro-imidazol-4-one was separated by chiral HPLC using a Chiralpak AD, 0.46×25 cm; mobile phase hexane/isopropanol 7/3 with 0.1% DEA and a flow rate of 1.0 mL/min to give the title enantiomeric products: A (5S) isomer, mp 99° C.; $[\alpha]_D$=−78.4 (c 1.0, MeOH); m/e (M−H)⁻ 446.2; ¹H NMR (400 MHZ, DMSO-d₆) δ 0.73 (t, 3H), 0.96 (t, 3H), 1.54 (m, 2H), 2.67 (m, 2H), 2.92 (s, 3H), 4.13 (m, 2H), 6.60 (bs, 2H), 6.92 (s, 1H), 7.01 (s, 1H), 7.41 (m, 3H), 7.53 (m, 1H), 7.67 (m, 1H), 7.97 (m, 1H), 8.19, (m, 1H) and B: (5R) isomer,; mp 99° C.; $[\alpha]_D$=+77.1 (c 1.0, MeOH); m/e (M−H)⁻ 446.2; ¹H NMR (400 MHZ, DMSO-d₆) δ 0.73 (t, 3H), 0.96 (t, 3H), 1.54 (m, 2H), 2.67 (m, 2H), 2.92 (s, 3H), 4.13 (m, 2H), 6.60 (bs, 2H), 6.92 (s, 1H), 7.01 (s, 1H), 7.41 (m, 3H), 7.53 (m, 1H), 7.67 (m, 1H), 7.97 (m, 1H), 8.19, (m, 1H).

EXAMPLE 255

Preparation of (5S) 2-Amino-5-[1-(3-fluoropropyl)-5-propionyl-1H-pyrrol-3-yl]-5-[3-(2-fluoropyridin-3-yl)phenyl]-3-methyl-3,5-dihydro-4H-imidazol-4-one (A) and (5R) 2-Amino-5-[1-(3-fluoropropyl)-5-propionyl-1H-pyrrol-3-yl]-5-[3-(2-fluoropyridin-3-yl)phenyl]-3-methyl-3,5-dihydro-4H-imidazol-4-one (B)

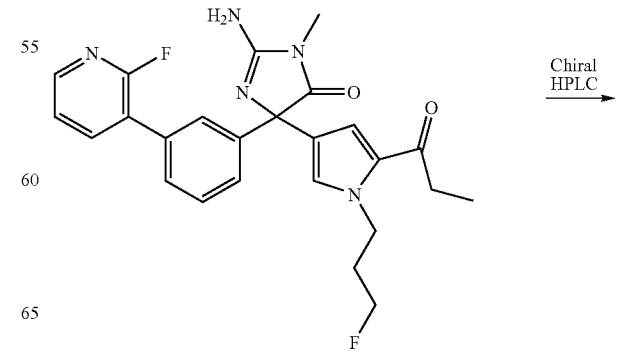

-continued

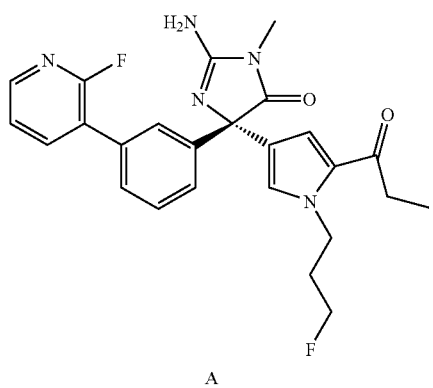

A

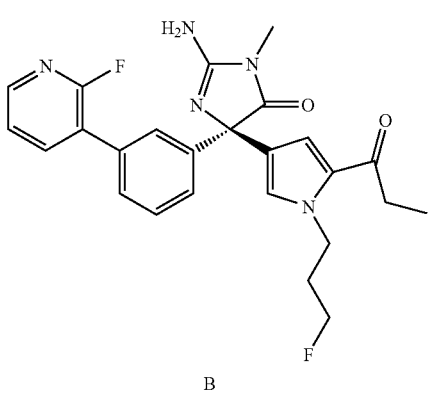

B

A racemic mixture of 2-amino-5-[1-(3-fluoropropyl)-5-propionyl-1H-pyrrol-3-yl]-5-[3-(2-fluoropyridin-3-yl)phenyl]-3-methyl-3,5-dihydro-4H-imidazol-4-one was separated by HPLC using a Chiralpak AD, 0.46×25 cm column; mobile phase hexane/isopropanol 7/3 with 0.1% DEA and a flow rate of 1.0 mL/min to give the title enantiomeric products: A (5S) isomer, mp 102° C., $[\alpha]_D$=−63.0 (c 1.0, MeOH); m/e (M−H)⁻ 464.2; ¹H NMR (400 MHZ, DMSO-d₆) δ 0.97 (t, 3H), 1.96-1.98 (m, 2H), 2.68 (q, 2H), 2.92 (s, 3H), 4.26 (m, 3H), 4.38 (m, 1H) 6.57 (bs, 2H), 7.02 (s, 1H), 7.03 (s, 1H), 7.41-7.42 (m, 3H), 7.55 (m, 1H), 7.68 (m, 1H), 7.98 (m, 1H), 8.12, (m, 1H) and B (5R) isomer, mp 102° C.; $[\alpha]_D$=+76.0 (c 1.0, MeOH); m/e (M−H)⁻ 464.2; ¹H NMR (400 MHZ, DMSO-d₆) δ 0.97 (t, 3H), 1.96-1.98 (m, 2H), 2.68 (q, 2H), 2.92 (s, 3H), 4.26 (m, 3H), 4.38 (m, 1H) 6.57 (bs, 2H), 7.02 (s, 1H), 7.03 (s, 1H), 7.41-7.42 (m, 3H), 7.55 (m, 1H), 7.68 (m, 1H), 7.98 (m, 1H), 8.12, (m, 1H).

EXAMPLE 256

Preparation of (5S) 2-Amino-5-[1-(2-fluoroethyl)-5-propionyl-1H-pyrrol-3-yl]-5-[3-(2-fluoropyridin-3-yl)phenyl]-3-methyl-3,5-dihydro-4H-imidazol-4-one (A) and (5R) 2-Amino-5-[1-(2-fluoroethyl)-5-propionyl-1H-pyrrol-3-yl]-5-[3-(2-fluoropyridin-3-yl)phenyl]-3-methyl-3,5-dihydro-4H-imidazol-4-one (B)

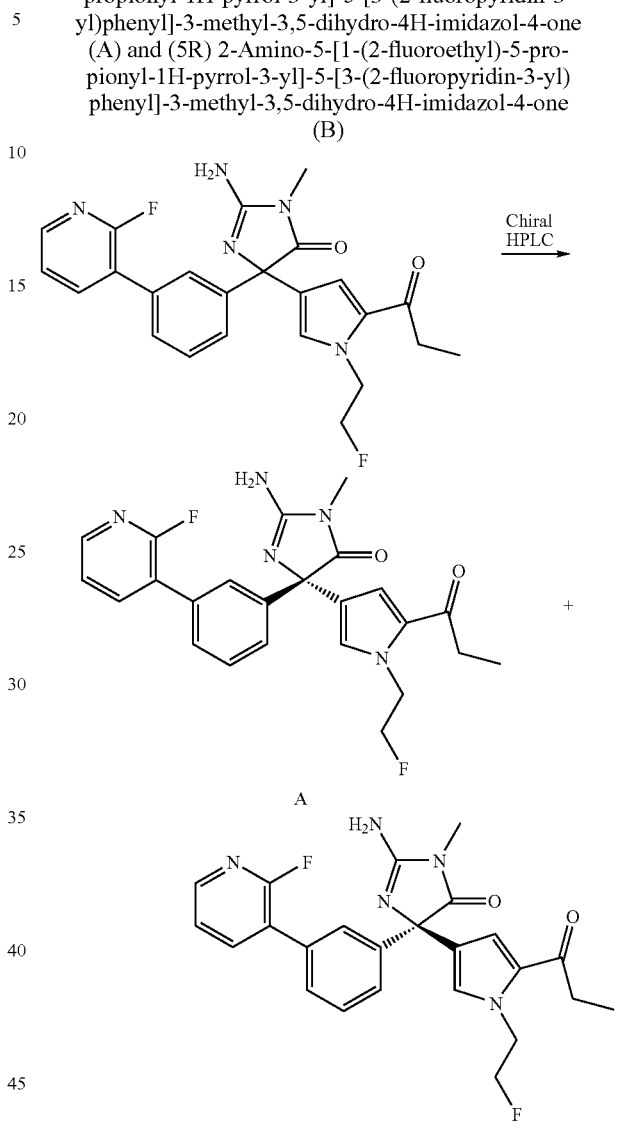

A racemic mixture of 2-amino-5-[1-(2-fluoroethyl)-5-propionyl-1H-pyrrol-3-yl]-5-[3-(2-fluoropyridin-3-yl)phenyl]-3-methyl-3,5-dihydro-4H-imidazol-4-one was separated by chiral HPLC using a Chiralpak AD, 0.46×25 cm column, mobile phase hexane/isopropanol 7/3 with 0.1% DEA and a flow rate of 1.0 mL/min to give the title enantiomeric products: A (5S) isomer, mp 110° C.; $[\alpha]_D$=−69.6 (c 1.0, MeOH); m/e (M−H)⁻ 450.2; ¹H NMR (400 MHZ, DMSO-d₆) δ 0.81 (m, 1H), 0.95-0.97 (t, 3H), 1.20 (m, 1H), 2.70 (q, 2H), 2.93 (s, 3H), 4.48-4.55 (m, 2H), 6.58 (bs, 2H), 6.99 (s, 1H), 7.05 (s, 1H), 7.41-7.43 (m, 3H), 7.57 (m, 1H), 7.69 (s, 1H), 7.98 (m, 1H), 8.20, (m, 1H) and B (5R) isomer, mp 105° C., $[\alpha]_D$=+82.6 (c 1.0, MeOH); m/e (M−H)⁻ 450.2; ¹H NMR (400 MHZ, DMSO-d₆) δ 0.81 (m, 1H), 0.95-0.97 (t, 3H), 1.20 (m, 1H), 2.70 (q, 2H), 2.93 (s, 3H), 4.48-4.55 (m, 2H), 6.58 (bs, 2H), 6.99 (s, 1H), 7.05 (s, 1H), 7.41-7.43 (m, 3H), 7.57 (m, 1H), 7.69 (s, 1H), 7.98 (m, 1H), 8.20, (m, 1H).

EXAMPLE 257

Preparation of Methyl 4-{(4S)-2-amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carboxylate (A) and Methyl 4-{(4R)-2-amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carboxylate (B)

EXAMPLE 258

Preparation of Methyl 4-[(4S)-2-amino-4-(4-fluoro-3-pyrimidin-5-ylphenyl)-1-methyl-5-oxo-4,5-dihydro-1H-imidazol-4-yl]-1-(2,2,2-trifluoroethyl)-1H-pyrrole-2-carboxylate (A) and Methyl 4-[(4R)-2-amino-4-(4-fluoro-3-pyrimidin-5-ylphenyl)-1-methyl-5-oxo-4,5-dihydro-1H-imidazol-4-yl]-1-(2,2,2-trifluoroethyl)-1H-pyrrole-2-carboxylate (B)

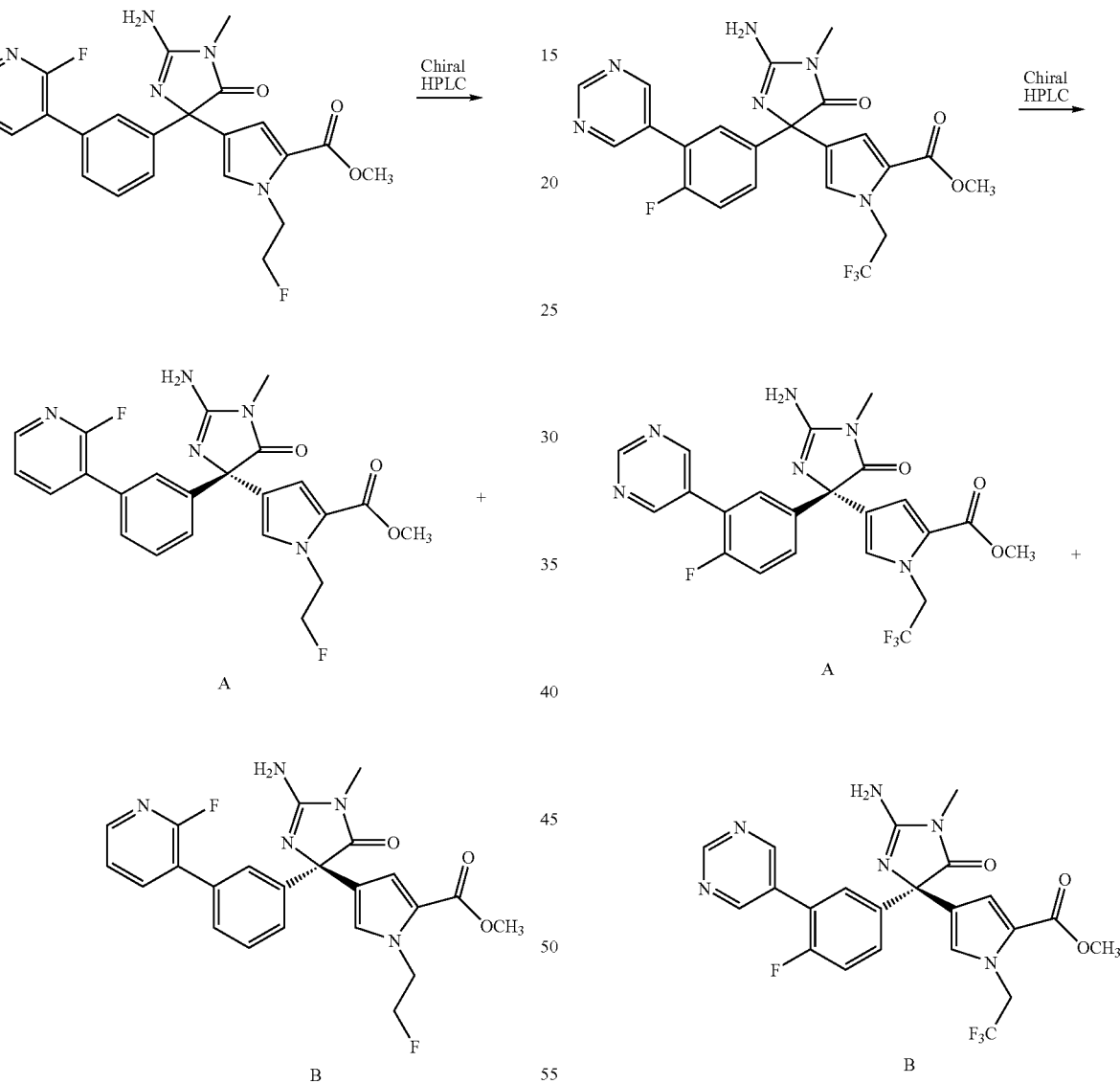

A racemic mixture of methyl 4-{2-amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carboxylate was separated by chiral HPLC to give the title enantiomeric products: A (5S) isomer, mp 174-176° C.; $[\alpha]_D$=−68.00 (c 1.0, MeOH); and B (5R) isomer, mp 174-176° C., $[\alpha]_D$=+60.2 (c 1.0, MeOH). Both isomers were identified by NMR and mass spectral analyses.

A racemic mixture of methyl 4-[2-amino-4-(4-fluoro-3-pyrimidin-5-ylphenyl)-1-methyl-5-oxo-4,5-dihydro-1H-imidazol-4-yl]-1-(2,2,2-trifluoroethyl)-1H-pyrrole-2-carboxylate was separated by chiral HPLC to give the title enantiomeric products: A (5S) isomer, mp 128-131° C.; $[\alpha]_D$=−65.00 (c 1.0, MeOH); and B (5R) isomer, mp 128-131° C., $[\alpha]_D$=+73.20 (c 1.0, MeOH). Both isomers were identified by NMR and mass spectral analyses.

EXAMPLE 259

Evaluation of BACE-1 Binding Affinity of Test Compounds

Fluorescent Kinetic Assays

Final Assay Conditions: 10 nM human BACE1 (or 10 nM Murine BACE1, 1.5 nM human BACE2), 25 µM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat.# 24, 124-5, CHAPS was from Research Organics, Cat. # 1304C 1×, PBS was from Mediatech (Cellgro), Cat# 21-031-CV, peptide substrate AbzSEVNLDAEFRDpa was from AnaSpec, Peptide Name: WABC-6

Determination of stock substrate (AbzSEVNLDAE-FRDpa) concentration: ~25 mM stock solution is made in DMSO using the peptide weight and MW, and diluted to ~25 µM (1:1000) in 1×PBS. Concentration is determined by absorbance at 354 nm using an extinction coefficient $\epsilon$ of 18172 M$^{-1}$ cm$^{-1}$, the concentration of stock substrate is corrected, and the substrate stock stored in small aliquots in −80° C. [Substrate Stock]=ABS$^{354\ nm}$ *10$^6$/18172 (in mM)

The extinction coefficient $\epsilon^{354\ nm}$ was adapted from TACE peptide substrate, which had the same quencher-fluorophore pair.

Determination of Stock Enzyme Concentration: the stock concentration of each enzyme is determined by absorbance at 280 nm using an $\epsilon$ of 64150 M$^{-1}$ cm$^{-1}$ for hBACE1 and MuBACE1, 62870 M$^{-1}$ cm$^{-1}$ for hBACE2 in 6 M Guanidinium Hydrochloride (from Research Organics, Cat. # 5134G-2), pH ~6. The extinction coefficient $\epsilon^{0.281\ nm}$ for each enzyme was calculated based on known amino acid composition and published extinction coefficients for Trp (5.69 M$^{-1}$ cm$^{-1}$) and Tyr (1.28 M$^{-1}$ cm$^{-1}$) residues (*Anal. Biochem.* 182, 319-326).

Dilution and mixing steps: total reaction volume: 100 µL

2× inhibitor dilutions in buffer A(66.7 mM Na-Acetate, pH 4.5, 0.0667% CHAPS) were prepared, 4× enzyme dilution in buffer A(66.7 mM Na-Acetate, pH 4.5, 0.0667% CHAPS) were prepared, 100 µM substrate dilution in 1×PBS was prepared, and 50 µL 2× Inhibitor, 25 µL 100 µM substrate are added to each well of 96-well plate (from DYNEX Technologies, VWR #: 11311-046), immediately followed by 25 µL 4× enzyme (added to the inhibitor and substrate mix), and the fluorescence readings are initiated.

Fluorescence Readings: Readings at $\lambda_{ex}$ 320 nm and $\lambda_{em}$ 420 nm are taken every 40 sec for 30 min at room temperature and the linear slope for substrate cleavage rate ($v_i$) determined.

Calculation of % Inhibition:

% Inhibition=100*(1−$v_i$/$v_0$)

$v_i$: substrate cleavage rate in the presence of inhibitor $v_0$: substrate cleavage rate in the absence of inhibitor IC$_{50}$ Determination:

% Inhibition=((B*IC$_{50}^n$)+(100*I$_0^n$))/(IC$_{50}^n$+I$_0^n$)

(Model # 39 from LSW Tool Bar in Excel where B is the % inhibition from the enzyme control, which should be close to 0.) % Inhibition is plotted vs. Inhibitor Concentration (I$_0$) and the data fit to the above equation to obtain IC$_{50}$ value and Hill number (n) for each compound. Testing at least 10 different inhibitor concentrations is preferred.

Results are shown in Table XX.

TABLE XX

| Example No. | BACE-1 IC$_{50}$ µM |
|---|---|
| 1 | B |
| 2 | B |
| 3 | A |
| 4 | A |
| 5 | A |
| 6 | A |
| 7 | B |
| 8 | B |
| 9 | A |
| 10 | A |
| 11 | B |
| 12 | A |
| 13 | A |
| 14 | B |
| 16 | B |
| 18 | B |
| 19 | B |
| 20 | A |
| 21 | B |
| 22 | B |
| 23 | B |
| 24 | A |
| 25 | A |
| 26 | B |
| 27 | B |
| 29 | A |
| 31 | B |
| 32 | A |
| 33 | A |
| 34 | A |
| 35 | B |
| 36 | C |
| 37 | A |
| 38 | B |
| 39 | A |
| 40 | A |
| 41 | B |
| 42 | A |
| 43 | A |
| 44A | C |
| 44B | A |
| 45 | A |
| 46 | A |
| 52 | B |
| 53 | B |
| 54 | B |
| 55 | B |
| 58 | C |
| 59 | C |
| 68 | A |
| 69 | A |
| 70 | B |
| 71 | B |
| 73 | C |
| 74 | C |
| 75 | C |
| 76 | C |
| 77 | C |
| 78 | C |
| 82 | A |
| 83 | A |
| 84 | B |
| 85 | B |
| 86 | B |
| 87 | A |
| 88 | B |
| 89 | B |
| 92 | C |
| 93 | C |
| 94 | A |
| 97 | A |
| 98 | A |
| 99 | A |
| 100 | A |

TABLE XX-continued

| Example No. | BACE-1 IC$_{50}$ μM |
|---|---|
| 101 | A |
| 102 | A |
| 103 | A |
| 104 | A |
| 105 | A |
| 106 | A |
| 107 | A |
| 108 | A |
| 109 | C |
| 110 | B |
| 111 | B |
| 114 | A |
| 116 | A |
| 118 | A |
| 119A | A |
| 119B | B |
| 120 | — |
| 121 | A |
| 122 | A |
| 123 | A |
| 124 | B |
| 125 | A |
| 26 | B |
| 127 | B |
| 128 | C |
| 129 | B |
| 130 | B |
| 131 | A |
| 132 | A |
| 133 | A |
| 134 | B |
| 135 | B |
| 136 | B |
| 137 | A |
| 138 | A |
| 139 | B |
| 140 | A |
| 141 | B |
| 143 | B |
| 144 | B |
| 147 | C |
| 148 | B |
| 149 | A |
| 150 | B |
| 151 | A |
| 152 | A |
| 153 | A |
| 154 | A |
| 155 | A |
| 156 | A |
| 157 | A |
| 158 | A |
| 159 | B |
| 160 | A |
| 161 | B |
| 162 | B |
| 163 | A |
| 164 | A |
| 165 | B |
| 166 | B |
| 167 | A |
| 168 | A |
| 169 | A |
| 170 | A |
| 171 | A |
| 172 | A |
| 173 | A |
| 174 | A |
| 176 | A |
| 177 | A |
| 178 | A |
| 179 | A |
| 180 | A |
| 181 | A |
| 182 | A |
| 183A | A |
| 183B | C |
| 184A | A |
| 184B | B |
| 185 | A |
| 186 | A |
| 187 | A |
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | B |
| 200 | A |
| 201 | A |
| 202 | A |
| 203 | A |
| 204 | A |
| 205 | A |
| 206 | A |
| 207 | A |
| 208 | A |
| 224A | A |
| 224B | C |
| 225 | B |
| 226 | B |
| 227 | B |
| 228 | B |
| 229 | A |
| 230 | A |
| 231 | A |
| 232 | B |
| 233 | A |
| 234 | A |
| 235 | C |
| 236 | C |
| 237 | C |
| 238 | B |
| 239 | A |
| 240 | B |
| 241 | A |
| 242A | A |
| 242B | C |
| 243A | A |
| 243B | C |
| 244A | A |
| 244B | B |
| 247 | A |
| 248 | A |
| 249A | C |
| 249B | C |
| 250A | A |
| 250B | C |
| 251A | A |
| 251B | C |
| 252A | A |
| 252B | C |
| 253A | A |
| 253B | C |
| 254A | A |
| 254B | C |
| 255A | A |
| 255B | C |
| 256A | A |
| 256B | C |
| 257A | A |

TABLE XX-continued

| Example No. | BACE-1 IC$_{50}$ µM |
|---|---|
| 257B | B |
| 258A | A |
| 258B | C |

For Table XX
A = 0.01 µM-0.10 µM
B = 0.11 µM-1.00 µM
C = >1.00 µM

What is claimed is:

1. A compound of formula I

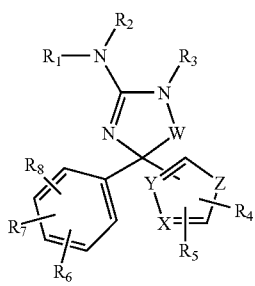

wherein W is CO;
X is CR$_9$;
Y is CR$_{10}$;
Z is N, NR, or NO;
p is 1 or 2;
R is H or a C$_1$-C$_6$alkyl, C$_1$-C$_6$haloalkyl, C$_2$-C$_6$alkenyl, C$_2$-C$_6$alkynyl, C$_3$-C$_8$cycloalkyl or aryl(C$_1$-C$_6$)alkyl group each optionally substituted;
R$_1$ and R$_2$ are each independently H, COR$_{14}$, CO$_2$R$_{15}$ or an optionally substituted C$_1$-C$_4$alkyl group;
R$_3$ is H, OR$_{13}$ or a C$_1$-C$_6$alkyl, C$_1$-C$_6$haloalkyl, C$_2$-C$_6$alkenyl, C$_2$-C$_6$alkynyl, C$_3$-C$_8$cycloalkyl or aryl (C$_1$-C$_6$)alkyl group each optionally substituted;
R$_4$, R$_5$, R$_9$ and R$_{10}$ are each independently H, halogen, NO$_2$, CN, OR$_{14}$, CO$_2$R$_{15}$, COR$_{16}$, NR$_{17}$R$_{18}$, SO$_p$NR$_{19}$R$_{20}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted;
R$_6$ and R$_8$ are each independently H, halogen, NO$_2$, CN, OR$_{21}$, NR$_{22}$R$_{23}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted;
R$_7$ is H, halogen, NO$_2$, CN, OR$_{24}$, NR$_{25}$R$_{26}$ or a C$_1$-C$_6$alkyl, C$_1$-C$_6$haloalkyl, C$_2$-C$_6$alkenyl, C$_2$-C$_6$alkynyl, C$_3$-C$_8$cycloalkyl, aryl or heteroaryl group each optionally substituted;
R$_{13}$, R$_{14}$, R$_{15}$, R$_{16}$, R$_{21}$, and R$_{24}$ are each independently H or a C$_1$-C$_6$alkyl, C$_1$-C$_6$haloalkyl, C$_2$-C$_6$alkenyl, C$_2$-C$_6$alkynyl, C$_3$-C$_8$cycloalkyl, cycloheteroalkyl or aryl group each optionally substituted;
R$_{17}$, R$_{18}$, R$_{19}$, R$_{20}$, R$_{22}$, R$_{23}$, R$_{25}$ and R$_{26}$ are each independently H, COR$_{34}$, SO$_p$R$_{35}$ or a C$_1$-C$_4$alkyl, C$_2$-C$_6$alkenyl, C$_2$-C$_6$alkynyl, C$_3$-C$_8$ cycloalkyl, cycloheteroalkyl, aryl or heteroaryl group each optionally substituted or R$_{17}$, R$_{18}$;
or R$_{19}$, R$_{20}$, or R$_{22}$, R$_{23}$, or R$_{25}$, R$_{26}$ may be taken together with the atom to which they are attached to form an optionally substituted 5- to 7-membered ring optionally containing an additional heteroatom selected from O, N or S;
R$_{34}$ is H, or a C$_1$-C$_6$alkyl, C$_1$-C$_6$haloalkyl, C$_2$-C$_6$alkenyl, C$_2$-C$_6$alkynyl, C$_3$-C$_8$cycloalkyl, cycloheteroalkyl, aryl or heteroaryl group each optionally substituted; and
R$_{35}$ is a C$_1$-C$_6$alkyl, C$_1$-C$_6$haloalkyl, C$_2$-C$_6$alkenyl, C$_2$-C$_6$alkynyl, C$_3$-C$_8$cycloalkyl, cycloheteroalkyl, aryl or heteroaryl group each optionally substituted; or
a tautomer thereof, a stereoisomer thereof or a pharmaceutically acceptable salt thereof.

2. The compound according to claim 1 wherein R$_7$ is phenyl or heteroaryl.

3. The compound according to claim 2 wherein R is H or C$_1$-C$_4$alkyl and R$_4$ is CN or COR$_{16}$.

4. The compound according to claim 2 wherein R$_1$ and R$_2$ are H; and R$_3$ is methyl.

5. The compound according to claim 1 selected from the group consisting of:
(5S)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;
(5S)-2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one;
2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;
2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one;
Methyl 4-[2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;
Methyl 4-[(4S)-2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;
Methyl 4-[(4R)-2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;
Methyl 4-[2-amino-4-(4-fluoro-3-pyrimidin-5-ylphenyl)-1-methyl-5-oxo-4,5-dihydro-1H-imidazol-4-yl]-1-(2,2,2-trifluoroethyl)-1H-pyrrole-2-carboxylate;
Methyl 4-{2-amino-4-[4-fluoro-3-(2-fluoropyridin-3-yl)phenyl]-1-methyl-5-oxo-4,5-dihydro-1H-imidazol-4-yl}-1-(2,2,2-trifluoroethyl)-1H-pyrrole-2-carboxylate;
Methyl 4-{2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;
Methyl 4-{2-amino-4-[4-fluoro-3-(2-fluoropyridin-3-yl)phenyl]-1-methyl-5-oxo-4,5-dihydro-1H-imidazol-4-yl}-1-ethyl-1H-pyrrole-2-carboxylate;
Isopropyl 4-{2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;
2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;
Methyl 4-{(4S)-2-amino-4-[4-fluoro-3-(2-fluoropyridin-3-yl)phenyl]-1-methyl-5-oxo-4,5-dihydro-1H-imidazol-4-yl}-1-(2,2,2-trifluoroethyl)-1H-pyrrole-2-carboxylate;
Methyl 4-{(4R)-2-amino-4-[4-fluoro-3-(2-fluoropyridin-3-yl)phenyl]-1-methyl-5-oxo-4,5-dihydro-1H-imidazol-4-yl}-1-(2,2,2-trifluoroethyl)-1H-pyrrole-2-carboxylate;

Isopropyl 4-[2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;

N-{3-[2-Amino-4-(1-ethyl-5-propionyl-1H-pyrrol-3-yl)-1-methyl-5-oxo-4,5-dihydro-1H-imidazol-4-yl]-phenyl}-butyramide;

N-{3-[2-Amino-4-(1-ethyl-5-propionyl-1H-pyrrol-3-yl)-1-methyl-5-oxo-4,5-dihydro-1H-imidazol-4-yl]-phenyl}-propionamide;

2-Amino-5-(1-ethyl-5-propionyl-1H-pyrrol-3-yl)-3-methyl-5-(3-propoxyphenyl)-3,5-dihydro-4H-imidazol-4-one;

2-Amino-5-(1-ethyl-5-propionyl-1H-pyrrol-3-yl)-3-methyl-5-[3-(pentyloxy)phenyl]-3,5-dihydro-4H-imidazol-4-one;

2-Amino-5-[3-(3,3-dimethylbutoxy)phenyl]-5-(1-ethyl-5-propionyl-1H-pyrrol-3-yl)-3-methyl-3,5-dihydro-4H-imidazol-4-one;

2-Amino-5-(1-ethyl-5-propionyl-1H-pyrrol-3-yl)-5-[3-(2-fluoroethoxy)phenyl]-3-methyl-3,5-dihydro-4H-imidazol-4-one;

2-Amino-5-(3-butoxyphenyl)-5-(1-ethyl-5-propionyl-1H-pyrrol-3-yl)-3-methyl-3,5-dihydro-4H-imidazol-4-one;

2-Amino-5-[3-(cyclopropylmethoxy)phenyl]-5-(1-ethyl-5-propionyl-1H-pyrrol-3-yl)-3-methyl-3,5-dihydro-4H-imidazol-4-one;

2-Amino-5-(1-ethyl-5-propionyl-1H-pyrrol-3-yl)-5-(3-isobutoxyphenyl)-3-methyl-3,5-dihydro-4H-imidazol-4-one;

4-{3-[2-Amino-4-(1-ethyl-5-propionyl-1H-pyrrol-3-yl)-1-methyl-5-oxo-4,5-dihydro-H-imidazol-4-yl]phenoxy}butanenitrile;

2-Amino-5-[3-(2-fluoropyridin-3-yl)phenyl]-3-methyl-5-[1-(3-methylbutyl)-5-propionyl-1H-pyrrol-3-yl]-3,5-dihydro-4H-imidazol-4-one;

2-Amino-5-[1-(3-fluoropropyl)-5-propionyl-1H-pyrrol-3-yl]-5-[3-(2-fluoropyridin-3-yl)phenyl]-3-methyl-3,5-dihydro-4H-imidazol-4-one;

2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one;

2-Amino-5-[3-(2-fluoropyridin-3-yl)phenyl]-3-methyl-5-(5-propionyl-1H-pyrrol-3-yl)-3,5-dihydro-4H-imidazol-4-one;

(5S)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

(5R)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one;

5-(5-Acetyl-1-ethyl-1H-pyrrol-3-yl)-2-amino-5-[3-(2-fluoropyridin-3-yl)phenyl]-3-methyl-3,5-dihydro-4H-imidazol-4-one;

Methyl 4-{(4S)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

Methyl 4-{(4R)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

2-Amino-5-[1-ethyl-5-(piperidin-1-ylcarbonyl)-1H-pyrrol-3-yl]-5-[3-(2-fluoropyridin-3-yl)phenyl]-3-methyl-3,5-dihydro-4H-imidazol-4-one;

2-Amino-5-[1-ethyl-5-(morpholin-4-ylcarbonyl)-1H-pyrrol-3-yl]-5-[3-(2-fluoropyridin-3-yl)phenyl]-3-methyl-3,5-dihydro-4H-imidazol-4-one;

(5S)-2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one;

Methyl 4-{(4S)-2-amino-4-[4-fluoro-3-(2-fluoropyridin-3-yl)phenyl]-1-methyl-5-oxo-4,5-dihydro-1H-imidazol-4-yl}-1-ethyl-1H-pyrrole-2-carboxylate;

(5S)-5-(5-Acetyl-1-ethyl-1H-pyrrol-3-yl)-2-amino-5-[3-(2-fluoropyridin-3-yl)phenyl]-3-methyl-3,5-dihydro-4H-imidazol-4-one;

Methyl 4-[2-amino-1-methyl-5-oxo-4-(3-pyrimidin-5-ylphenyl)-4,5-dihydro-1H-imidazol-4-yl]-1-(2-fluoroethyl)-1H-pyrrole-2-carboxylate;

Methyl 4-{2-amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

Methyl 4-{2-amino-4-[3-(6-fluoropyridin-3-yl)phenyl]-1-methyl-5-oxo-4,5-dihydro-1H-imidazol-4-yl}-1-(2-fluoroethyl)-1H-pyrrole-2-carboxylate;

Methyl 4-[2-amino-4-(2',5'-difluorobiphenyl-3-yl)-1-methyl-5-oxo-4,5-dihydro-1H-imidazol-4-yl]-1-(2-fluoroethyl)-1H-pyrrole-2-carboxylate;

Methyl 4-[2-amino-4-(3',5'-difluorobiphenyl-3-yl)-1-methyl-5-oxo-4,5-dihydro-1H-imidazol-4-yl]-1-(2-fluoroethyl)-1H-pyrrole-2-carboxylate;

Methyl 4-[2-amino-4-(3'-cyanobiphenyl-3-yl)-1-methyl-5-oxo-4,5-dihydro-1H-imidazol-4-yl]-1-(2-fluoroethyl)-1H-pyrrole-2-carboxylate;

Methyl 4-[2-amino-4-(5'-cyano-2'-fluorobiphenyl-3-yl)-1-methyl-5-oxo-4,5-dihydro-1H-imidazol-4-yl]-1-(2-fluoroethyl)-1H-pyrrole-2-carboxylate;

Methyl 4-[2-amino-4-(3'-methoxybiphenyl-3-yl)-1-methyl-5-oxo-4,5-dihydro-1H-imidazol-4-yl]-1-(2-fluoroethyl)-1H-pyrrole-2-carboxylate;

Methyl 4-{2-amino-1-methyl-5-oxo-4-[3'-(trifluoromethoxy)biphenyl-3-yl]-4,5-dihydro-1H-imidazol-4-yl}-1-(2-fluoroethyl)-1H-pyrrole-2-carboxylate;

Methyl 4-[2-amino-4-(3',4'-difluorobiphenyl-3-yl)-1-methyl-5-oxo-4,5-dihydro-1H-imidazol-4-yl]-1-(2-fluoroethyl)-1H-pyrrole-2-carboxylate;

Methyl 4-{2-amino-4-[3-(1,3-benzodioxol-5-yl)phenyl]-1-methyl-5-oxo-4,5-dihydro-1H-imidazol-4-yl}-1-(2-fluoroethyl)-1H-pyrrole-2-carboxylate;

4-[2-Amino-4-(3-bromophenyl)-1-methyl-5-oxo-4,5-dihydro-1H-imidazol-4-yl]-1-methyl-1H-pyrrole-2-carbonitrile;

4-[2-Amino-4-(3-bromophenyl)-1-methyl-5-oxo-4,5-dihydro-1H-imidazol-4-yl]-1-(2-fluoroethyl)-1H-pyrrole-2-carbonitrile;

4-[2-Amino-4-(3-bromophenyl)-1-methyl-5-oxo-4,5-dihydro-1H-imidazol-4-yl]-1-propyl-1H-pyrrole-2-carbonitrile;

4-[2-Amino-1-methyl-5-oxo-4-(3-pyrimidin-5-ylphenyl)-4,5-dihydro-1H-imidazol-4-yl]-1-methyl-1H-pyrrole-2-carbonitrile;

4-{2-Amino-4-[3-(2-fluoropyridin-3-yl)phenyl]-1-methyl-5-oxo-4,5-dihydro-1H-imidazol-4-yl}-1-methyl-1H-pyrrole-2-carbonitrile;

4-{2-Amino-4-[3-(2-chloro-5-fluoropyridin-3-yl)phenyl]-1-methyl-5-oxo-4,5-dihydro-1H-imidazol-4-yl}-1-methyl-1H-pyrrole-2-carbonitrile;

4-[2-Amino-1-methyl-5-oxo-4-(3-pyrimidin-5-ylphenyl)-4,5-dihydro-1H-imidazol-4-yl]-1-(2-fluoroethyl)-1H-pyrrole-2-carbonitrile;

4-[2-Amino-1-methyl-5-oxo-4-(3-pyrimidin-5-ylphenyl)-4,5-dihydro-1H-imidazol-4-yl]-1-propyl-1H-pyrrole-2-carbonitrile;
4-{2-Amino-4-[3-(2-fluoropyridin-3-yl)phenyl]-1-methyl-5-oxo-4,5-dihydro-1H-imidazol-4-yl}-1-propyl-1H-pyrrole-2-carbonitrile;
4-{2-Amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carbonitrile;
4-{2-Amino-4-[3-(2-chloro-5-fluoropyridin-3-yl)phenyl]-1-methyl-5-oxo-4,5-dihydro-1H-imidazol-4-yl}-1-propyl-1H-pyrrole-2-carbonitrile;
5-(5-Acetyl-1H-pyrrol-3-yl)-2-amino-5-(3-bromophenyl)-3-methyl-3,5-dihydro-imidazol-4-one;
4-{2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde;
4-[2-Amino-4-(3-bromophenyl)-1-methyl-5-oxo-4,5-dihydro-1H-imidazol-4-yl]-1H-pyrrole-2-carbaldehyde;
4-[2-Amino-4-(3-bromophenyl)-1-methyl-5-oxo-4,5-dihydro-1H-imidazol-4-yl]-1-ethyl-1H-pyrrole-2-carbaldehyde;
4-[2-Amino-4-(3-bromophenyl)-1-methyl-5-oxo-4,5-dihydro-1H-imidazol-4-yl]-1-(2-fluoroethyl)-1H-pyrrole-2-carbaldehyde;
4-{2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde;
4-{2-Amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carbaldehyde;
2-Amino-5-[5-[(diethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one;
2-Amino-5-{1-(2-fluoroethyl)-5-[(isopropylamino)methyl]-1H-pyrrol-3-yl}-5-[3-(2-fluoropyridin-3-yl)phenyl]-3-methyl-3,5-dihydro-4H-imidazol-4-one;
2-Amino-5-[1-(2-fluoroethyl)-5-(pyrrolidin-1-ylmethyl)-1H-pyrrol-3-yl]-5-[3-(2-fluoropyridin-3-yl)phenyl]-3-methyl-3,5-dihydro-4H-imidazol-4-one;
2-Amino-5-[5-[(dimethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one;
2-Amino-5-[5-[(dimethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one;
2-Amino-5-[1-ethyl-5-(1-hydroxypropyl)-1H-pyrrol-3-yl]-5-[3-(2-fluoropyridin-3-yl)phenyl]-3-methyl-3,5-dihydro-4H-imidazol-4-one;
2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one;
2-Amino-5-(3-bromophenyl)-5-(1-ethyl-5-propionyl-1H-pyrrol-3-yl)-3-methyl-3,5-dihydro-4H-imidazol-4-one;
(5S)-2-Amino-5-[3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one;
(5R)-2-Amino-5-[3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one;
2-Amino-5-(1-ethyl-5-propionyl-1H-pyrrol-3-yl)-3-methyl-5-(3-pyrimidin-5-ylphenyl)-3,5-dihydro-4H-imidazol-4-one;
2-Amino-5-(3'-methoxybiphenyl-3-yl)-3-methyl-5-[5-propionyl-1-(2,2,2-trifluoroethyl)-1H-pyrrol-3-yl]-3,5-dihydro-4H-imidazol-4-one;
2-Amino-5-(3',5'-difluorobiphenyl-3-yl)-3-methyl-5-[5-propionyl-1-(2,2,2-trifluoroethyl)-1H-pyrrol-3-yl]-3,5-dihydro-4H-imidazol-4-one;
2-Amino-5-(3'-chlorobiphenyl-3-yl)-3-methyl-5-[5-propionyl-1-(2,2,2-trifluoroethyl)-1H-pyrrol-3-yl]-3,5-dihydro-4H-imidazol-4-one;
2-Amino-5-(3'-chloro-4'-fluorobiphenyl-3-yl)-3-methyl-5-[5-propionyl-1-(2,2,2-trifluoroethyl)-1H-pyrrol-3-yl]-3,5-dihydro-4H-imidazol-4-one;
3'-{2-Amino-1-methyl-5-oxo-4-[5-propionyl-1-(2,2,2-trifluoroethyl)-1H-pyrrol-3-yl]-4,5-dihydro-1H-imidazol-4-yl}biphenyl-3-carbonitrile;
2-Amino-5-(3-bromo-4-fluorophenyl)-3-methyl-5-[5-propionyl-1-(2,2,2-trifluoroethyl)-1H-pyrrol-3-yl]-3,5-dihydro-4H-imidazol-4-one;
2-Amino-5-[4-fluoro-3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one; and
2-Amino-5-(4-fluoro-3-pyrimidin-5-ylphenyl)-3-methyl-5-[5-propionyl-1-(2,2,2-trifluoroethyl)-1H-pyrrol-3-yl]-3,5-dihydro-4H-imidazol-4-one; or a tautomer thereof,
a stereoisomer thereof; or
a pharmaceutically acceptable salt thereof.

6. A method for the treatment of Alzheimer's disease in a patient in need thereof which comprises providing to said patient a therapeutically effective amount of a compound of formula I wherein W is CO;
X is $CR_9$;
Y is $CR_{10}$;
Z is N, NR, or NO;
p is 1 or 2;
R is H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl($C_1$-$C_6$)alkyl group each optionally substituted;
$R_1$ and $R_2$ are each independently H, $COR_{14}$, $CO_2R_{15}$ or an optionally substituted $C_1$-$C_4$alkyl group;
$R_3$ is H, $OR_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl ($C_1$-$C_6$)alkyl group each optionally substituted;
$R_4$, $R_5$, $R_9$ and $R_{10}$ are each independently H, halogen, $NO_2$, CN, $OR_{14}$, $CO_2R_{15}$, $COR_{16}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_6$ and $R_8$ are each independently H, halogen, $NO_2$, CN, $OR_{21}$, $NR_{22}R_{23}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_7$ is H, halogen, $NO_2$, CN, $OR_{24}$, $NR_{25}R_{26}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, aryl or heteroaryl group each optionally substituted;

$R_{13}$, $R_{14}$, $R_{15}$, $R_{16}$, $R_{21}$ and $R_{24}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted;

$R_{17}$, $R_{18}$, $R_{19}$, $R_{20}$, $R_{22}$, $R_{23}$, $R_{25}$ and $R_{26}$ are each independently H, $COR_{34}$, $SO_pR_{35}$ or a $C_1$-$C_4$alkyl, $C_2$-$C_6$alkenyl, $C_2$-$C_6$alkynyl, $C_3$-$C_8$ cycloalkyl, cycloheteroalkyl, aryl or heteroaryl group each optionally substituted or $R_{17}$, $R_{18}$;

or $R_{19}$, $R_{20}$, or $R_{22}$, $R_{23}$, or $R_{25}$, $R_{26}$ may be taken together with the atom to which they are attached to form an optionally substituted 5- to 7-membered ring optionally containing an additional heteroatom selected from O, N or S;

$R_{34}$ is H, or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; and $R_{35}$ is a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; or a tautomer thereof, a stereoisomer thereof or a pharmaceutically acceptable salt thereof.

7. The method according to claim 6 wherein Alzheimer's disease is characterized by the production of β-amyloid deposits or neurofibrillary tangles.

8. A pharmaceutical composition which comprises a pharmaceutically acceptable carrier and an effective amount of a compound of formula I

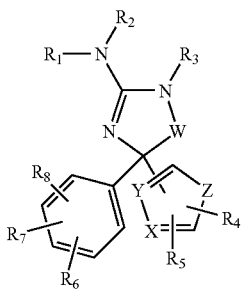

I wherein W is CO;

X is $CR_9$;

Y is $CR_{10}$;

Z is N, NR, or NO;

p is 1 or 2;

R is H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl($C_1$-$C_6$)alkyl group each optionally substituted;

$R_1$ and $R_2$ are each independently H, $COR_{14}$, $CO_2R_{15}$ or an optionally substituted $C_1$-$C_4$alkyl group;

$R_3$ is H, $OR_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl ($C_1$-$C_6$)alkyl group each optionally substituted;

$R_4$, $R_5$, $R_9$ and $R_{10}$ are each independently H, halogen, $NO_2$, CN, $OR_{14}$, $CO_2R_{15}$, $COR_{16}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

$R_6$ and $R_8$ are each independently H, halogen, $NO_2$, CN, $OR_{21}$, $NR_{22}R_{23}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

$R_7$ is H, halogen, $NO_2$, CN, $OR_{24}$, $NR_{25}R_{26}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, aryl or heteroaryl group each optionally substituted;

$R_{13}$, $R_{14}$, $R_{15}$, $R_{16}$, $R_{21}$ and $R_{24}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted;

$R_{17}$, $R_{18}$, $R_{19}$, $R_{20}$, $R_{22}$, $R_{23}$, $R_{25}$ and $R_{26}$ are each independently H, $COR_{34}$, $SO_pR_{35}$ or a $C_1$-$C_4$alkyl, $C_2$-$C_6$alkenyl, $C_2$-$C_6$alkynyl, $C_3$-$C_8$ cycloalkyl, cycloheteroalkyl, aryl or heteroaryl group each optionally substituted or $R_{17}$, $R_{18}$; or $R_{19}$, $R_{20}$, or $R_{22}$, $R_{23}$, or $R_{25}$, $R_{26}$ may be taken together with the atom to which they are attached to form an optionally substituted 5- to 7-membered ring optionally containing an additional heteroatom selected from O, N or S;

$R_{34}$ is H, or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; and $R_{35}$ is a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; or a tautomer thereof, a stereoisomer thereof or a pharmaceutically acceptable salt thereof.

9. The composition according to claim 8 having a formula I compound wherein $R_7$ is phenyl or heteroaryl.

10. The composition according to claim 9 having a formula I compound wherein R is H or $C_1$-$C_4$alkyl; $R_4$ is $COR_{16}$; $R_1$ and $R_2$ are H; and $R_3$ is methyl.

11. The composition according to claim 8 having a formula I compound selected from the group consisting of:

(5S)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

(5S)-2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one;

2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one;

Methyl 4-[2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;

Methyl 4-[(4S)-2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;

Methyl 4-[(4R)-2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;

Methyl 4-[2-amino-4-(4-fluoro-3-pyrimidin-5-ylphenyl)-1-methyl-5-oxo-4,5-dihydro-1H-imidazol-4-yl]-1-(2,2,2-trifluoroethyl)-1H-pyrrole-2-carboxylate;

Methyl 4-{2-amino-4-[4-fluoro-3-(2-fluoropyridin-3-yl)phenyl]-1-methyl-5-oxo-4,5-dihydro-1H-imidazol-4-yl}-1-(2,2,2-trifluoroethyl)-1H-pyrrole-2-carboxylate;

Methyl 4-{2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

Methyl 4-{2-amino-4-[4-fluoro-3-(2-fluoropyridin-3-yl)phenyl]-1-methyl-5-oxo-4,5-dihydro-1H-imidazol-4-yl}-1-ethyl-1H-pyrrole-2-carboxylate;

Isopropyl 4-{2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

Methyl 4-{(4S)-2-amino-4-[4-fluoro-3-(2-fluoropyridin-3-yl)phenyl]-1-methyl-5-oxo-4,5-dihydro-1H-imidazol-4-yl}-1-(2,2,2-trifluoroethyl)-1H-pyrrole-2-carboxylate;

Methyl 4-{(4R)-2-amino-4-[4-fluoro-3-(2-fluoropyridin-3-yl)phenyl]-1-methyl-5-oxo-4,5-dihydro-1H-imidazol-4-yl}-1-(2,2,2-trifluoroethyl)-1H-pyrrole-2-carboxylate;

Isopropyl 4-[2-amino-4-(4-fluoro-3-pyrimidin-5-ylphenyl)-1-methyl-5-oxo-4,5-dihydro-1H-imidazol-4-yl]-1-(2-fluoroethyl)-1H-pyrrole-2-carboxylate;

N-{3-[2-Amino-4-(1-ethyl-5-propionyl-1H-pyrrol-3-yl)-1-methyl-5-oxo-4,5-dihydro-1H-imidazol-4-yl]-phenyl}-butyramide;

N-{3-[2-Amino-4-(1-ethyl-5-propionyl-1H-pyrrol-3-yl)-1-methyl-5-oxo-4,5-dihydro-1H-imidazol-4-yl]-phenyl}-propionamide;

2-Amino-5-(1-ethyl-5-propionyl-1H-pyrrol-3-yl)-3-methyl-5-(3-propoxyphenyl)-3,5-dihydro-4H-imidazol-4-one;

2-Amino-5-(1-ethyl-5-propionyl-1H-pyrrol-3-yl)-3-methyl-5-[3-(pentyloxy)phenyl]-3,5-dihydro-4H-imidazol-4-one;

2-Amino-5-[3-(3,3-dimethylbutoxy)phenyl]-5-(1-ethyl-5-propionyl-1H-pyrrol-3-yl)-3-methyl-3,5-dihydro-4H-imidazol-4-one;

2-Amino-5-(1-ethyl-5-propionyl-1H-pyrrol-3-yl)-5-[3-(2-fluoroethoxy)phenyl]-3-methyl-3,5-dihydro-4H-imidazol-4-one;

2-Amino-5-(3-butoxyphenyl)-5-(1-ethyl-5-propionyl-1H-pyrrol-3-yl)-3-methyl-3,5-dihydro-4H-imidazol-4-one;

2-Amino-5-[3-(cyclopropylmethoxy)phenyl]-5-(1-ethyl-5-propionyl-1H-pyrrol-3-yl)-3-methyl-3,5-dihydro-4H-imidazol-4-one;

2-Amino-5-(1-ethyl-5-propionyl-1H-pyrrol-3-yl)-5-(3-isobutoxyphenyl)-3-methyl-3,5-dihydro-4H-imidazol-4-one;

4-{3-[2-Amino-4-(1-ethyl-5-propionyl-1H-pyrrol-3-yl)-1-methyl-5-oxo-4,5-dihydro-H-imidazol-4-yl]phenoxy}butanenitrile;

2-Amino-5-[3-(2-fluoropyridin-3-yl)phenyl]-3-methyl-5-[1-(3-methylbutyl)-5-propionyl-1H-pyrrol-3-yl]-3,5-dihydro-4H-imidazol-4-one;

2-Amino-5-[1-(3-fluoropropyl)-5-propionyl-1H-pyrrol-3-yl]-5-[3-(2-fluoropyridin-3-yl)phenyl]-3-methyl-3,5-dihydro-4H-imidazol-4-one;

2-Amino-5-[3-(2-fluoropyridin-3-yl)phenyl]-3-methyl-5-(5-propionyl-1-propyl-1H-pyrrol-3-yl)-3,5-dihydro-4H-imidazol-4-one;

2-Amino-5-[3-(2-fluoropyridin-3-yl)phenyl]-3-methyl-5-(5-propionyl-1H-pyrrol-3-yl)-3,5-dihydro-4H-imidazol-4-one;

(5S)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

(5R)-2-Amino-5-(1-ethyl-5-propionyl-1H-pyrrol-3-yl)-5-[4-fluoro-3-(2-fluoropyridin-3-yl)phenyl]-3-methyl-3,5-dihydro-4H-imidazol-4-one;

2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one;

5-(5-Acetyl-1-ethyl-1H-pyrrol-3-yl)-2-amino-5-[3-(2-fluoropyridin-3-yl)phenyl]-3-methyl-3,5-dihydro-4H-imidazol-4-one;

Methyl 4-{(4S)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

Methyl 4-{(4R)-2-amino-4-[4-fluoro-3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

2-Amino-5-[1-ethyl-5-(piperidin-1-ylcarbonyl)-1H-pyrrol-3-yl]-5-[3-(2-fluoropyridin-3-yl)phenyl]-3-methyl-3,5-dihydro-4H-imidazol-4-one;

2-Amino-5-[1-ethyl-5-(morpholin-4-ylcarbonyl)-1H-pyrrol-3-yl]-5-[3-(2-fluoropyridin-3-yl)phenyl]-3-methyl-3,5-dihydro-4H-imidazol-4-one;

(5S)-2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one;

Methyl 4-{(4S)-2-amino-4-[4-fluoro-3-(2-fluoropyridin-3-yl)phenyl]-1-methyl-5-oxo-4,5-dihydro-1H-imidazol-4-yl}-1-ethyl-1H-pyrrole-2-carboxylate;

(5S)-5-(5-Acetyl-1-ethyl-1H-pyrrol-3-yl)-2-amino-5-[3-(2-fluoropyridin-3-yl)phenyl]-3-methyl-3,5-dihydro-4H-imidazol-4-one;

Methyl 4-[2-amino-1-methyl-5-oxo-4-(3-pyrimidin-5-ylphenyl)-4,5-dihydro-1H-imidazol-4-yl]-1-(2-fluoroethyl)-1H-pyrrole-2-carboxylate;

Methyl 4-{2-amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carboxylate;

Methyl 4-{2-amino-4-[3-(6-fluoropyridin-3-yl)phenyl]-1-methyl-5-oxo-4,5-dihydro-1H-imidazol-4-yl}-1-(2-fluoroethyl)-1H-pyrrole-2-carboxylate;

Methyl 4-[2-amino-4-(2',5'-difluorobiphenyl-3-yl)-1-methyl-5-oxo-4,5-dihydro-1H-imidazol-4-yl]-1-(2-fluoroethyl)-1H-pyrrole-2-carboxylate;

Methyl 4-[2-amino-4-(3',5'-difluorobiphenyl-3-yl)-1-methyl-5-oxo-4,5-dihydro-1H-imidazol-4-yl]-1-(2-fluoroethyl)-1H-pyrrole-2-carboxylate;

Methyl 4-[2-amino-4-(3'-cyanobiphenyl-3-yl)-1-methyl-5-oxo-4,5-dihydro-1H-imidazol-4-yl]-1-(2-fluoroethyl)-1H-pyrrole-2-carboxylate;

Methyl 4-[2-amino-4-(5'-cyano-2'-fluorobiphenyl-3-yl)-1-methyl-5-oxo-4,5-dihydro-1H-imidazol-4-yl]-1-(2-fluoroethyl)-1H-pyrrole-2-carboxylate;

Methyl 4-[2-amino-4-(3'-methoxybiphenyl-3-yl)-1-methyl-5-oxo-4,5-dihydro-1H-imidazol-4-yl]-1-(2-fluoroethyl)-1H-pyrrole-2-carboxylate;

Methyl 4-{2-amino-1-methyl-5-oxo-4-[3'-(trifluoromethoxy)biphenyl-3-yl]-4,5-dihydro-1H-imidazol-4-yl}-1-(2-fluoroethyl)-1H-pyrrole-2-carboxylate;

Methyl 4-[2-amino-4-(3',4'-difluorobiphenyl-3-yl)-1-methyl-5-oxo-4,5-dihydro-1H-imidazol-4-yl]-1-(2-fluoroethyl)-1H-pyrrole-2-carboxylate;

Methyl 4-{2-amino-4-[3-(1,3-benzodioxol-5-yl)phenyl]-1-methyl-5-oxo-4,5-dihydro-1H-imidazol-4-yl}-1-(2-fluoroethyl)-1H-pyrrole-2-carboxylate;

4-[2-Amino-4-(3-bromophenyl)-1-methyl-5-oxo-4,5-dihydro-1H-imidazol-4-yl]-1-methyl-1H-pyrrole-2-carbonitrile;

4-[2-Amino-4-(3-bromophenyl)-1-methyl-5-oxo-4,5-dihydro-1H-imidazol-4-yl]-1-(2-fluoroethyl)-1H-pyrrole-2-carbonitrile;

4-[2-Amino-4-(3-bromophenyl)-1-methyl-5-oxo-4,5-dihydro-1H-imidazol-4-yl]-1-propyl-1H-pyrrole-2-carbonitrile;

4-[2-Amino-1-methyl-5-oxo-4-(3-pyrimidin-5-ylphenyl)-4,5-dihydro-1H-imidazol-4-yl]-1-methyl-1H-pyrrole-2-carbonitrile;

4-{2-Amino-4-[3-(2-fluoropyridin-3-yl)phenyl]-1-methyl-5-oxo-4,5-dihydro-1H-imidazol-4-yl}-1-methyl-1H-pyrrole-2-carbonitrile;

4-{2-Amino-4-[3-(2-chloro-5-fluoropyridin-3-yl)phenyl]-1-methyl-5-oxo-4,5-dihydro-1H-imidazol-4-yl}-1-methyl-1H-pyrrole-2-carbonitrile;

4-[2-Amino-1-methyl-5-oxo-4-(3-pyrimidin-5-ylphenyl)-4,5-dihydro-1H-imidazol-4-yl]-1-(2-fluoroethyl)-1H-pyrrole-2-carbonitrile;

4-[2-Amino-1-methyl-5-oxo-4-(3-pyrimidin-5-ylphenyl)-4,5-dihydro-1H-imidazol-4-yl]-1-propyl-1H-pyrrole-2-carbonitrile;

4-{2-Amino-4-[3-(2-fluoropyridin-3-yl)phenyl]-1-methyl-5-oxo-4,5-dihydro-1H-imidazol-4-yl}-1-propyl-1H-pyrrole-2-carbonitrile;

4-{2-Amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carbonitrile;

4-{2-Amino-4-[3-(2-chloro-5-fluoropyridin-3-yl)phenyl]-1-methyl-5-oxo-4,5-dihydro-1H-imidazol-4-yl}-1-propyl-1H-pyrrole-2-carbonitrile;

5-(5-Acetyl-1H-pyrrol-3-yl)-2-amino-5-(3-bromophenyl)-3-methyl-3,5-dihydro-imidazol-4-one;

4-{2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde;

4-[2-Amino-4-(3-bromophenyl)-1-methyl-5-oxo-4,5-dihydro-1H-imidazol-4-yl]-1H-pyrrole-2-carbaldehyde;

4-[2-Amino-4-(3-bromophenyl)-1-methyl-5-oxo-4,5-dihydro-1H-imidazol-4-yl]-1-ethyl-1H-pyrrole-2-carbaldehyde;

4-[2-Amino-4-(3-bromophenyl)-1-methyl-5-oxo-4,5-dihydro-1H-imidazol-4-yl]-1-(2-fluoroethyl)-1H-pyrrole-2-carbaldehyde;

4-{2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde;

4-{2-Amino-4-[3-(2-fluoropyridin-3-yl)phenyl]-1-methyl-5-oxo-4,5-dihydro-1H-imidazol-4-yl}-1-(2-fluoroethyl)-1H-pyrrole-2-carbaldehyde;

2-Amino-5-[5-[(diethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one;

2-Amino-5-{1-(2-fluoroethyl)-5-[(isopropylamino)methyl]-1H-pyrrol-3-yl}-5-[3-(2-fluoropyridin-3-yl)phenyl]-3-methyl-3,5-dihydro-4H-imidazol-4-one;

2-Amino-5-[1-(2-fluoroethyl)-5-(pyrrolidin-1-ylmethyl)-1H-pyrrol-3-yl]-5-[3-(2-fluoropyridin-3-yl)phenyl]-3-methyl-3,5-dihydro-4H-imidazol-4-one;

2-Amino-5-[5-[(dimethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one;

2-Amino-5-[5-[(dimethylamino)methyl]-1-(2-fluoroethyl)-1H-pyrrol-3-yl]-5-[3-(2-fluoropyridin-3-yl)phenyl]-3-methyl-3,5-dihydro-4H-imidazol-4-one;

2-Amino-5-[1-ethyl-5-(1-hydroxypropyl)-1H-pyrrol-3-yl]-5-[3-(2-fluoropyridin-3-yl)phenyl]-3-methyl-3,5-dihydro-4H-imidazol-4-one;

2-Amino-5-(1-ethyl-5-propionyl-1H-pyrrol-3-yl)-5-[3-(2-fluoropyridin-3-yl)phenyl]-3-methyl-3,5-dihydro-4H-imidazol-4-one;

2-Amino-5-(3-bromophenyl)-5-(1-ethyl-5-propionyl-1H-pyrrol-3-yl)-3-methyl-3,5-dihydro-4H-imidazol-4-one;

(5S)-2-Amino-5-[3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one;

(5R)-2-Amino-5-[3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one;

2-Amino-5-(1-ethyl-5-propionyl-1H-pyrrol-3-yl)-3-methyl-5-(3-pyrimidin-5-ylphenyl)-3,5-dihydro-4H-imidazol-4-one;

2-Amino-5-(3'-methoxybiphenyl-3-yl)-3-methyl-5-[5-propionyl-1-(2,2,2-trifluoroethyl)-1H-pyrrol-3-yl]-3,5-dihydro-4H-imidazol-4-one;

2-Amino-5-(3',5'-difluorobiphenyl-3-yl)-3-methyl-5-[5-propionyl-1-(2,2,2-trifluoroethyl)-1H-pyrrol-3-yl]-3,5-dihydro-4H-imidazol-4-one;

2-Amino-5-(3'-chlorobiphenyl-3-yl)-3-methyl-5-[5-propionyl-1-(2,2,2-trifluoroethyl)-1H-pyrrol-3-yl]-3,5-dihydro-4H-imidazol-4-one;

2-Amino-5-(3'-chloro-4'-fluorobiphenyl-3-yl)-3-methyl-5-[5-propionyl-1-(2,2,2-trifluoroethyl)-1H-pyrrol-3-yl]-3,5-dihydro-4H-imidazol-4-one;

3'-{2-Amino-1-methyl-5-oxo-4-[5-propionyl-1-(2,2,2-trifluoroethyl)-1H-pyrrol-3-yl]-4,5-dihydro-1H-imidazol-4-yl}biphenyl-3-carbonitrile;

2-Amino-5-(3-bromo-4-fluorophenyl)-3-methyl-5-[5-propionyl-1-(2,2,2-trifluoroethyl)-1H-pyrrol-3-yl]-3,5-dihydro-4H-imidazol-4-one;

2-Amino-5-[4-fluoro-3-(2-fluoropyridin-3-yl)phenyl]-3-methyl-5-[5-propionyl-1-(2,2,2-trifluoroethyl)-1H-pyrrol-3-yl]-3,5-dihydro-4H-imidazol-4-one; and 2-Amino-5-(4-fluoro-3-pyrimidin-5-ylphenyl)-3-methyl-5-[5-propionyl-1-(2,2,2-trifluoroethyl)-1H-pyrrol-3-yl]-3,5-dihydro-4H-imidazol-4-one; or a tautomer thereof, a stereoisomer thereof; or a pharmaceutically acceptable salt thereof.

12. A compound selected from the group consisting of:

4-{2-Amino-4-[4-ethoxy-3-(2-fluoropyridin-3-yl)phenyl]-1-methyl-5-oxo-4,5-dihydro-1H-imidazol-4-yl}-1-ethyl-N-methyl-1H-pyrrole-2-carboxamide;

N-{3-[2-Amino-4-(1-ethyl-5-propionyl-1H-pyrrol-3-yl)-1-methyl-5-oxo-4,5-dihydro-1H-imidazol-4-yl]-phenyl}-2-methoxy-acetamide;

4-{2-Amino-4-[3-(2-fluoropyridin-3-yl)phenyl]-1-methyl-5-oxo-4,5-dihydro-1H-imidazol-4-yl}-1-ethyl-N-methyl-1H-pyrrole-2-carboxamide;

4-{2-Amino-4-[3-(2-fluoropyridin-3-yl)phenyl]-1-methyl-5-oxo-4,5-dihydro-1H-imidazol-4-yl}-N, 1-diethyl-1H-pyrrole-2-carboxamide;

4-{2-Amino-4-[3-(2-fluoropyridin-3-yl)phenyl]-1-methyl-5-oxo-4,5-dihydro-1H-imidazol-4-yl}-1-ethyl-N-propyl-1H-pyrrole-2-carboxamide;

4-{2-Amino-4-[3-(2-fluoropyridin-3-yl)phenyl]-1-methyl-5-oxo-4,5-dihydro-1H-imidazol-4-yl}-N-butyl-1-ethyl-1H-pyrrole-2-carboxamide;

4-{2-Amino-4-[3-(2-fluoropyridin-3-yl)phenyl]-1-methyl-5-oxo-4,5-dihydro-1H-imidazol-4-yl}-1-ethyl-N-isopropyl-1H-pyrrole-2-carboxamide;

4-{2-Amino-4-[3-(2-fluoropyridin-3-yl)phenyl]-1-methyl-5-oxo-4,5-dihydro-1H-imidazol-4-yl}-N-cyclopentyl-1-ethyl-1H-pyrrole-2-carboxamide;

4-{2-Amino-4-[3-(2-fluoropyridin-3-yl)phenyl]-1-methyl-5-oxo-4,5-dihydro-1H-imidazol-4-yl}-1-ethyl-N,N-dimethyl-1H-pyrrole-2-carboxamide;

4-{2-Amino-4-[3-(2-fluoropyridin-3-yl)phenyl]-1-methyl-5-oxo-4,5-dihydro-1H-imidazol-4-yl}-1-ethyl-N-(4-fluorobenzyl)-1H-pyrrole-2-carboxamide;

2-Amino-5-[1-ethyl-5-(methylsulfonyl)-1H-pyrrol-3-yl]-5-[4-fluoro-3-(2-fluoropyridin-3-yl)phenyl]-3-methyl-3,5-dihydro-4H-imidazol-4-one; and 4-{2-Amino-4-[3-(2-fluoropyridin-3-yl)phenyl]-1-methyl-5-oxo-4,5-dihydro-1H-imidazol-4-yl}-1-ethyl-1H-pyrrole-2-carbaldehyde 0-methyloxime; or a tautomer thereof, a stereoisomer thereof; or a pharmaceutically acceptable salt thereof.

* * * * *